(12) United States Patent
Flynn et al.

(10) Patent No.: US 11,912,668 B2
(45) Date of Patent: Feb. 27, 2024

(54) GCN2 AND PERK KINASE INHIBITORS AND METHODS OF USE THEREOF

(71) Applicant: Deciphera Pharmaceuticals, LLC, Waltham, MA (US)

(72) Inventors: Daniel L. Flynn, Waltham, MA (US); Patrick Kearney, Waltham, MA (US); Jeffery Zwicker, Waltham, MA (US); Gada Al-Ani, Waltham, MA (US); Salim Javed, Waltham, MA (US); Yu Mi Ahn, Waltham, MA (US); Kristen Stoltz, Waltham, MA (US); Bertrand Le Bourdonnec, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 17/528,478

(22) Filed: Nov. 17, 2021

(65) Prior Publication Data
US 2022/0274934 A1 Sep. 1, 2022

Related U.S. Application Data

(60) Provisional application No. 63/185,846, filed on May 7, 2021, provisional application No. 63/115,496, filed on Nov. 18, 2020.

(51) Int. Cl.
| | |
|---|---|
| *C07D 471/04* | (2006.01) |
| *C07D 239/84* | (2006.01) |
| *A61P 35/00* | (2006.01) |
| *C07D 401/12* | (2006.01) |

(52) U.S. Cl.
CPC ............ *C07D 239/84* (2013.01); *A61P 35/00* (2018.01); *C07D 401/12* (2013.01); *C07D 471/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 6,001,839 A | 12/1999 | Calderwood et al. |
| 6,391,885 B1 | 5/2002 | Piazza et al. |
| 6,660,744 B1 | 12/2003 | Hirst et al. |
| 6,713,474 B2 | 3/2004 | Hirst et al. |
| 6,921,763 B2 | 7/2005 | Hirst et al. |
| 7,071,199 B1 | 7/2006 | Hirst et al. |
| 7,144,911 B2 | 12/2006 | Flynn et al. |
| 7,202,257 B2 | 4/2007 | Flynn et al. |
| 7,202,363 B2 | 4/2007 | Betschmann et al. |
| 7,276,506 B2 | 10/2007 | Waer et al. |
| 7,279,576 B2 | 10/2007 | Flynn et al. |
| 7,342,037 B2 | 3/2008 | Flynn et al. |
| 7,423,038 B2 | 9/2008 | Ren et al. |
| 7,446,112 B2 | 11/2008 | Grootenhuis et al. |
| 7,449,582 B2 | 11/2008 | Ding et al. |
| 7,501,513 B2 | 3/2009 | Waer et al. |
| 7,531,566 B2 | 5/2009 | Flynn et al. |
| 7,592,352 B2 | 9/2009 | Miyazaki |
| 7,662,819 B2 | 2/2010 | Chisholm et al. |
| 7,666,895 B2 | 2/2010 | Flynn et al. |
| 7,678,792 B2 | 3/2010 | Chianelli et al. |
| 7,696,213 B2 | 4/2010 | Cheng et al. |
| 7,737,283 B2 | 6/2010 | Flynn et al. |
| 7,790,756 B2 | 9/2010 | Flynn et al. |
| 7,829,570 B2 | 11/2010 | Hirst et al. |
| 7,893,066 B2 | 2/2011 | Koltun et al. |
| 7,897,762 B2 | 3/2011 | Flynn et al. |
| 8,143,293 B2 | 3/2012 | Flynn et al. |
| 8,143,394 B2 | 3/2012 | Watkins et al. |
| 8,163,756 B2 | 4/2012 | Flynn et al. |
| 8,188,113 B2 | 5/2012 | Flynn et al. |
| 8,278,331 B2 | 10/2012 | Flynn et al. |
| 8,461,179 B1 | 6/2013 | Flynn et al. |
| 8,486,951 B2 | 7/2013 | Flynn et al. |

(Continued)

FOREIGN PATENT DOCUMENTS

| | | |
|---|---|---|
| CN | 102746241 B | 11/2014 |
| CN | 109721531 A | 5/2019 |

(Continued)

OTHER PUBLICATIONS

U.S. Appl. No. 11/963,740, filed Dec. 21, 2007, Granted, U.S. Pat. No. 8,163,756.

(Continued)

*Primary Examiner* — Brian E McDowell
(74) *Attorney, Agent, or Firm* — Goodwin Procter LLP

(57) ABSTRACT

Described herein are compounds, such as compounds represented by Formula I-R:

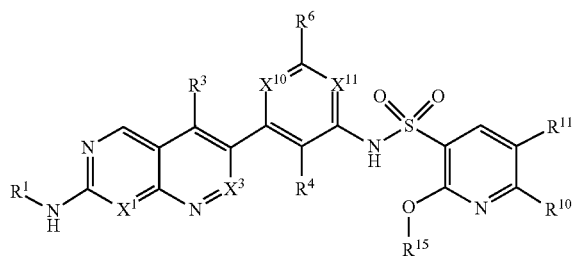

Formula I-R and pharmaceutically acceptable salts, enantiomers, stereoisomers, and tautomers thereof, that are inhibitors of GCN2 kinase or PERK kinase, and methods of treating diseases, including diseases associated with GCN2 kinase or PERK kinase, with said compounds.

15 Claims, 8 Drawing Sheets

Specification includes a Sequence Listing.

(56) References Cited

U.S. PATENT DOCUMENTS

| | | |
|---|---|---|
| 8,536,187 B2 | 9/2013 | Canales et al. |
| 8,569,319 B2 | 10/2013 | Flynn et al. |
| 8,586,565 B2 | 11/2013 | Flynn et al. |
| 8,637,549 B2 | 1/2014 | Engelhardt et al. |
| 8,637,672 B2 | 1/2014 | Flynn et al. |
| 8,697,709 B2 | 4/2014 | Dar et al. |
| 8,741,911 B2 | 6/2014 | Allgeier et al. |
| 8,921,565 B2 | 12/2014 | Flynn et al. |
| 8,940,756 B2 | 1/2015 | Flynn et al. |
| 8,940,893 B2 | 1/2015 | Bosanac et al. |
| 8,980,899 B2 | 3/2015 | Korennykh et al. |
| 9,012,635 B2 | 4/2015 | Flynn et al. |
| 9,133,183 B2 | 9/2015 | Flynn et al. |
| 9,181,223 B2 | 11/2015 | Kaufman et al. |
| 9,187,474 B2 | 11/2015 | Flynn et al. |
| 9,193,719 B2 | 11/2015 | Flynn et al. |
| 9,309,224 B2 | 4/2016 | Flynn et al. |
| 9,334,267 B2 | 5/2016 | Flynn et al. |
| 9,376,438 B2 | 6/2016 | Goldstein et al. |
| 9,382,228 B2 | 7/2016 | Flynn et al. |
| 9,387,202 B2 | 7/2016 | Flynn et al. |
| 9,457,019 B2 | 10/2016 | Flynn et al. |
| 10,399,988 B2 | 9/2019 | Yoon et al. |
| 10,544,104 B2 | 1/2020 | Van Voorhis et al. |
| 10,561,660 B2 | 2/2020 | Bindi et al. |
| 10,745,379 B2 | 8/2020 | Vacca et al. |
| 10,966,966 B2 | 4/2021 | Soto et al. |
| 11,103,507 B2 | 8/2021 | Flynn et al. |
| RE48,731 E | 9/2021 | Flynn et al. |
| 11,185,535 B2 | 11/2021 | Kaufman et al. |
| 11,266,635 B2 | 3/2022 | Soto et al. |
| 11,344,536 B1 | 5/2022 | Soto et al. |
| 11,395,818 B2 | 7/2022 | Kaufman et al. |
| 11,426,390 B2 | 8/2022 | Soto et al. |
| 11,433,056 B1 | 9/2022 | Soto et al. |
| 11,518,758 B2 | 12/2022 | Flynn et al. |
| 11,529,336 B2 | 12/2022 | Soto et al. |
| 11,530,206 B2 | 12/2022 | Flynn et al. |
| 11,534,432 B2 | 12/2022 | Soto et al. |
| 11,576,903 B2 | 2/2023 | Kaufman et al. |
| 11,576,904 B2 | 2/2023 | Soto et al. |
| 11,590,134 B2 | 2/2023 | Flynn et al. |
| 11,612,591 B2 | 3/2023 | Kaufman et al. |
| 11,679,110 B2 | 6/2023 | Flynn et al. |
| 2003/0199525 A1 | 10/2003 | Hirst et al. |
| 2005/0008640 A1 | 1/2005 | Waegell et al. |
| 2005/0026944 A1 | 2/2005 | Betschmann et al. |
| 2006/0025383 A1 | 2/2006 | Wishart et al. |
| 2007/0004721 A1 | 1/2007 | Waer et al. |
| 2007/0054916 A1 | 3/2007 | Patel et al. |
| 2007/0060601 A1 | 3/2007 | Arrington et al. |
| 2009/0306107 A1 | 12/2009 | Perez et al. |
| 2009/0318456 A1 | 12/2009 | Herdewijn et al. |
| 2011/0136766 A1 | 6/2011 | Zhuang et al. |
| 2011/0313156 A1 | 12/2011 | Engelhardt et al. |
| 2013/0116263 A1 | 5/2013 | Campbell et al. |
| 2013/0267526 A1 | 10/2013 | Chen et al. |
| 2014/0038991 A1 | 2/2014 | Yu et al. |
| 2014/0163026 A1 | 6/2014 | Campbell et al. |
| 2015/0031693 A1 | 1/2015 | Mckew et al. |
| 2016/0045503 A1 | 2/2016 | Goldstein et al. |
| 2016/0257676 A1 | 9/2016 | Zhang et al. |
| 2020/0108075 A1 | 4/2020 | Liang et al. |
| 2020/0157079 A1 | 5/2020 | Vacca et al. |
| 2020/0352920 A1 | 11/2020 | Flynn et al. |
| 2021/0128559 A1 | 5/2021 | Xu et al. |
| 2021/0145805 A1 | 5/2021 | Flynn et al. |
| 2021/0261544 A1 | 8/2021 | Deng et al. |
| 2022/0047573 A1 | 2/2022 | Flynn et al. |
| 2022/0184050 A1 | 6/2022 | Flynn |
| 2022/0184054 A1 | 6/2022 | Flynn |
| 2022/0184077 A1 | 6/2022 | Flynn |
| 2022/0184092 A1 | 6/2022 | Flynn |
| 2022/0184093 A1 | 6/2022 | Flynn |
| 2022/0193083 A1 | 6/2022 | Flynn |
| 2022/0274934 A1 | 9/2022 | Flynn et al. |
| 2022/0370423 A1 | 11/2022 | Flynn et al. |
| 2022/0370424 A1 | 11/2022 | Flynn et al. |
| 2022/0370426 A1 | 11/2022 | Soto et al. |
| 2023/0039712 A1 | 2/2023 | Flynn et al. |
| 2023/0047915 A1 | 2/2023 | Flynn et al. |
| 2023/0145926 A1 | 5/2023 | Soto et al. |
| 2023/0201175 A1 | 6/2023 | Kaufman et al. |
| 2023/0201176 A1 | 6/2023 | Kaufman et al. |

FOREIGN PATENT DOCUMENTS

| | | |
|---|---|---|
| DE | 4038932 A1 | 6/1992 |
| EP | 3929195 A1 | 12/2021 |
| WO | WO-9841525 A1 | 9/1998 |
| WO | WO-2000017202 A1 | 3/2000 |
| WO | WO-2001019829 A3 | 9/2001 |
| WO | WO-2001072751 A1 | 10/2001 |
| WO | WO-2006/039718 A2 | 4/2006 |
| WO | WO-2008043087 A2 | 4/2008 |
| WO | WO-2009126123 A1 | 10/2009 |
| WO | WO-2016023401 A1 | 2/2016 |
| WO | WO-2017220477 A1 | 12/2017 |
| WO | WO-2020117635 A1 | 6/2020 |
| WO | WO-2020142612 A1 | 7/2020 |
| WO | WO-2020147097 A1 | 7/2020 |
| WO | WO-2020172093 A1 | 8/2020 |
| WO | WO-2020177729 A1 | 9/2020 |
| WO | WO-2020210828 A1 | 10/2020 |
| WO | WO-2020232401 A1 | 11/2020 |
| WO | WO-2020232403 A1 | 11/2020 |
| WO | WO-2020243376 A1 | 12/2020 |
| WO | WO-2020252165 A1 | 12/2020 |
| WO | WO-2021145521 A1 | 7/2021 |
| WO | WO-2021165346 A1 | 8/2021 |
| WO | WO-2022109001 A1 | 5/2022 |

OTHER PUBLICATIONS

U.S. Appl. No. 11/870,388, filed Oct. 10, 2007, Granted, U.S. Pat. No. 7,790,756.
U.S. Appl. No. 12/829,561, filed Jul. 2, 2010, Granted, U.S. Pat. No. 8,586,565.
U.S. Appl. No. 11/854,354, filed Sep. 12, 2007, Granted, U.S. Pat. No. 8,188,113.
U.S. Appl. No. 10/746,460, filed Dec. 24, 2003, Granted, U.S. Pat. No. 7,144,911.
U.S. Appl. No. 10/886,329, filed Jul. 6, 2004, Granted, U.S. Pat. No. 7,202,257.
U.S. Appl. No. 11/450,840, filed Jun. 9, 2006, Granted, U.S. Pat. No. 7,342,037.
U.S. Appl. No. 11/336,708, filed Jan. 20, 2006, Granted, U.S. Pat. No. 7,531,566.
U.S. Appl. No. 11/450,850, filed Jun. 9, 2006, Granted, U.S. Pat. No. 7,666,895.
U.S. Appl. No. 10/746,607, filed Dec. 24, 2003, Granted, U.S. Pat. No. 7,279,576.
U.S. Appl. No. 11/854,293, filed Sep. 12, 2007, Granted, U.S. Pat. No. 7,897,762.
U.S. Appl. No. 12/105,408, filed Apr. 18, 2008, Granted, U.S. Pat. No. 8,143,293.
U.S. Appl. No. 13/590,955, filed Aug. 21, 2012, Granted, U.S. Pat. No. 8,486,951.
U.S. Appl. No. 11/450,849, file Jun. 9, 2006, Granted, U.S. Pat. No. 7,737,283.
U.S. Appl. No. 13/785,575, filed Mar. 5, 2013, Granted, U.S. Pat. No. 8,741,911.
U.S. Appl. No. 12/608,578, filed Oct. 29, 2009, Granted, U.S. Pat. No. 8,278,331.
U.S. Appl. No. 13/098,247, filed Apr. 29, 2011, Granted, U.S. Pat. No. 8,569,319.
U.S. Appl. No. 13/559,170, filed Jul. 26, 2012, Granted, U.S. Pat. No. 8,637,672.
U.S. Appl. No. 14/214,134, filed Mar. 14, 2014, Granted, U.S. Pat. No. 9,133,183.

(56) References Cited

OTHER PUBLICATIONS

U.S. Appl. No. 14/383,803, filed Mar. 5, 2013, Granted, U.S. Pat. No. 9,187,474.
U.S. Appl. No. 13/491,394, filed Jun. 7, 2012, Granted, U.S. Pat. No. 8,461,179.
U.S. Appl. No. 13/801,753, filed Mar. 13, 2013, Granted, U.S. Pat. No. 8,940,756.
U.S. Appl. No. 16/387,315, filed Apr. 17, 2019, Granted, Re. 48731.
U.S. Appl. No. 14/214,127, filed Mar. 14, 2014, Granted, U.S. Pat. No. 9,012,635.
U.S. Appl. No. 13/683,277, filed Nov. 21, 2012, Granted, U.S. Pat. No. 8,921,565.
U.S. Appl. No. 14/549,125, filed Nov. 20, 2014, Granted, U.S. Pat. No. 9,387,202.
U.S. Appl. No. 14/214,160, filed Mar. 14, 2014, Granted, U.S. Pat. No. 9,193,719.
U.S. Appl. No. 14/214,171, filed Mar. 14, 2014, Granted, U.S. Pat. No. 9,181,223.
U.S. Appl. No. 14/214,185, filed Mar. 14, 2014, Granted, U.S. Pat. No. 9,382,228.
U.S. Appl. No. 14/214,179, filed Mar. 14, 2014, Granted, U.S. Pat. No. 9,309,224.
U.S. Appl. No. 14/383,799, filed Mar. 5, 2013, Granted, U.S. Pat. No. 9,334,267.
U.S. Appl. No. 14/535,900, filed Nov. 7, 2014, Granted, U.S. Pat. No. 9,457,019.
U.S. Appl. No. 17/374,446, filed Jul. 13, 2021, Pending.
U.S. Appl. No. 16/617,721, filed Nov. 27, 2019, Published, US 2020-0129489 A1.
U.S. Appl. No. 17/028,591, filed Sep. 22, 2020, Published, US 2021-0015801 A1.
U.S. Appl. No. 17/506,772, filed Oct. 21, 2021, Pending.
U.S. Appl. No. 16/943,821, filed Jul. 30, 2020, Published, US 2021-0145805 A1.
U.S. Appl. No. 16/943,871, filed Jul. 30, 2020, Published, US 2020-0352920 A1.
U.S. Appl. No. 16/725,282, filed Dec. 23, 2019, Granted, U.S. Pat. No. 11,103,507.
U.S. Appl. No. 17/358,137, filed Jun. 25, 2021, Pending.
U.S. Appl. No. 16/870,384, filed May 8, 2020, Published, US 2020-0354352 A1.
U.S. Appl. No. 16/902,989, filed Jun. 16, 2020, Pending, US 2021-0128556 A1.
U.S. Appl. No. 16/991,644, filed Aug. 12, 2020, Pending, US 2022-0047573 A1.
U.S. Appl. No. 17/180,234, filed Feb. 19, 2021, Granted, U.S. Pat. No. 11,185,535.
U.S. Appl. No. 17/504,133, filed Oct. 18, 2021, Pending.
U.S. Appl. No. 17/028,640, filed Sep. 22, 2020, Granted, U.S. Pat. No. 10,966,966.
U.S. Appl. No. 17/180,218, filed Feb. 19, 2021, Granted, U.S. Pat. No. 11,266,635.
U.S. Appl. No. 17/180,241, filed Feb. 19, 2021, Published, US 2021-0196693 A1.
U.S. Appl. No. 17/193,707, filed Mar. 5, 2021, Published, US 2021-0275518 A1.
U.S. Appl. No. 17/528,478, filed Nov. 17, 2021, Pending.
U.S. Appl. No. 17/534,795, filed Nov. 24, 2021, Pending.
U.S. Appl. No. 17/534,762, filed Nov. 24, 2021, Pending.
U.S. Appl. No. 17/534,764, filed Nov. 24, 2021, Pending.
U.S. Appl. No. 17/534,768, filed Nov. 24, 2021, Pending.
U.S. Appl. No. 17/534,769, filed Nov. 24, 2021, Pending.
U.S. Appl. No. 17/534,771, filed Nov. 24, 2021, Pending.
U.S. Appl. No. 17/583,977, filed Jan. 25, 2022, Pending.
U.S. Appl. No. 17/583,985, filed Jan. 25, 2022, Pending.
Alberga, Domenico et al. A New Approach for Drug Target and Bioactivity Prediction: The Multifingerprint Similarity Search Algorithm (MuSSeL); Journal of Chemical Information and Modeling (2019), 59(1), 586-596.
International Search Report and Written Opinion of PCT/US2021/059678 dated Mar. 15, 2022, 15 pages.
Lin, Songwen, et al. 2-Amino-4-methylquinazoline Derivatives as Highly Potent Phosphatidylinositol 3-Kinase Inhibitors for Cancer Treatment; Journal of Medicinal Chemistry (2018), 61(14), 6087-6109.
Lin, Songwen, et al. Discovery of 4-Methylquinazoline Based PI3K Inhibitors for the Potential Treatment of Idiopathic Pulmonary Fibrosis; Journal of Medicinal Chemistry (2019), 62(19), 8873-8879.
Smith, A. L et al., "Discovery of 1H-Pyrazol-3(2H)-ones as Potent and Selective Inhibitors of Protein Kinase R-like Endoplasmic Reticulum Kinase (PERK)", Journal of Medicinal Chemistry, 2015, 58, pp. 1426-1441.
Lehman, S. L., "The Role of the Integrated Stress Response Kinase Gen2 in Cell Regulation and Tumorigenesis", Univ. of Pennsylvania Scholarly Commons, 2015, 102 pages.
Hamanaka, R. B. et al., "PERK and GCN2 Contribute to eIF2α Phosphorylation and Cell Cycle Arrest after Activation of the Unfolded Protein Response Pathway", Molecular Biology of the Cell, vol. 16, pp. 5493-5501, Dec. 2005.
Giglio, P. et al., "PKR and GCN2 stress kinases promote an ER stress-independent eIF2α phosphorylation responsible for calreticulin exposure in melanoma cells", Oncoimmunology, 2018, vol. 7, e1466765, 14 pages.
Fujimoto, J. et al., "Identification of novel, potent and orally available GCN2 inhibitors with type I half binding mode", ACS Medicinal Chemistry Letters, Sep. 19, 2019, 50 pages.
Axten, J. M. et al., "Discovery of GSK2656157: An Optimized PERK Inhibitors Selected for Preclinical Development", ACS Medicinal Chemistry Letters, 2013, 4, pp. 964-968.
Axten, J. M. et al., "Discovery of 7-Methyl-5-(1 {[3-(trifluoromethyl)phenyl]}-2,3-dihydro-1H-indol-5-yl)-7H-pyrrolo[2,3-d]pyrimidin-4-amine(GSK2606414), a Potent and Selective First-in-Class Inhibitor of Protein Kinase R (PKR)-like Endoplasmic Reticulum Kinase (Perk)", J. Med. Chem., 2012, 25 pages.
Alasiri, G. et al., "Reciprocal regulation between GCN2 (eIF2AK4) and PERK (eIF2AK3) through the JNK-FOXO3 axis to modulate cancer drug resistance and clonal survival", Molecular and Cellular Endocrinology, 2020, 515, 15 pages.
International Search Report and Written Opinion of PCT/US2022/051717 dated Mar. 31, 2023, 11 pages.

6 A 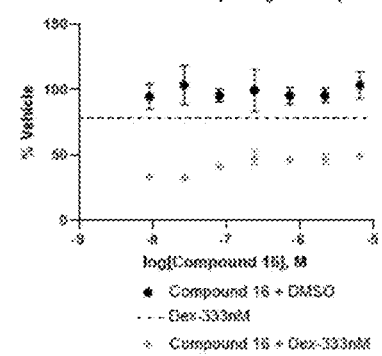
6 B 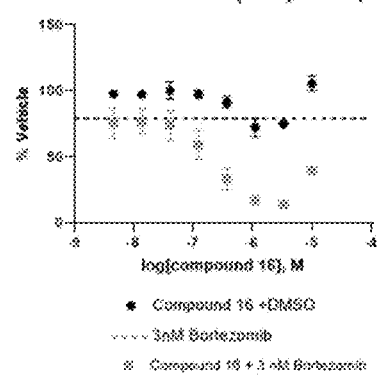
6 C 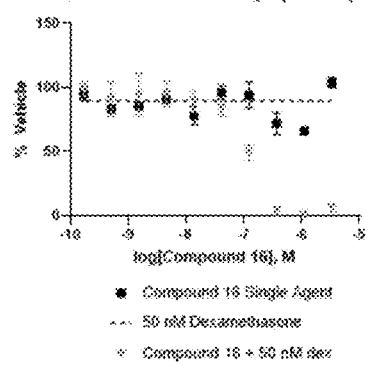
6 D 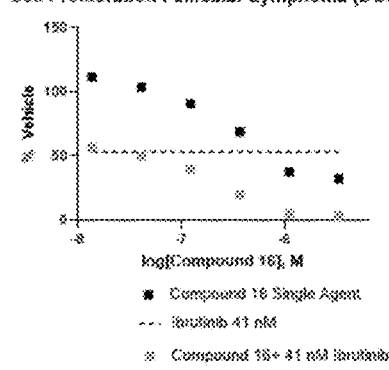
Figures 6A, 6B, 6C, and 6D

| Dose (mg/kg) | Time point (h) | Compound 16 plasma level (ng/mL) | % inhibition of ATF4 |
|---|---|---|---|
| 50 | 2 | 170573 | 81 |
| 50 | 6 | 158460 | 90 |
| 50 | 10 | 148626 | 98 |
| 25 | 2 | 138922 | 69 |
| 25 | 6 | 130077 | 92 |
| 25 | 10 | 90146 | 88 |

GCN2 AND PERK KINASE INHIBITORS AND METHODS OF USE THEREOF

CROSS-REFERENCE

This application claims priority to U.S. Provisional Application No. 63/115,496 filed Nov. 18, 2020 and U.S. Provisional Application No. 63/185,846 filed May 7, 2021, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 28, 2021, is named DCP_098_SL.txt and is 23,646 bytes in size.

BACKGROUND

Cancer cells need a continuous supply of nutrients to maintain their abnormal growth and rapid division. As part of these nutrients, amino acids are essential to support the high metabolic demands of tumor cells.

GCN2 is a serine/threonine protein kinase, one of the eukaryotic initiation factor 2α (eIF2α) kinases that are master regulators in the integrated stress response (ISR). The ISR is essential for maintaining cellular homeostasis under a wide range of stressors and is activated when cells adapt to stress conditions such as hypoxia and amino acid deprivation. The ISR is regulated by phosphorylation and activation of eIF2α kinases, including GCN2, that act as early responders to disturbances in cellular homeostasis. In addition to GCN2, there are three other eIF2α kinases family including PKR-like ER kinase (PERK), double-stranded RNA-dependent protein kinase (PKR), and heme-regulated eIF2α kinase (HRI). All four eIF2α kinases share extensive homology in their kinase catalytic domains but possess distinct regulatory domains. Each of the IF2α kinases responds to distinct environmental and physiological stresses, which reflect their unique regulatory mechanisms. PERK kinase is activated under stress conditions including ATP depletion and the unfolded protein response, and like GCN2, PERK kinase activation leads to up-regulation of the key ISR transcription factor ATF4.

Under conditions of essential amino-acid limitation or other stressors (UV irradiation, redox stress or proteasome inhibition), GCN2 phosphorylates eIF2α, which inhibits the formation of a new ternary complex and hence inhibition of mRNA translation initiation. While decreasing global mRNA translation, in tumor cells eIF2α phosphorylation also increases the translation of the ISR transcription factor ATF4, which increases the expression of many stress response genes including genes dedicated to providing amino acids to the tumor cell: i.e., amino acid synthesis enzymes and transporters that mediate influx of amino acids into the tumor cell. ATF4 is over-expressed in human solid and liquid tumors suggesting an important function in tumor progression.

Asparagine is an important amino acid involved in several biosynthetic pathways that significantly influence carcinogenesis and tumor biology. All cells need asparagine for their protein synthesis and growth. Normal cells will obtain most of their asparagine requirements through internal synthesis. Compared to normal cells, cancer cells require elevated amounts of asparagine to grow and proliferate, cannot produce that required amount themselves, and must rely on circulating asparagine in order to survive. Asparagine Synthetase (ASNS) catalyzes the synthesis of asparagine from aspartate and glutamine. L-asparaginase (ASNase) removes circulating asparagine, thereby depriving cancer cells of a key nutrient and causing them to die. The use of L-asparaginase, the first example of anti-cancer treatment targeting a tumor-specific metabolic feature, is a well-established treatment in pediatric acute lymphoblastic leukemia (ALL), but toxicity has limited its use beyond this patient population. The particularly low-level expression of ASNS in numerous ALL cell lines, as compared to that of normal cells, makes asparagine depletion an effective method of treatment due to the cells' unusual dependency on circulating serum asparagine as a necessary nutrition for growth. A poor response to asparaginase is associated with increased relapse risk. Other hematological and solid cancers express low levels of ASNS and, therefore, should also be asparagine auxotroph and asparaginase sensitive. Conversely, in some cancer types ASNS is overexpressed, promoting cell proliferation, chemoresistance, and a metastatic behavior. In case of asparaginase resistant cancers, the effect of blood asparagine depletion through L-asparaginase instead leads to significant ASNS overexpression to compensate, effectively nullifying the effect of the chemotherapy drug. Numerous studies have shown that ASNS is at the center of the cell response to amino acid deprivation and other forms of cellular stress. Through transcriptional regulation, the ASNS gene is a target of two signaling pathways aimed at ensuring cell survival. The first, named Amino Acid Response (AAR), is activated by the GCN2 kinase under conditions of imbalanced amino acid availability. The second pathway, named the Unfolded Protein Response (UPR), is activated by the PERK kinase under conditions of increased endoplasmic reticulum stress. The AAR and UPR pathways converge on the phosphorylation of eIF2α, which provokes the attenuation of global protein synthesis and, at the same time, the preferential translation of a selected population of mRNAs, including the transcription factor ATF4. ATF4 is the major factor for ASNS induction, working as a trans-activator through the binding to an enhancer element within ASNS promoter.

GCN2 sensitizes cancer cells with low basal level expression of ASNS to the antileukemic agent L-asparaginase in vitro and in vivo. Treatment with GCN2 inhibitors rendered acute lymphoblastic leukemia cells sensitive to L-asparaginase by preventing the induction of ASNS. GCN2 inhibitors exhibit synergistic antiproliferative effects with L-asparaginase in ASNS-low/deficient cancers. Therefore, combined treatment with GCN2 inhibitors and L-asparaginase shows promise for achieving improved outcomes in acute lymphoblastic leukemia and other types of cancer. Acute lymphoblastic leukemia, acute myeloid leukemia, and pancreatic cancer cells are particularly sensitive to combined treatment with L-asparaginase and GCN2 inhibitors. Previously reported studies demonstrated robust antitumor activities of combined treatment with ASNase and GCN2 inhibitors in acute lymphoblastic leukemia, acute myeloid leukemia, and pancreatic cancer cells compared with the results of single-agent L-asparaginase or GCN2 inhibitor treatment. Thus, GCN2 inhibitors may represent sensitizing agents to L-asparaginase used for treating these tumors. In summary, GCN2 inhibition enhances the sensitivity to L-asparaginase treatment by preventing ASNS induction in cancer cells with low ASNS expression at basal levels.

Inhibition of GCN2 may also be an effective strategy for targeting the tumor microenvironment, including the immune system, including tryptophan-dependent immunosurveillance of tumor cells.

The tumor microenvironment [TME; a series of extracellular components and stromal cells (endothelial cells, cancer-associated fibroblasts, tumor-associated macrophages, tumor-infiltrating T cells) that surround the tumor cells] is characterized by deficiencies in oxygen and key nutrients, such as glucose and amino acids, resulting in an overall immune suppressive environment.

Many tumors evolved to escape immune surveillance by taking advantage of their metabolic flexibility and redirecting nutrients for their own advantage. Stromal cells and myeloid-derived suppressor cells (MDSC) within the tumor create a nutrient-poor environment that inhibits immune function and supports tumor growth.

Elevated catabolism of tryptophan, one of the essential amino acids, driven by overexpression of critical enzymes in tryptophan metabolism [Indoleamine-2,3-dioxygenase (IDO) and tryptophan-2,3-dioxygenase (TDO)] is driven by cells of the tumor microenvironment, leading to an immunosuppressive microenvironment in many types of cancer. Local tryptophan depletion is considered to be a crucial T-cell immunosuppressive mechanism. In T cells, the GCN2 kinase has been identified as a molecular sensor of tryptophan deprivation. GCN2 activation by tryptophan depletion induces apoptosis and mitigates T cell proliferation. GCN2 is a key effector signaling component for IDO/TDO and is considered a metabolic checkpoint of highly tryptophan-dependent T-cells.

The GCN2 pathway is not only important for tumoral immune escape but also plays an active role in modulating other aspects of the tumor microenvironment. GCN2 knockdown has been demonstrated to prevent amino acid deprivation (AAD)-induced expression of Vascular Endothelial Growth Factor (VEGF) which tumors use to enhance nutrient supply via increased vascularization. Thus, activation of the GCN2/ATF4 pathway promotes tumor growth and angiogenesis through AAD-mediated VEGF expression. Abrogation of ATF4 or GCN2 expression significantly inhibited tumor growth in vivo.

Therefore, selective inhibition of GCN2 can both increase the activity of the immune system and decrease vascularization in the tumor microenvironment. The GCN2-eIF2α-ATF4 pathway is critical for maintaining metabolic homeostasis in tumor cells under conditions of stress, and for maintaining an immunosuppressed immune cell microenvironment. The PERK-ATF4 pathway is also critical for maintaining homeostasis in tumors cells under conditions of stress. It has been reported that there is cross talk regulation of both the GCN2 and PERK signaling pathways, such that inhibition of GCN2 can activate PERK as a compensatory mechanism, and vice versa, that inhibition of PERK an activate GCN2 as a compensatory mechanism.

There is a need for inhibitors of GCN2 and/or PERK that block the pro-tumoral aspects of GCN2 and/or PERK, both in the tumor cell (tumor cell autonomous) and in the tumor immune cell microenvironment.

SUMMARY

Described herein are compounds which display inhibitory activity of the GCN2 (general control nonderepressible 2) kinase and/or PERK (PKR-like ER kinase) kinase and methods of use thereof for the treatment of disorders, including GCN2 or PERK associated diseases.

In one embodiment, described herein is a compound represented by Formula I:

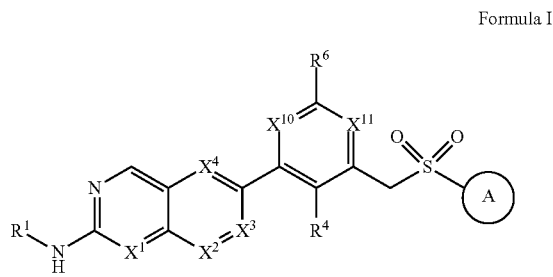

Formula I or a pharmaceutically acceptable salt, enantiomer, stereoisomer, or tautomer thereof, wherein:
$X^1$ is selected from the group consisting of CH and N; $X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, C-$L^2$-$E^2$, and C—N($R^2$)-$L^2$-$E^2$; provided that $X^2$ is selected from the group consisting of CH, C—O-$L^2$-$E^2$, C-$L^2$-$E^2$, and C—N($R^2$)-$L^2$-$E^2$ and $X^3$ is selected from the group consisting of CH and N; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; A is selected from the group consisting of a substituted 5-membered heteroaryl, a substituted 6-membered heteroaryl, a pyridone, and a substituted aryl ring; $L^2$ is selected from the group consisting of a direct bond and alkyl, wherein alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2; provided that the compound is not:

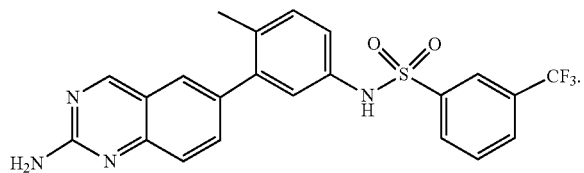 [SMILES: Cc1ccc(NS(=O)(=O)c2cccc(C(F)(F)F)c2)cc1-c1ccc2nc(N)ncc2c1]

In another embodiment, described herein is a pharmaceutical composition comprising a compound described herein (e.g., a compound of Formula I described herein) and a pharmaceutically acceptable carrier or excipient.

In another embodiment, described herein is a method of treating a disease caused by a dysregulation of an integrated stress response in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a disease caused by a dysregulation of an integrated stress response and/or an unfolded protein response in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting GCN2 kinase and inhibiting PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a disease selected from a GCN2 associated disease and a PERK associated disease, in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a disease selected from a GCN2 associated disease and a PERK associated disease, in a patient in need thereof, comprising administering to the patient a therapeutically effective amount of a compound described herein, or a pharmaceutically acceptable salt thereof, and a therapeutically effective amount of one or more therapeutic agents.

In another embodiment, described herein is a method of treating a cancer in a patient in need thereof, comprising administering to the patient a therapeutically effective amount of a compound described herein (e.g., a compound of Formula I described herein) or a pharmaceutically acceptable salt thereof, or pharmaceutical composition described herein.

In another embodiment, described herein is a method of treating a disorder selected from the group consisting of melanoma, fibrosarcoma, thyroid cancer, ovarian cancer, colon cancer, pancreatic cancer, lung cancer, bladder cancer, gastrointestinal stromal tumors, solid tumors, blood-borne cancers, acute myelogenous leukemia (AML), acute lymphoblastic leukemia (ALL) and other cancers caused by activation of the GCN2 signaling pathway in a patient in need thereof, comprising administering to the patient a therapeutically effective amount of a compound described herein (e.g., a compound of Formula I described herein) or a pharmaceutically acceptable salt thereof.

BRIEF DESCRIPTION OF THE DRAWINGS

FIGS. 6A, 6B, 6C, and 6D show effects of Compound 16, as a single agent and in combination with standard of care treatment, on cell proliferation of RPMI8226 multiple myeloma cells (FIG. 6A), H929 multiple myeloma cells (FIG. 6B), GA-10 Burkitts lymphoma cells (FIG. 6C), and DOHH-2 follicular lymphoma cells (FIG. 6D).

FIG. 7A shows data plots of results obtained from the PK/PD model studies and FIG. 7B depicts results in tabular form.

DETAILED DESCRIPTION

Figure 1:
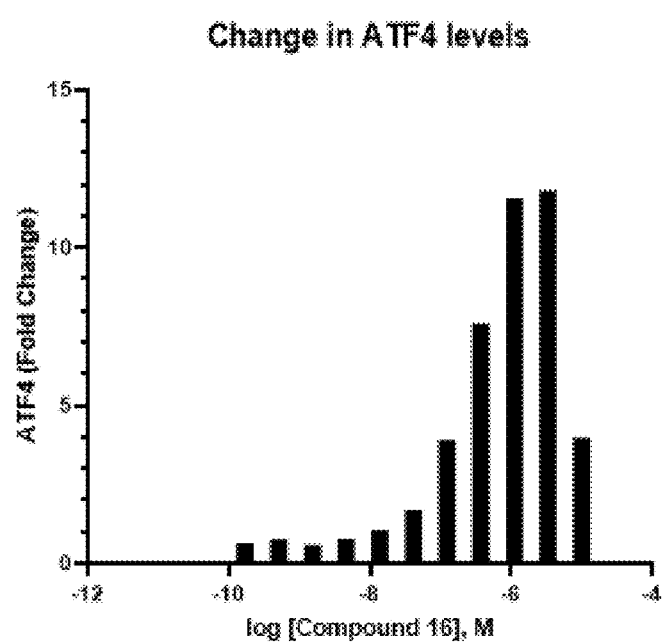
FIG. 1 depicts a graph of the stimulation of cellular ATF4 in H929 multiple myeloma cells induced by Compound 16.

The features and other details of the disclosure are more particularly described below. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The definitions set forth in this application are intended to clarify terms used throughout this application.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present disclosure.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible if such combinations result in stable compounds.

As used herein, the singular forms "a", "an" and "the" encompass plural references unless the context clearly indicates otherwise.

As used herein, the term "herein" means the entire application.

As used herein, "deuterated" mean that at least one hydrogen atom is replaced by deuterium. In any sample of a deuterated compound, some discrete molecules of the compound will likely have hydrogen, rather than deuterium, at the specified position. However, the percent of molecules of the deuterated compound which have deuterium at the specified position will be much greater than would naturally occur. The deuterium at the deuterated position is enriched.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the disclosed compounds can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure result.

As used herein, the term "optionally substituted" refers to the replacement of one to six hydrogen atoms in a given structure with the radical of a specified substituent including, but not limited to: hydroxy, hydroxyalkyl, alkoxy, halogen, alkyl, aryl, cycloalkyl, heterocyclyl, amino, aminoalkyl, cyano, haloalkyl, haloalkoxy, —OC(=O)—CH$_2$—Oalkyl. Preferably, "optionally substituted" refers to the replacement of one to four hydrogen atoms in a given structure with the substituents mentioned above. More preferably, one to three hydrogen atoms are replaced by the substituents as mentioned above. It is understood that the substituent can be further substituted.

As used herein, the term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, such substituents, if not otherwise specified, can include, for example, a halogen, a hydroxy, a carbonyl (such as a carboxyl, an alkoxycarbonyl, a formyl, or an acyl), an alkoxy, an amino, an amido, an imine, a cyano, a sulfonyl, a heterocyclyl, an aralkyl, a heteroaralkyl, or an aromatic or heteroaromatic moiety. It will be understood by those skilled in the art that substituents can themselves be substituted, if appropriate. For instance, the substituents of a substituted alkyl may include substituted and unsubstituted forms of amino, amido, sulfonyl and as well as ethers, carbonyls (including carboxylates, and esters), —CF$_3$, —CN and the like. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to a straight chained or branched non-aromatic hydrocarbon which is completely saturated. Typically, a straight chained or branched alkyl group has from 1 to about 20 carbon atoms, preferably from 1 to about 10, e.g., may be $C_1$-$C_{10}$alkyl or e.g., $C_1$-$C_6$alkyl unless otherwise defined. Examples of straight chained and branched alkyl groups include, but are not limited to, methyl, ethyl, 1-propyl (n-propyl), 2-propyl, n-butyl, sec-butyl, tertbutyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. Moreover, the term "alkyl" used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. The "alkyl" group may be optionally substituted.

The term "$C_x$-$C_y$" when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal.

As used herein, the term "alkoxy" refers to a straight or branched, saturated aliphatic (alkyl) hydrocarbon radical bonded to an oxygen atom that is attached to a core structure. Preferably, alkoxy groups have one to six carbon atoms, i.e. may be $C_1$-$C_6$ alkoxy. Examples of alkoxy groups include but are not limited to methoxy, ethoxy, propoxy, isopropoxy, butoxy, isobutoxy, tert-butoxy, pentoxy, 3-methyl butoxy and the like.

As used herein, the term "alkoxyalkyl" refers to an alkyl group (as defined above) substituted with an alkoxy group and may be represented by the general formula alkyl-O-alkyl. Examples of alkoxyalkyl groups include but are not limited to methyl-O-ethylene-, ethyl-O-ethylene-.

As used herein, the term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like.

As used herein, the term "haloalkoxy" refers to radicals wherein one or more of the hydrogen atoms of the alkoxy group are substituted with one or more halogens. Representative examples of "haloalkoxy" groups include, but not limited to, difluoromethoxy (—$OCHF_2$), trifluoromethoxy (—$OCF_3$) or trifluoroethoxy (—$OCH_2CF_3$).

As used herein, the term "aryl" includes substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings (fused rings) wherein at least one of the rings is aromatic. e.g., the other cyclic rings can be cycloalkyls, cycloalkenyls, cycloalkynyls, aryls, heteroaryls, and/or heterocyclyls. The term "fused" means that the second ring is attached or formed by having two adjacent atoms in common with the first ring. The term "fused" is equivalent to the term "condensed". Examples of aryl groups include but are not limited to phenyl, naphthyl, phenanthryl, phenol, aniline, indanyl, dihydrobenzofuranyl, dihydroisobenzofuranyl, indolinyl, isoindolinyl, and the like. Unless otherwise specified, aryl groups described herein may be optionally substituted.

As used herein, the terms "polycyclyl", "polycycle", and "polycyclic" refer to two or more rings (e.g., cycloalkyls, cycloalkenyls, cycloalkynyls, aryls, heteroaryls, and/or heterocyclyls) in which one or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

As used herein, the term "acyl" refers to a group —C(=O)—$R^w$ wherein $R^w$ is optionally substituted alkyl. Examples of "acyl" include, but are not limited to, instances where $R^w$ is $C_1$-$C_{10}$alkyl ($C_1$-$C_{10}$acyl) or $C_1$-$C_6$-alkyl ($C_1$-$C_6$acyl). In some embodiments, each occurrence of the optionally substituted substituent is independently selected from the group consisting of H, OH, alkoxy, cyano, F, and amino. Additional examples of "acyl" include —C(=O)—$CH_3$, —C(=O)—$CH_2$—$CH_3$, —C(=O)—$CH_2$—$CH_2$—$CH_3$, or —C(=O)—$CH(CH_3)_2$.

As used herein, the terms "amine" and "amino" refer to both unsubstituted and substituted amines and salts thereof, e.g., a moiety that can be represented by:

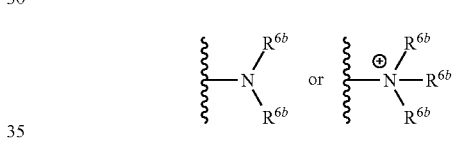

wherein $R^{6b}$ independently represent a hydrogen, alkyl or a cycloalkyl group, or $R^{6b}$ groups are taken together with the N atom to which they are attached complete a heterocycle having from 4 to 8 atoms in the ring structure.

As used herein, the terms "amide" and "amido" refers to a group represented by

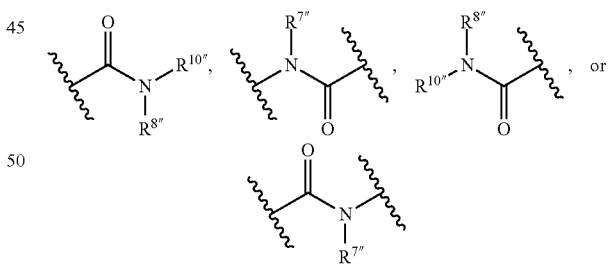

wherein $R^{7''}$, $R^{8''}$, and $R^{10''}$ each independently represents a hydrogen or hydrocarbyl group, or $R^{8''}$ and $R^{10''}$ are taken together with the N atom to which they are attached complete a heterocyclyl having from 4 to 8 atoms in the ring structure.

As used herein, the term "acylamino" refers to an amino group, as defined above, substituted with an acyl group.

As used herein, the term "aminocarbonyl" refers to a carbonyl group substituted with an amino group.

As used herein, the term "alkylamino" refers to an amino group, as defined above, substituted with at least one alkyl group.

As used herein, the term "aminoalkyl" refers to an alkyl group substituted with an amino group.

As used herein, the term "amidoalkyl" refers to an alkyl group substituted with an amido group.

As used herein, the term "cyanoalkyl" refers to an alkyl group substituted with a cyano group.

As used herein, the term "cycloalkoxyalkyl" refers to an alkyl group (as defined above) substituted with a cycloalkoxy group and may be represented by the general formula cycloalkyl-O-alkyl. Examples of cycloalkoxyalkyl groups include but are not limited to cyclopropyl-O-methylene-, cyclopropyl-O-ethylene.

As used herein, the term "heteroarylalkyl" refers to an alkyl group substituted with heteroaryl group.

As used herein, the term "heterocyclylalkyl" refers to an alkyl group substituted with a heterocyclyl group.

As used herein, the term "hydroxyalkyl" refers to an alkyl group substituted with a hydroxy group.

As used herein, the term "cycloalkyl" alone or in combination with other term(s) refers to a cyclic hydrocarbon which is completely saturated. "Cycloalkyl" includes monocyclic, bicyclic, and tricyclic rings. Typically, a monocyclic cycloalkyl group has from 3 to about 10 carbon atoms, more typically 3 to 8 carbon atoms (e.g., $C_3$-$C_{10}$cycloalkyl or e.g., $C_3$-$C_6$cycloalkyl unless otherwise defined. Examples of monocyclic cycloalkyls include cyclopropyl, cyclobutyl, cyclopentyl, cyclohexyl, cycloheptyl and the like. The second ring of a bicyclic cycloalkyl or, the second or third rings of a tricyclic cycloalkyl, may be selected from saturated, unsaturated and aromatic rings. Cycloalkyl includes bicyclic and tricyclic molecules in which one, two or three or more atoms are shared between the two rings. Cycloalkyls can be further substituted with alkyls, alkenyls, alkoxys, aminoalkyls, carbonyl-substituted alkyls, —$CF_3$, —CN, and the like.

As used herein, the term "cycloalkylalkyl" refers to an alkyl group substituted with a cycloalkyl group.

As used herein, the term "cyano" refers to —CN group.

As used herein, the term "hydroxy" or "hydroxyl" refers to —OH group.

As used herein, the term "halo" or "halogen" alone or in combination with other term(s) means chloro, fluoro, bromo, and iodo.

As used herein, the term "heteroatom" refers an atom of any element other than carbon or hydrogen. Exemplary heteroatoms are nitrogen (N), oxygen (O), sulfur (S), and silicon (Si).

As used herein, the terms "heterocyclyl", "heterocycloalkyl", "heterocycle", and "heterocyclic" refer to a non-aromatic, saturated or partially saturated, including monocyclic, polycyclic (e.g., bicyclic, tricyclic) bridged, or fused, ring system of 3 to 15 member having at least one heteroatom or heterogroup selected from O, N, S, S(O), S(O)$_2$, NH or C(O) with the remaining ring atoms being independently selected from the group consisting of carbon, oxygen, nitrogen, and sulfur. Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, 2-azabicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocycloalkyl" includes azetidinyl, pyrrolidinyl, morpholinyl and piperidinyl. Heterocycloalkyl are optionally substituted by one or more aforesaid groups.

As used herein, the term "heteroaryl" refers to substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also refers to substituted or unsubstituted aromatic or partly aromatic ring systems containing at least one heteroatom and having two or more cyclic rings (bicyclic, tricyclic, or polycyclic), containing 8 to 20 ring atoms, suitably 5 to 10 ring atoms, which may be linked covalently, or fused in which two or more atoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. The rings may contain an N or S atom, wherein the N or S atom is optionally oxidized, or the N atom is optionally quaternized. All heteroaryls are optionally substituted. Any suitable ring position of the heteroaryl moiety may be covalently linked to a defined chemical structure. Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, thiadiazolyl, triazolyl, pyridyl, pyrimidinyl, pyrazinyl, pyridazinyl, triazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, alpha-carboline, indolizinyl, benzoisothiazolyl, benzoxazolyl, pyrrolopyridyl, furopyridinyl, purinyl, benzothiadiazolyl, benzoxadiazolyl, benzotriazolyl, benzotriadiazolyl, carbazolyl, dibenzothienyl, acridinyl and the like.

As used herein, the term "sulfonamide" is represented by:

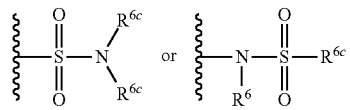

wherein $R^{6c}$, at each occurrence, independently represents a hydrogen, alkyl or cycloalkyl group, or $R^{6c}$ groups taken together with the N atom to which they are attached complete a heterocycle having from 4 to 8 atoms in the ring structure.

As used herein, the terms "sulfonyl" refers to the group —S(O)$_2$—$R^{6d}$ wherein $R^{6d}$ represents alkyl or cycloalkyl.

A "combination therapy" is a treatment that includes the administration of two or more therapeutic agents, e.g., a compound of Formula I and the enzyme asparaginase (ASNase) or a derivative thereof, to a patient in need thereof.

"Disease," "disorder," and "condition" are used interchangeably herein.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

The compounds described herein are useful for the treatment of diseases driven by GCN2 (sometimes to be abbreviated as "GCN2 associated disease" in the present specification), for example, cancer [e.g., colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell renal cell carcinoma), transitional cell carcinoma of renal pelvis and ureter), uterine cancer (e.g., cervical cancer, uterine body cancer, uterus sarcoma), gestational choriocarcinoma, brain tumor (e.g., medulloblastoma, glioma, pineal astrocytoma, pilocytic astrocytoma, diffuse astrocytoma, anaplastic astrocytoma, hypophyseal adenoma), retina blastoma, skin cancer (e.g., basal cell carcinoma, malignant melanoma (melanoma)), sarcoma (e.g., rhabdomyosarcoma, leiomyosarcoma, soft tissue sarcoma, spindle cell sarcoma, osteosarcoma), malignant bone tumor, urinary bladder cancer, hematologic cancer (e.g., multiple myeloma, leukemia (e.g., acute myeloid leukemia, acute lymphocytic leukemia (including blast crisis of chronic leukemia)), malignant lymphoma, Hodgkin's disease, chronic myeloproliferative disease), cancer of unknown primary nucleus], cancer growth inhibitor, cancer metastasis inhibitor, apoptosis promoter, and for the prophylaxis or treatment of precancerous lesion (e.g., bone marrow myelodysplastic syndrome).

The compounds described herein, e.g., a compound of Formula I as defined herein, may be used in combination with one or more additional therapeutic agents to treat a disorder described herein, such as a cancer described herein. In some embodiments, the compounds described herein may be used in combination with hormonal therapeutic agents, chemotherapeutic agents, immunotherapeutic agents, medicaments inhibiting actions of cell growth factor and receptor thereof, such as PERK inhibitors and autophagy inhibitors, the enzyme asparaginase (ASNase), and the like.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbol "R" or "S" depending on the configuration of substituents around the stereogenic carbon atom, but the skilled artisan will recognize that a structure may denote a chiral center implicitly. These compounds may also be designated by "(+)" and "(−)" based on their optical rotation properties. The presently described compounds encompasses various stereoisomers of these compounds and mixtures thereof. Mixtures of enantiomers or diastereomers may be designated by the symbol "(±)" in nomenclature, but the skilled artisan will recognize that a structure may denote a chiral center implicitly.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds described herein are administered in therapeutically effective amounts to treat a disorder.

"Treating" includes any effect, e.g., lessening, reducing, modulating, or eliminating, that results in the improvement of the condition, disease, disorder and the like.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into the disclosed compounds include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the disclosure may have one or more H atom replaced with deuterium.

Individual enantiomers and diastereomers of the disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations and may involve the use of chiral auxiliaries. For examples, see Carreira and Kvaerno, *Classics in Stereoselective Synthesis*, Wiley-VCH: Weinheim, 2009.

Compounds

In one embodiment, described herein is a compound represented by Formula I:

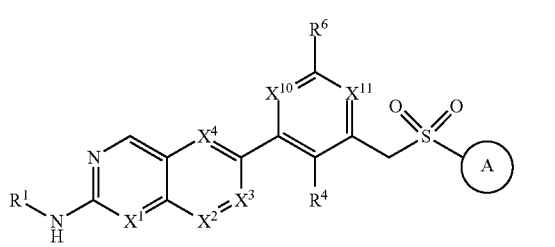

Formula I or a pharmaceutically acceptable salt, enantiomer, stereoisomer, or tautomer thereof, wherein:
$X^1$ is selected from the group consisting of CH and N; $X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, C-$L^2$-$E^2$, and C—N($R^2$)-$L^2$-$E^2$; provided that $X^2$ is selected from the group consisting of CH, C—O-$L^2$-$E^2$, C-$L^2$-$E^2$, and C—N($R^2$)-$L^2$-$E^2$ and $X^3$ is selected from the group consisting of CH and N; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; A is selected from the group consisting of a substituted 5-membered heteroaryl, a substituted 6-membered heteroaryl, a pyridone, and a substituted aryl ring; $L^2$ is selected from the group consisting of a direct bond and alkyl, wherein alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2; provided that the compound is not:

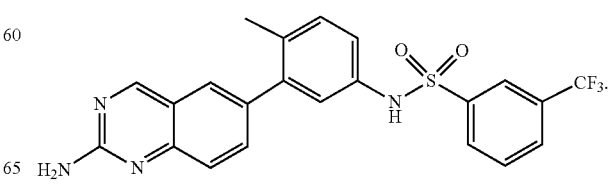

In some embodiments, the compound is represented by Formula I-A:

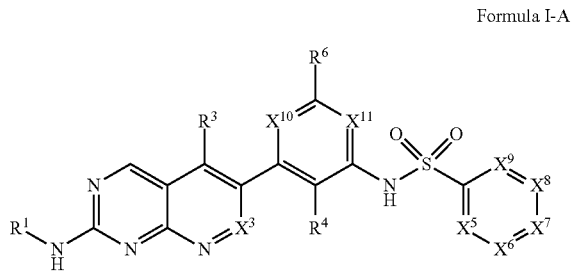

Formula I-A or a pharmaceutically acceptable salt, enantiomer, stereoisomer, or tautomer thereof, wherein: $X^3$ is selected from the group consisting of CH, C—O-$L^2$-$E^2$, C-$L^2$-$E^2$, and C—N($R^2$)-$L^2$-$E^2$; $X^5$ is selected from the group consisting of $CR^8$ and N; $X^6$ is selected from the group consisting of $CR^9$ and N; $X^7$ is selected from the group consisting of $CR^{10}$ and N; $X^8$ is selected from the group consisting of $CR^{11}$ and N; $X^9$ is selected from the group consisting of $CR^8$ and N, provided that not more than three of $X^5$, $X^6$, $X^7$, $X^8$, and $X^9$ is N; $X^{10}$ is selected from the group consisting of $CR^5$ and N; $X^{11}$ is selected from the group consisting of $CR^7$ and N; $R^1$ is selected from the group consisting of H, alkyl, (C═O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxy, and CN; $R^9$, $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-B:

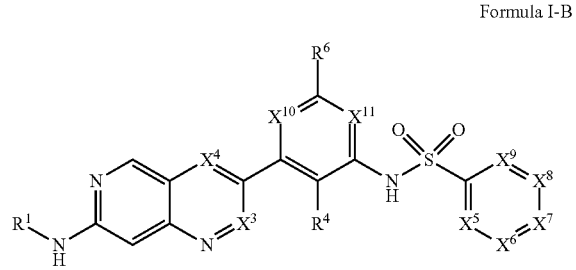

Formula I-B or a pharmaceutically acceptable salt, enantiomer, stereoisomer, or tautomer thereof, wherein: $X^3$ is selected from the group consisting of CH, C—O-$L^2$-$E^2$, C-$L^2$-$E^2$, and C—N($R^2$)-$L^2$-$E^2$; $X^4$ is selected from the group consisting of $CR^3$ and N; $X^5$ is selected from the group consisting of $CR^8$ and N; $X^6$ is selected from the group consisting of $CR^9$ and N; $X^7$ is selected from the group consisting of $CR^{10}$ and N; $X^8$ is selected from the group consisting of $CR^{11}$ and N; $X^9$ is selected from the group consisting of $CR^8$ and N, provided that not more than three of $X^5$, $X^6$, $X^7$, $X^8$, and $X^9$ is N; $X^{10}$ is selected from the group consisting of $CR^5$ and N; $X^{11}$ is selected from the group consisting of $CR^7$ and N; $R^1$ is selected from the group consisting of H, alkyl, (C═O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxy, and CN; $R^9$, $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-C:

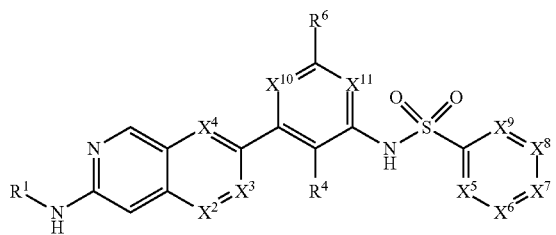

Formula I-C or a pharmaceutically acceptable salt, enantiomer, stereoisomer, or tautomer thereof, wherein:
$X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, C-$L^2$-$E^2$; and C—N($R^2$)-$L^2$-$E^2$; provided that $X^2$ is selected from the group consisting of CH, C—O-$L^2$-$E^2$, C-$L^2$-$E^2$, and C—N($R^2$)-$L^2$-$E^2$ and $X^3$ is selected from the group consisting of CH and N; $X^4$ is selected from the group consisting of CR$^3$ and N; $X^5$ is selected from the group consisting of CR$^8$ and N; $X^6$ is selected from the group consisting of CR$^9$ and N; $X^7$ is selected from the group consisting of CR$^{10}$ and N; $X^8$ is selected from the group consisting of CR$^{11}$ and N; $X^9$ is selected from the group consisting of CR$^8$ and N, provided that not more than three of $X^5$, $X^6$, $X^7$, $X^8$, and $X^9$ is N; $X^{10}$ is selected from the group consisting of CR$^5$ and N; $X^{11}$ is selected from the group consisting of CR$^7$ and N; $R^1$ is selected from the group consisting of H, alkyl, (C=O)R$^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxy, and CN; $R^9$, $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-D:

Formula I-D

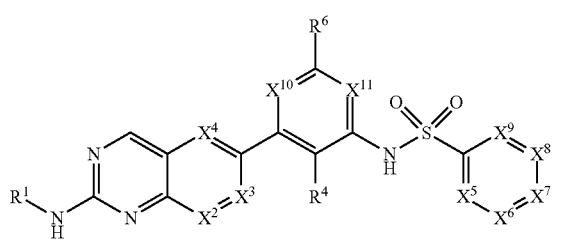

or a pharmaceutically acceptable salt, enantiomer, stereoisomer, or tautomer thereof, wherein:

$X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, C-$L^2$-$E^2$, and C—N($R^2$)-$L^2$-$E^2$; provided that $X^2$ is selected from the group consisting of CH, C—O-$L^2$-$E^2$, C-$L^2$-$E^2$ and C—N($R^2$)-$L^2$-$E^2$ and $X^3$ is selected from the group consisting of CH and N; $X^4$ is selected from the group consisting of $CR^3$ and N; $X^5$ is selected from the group consisting of $CR^8$ and N; $X^6$ is selected from the group consisting of $CR^9$ and N; $X^7$ is selected from the group consisting of $CR^{10}$ and N; $X^8$ is selected from the group consisting of $CR^{11}$ and N; $X^9$ is selected from the group consisting of $CR^8$ and N, provided that not more than three of $X^5$, $X^6$, $X^7$, $X^8$, and $X^9$ is N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxy, and CN; $R^9$, $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-E:

Formula I-E

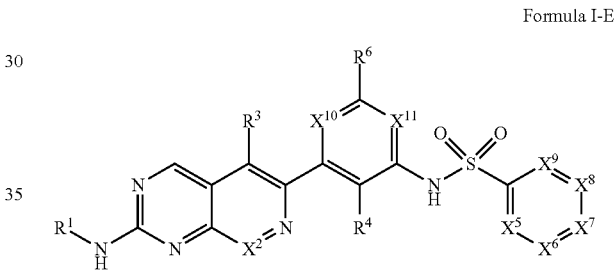

or a pharmaceutically acceptable salt, enantiomer, stereoisomer, or tautomer thereof, wherein:

$X^2$ is selected from the group consisting of CH, C—O-$L^2$-$E^2$, C-$L^2$-$E^2$, and C—N($R^2$)-$L^2$-$E^2$; $X^5$ is selected from the group consisting of $CR^8$ and N; $X^6$ is selected from the group consisting of $CR^9$ and N; $X^7$ is selected from the group consisting of $CR^{10}$ and N; $X^8$ is selected from the group consisting of $CR^{11}$ and N; $X^9$ is selected from the group consisting of $CR^8$ and N, provided that not more than three of $X^5$, $X^6$, $X^7$, $X^8$, and $X^9$ is N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxy, and CN; $R^9$, $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-F:

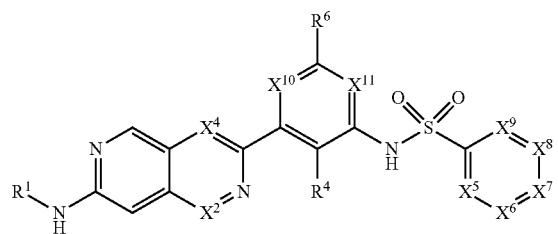

Formula I-F or a pharmaceutically acceptable salt, enantiomer, stereoisomer, or tautomer thereof, wherein:

$X^2$ is selected from the group consisting of CH, C—O-$L^2$-$E^2$, C-$L^2$-$E^2$, and C—N($R^2$)-$L^2$-$E^2$; $X^4$ is selected from the group consisting of $CR^3$ and N; $X^5$ is selected from the group consisting of $CR^8$ and N; $X^6$ is selected from the group consisting of $CR^9$ and N; $X^7$ is selected from the group consisting of $CR^{10}$ and N; $X^8$ is selected from the group consisting of $CR^{11}$ and N; $X^9$ is selected from the group consisting of $CR^8$ and N, provided that not more than three of $X^5$, $X^6$, $X^7$, $X^8$, and $X^9$ is N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxy, and CN; $R^9$, $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-G:

Formula I-G

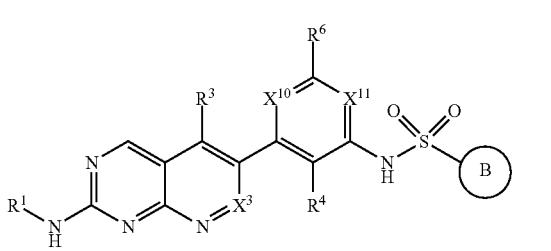

or a pharmaceutically acceptable salt, enantiomer, stereoisomer, or tautomer thereof, wherein:

$X^3$ is selected from the group consisting of CH, C—O-$L^2$-$E^2$, C-$L^2$-$E^2$, and C—N($R^2$)-$L^2$-$E^2$; $X^{10}$ is selected from the group consisting of $CR^5$ and N; $X^{11}$ is selected from the group consisting of $CR^7$ and N; $R^1$ is selected from the group consisting of H, alkyl, (C═O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{12}$ is individually and independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, haloalkyl, alkoxy, alkylamino, H, cyanoalkyl, alkyl, cycloalkyl, cycloalkoxy, cycloalkylamino, heterocyclyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; B is selected from the group consisting of a five-membered heteroaryl, a six-membered heteroaryl, and a pyridone, wherein the five- or six-membered heteroaryl ring, or the pyridone is optionally substituted by $R^{12}$ at each substitutable position; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-H:

Formula I-H

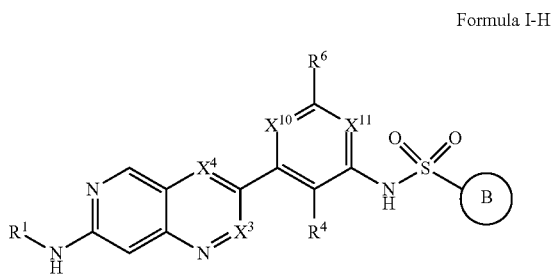

or a pharmaceutically acceptable salt, enantiomer, stereoisomer, or tautomer thereof, wherein:

$X^3$ is selected from the group consisting of CH, C—O-$L^2$-$E^2$, C-$L^2$-$E^2$, and C—N($R^2$)-$L^2$-$E^2$; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C═O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{12}$ is individually and independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, haloalkyl, alkoxy, alkylamino, H, cyanoalkyl, alkyl, cycloalkyl, cycloalkoxy, cycloalkylamino, heterocyclyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; B is selected from the group consisting of a five-membered heteroaryl, a six-membered heteroaryl, and a pyridone, wherein the five- or six-membered heteroaryl ring, or the pyridone, is optionally substituted by $R^{12}$ at each substitutable position; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-J:

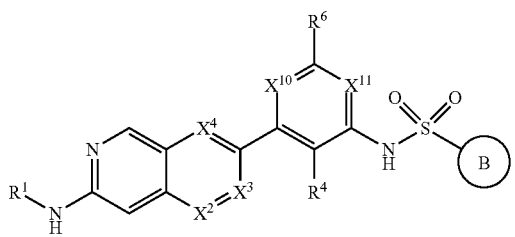

Formula I-J or a pharmaceutically acceptable salt, enantiomer, stereoisomer, or tautomer thereof, wherein:
$X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, and C—N($R^2$)-$L^2$-$E^2$; provided that $X^2$ is selected from the group consisting of CH, C—O-$L^2$-$E^2$; C-$L^2$-$E^2$, and C—N($R^2$)-$L^2$-$E^2$ and $X^3$ is selected from the group consisting of CH and N; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{12}$ is individually and independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, haloalkyl, alkoxy, alkylamino, H, cyanoalkyl, alkyl, cycloalkyl, heterocyclyl, and heterocyclylalkyl; $R^{13}$ is selected from the group consisting of H, alkyl, cycloalkyl, cycloalkoxy, cycloalkylamino, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; B is selected from the group consisting of a five-membered heteroaryl, a six-membered heteroaryl, and a pyridone, wherein the five- or six-membered heteroaryl ring, or the pyridone, is optionally substituted by $R^{12}$ at each substitutable position; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-K:

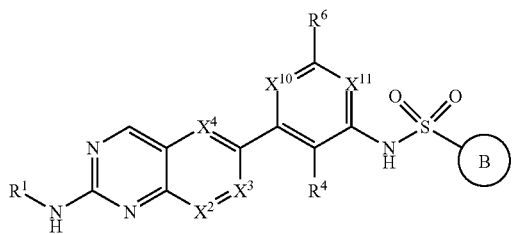

Formula I-K or a pharmaceutically acceptable salt, enantiomer, stereoisomer, or tautomer thereof, wherein:
$X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, C-$L^2$-$E^2$, and C—N($R^2$)-$L^2$-$E^2$; provided that $X^2$ is selected from the group consisting of CH, C-O-$L^2$-$E^2$, C-$L^2$-$E^2$, and C—N($R^2$)-$L^2$-$E^2$ and $X^3$ is selected from the group consisting of CH and N; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{12}$ is individually and independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, haloalkyl, alkoxy, alkylamino, H, cyanoalkyl, alkyl, cycloalkyl, cycloalkoxy, cycloalkylamino, heterocyclyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; B is selected from the group consisting of a five-membered heteroaryl, a six-membered heteroaryl, and a pyridone, wherein the five- or six-membered heteroaryl ring, or the pyridone, is optionally substituted by $R^{12}$ at each substitutable position; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-L:

Formula I-L or a pharmaceutically acceptable salt, enantiomer, stereoisomer, or tautomer thereof, wherein:

$X^2$ is selected from the group consisting of CH, C—O-$L^2$-$E^2$, C-$L^2$-$E^2$, and C—N($R^2$)-$L^2$-$E^2$; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{12}$ is individually and independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, haloalkyl, alkoxy, alkylamino, H, cyanoalkyl, alkyl, cycloalkyl, heterocyclyl, and heterocyclylalkyl; $R^{13}$ is selected from the group consisting of H, alkyl, cycloalkyl, cycloalkoxy, cycloalkylamino, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; B is selected from the group consisting of a five-membered heteroaryl, a six-membered heteroaryl, and a pyridone, wherein the five- or six-membered heteroaryl ring, or the pyridone, is optionally substituted by $R^{12}$ at each substitutable position; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-M:

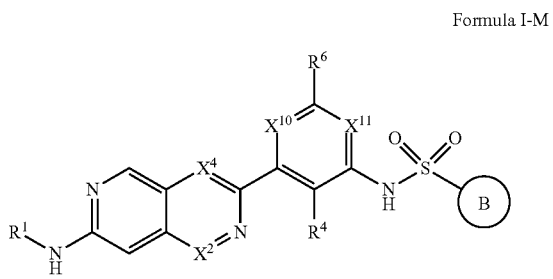

Formula I-M or a pharmaceutically acceptable salt, enantiomer, stereoisomer, or tautomer thereof, wherein:

$X^2$ is selected from the group consisting of CH, C—O-$L^2$-$E^2$, C-$L^2$-$E^2$, and C—N($R^2$)-$L^2$-$E^2$; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{12}$ is individually and independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, haloalkyl, alkoxy, alkylamino, H, cyanoalkyl, alkyl, cycloalkyl, cycloalkoxy, cycloalkylamino, heterocyclyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; B is selected from the group consisting of a five-membered heteroaryl, a six-membered heteroaryl, and a pyridone, wherein the five- or six-membered heteroaryl ring, or the pyridone, is optionally substituted by $R^{12}$ at each substitutable position; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-N:

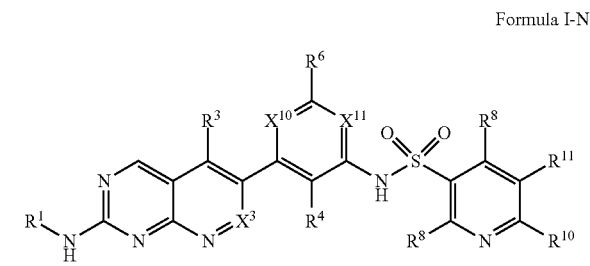

Formula I-N or a pharmaceutically acceptable salt, enantiomer, stereoisomer, or tautomer thereof, wherein:

$X^3$ is selected from the group consisting of CH, C—O-$L^2$-$E^2$, C-$L^2$-$E^2$, and C—N($R^2$)-$L^2$-$E^2$; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-O:

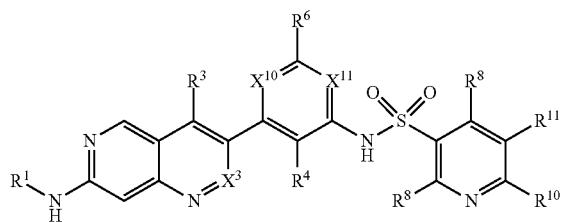

Formula I-O or a pharmaceutically acceptable salt, enantiomer, stereoisomer, or tautomer thereof, wherein:
$X^3$ is selected from the group consisting of CH, C—O-$L^2$-$E^2$, C-$L^2$-$E^2$, and C—N($R^2$)-$L^2$-$E^2$; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-P:

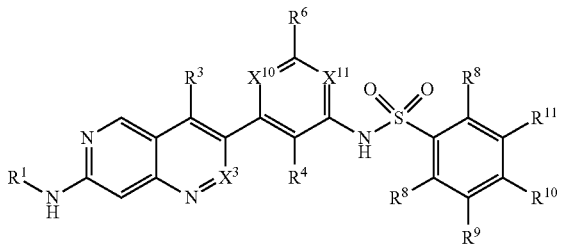

Formula I-P or a pharmaceutically acceptable salt, enantiomer, stereoisomer, or tautomer thereof, wherein: $X^3$ is selected from the group consisting of CH, C—O-L$^2$-E$^2$, C-L$^2$-E$^2$, and C—N(R$^2$)-L$^2$-E$^2$; X$^{10}$ is selected from the group consisting of CR$^5$ and N; X$^{11}$ is selected from the group consisting of CR$^7$ and N; R$^1$ is selected from the group consisting of H, alkyl, (C=O)R$^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; R$^2$ is selected from the group consisting of H and alkyl; R$^3$ is selected from the group consisting of H, alkyl, and halogen; R$^4$ and R$^5$ are each independently selected from the group consisting of halogen, H, alkoxy, alkylamino, amino, alkyl, haloalkyl and CN; R$^6$ is selected from the group consisting of halogen, H, and alkyl; R$^7$ is selected from the group consisting of H and F; R$^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; R$^9$, R$^{10}$, and R$^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; R$^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; L$^2$ is selected from the group consisting of a direct bond and C$_1$-C$_6$alkyl, wherein C$_1$-C$_6$alkyl is optionally substituted with (E$^{21}$)$_p$; E$^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; E$^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I-Q:

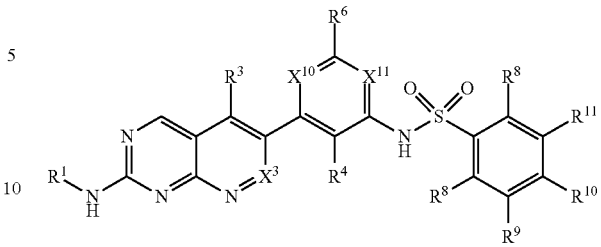

Formula I-Q or a pharmaceutically acceptable salt, enantiomer, stereoisomer, or tautomer thereof, wherein:

X$^3$ is selected from the group consisting of CH, C—O-L$^2$-E$^2$, C-L$^2$-E$^2$, and C—N(R$^2$)-L$^2$-E$^2$; X$^{10}$ is selected from the group consisting of CR$^5$ and N; X$^{11}$ is selected from the group consisting of CR$^7$ and N; R$^1$ is selected from the group consisting of H, alkyl, (C=O)R$^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; R$^2$ is selected from the group consisting of H and alkyl; R$^3$ is selected from the group consisting of H, alkyl, and halogen; R$^4$ and R$^5$ are each independently selected from the group consisting of halogen, H, alkoxy, alkylamino, amino, alkyl, haloalkyl and CN; R$^6$ is selected from the group consisting of halogen, H, and alkyl; R$^7$ is selected from the group consisting of H and F; R$^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; R$^9$, R$^{10}$, and R$^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, cycloalkoxy, cycloalkylamino, haloalkyl, heterocyclyl, alkoxycarbonyl, and heterocyclylalkyl; R$^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; L$^2$ is selected from the group consisting of a direct bond and C$_1$-C$_6$alkyl, wherein C$_1$-C$_6$alkyl is optionally substituted with (E$^{21}$)$_p$; E$^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, the compound is represented by Formula I:

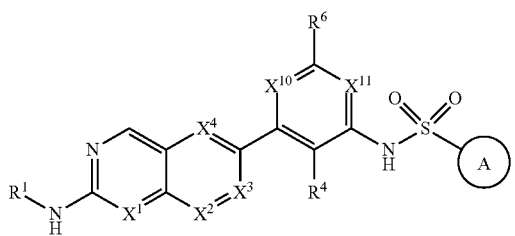

Formula I or a pharmaceutically acceptable salt, enantiomer, stereoisomer, or tautomer thereof, wherein: $X^1$ is selected from the group consisting of CH and N; $X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, C-$L^2$-$E^2$, and C—N($R^2$)-$L^2$-$E^2$; provided that $X^2$ is selected from the group consisting of CH, C—O-$L^2$-$E^2$, C-$L^2$-$E^2$, and C—N($R^2$)-$L^2$-$E^2$ and $X^3$ is selected from the group consisting of CH and N; $X^4$ is selected from the group consisting of $CR^3$ and N; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, alkoxyalkyl, cycloalkoxyalkyl, aminoalkyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; A is selected from the group consisting of a substituted 5-membered heteroaryl, a substituted 6-membered heteroaryl, a pyridone, and a substituted aryl ring; $L^2$ is selected from the group consisting of a direct bond and $C_1$-$C_6$alkyl, wherein $C_1$-$C_6$alkyl is optionally substituted with ($E^{21}$)$_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2; provided that the compound is not:

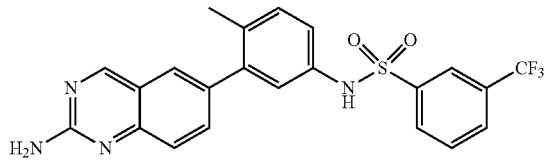 [SMILES: Cc1ccc(NS(=O)(=O)c2cccc(C(F)(F)F)c2)cc1-c1ccc2nc(N)ncc2c1]

In some embodiments, the compound is represented by Formula I:

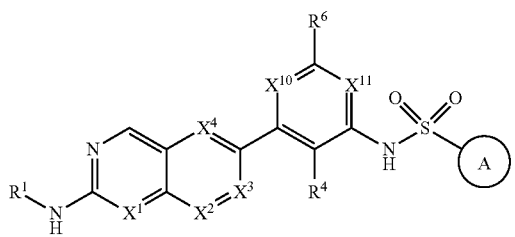

Formula I or a pharmaceutically acceptable salt, enantiomer, stereoisomer, or tautomer thereof, wherein:
$X^1$ is selected from the group consisting of CH and N; $X^2$ is selected from the group consisting of N, CH, C—O-$L^2$-$E^2$, and C-$L^2$-$E^2$; $X^3$ is C—N($R^2$)-$L^2$-$E^2$; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; A is selected from the group consisting of a substituted 5-membered heteroaryl, a substituted 6-membered heteroaryl, a pyridone, and a substituted aryl ring; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In one embodiment, described herein is a compound represented by Formula I:

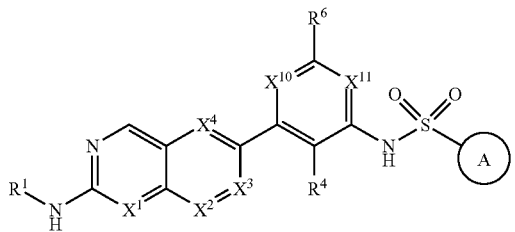

Formula I or a pharmaceutically acceptable salt, enantiomer, stereoisomer, or tautomer thereof, wherein:
$X^1$ is CH; $X^2$ and $X^3$ are each independently selected from the group consisting of N, CH, C—O-$L^2$-$E^2$, C-$L^2$-$E^2$, and C—N($R^2$)-$L^2$-$E^2$, provided that $X^2$ is selected from the group consisting of CH and N, and $X^3$ is selected from the group consisting of CH, C—O-$L^2$-$E^2$, C-$L^2$-$E^2$, and C—N($R^2$)-$L^2$-$E^2$; provided that $X^2$ is selected from the group consisting of CH, C—O-$L^2$-$E^2$, C-$L^2$-$E^2$, and C—N($R^2$)-$L^2$-$E^2$ and $X^3$ is selected from the group consisting of CH and N; $X^4$ is selected from the group consisting of $CR^3$ and N; $X^{10}$ is selected from the group consisting of $CR^5$ and N; $X^{11}$ is selected from the group consisting of $CR^7$ and N; $R^1$ is selected from the group consisting of H, alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ and $R^7$ are each independently selected from the group consisting of halogen, H, and alkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; A is selected from the group consisting of a substituted 5-membered heteroaryl, a substituted 6-membered heteroaryl, a pyridone, and a substituted aryl ring; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen; and each p is independently 0, 1 or 2.

In some embodiments, $L^2$ is a direct bond. In some embodiments, $L^2$ is alkyl. In some embodiments, $L^2$ is $C_1$-$C_6$alkyl, wherein $C_1$-$C_6$alkyl is optionally substituted with $(E^{21})_p$.

In some embodiments, $X^2$ is N and $X^3$ is selected from the group consisting from CH, C—O-$L^2$-$E^2$, C-$L^2$-$E^2$, and C—N($R^2$)-$L^2$-$E^2$.

In some embodiments, $X^2$ is CH and $X^3$ is selected from the group consisting from N, C—O-$L^2$-$E^2$, C-$L^2$-$E^2$, and C—N($R^2$)-$L^2$-$E^2$.

In some embodiments, $X^2$ is selected from the group consisting of CH, C—O-$L^2$-$E^2$, C-$L^2$-$E^2$, and C—N($R^2$)-$L^2$-$E^2$, and $X^3$ is N.

In some embodiments, $X^2$ is selected from the group consisting of CH, C—O-$L^2$-$E^2$, C-$L^2$-$E^2$, and C—N($R^2$)-$L^2$-$E^2$, and $X^3$ is CH.

In some embodiments, $X^2$ is selected from the group consisting of N and CH, and $X^3$ is C—N($R^2$)-$L^2$-$E^2$.

In some embodiments, $X^2$ is N and $X^3$ is C—N($R^2$)-$L^2$-$E^2$.

In some embodiments, $X^2$ is CH and $X^3$ is C—N($R^2$)-$L^2$-$E^2$.

In some embodiments, $X^2$ is C—O-$L^2$-$E^2$ and $X^3$ is C—N($R^2$)-$L^2$-$E^2$.

In some embodiments, $X^2$ is C-$L^2$-$E^2$ and $X^3$ is C—N($R^2$)-$L^2$-$E^2$.

In some embodiments, $X^3$ is C—N($R^2$)-$L^2$-$E^2$.

In some embodiments, $X^2$ is N and $X^3$ is CCH$_3$.

In some embodiments, $X^2$ is N and $X^3$ is CN(H)CH$_3$.

In some embodiments, $X^2$ is CH and $X^3$ is N.

In some embodiments, $X^3$ is selected from the group consisting of

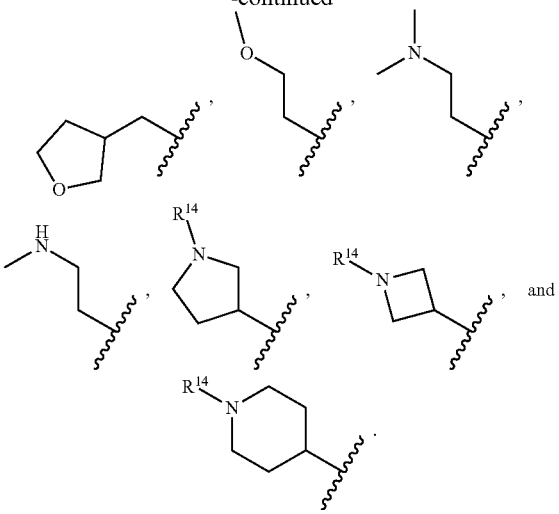

wherein $R^{14}$ is independently selected from the group consisting of H, alkyl, alkoxyalkyl, haloalkyl, hydroxyalkyl, and cyanoalkyl.

In some embodiments, $R^1$ is H.

In some embodiments, $R^1$ is methyl.

In some embodiments, $R^1$ is selected from the group consisting of H, alkyl, cycloalkyl, alkoxyalkyl, cycloalkoxyalkyl, aminoalkyl, heterocyclyl, and heterocyclylalkyl.

In some embodiments, the $R^1$ is selected from the group consisting of:

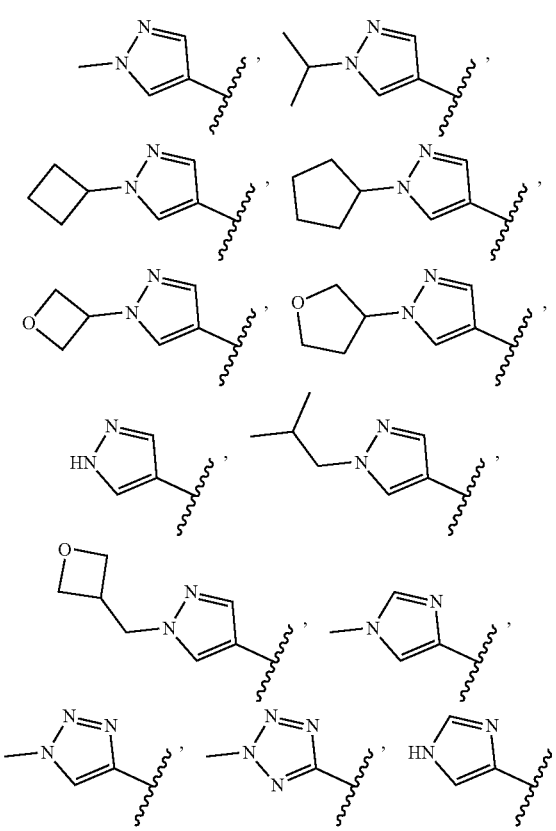

wherein each occurrence of $R^{14}$ is independently selected from the group consisting of H, alkyl, alkoxyalkyl, haloalkyl, hydroxyalkyl, and cyanoalkyl.

In some embodiments, $R^1$ is selected from the group consisting of aryl and heteroaryl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl.

In some embodiments, the $R^1$ is selected from the group consisting of:

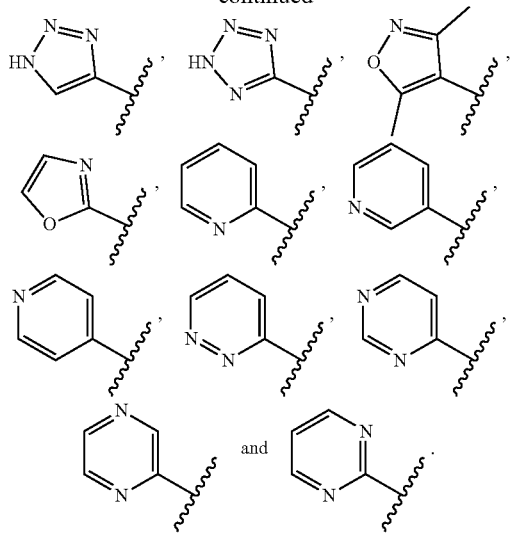

In some embodiments, R¹ is selected from the group consisting of (C=O)R¹³, wherein R¹³ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl.

In some embodiments, the R¹ is selected from the group consisting of:

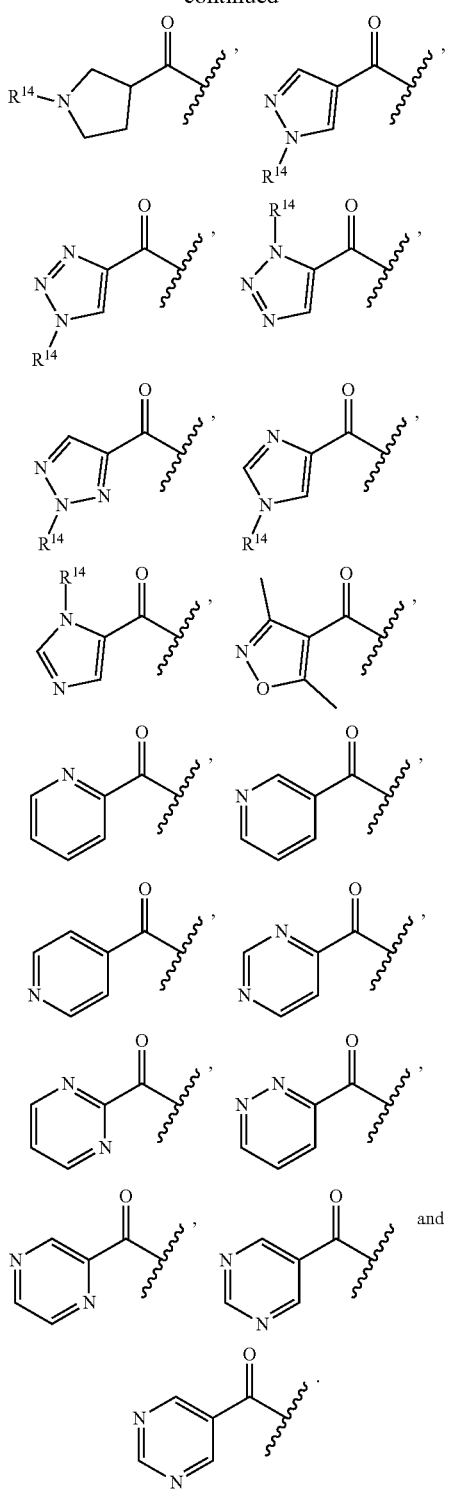

wherein each occurrence of R¹⁴ is independently selected from the group consisting of H, alkyl, alkoxyalkyl, haloalkyl, hydroxyalkyl, and cyanoalkyl.

In some embodiments, X¹ is N.

In some embodiments, X¹ is CH.

In some embodiments, X² is selected from the group consisting of:

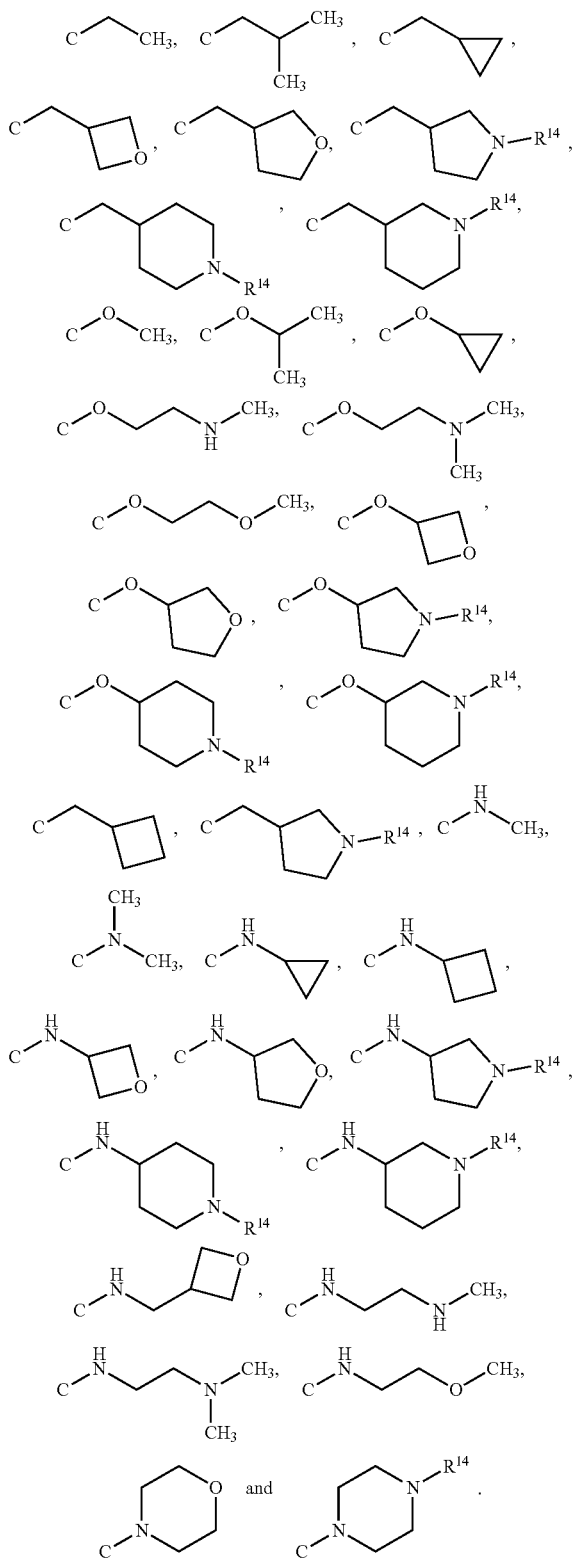

wherein each occurrence of $R^{14}$ is independently selected from the group consisting of H, alkyl, alkoxyalkyl, haloalkyl, hydroxyalkyl, and cyanoalkyl.

In some embodiments, $X^3$ is selected from the group consisting of:

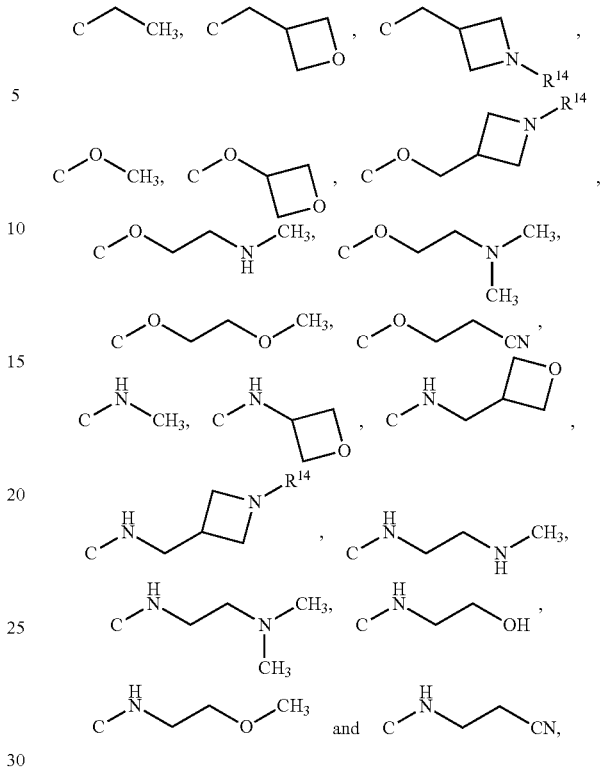

wherein each occurrence of $R^{14}$ is independently selected from the group consisting of H, alkyl, alkoxyalkyl, haloalkyl, hydroxyalkyl, and cyanoalkyl.

In some embodiments $X^4$ is selected from the group consisting of N and $CR^3$.

In some embodiments $X^{10}$ is selected from the group consisting of N and $CR^5$.

In some embodiments $X^{11}$ is selected from the group consisting of N and $CR^7$.

In some embodiments, $R^3$ is selected from the group consisting of H, alkyl, and halogen.

In some embodiments, $R^3$ is selected from the group consisting of H, $C_1$-$C_3$alkyl, and halogen. In some embodiments, $R^3$ is $C_1$-$C_3$alkyl.

In some embodiments, $R^3$ is selected from the group consisting of H, methyl, and F. In some embodiments, $R^3$ is H. In some embodiments, $R^3$ is F. In some embodiments, $R^3$ is Cl. In some embodiments, $R^3$ is methyl.

In some embodiments, $X^4$ is CH.

In some embodiments, $R^4$ and $R^5$ are each independently selected from the group consisting of halogen, H, alkoxy, alkylamino, amino, alkyl, and CN.

In some embodiments, $R^4$ is F, and $R^5$, $R^6$ and $R^7$ are each H.

In some embodiments, $R^6$ is F, and $R^4$, $R^5$ and $R^7$ are each H.

In some embodiments, $R^4$ and $R^5$ are each F, and $R^6$ and $R^7$ are each H.

In some embodiments, $R^5$ and $R^6$ are each F, and $R^4$ and $R^7$ are each H.

In some embodiments, $R^4$ and $R^6$ are each F, and $R^5$ and $R^7$ are each H.

In some embodiments, $R^4$ and $R^6$ are each H, and $R^5$ and $R^7$ are each F.

In some embodiments, A or B is selected from the group consisting of:

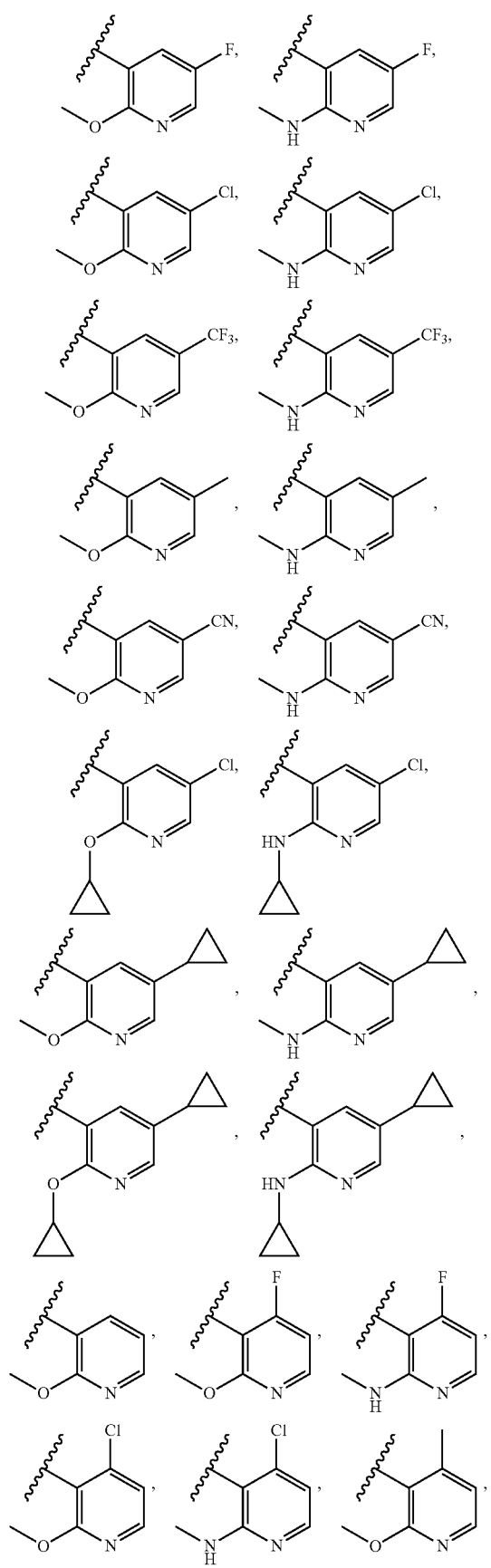
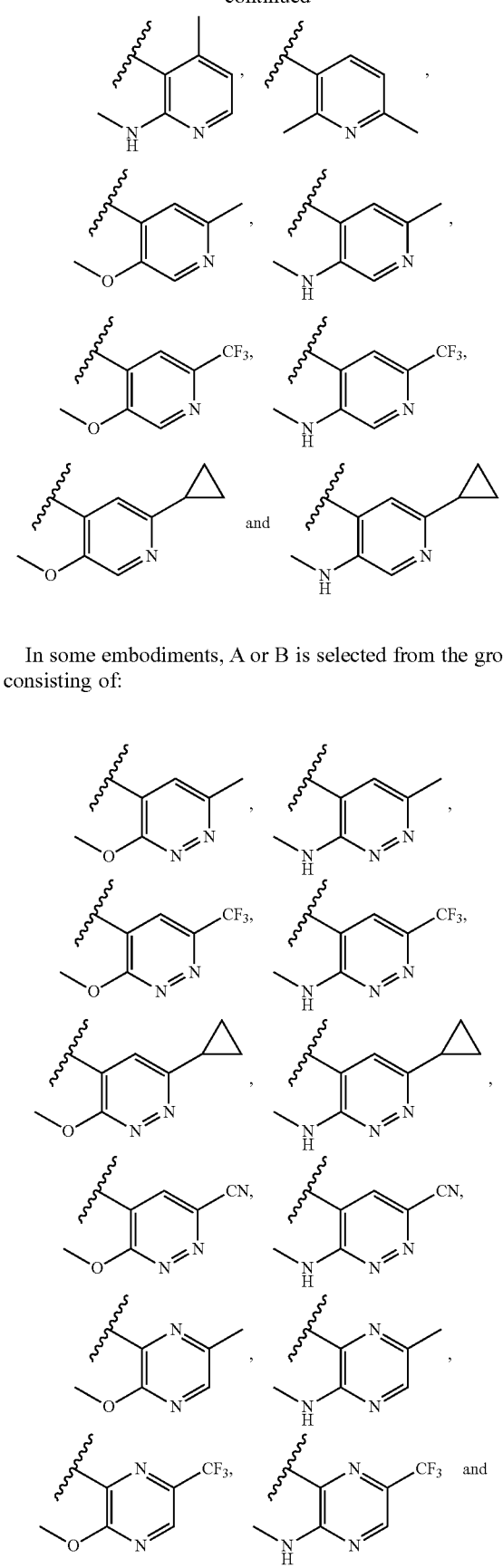
In some embodiments, A or B is selected from the group consisting of:

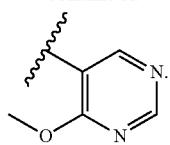
In some embodiments, A is selected from the group consisting of:
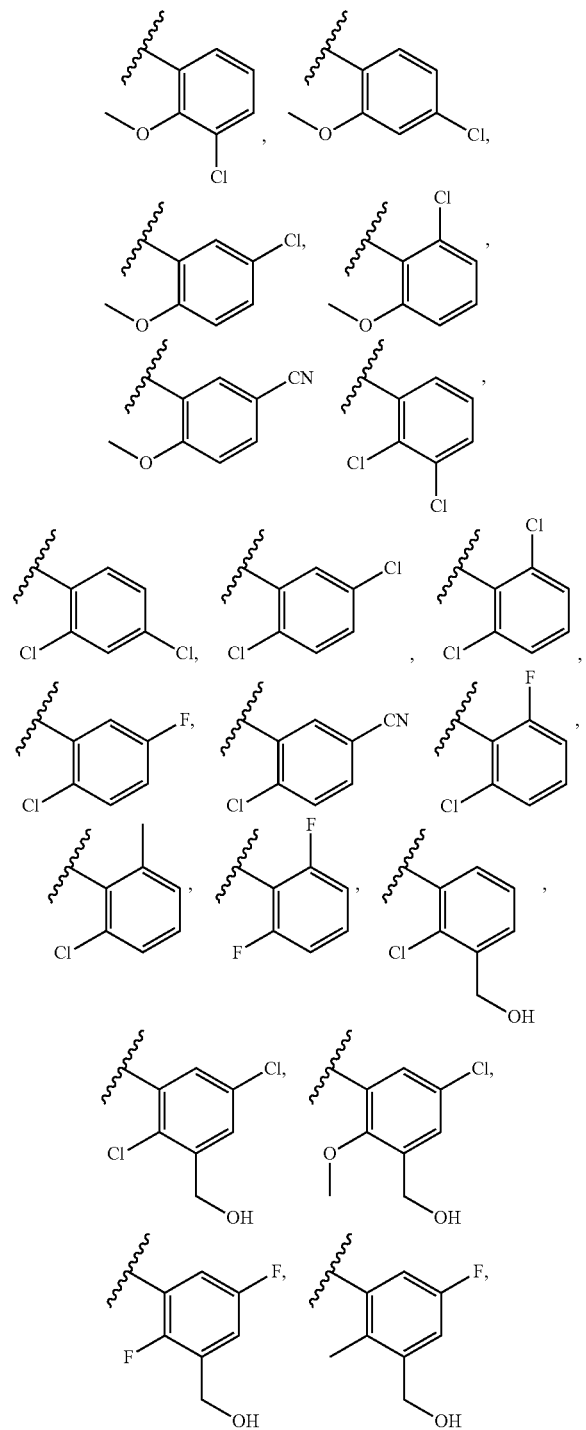
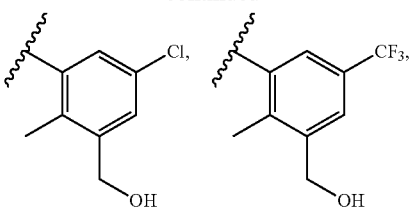
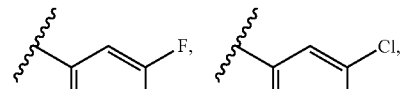
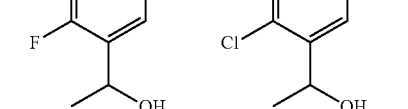
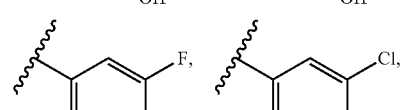
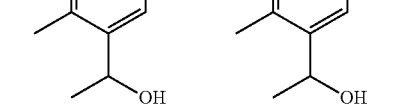
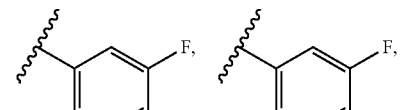
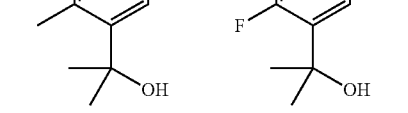
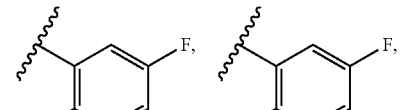
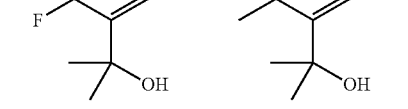
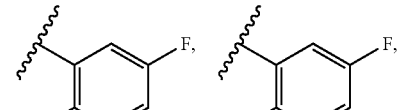
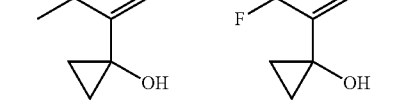
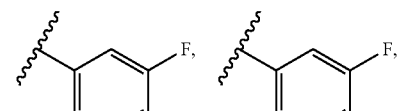
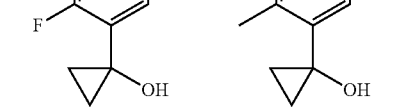
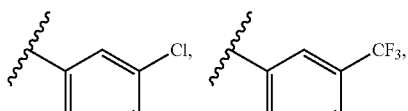
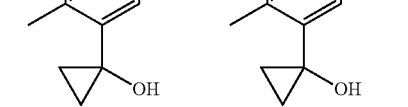

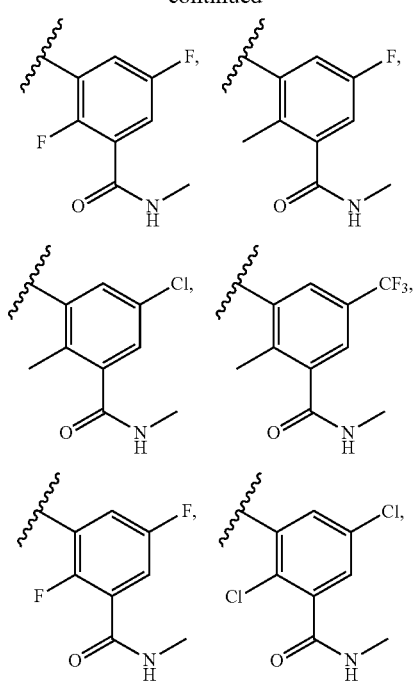
In some embodiments, A is selected from the group consisting of:
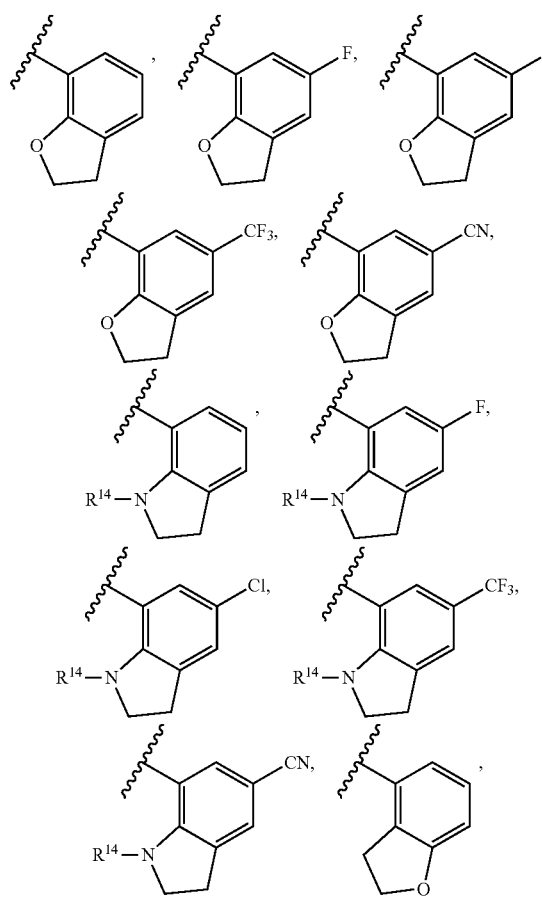
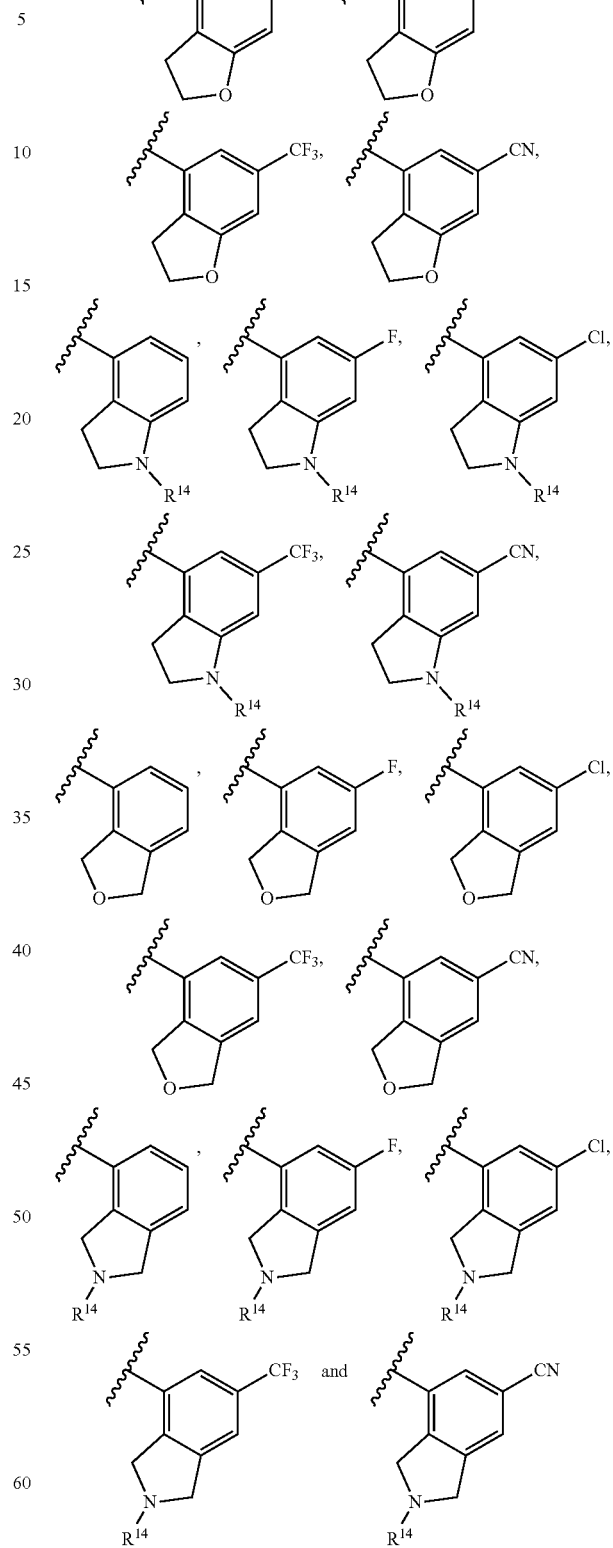
wherein each occurrence of $R^{14}$ is independently selected from the group consisting of H, alkyl, alkoxyalkyl, haloalkyl, hydroxyalkyl, and cyanoalkyl.

In some embodiments, A or B is selected from the group consisting of:

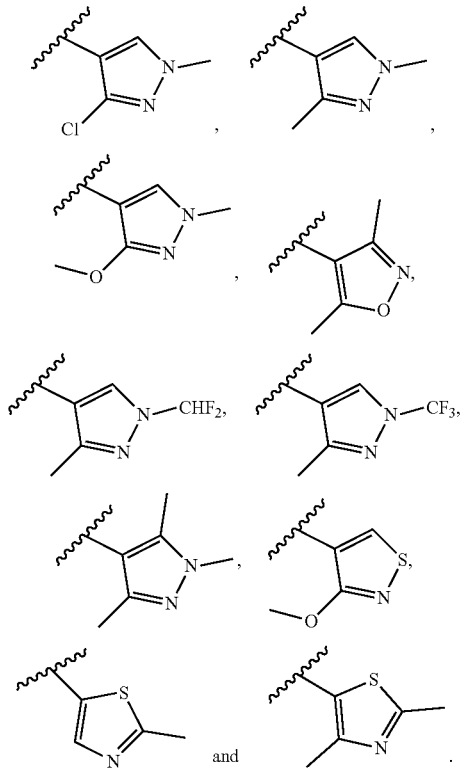

In some embodiments, A is an optionally substituted pyridone.

In some embodiments, A is selected from the group consisting of:

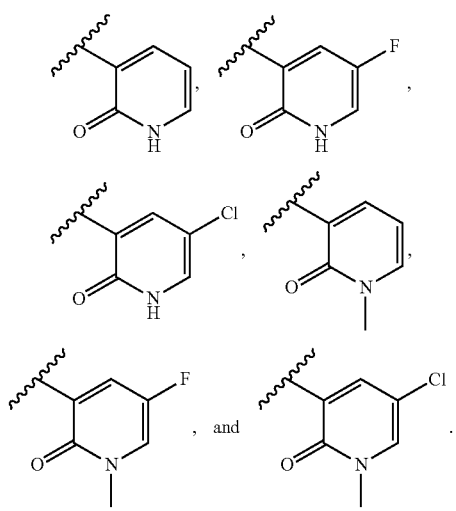

In some embodiments,

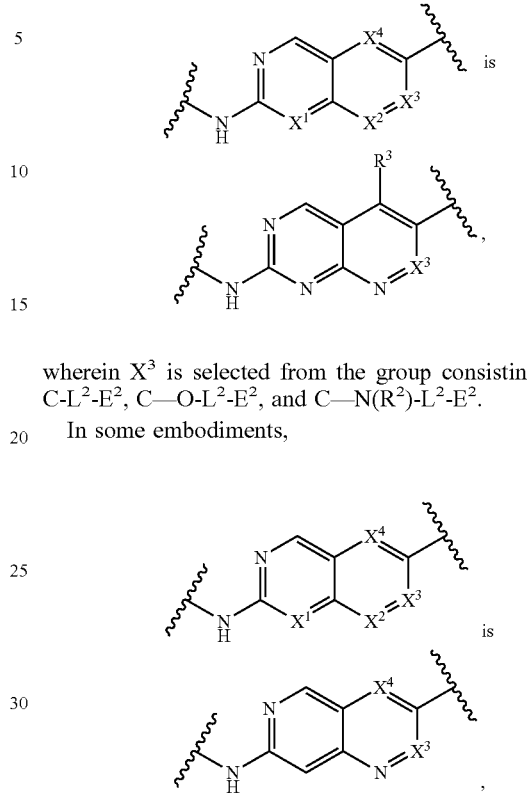

wherein $X^3$ is selected from the group consisting of CH, $C$-$L^2$-$E^2$, $C$—$O$-$L^2$-$E^2$, and $C$—$N(R^2)$-$L^2$-$E^2$.

In some embodiments,

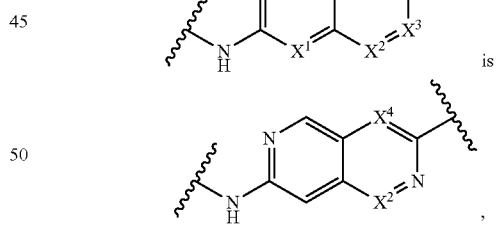

wherein $X^3$ is selected from the group consisting of CH, $C$-$L^2$-$E^2$, $C$—$O$-$L^2$-$E^2$, and $C$—$N(R^2)$-$L^2$-$E^2$ wherein $X^4$ is N or $CR^3$.

In some embodiments, wherein $X^2$ is selected from the group consisting of CH, $C$-$L^2$-$E^2$, $C$—$O$-$L^2$-$E^2$, and $C$—$N(R^2)$-$L^2$-$E^2$, wherein $X^4$ is N or $CR^3$.

In some embodiments,

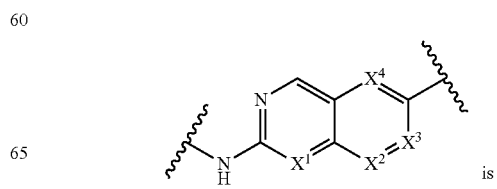

is

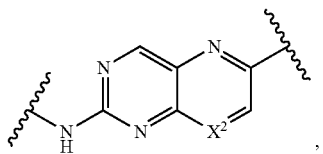

wherein $X^2$ is selected from the group consisting of CH, C-$L^2$-$E^2$, C—O-$L^2$-$E^2$, and C—N($R^2$)-$L^2$-$E^2$.

In some embodiments,

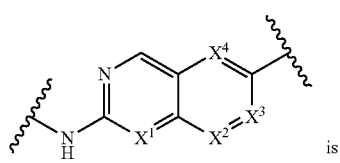 is

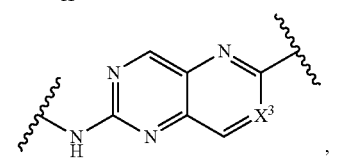, wherein $X^3$ is selected from the group consisting of CH, C-$L^2$-$E^2$, C—O-$L^2$-$E^2$, and C—N($R^2$)-$L^2$-$E^2$.

In some embodiments,

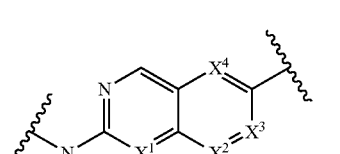 is

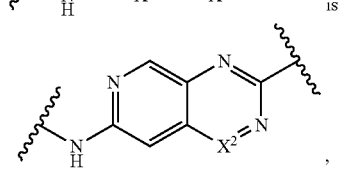, wherein $X^2$ is CH, C-$L^2$-$E^2$, C—O-$L^2$-$E^2$, and C—N($R^2$)-$L^2$-$E^2$, wherein $E^2$ is not F.

In some embodiments,

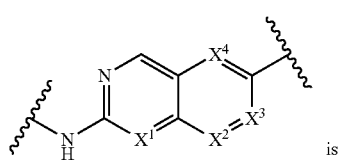 is

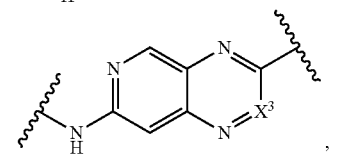, wherein $X^3$ is CH, C-$L^2$-$E^2$, C—O-$L^2$-$E^2$, and C—N($R^2$)-$L^2$-$E^2$, wherein $E^2$ is not F.

In some embodiments,

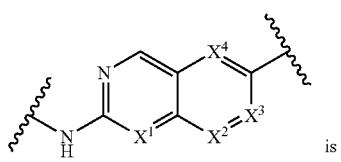 is

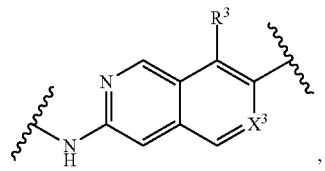, wherein $X^3$ is CH, C-$L^2$-$E^2$, C—O-$L^2$-$E^2$, and C—N($R^2$)-$L^2$-$E^2$.

In some embodiments,

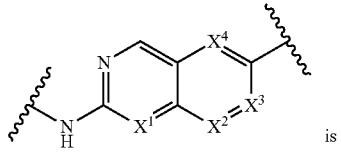 is

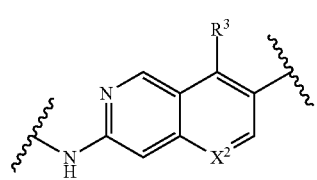, wherein $X^3$ is CH, C-$L^2$-$E^2$, C—O-$L^2$-$E^2$, and C—N($R^2$)-$L^2$-$E^2$.

In some embodiments,

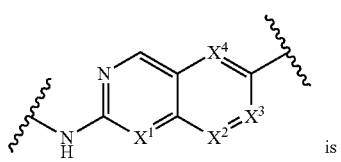 is

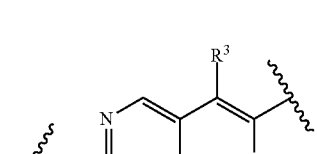, wherein $X^2$ is CH, C-$L^2$-$E^2$, C—O-$L^2$-$E^2$, and C—N($R^2$)-$L^2$-$E^2$.

In one embodiment, described herein is a compound represented by Formula I-R:

Formula I-R

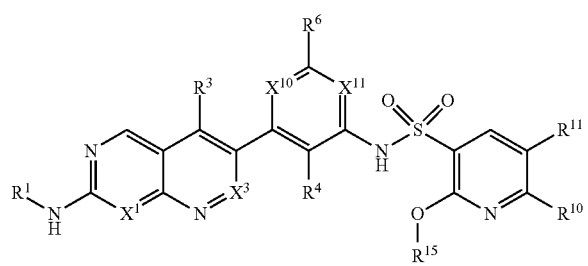

or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of $CR^5$ and N; $X^{11}$ is selected from the group consisting of $CR^7$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^{15}$ is selected from the group consisting of alkyl, cycloalkyl, and heterocycyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-S:

Formula I-S

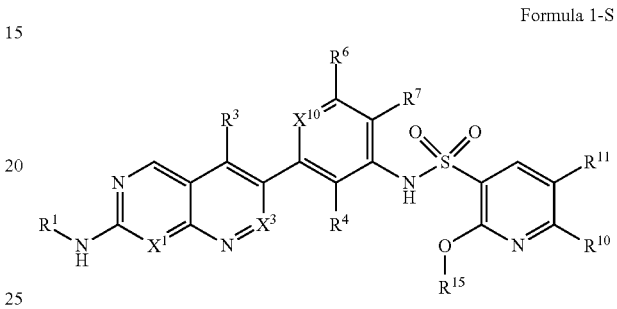

or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of $CR^5$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^{15}$ is selected from the group consisting of alkyl, cycloalkyl, and heterocycyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-T:

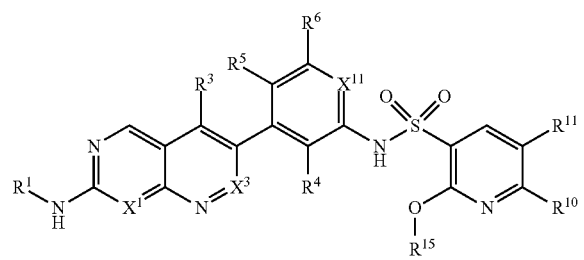

Formula I-T or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, cyanoalkyl, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^{15}$ is selected from the group consisting of alkyl, cycloalkyl, and heterocycyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-U:

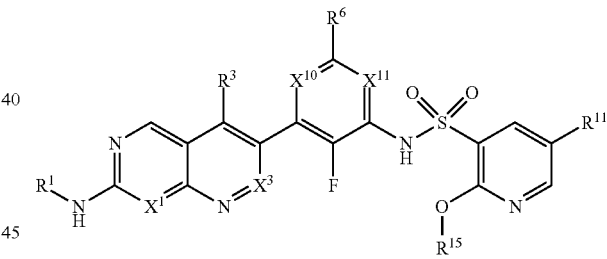

Formula I-U or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of C$R^5$ and N; $X^{11}$ is selected from the group consisting of C$R^7$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^{15}$ is selected from the group consisting of alkyl, cycloalkyl, and heterocycyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula 1-V:

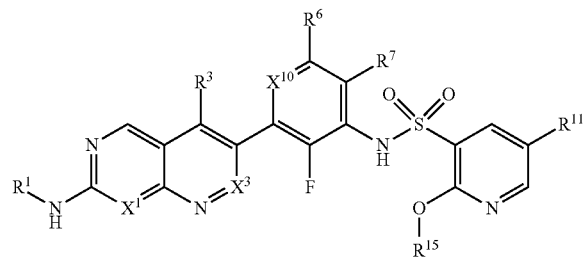

Formula 1-V or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of $CR^5$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^{15}$ is selected from the group consisting of alkyl, cycloalkyl, and heterocycyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula 1-W:

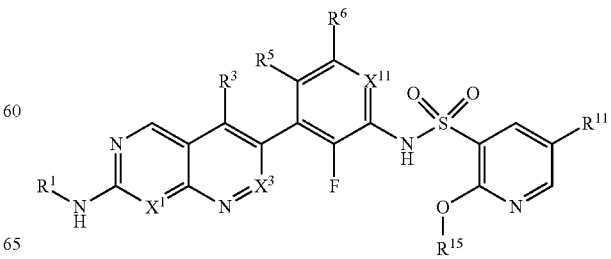

Formula 1-W or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{11}$ is selected from the group consisting of $CR^7$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^{15}$ is selected from the group consisting of alkyl, cycloalkyl, and heterocyyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-X:

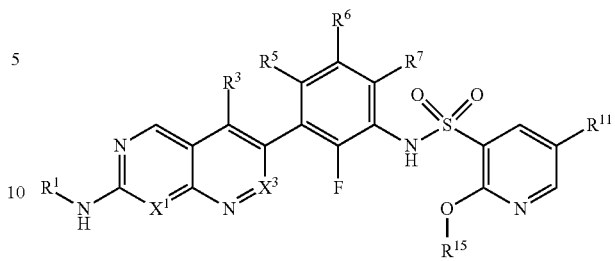

Formula 1-X or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^{15}$ is selected from the group consisting of alkyl, cycloalkyl, and heterocyyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a represented by Formula I-Y:

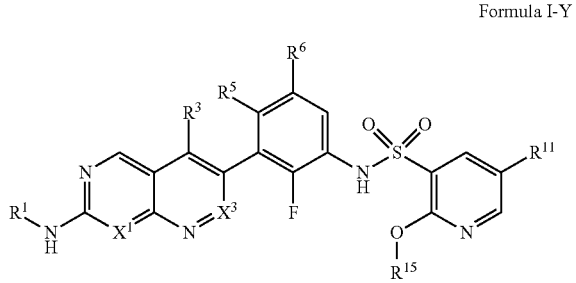

Formula I-Y or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is independently selected from the group consisting of halogen, H, alkoxy, alkylamino, amino, alkyl, haloalkyl and CN; $R^6$ is selected from the group consisting of halogen, H, and alkyl; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyanoalkyl, and sulfonyl; $R^{15}$ is selected from the group consisting of alkyl, cycloalkyl, and heterocycyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-Z:

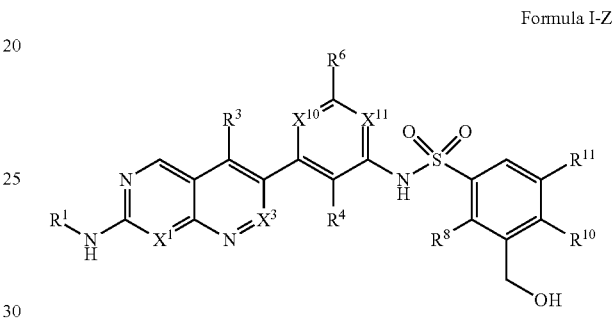

Formula I-Z or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of $CR^5$ and N; $X^{11}$ is selected from the group consisting of $CR^7$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-AA:

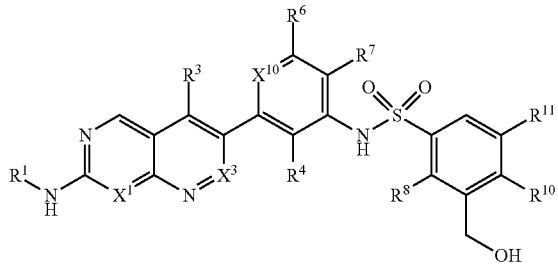

Formula I-AA or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of $CR^5$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{10}$ and $R^{11}$ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-AB:

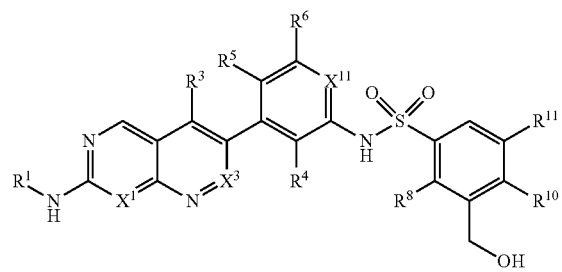

Formula I-AB or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{11}$ is selected from the group consisting of $CR^7$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^4$ and $R^5$ are each independently selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-AC:

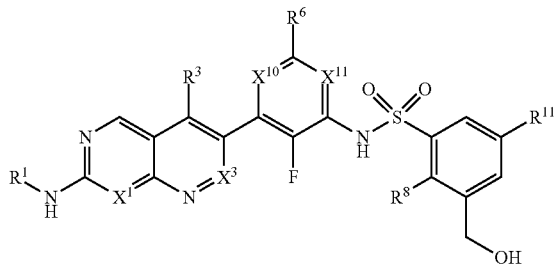

Formula I-AC or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of $CR^5$ and N; $X^{11}$ is selected from the group consisting of $CR^7$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-AD:

Formula I-AD

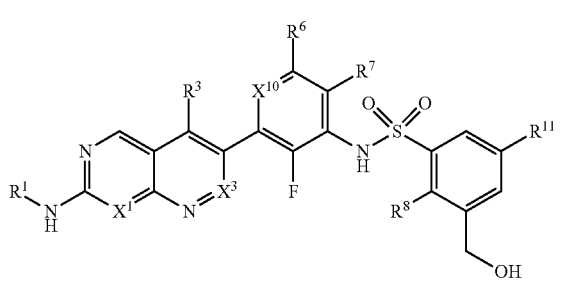

or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{10}$ is selected from the group consisting of $CR^5$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-AE:

Formula I-AE

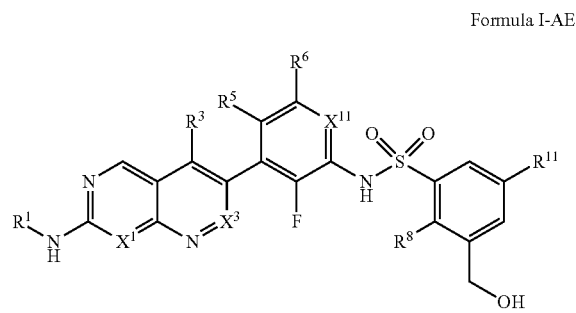

or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $X^{11}$ is selected from the group consisting of $CR^7$ and N; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-AF:

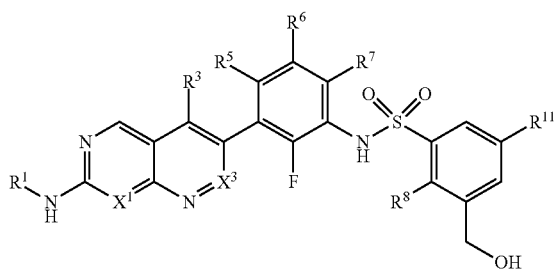

Formula I-AF or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; $R^3$ is selected from the group consisting of H, alkyl, and halogen; $R^5$ is selected from the group consisting of halogen, H, alkoxy, alkylamino, amino, alkyl, haloalkyl and CN; $R^6$ is selected from the group consisting of halogen, H, and alkyl; $R^7$ is selected from the group consisting of H and F; $R^8$ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; $R^{11}$ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; $R^{13}$ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $L^2$ is selected from the group consisting of a direct bond and $C_1$-$C_6$alkyl, wherein $C_1$-$C_6$alkyl is optionally substituted with $(E^{21})_p$; $E^2$ is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; $E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In one embodiment, described herein is a compound represented by Formula I-AG:

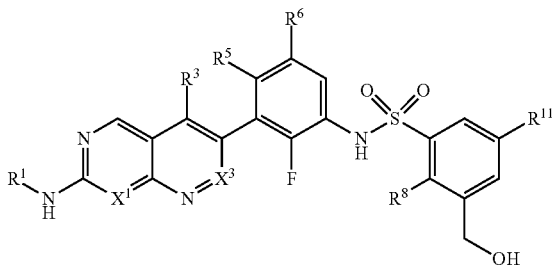

Formula I-AG or a pharmaceutically acceptable salt, enantiomer, stereoisomer, or tautomer thereof, wherein: $X^1$ is selected from the group consisting of CH and N; $X^3$ is selected from the group consisting of C—O-$L^2$-$E^2$, C-$L^2$-$E^2$, and C—N($R^2$)-$L^2$-$E^2$; $R^1$ is selected from the group consisting of alkyl, (C=O)$R^{13}$, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxyalkyl, amide, amine, aminoalkyl, acyl, haloalkyl, haloalkoxy, halogen, hydroxy, hydroxyalkyl, oxo, cyano, cyanoalkyl, and sulfonyl; $R^2$ is selected from the group consisting of H and alkyl; R³ is selected from the group consisting of H, alkyl, and halogen; R⁵ is selected from the group consisting of halogen, H, alkoxy, alkylamino, amino, alkyl, haloalkyl and CN; R⁶ is selected from the group consisting of halogen, H, and alkyl; R⁸ is selected from the group consisting of alkoxy, alkylamino, cycloalkoxy, cycloalkylamino, halogen, H, alkyl, haloalkoxy, haloalkyl, amide, alkoxycarbonyl, hydroxyalkyl, hydroxycycloalkyl, hydroxy, and CN; R¹¹ is selected from the group consisting of hydroxyalkyl, hydroxycycloalkyl, alkoxyalkyl, alkoxycycloalkyl, amino, aminoalkyl, aminocycloalkyl, aminocarbonyl, acylamino, halogen, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl; R¹³ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl, wherein each of aryl and heteroaryl is optionally substituted with one or more occurrences of a substituent independently selected from the group consisting of haloalkyl, alkyl, haloalkoxy, alkoxy, halogen, amine, amide, acyl, alkoxyalkyl, hydroxy, hydroxyalkyl, cyano, cyanoalkyl, and heterocyclyl, and wherein heterocyclyl is optionally substituted with one or more occurrences of a substituent independently selected from the group consisting of alkyl, alkoxy, alkoxyalkyl, amide, amine, aminoalkyl, acyl, haloalkyl, haloalkoxy, halogen, hydroxy, hydroxyalkyl, oxo, cyano, cyanoalkyl, and sulfonyl; L² is selected from the group consisting of a direct bond and C₁-C₆alkyl, wherein C₁-C₆alkyl is optionally substituted with (E²¹)ₚ; E² is selected from the group consisting of hydroxy, alkoxy, alkoxyalkyl, cyano, halogen, sulfonyl, H, alkyl, amine, amide, acyl, haloalkoxy, haloalkyl, and heterocyclyl, wherein heterocyclyl is optionally substituted with one or more occurrences of a substituent independently selected from the group consisting of alkyl, alkoxy, amide, amine, acyl, haloalkyl, haloalkoxy, halogen, hydroxy, hydroxyalkyl, oxo, cyano, and cyanoalkyl; E²¹, at each occurrence, is independently selected from the group consisting of H, alkyl, cycloalkyl, alkoxy, cyano, cyanoalkyl, haloalkoxy, haloalkyl, hydroxy, hydroxyalkyl, and halogen, and each p is independently 0, 1 or 2.

In some embodiments, R¹ is selected from the group consisting of

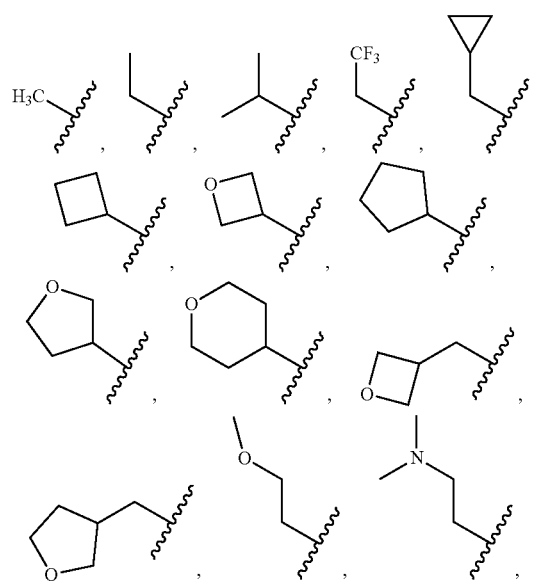

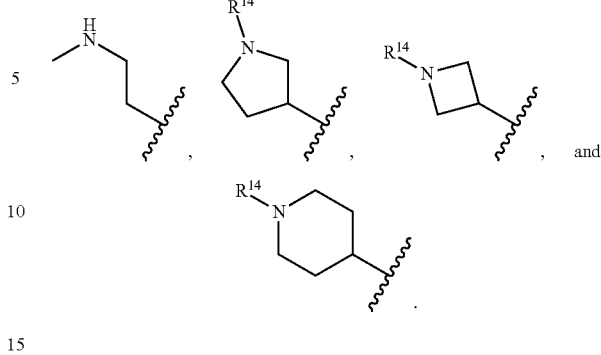

wherein each occurrence of R¹⁴ is independently selected from the group consisting of H, alkyl, alkoxyalkyl, haloalkyl, hydroxyalkyl, and cyanoalkyl.

In some embodiments, R¹ is selected from the group consisting of

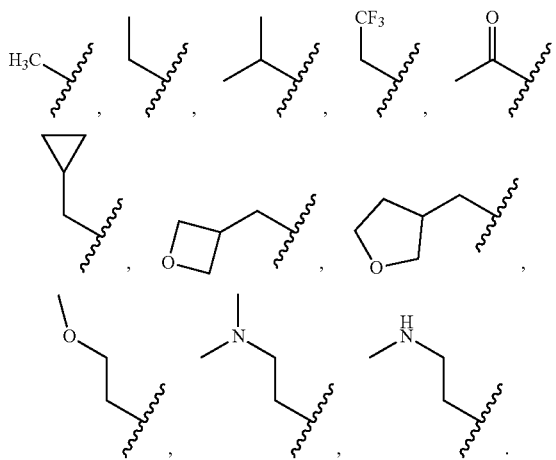

In some embodiments, R¹ is selected from the group consisting of H,

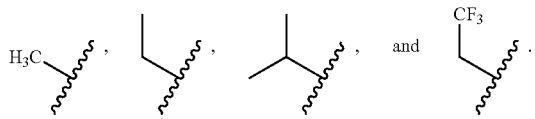

In some embodiments, R¹ is selected from the group consisting of

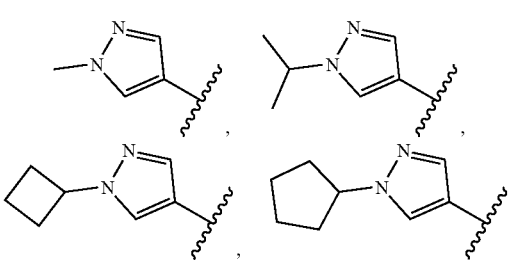

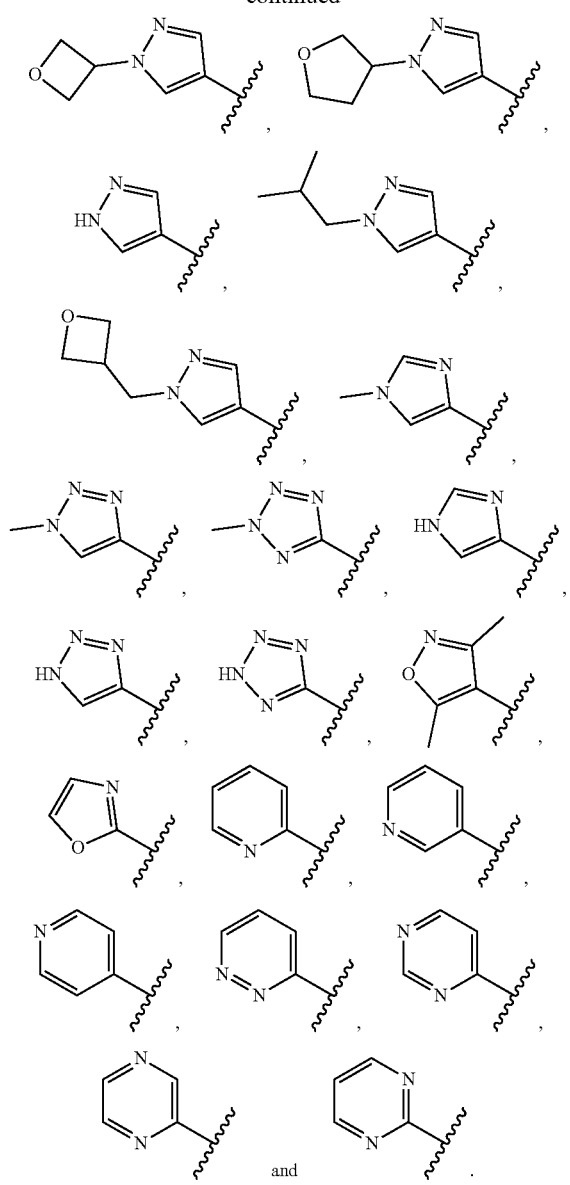

In some embodiments, $R^1$ is selected from the group consisting of

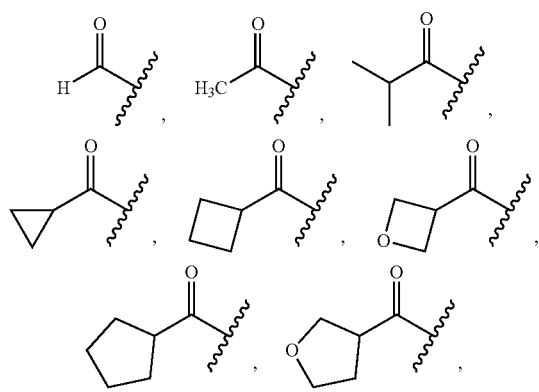

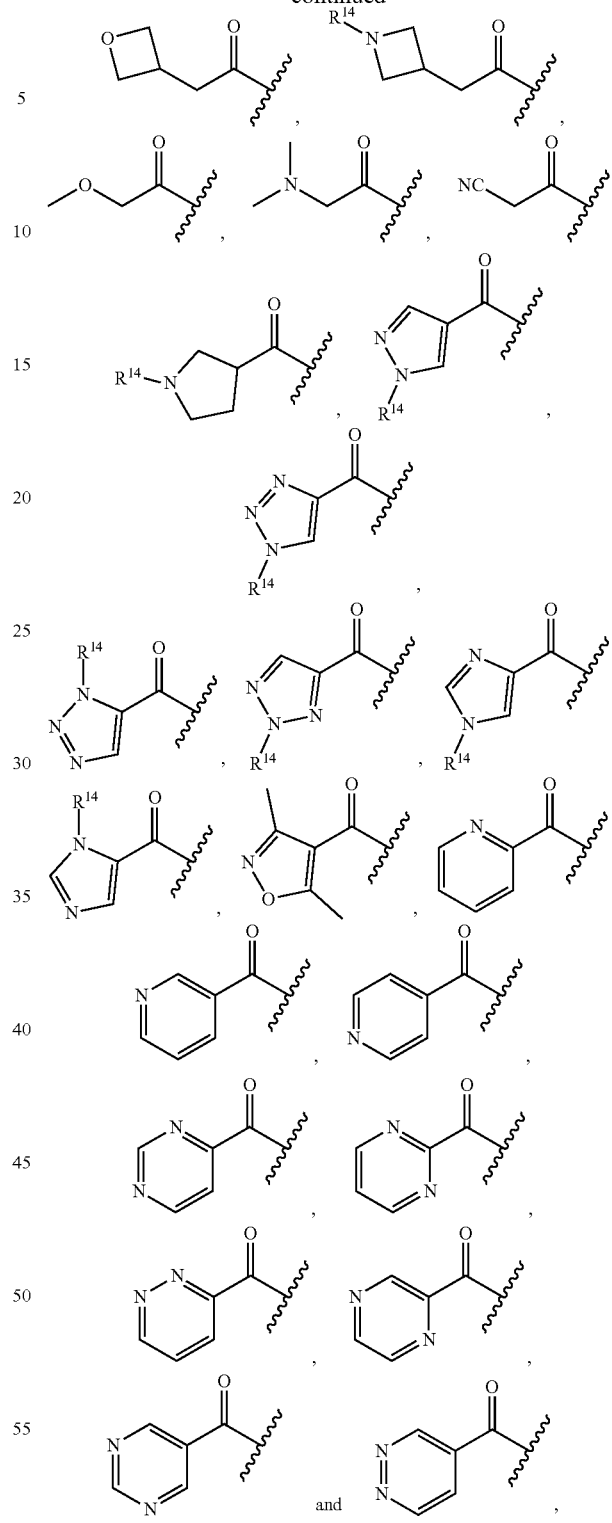

wherein each occurrence of $R^{14}$ is independently selected from the group consisting of H, alkyl, alkoxyalkyl, haloalkyl, hydroxyalkyl, and cyanoalkyl.

In some embodiments, $X^1$ is N. In some embodiments, $X^1$ is CH. In some embodiments, $X^3$ is C—N($R^2$)-$L^2$-$E^2$. In some embodiments, $X^3$ is CN(H)CH$_3$. In some embodiments, $X^3$ is CCH$_3$.

In some embodiments, $X^3$ is selected from the group consisting of:

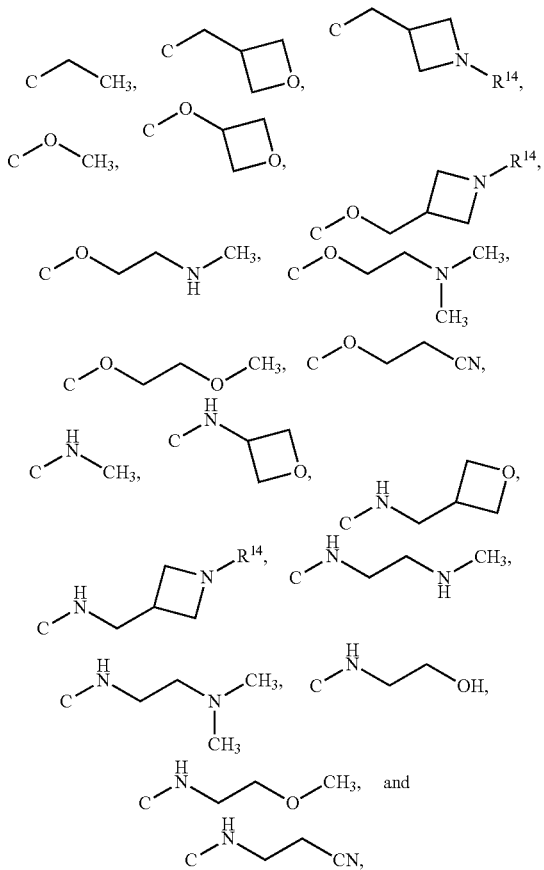

wherein each occurrence of $R^{14}$ is independently selected from the group consisting of H, alkyl, alkoxyalkyl, haloalkyl, hydroxyalkyl, and cyanoalkyl.

In some embodiments, $X^3$ is selected from the group consisting of

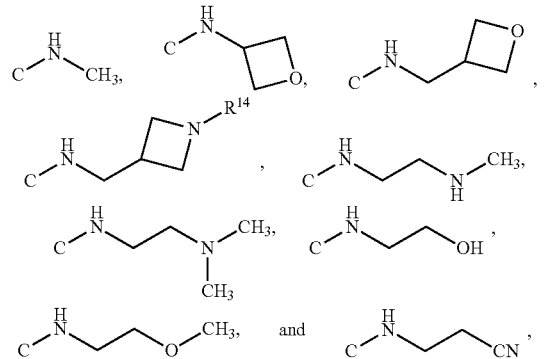

wherein each occurrence of $R^{14}$ is independently selected from the group consisting of H, alkyl, alkoxyalkyl, haloalkyl, hydroxyalkyl, and cyanoalkyl.

In some embodiments, $X^{10}$ is N and $X^{11}$ is $CR^7$. In some embodiments, $X^{10}$ and $X^{11}$ are N. In some embodiments, $X^{10}$ is $CR^5$ and $X^{11}$ is N. In some embodiments, $R^3$ is H, $C_1$-$C_6$ alkyl, and halogen. In some embodiments, $R^3$ is H. In some embodiments, $R^3$ is Me. In some embodiments, $R^3$ is F. In some embodiments, $R^3$ is Cl. In some embodiments, $R^4$ is selected from the group consisting of H, F, Cl, Me, OMe, $CF_3$, and CN. In some embodiments, $R^5$ is selected from the group consisting of H, F, Cl, Me, OMe, $CF_3$, and CN. In some embodiments, $R^6$ and $R^7$ are each independently selected from the group consisting of H, F, Cl, Me. In some embodiments, $R^4$, $R^5$, $R^6$, and $R^7$ are each independently H or F, and wherein at least one of $R^4$, $R^5$, $R^6$, and $R^7$ is F. In some embodiments, $R^6$ is F; and $R^4$, $R^5$, and $R^7$ are each H. In some embodiments, $R^4$ is F; and $R^5$, $R^6$, and $R^7$ are each H. In some embodiments, $R^4$ and $R^6$ are each F; and $R^5$ and $R^7$ are each H. In some embodiments, $R^4$ and $R^5$ are each F; and $R^6$ and $R^7$ are each H. In some embodiments, $R^5$ and $R^6$ are each F; and $R^4$ and $R^7$ are each H. In some embodiments, $R^{15}$ is selected from the group consisting of $C_1$-$C_6$ alkyl, $C_3$-$C_6$ cycloalkyl, and $C_3$-$C_6$ heterocyclyl. In some embodiments, $R^{15}$ is cyclopropyl. In some embodiments, $R^{15}$ is Me. In some embodiments, $R^{15}$ is oxetanyl. In some embodiments, $R^{15}$ is oxetan-2-yl. In some embodiments, $R^{15}$ is oxetan-3-yl.

In some embodiments, the compound is selected from the group consisting of:

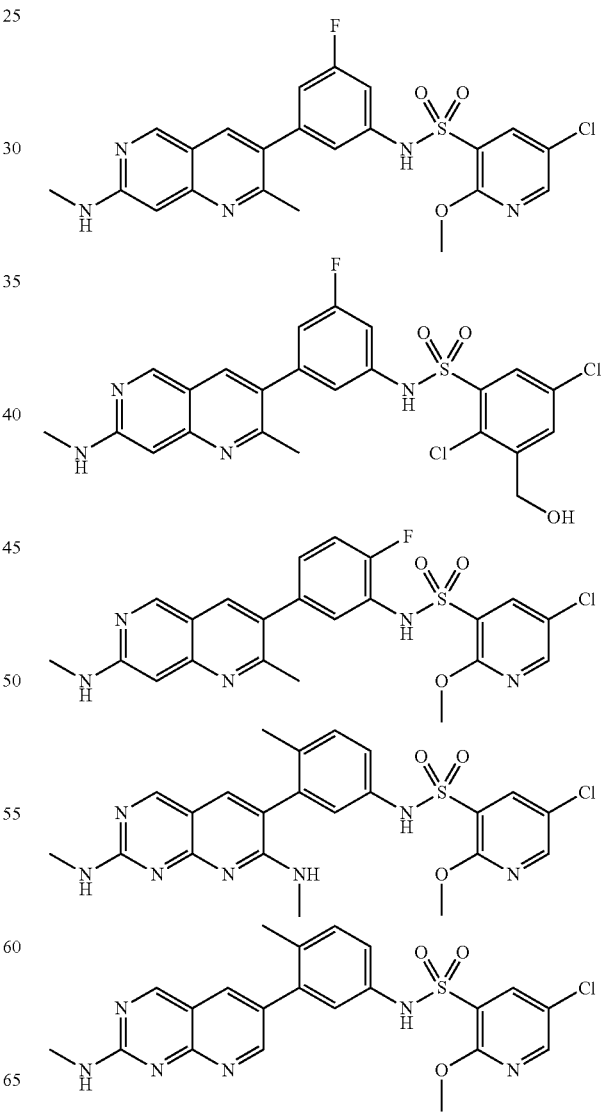

81
-continued
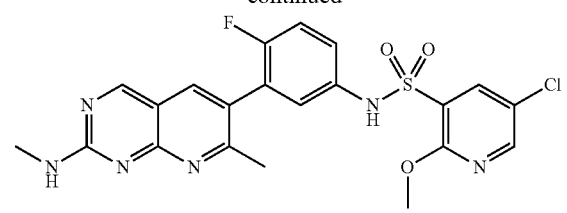
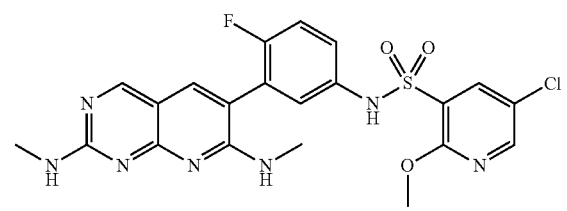
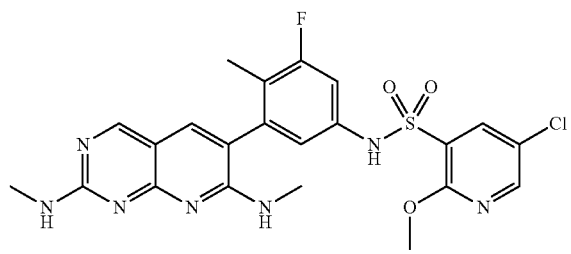
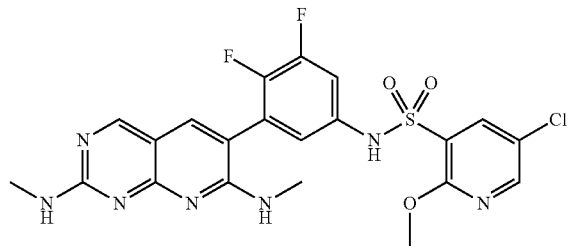
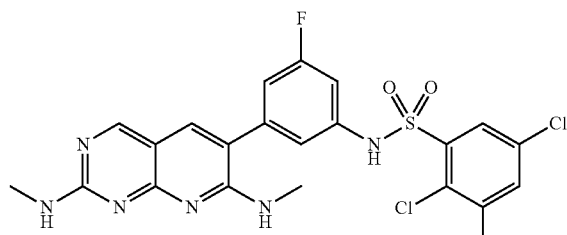
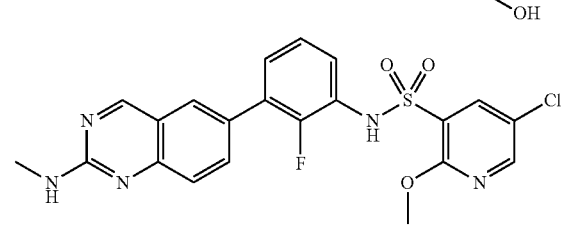
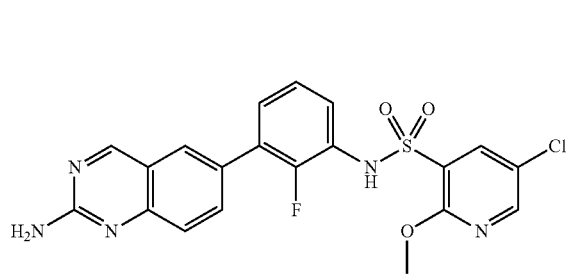
82
-continued
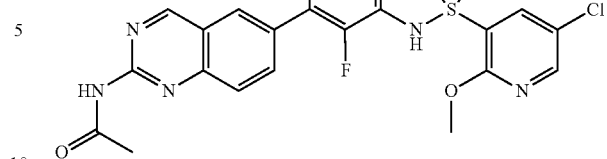
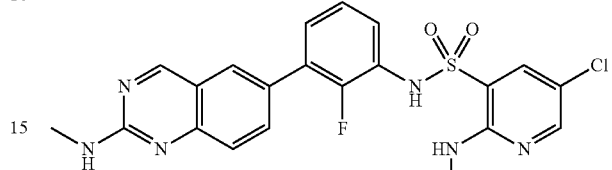
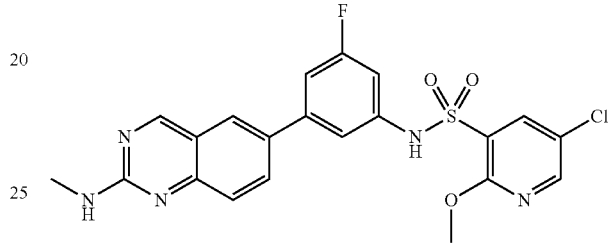
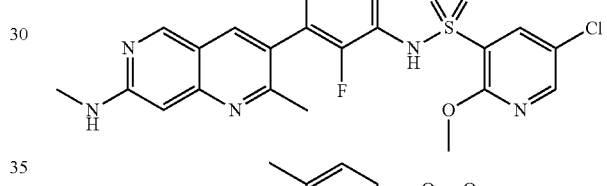
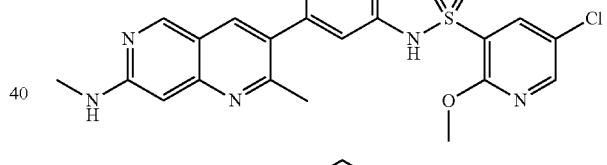
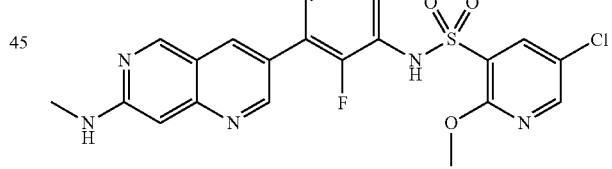
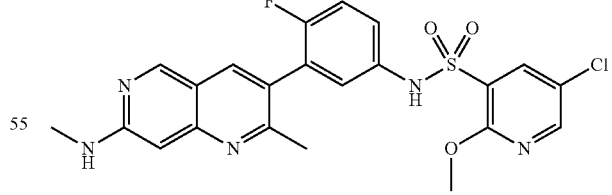
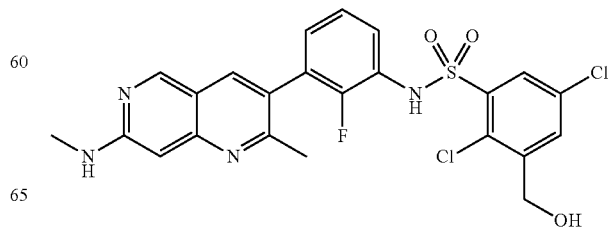

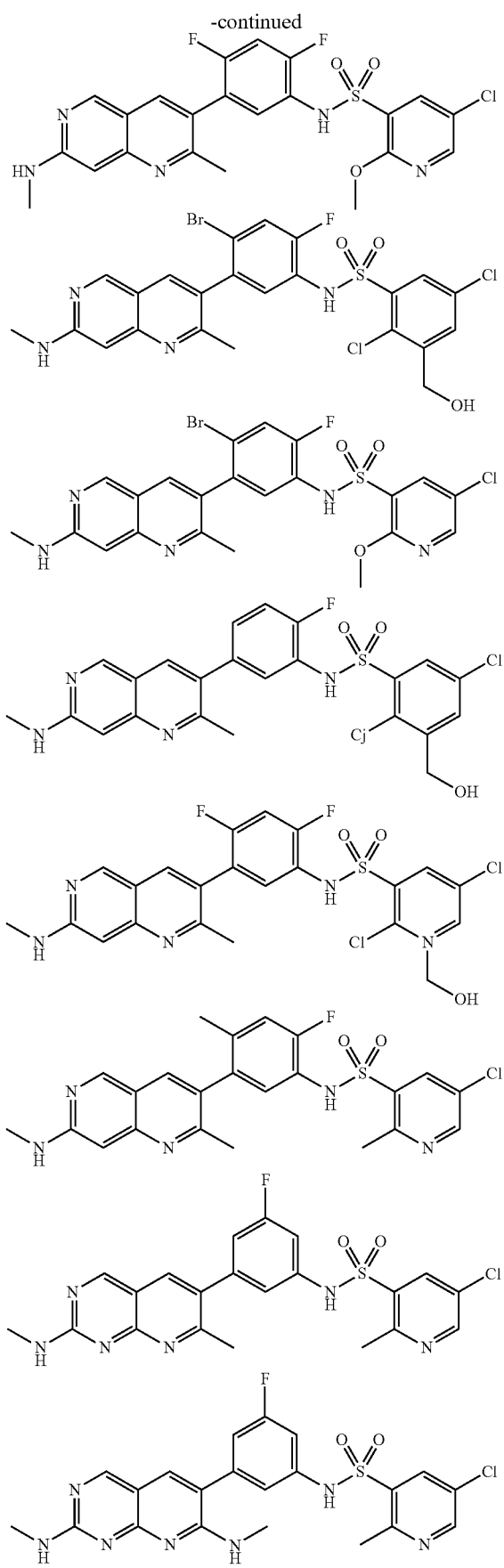
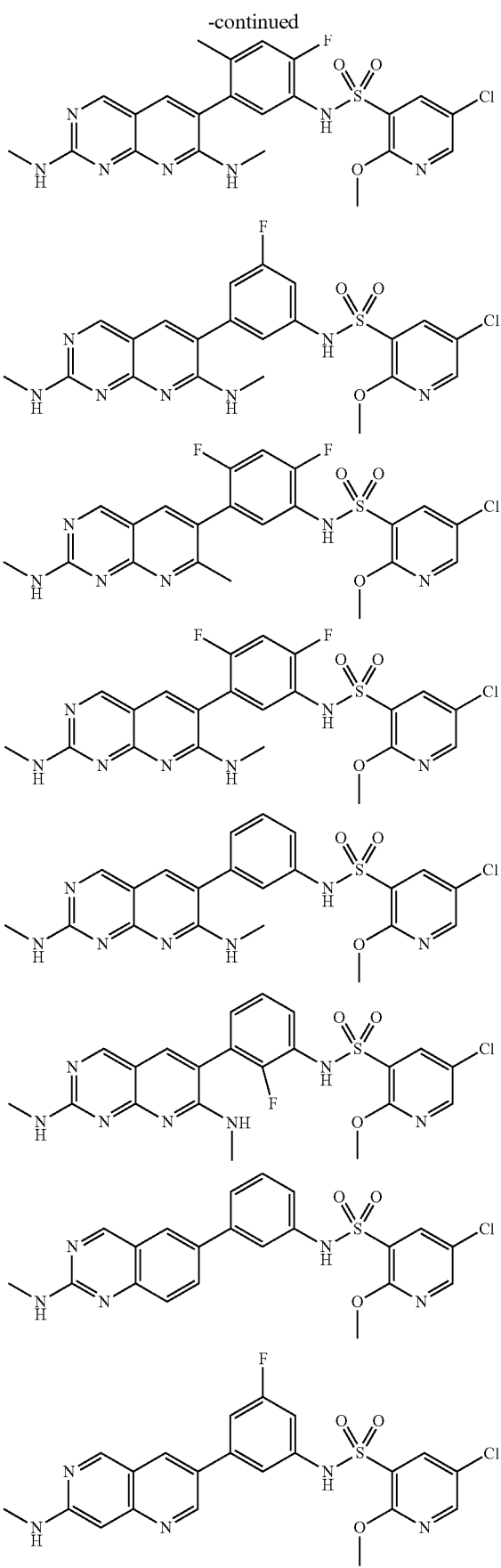

85
-continued
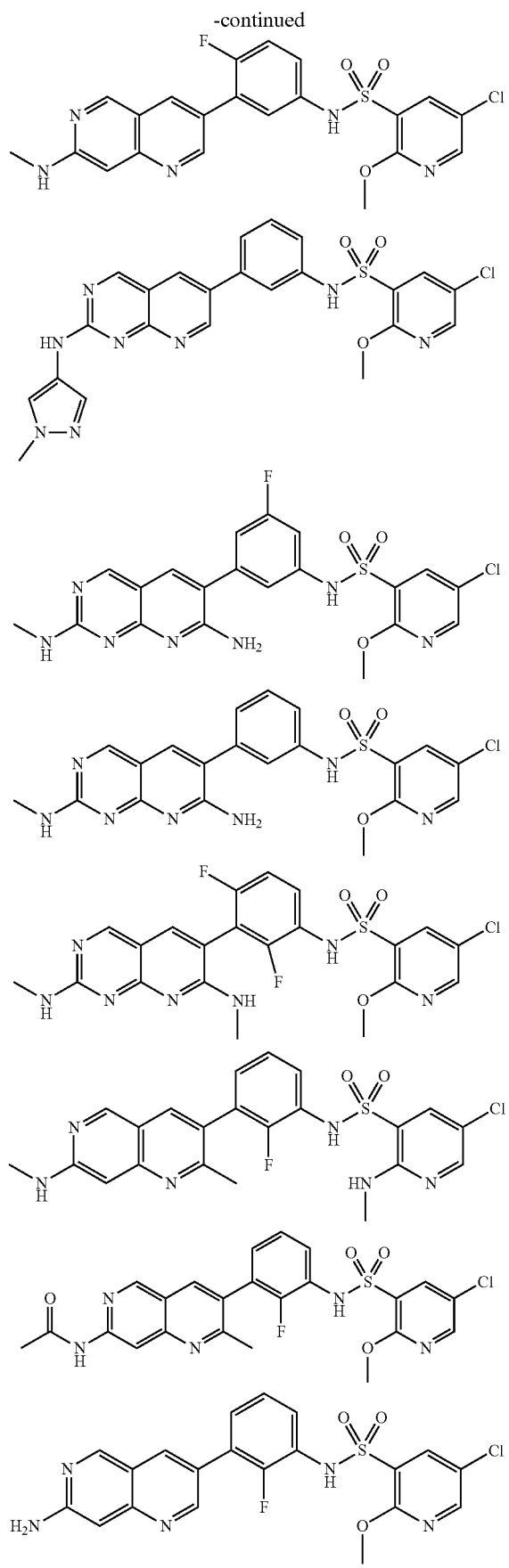
86
-continued
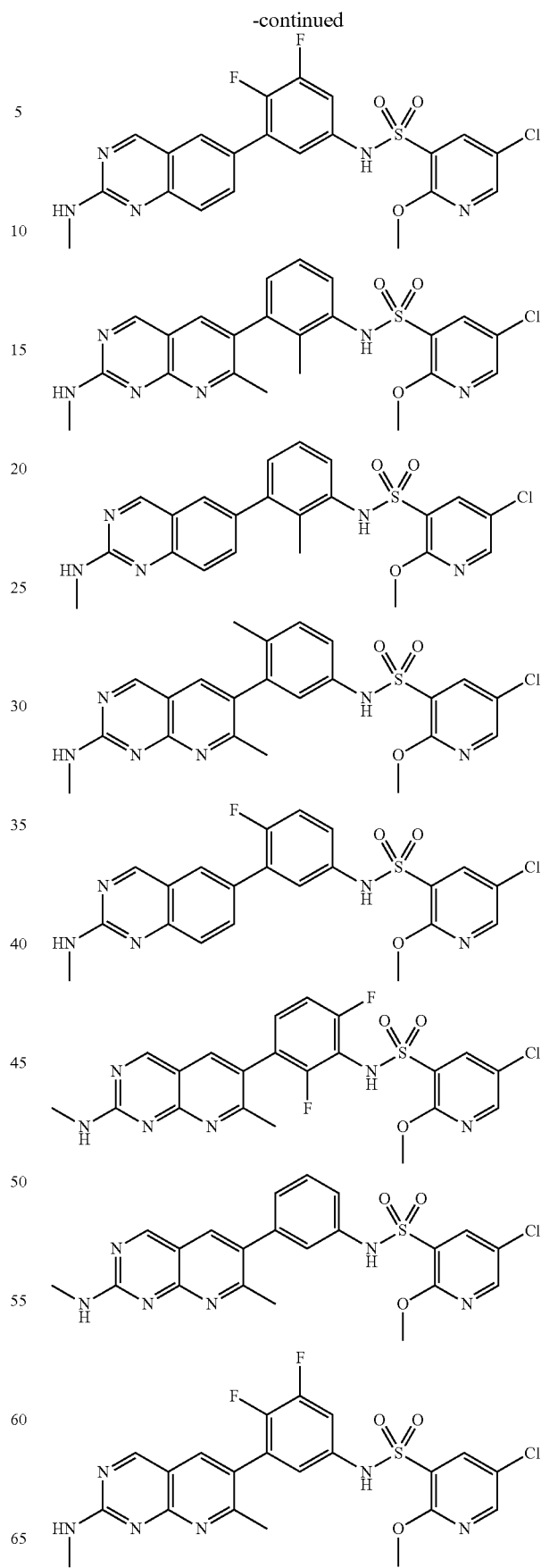

-continued
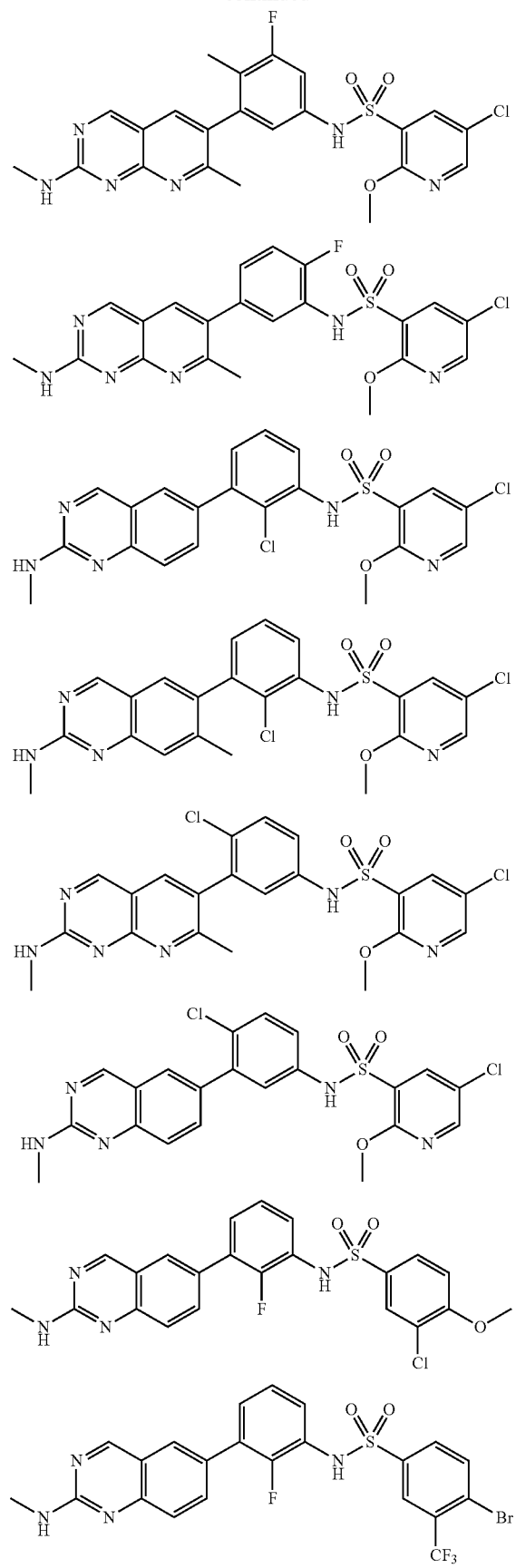
-continued
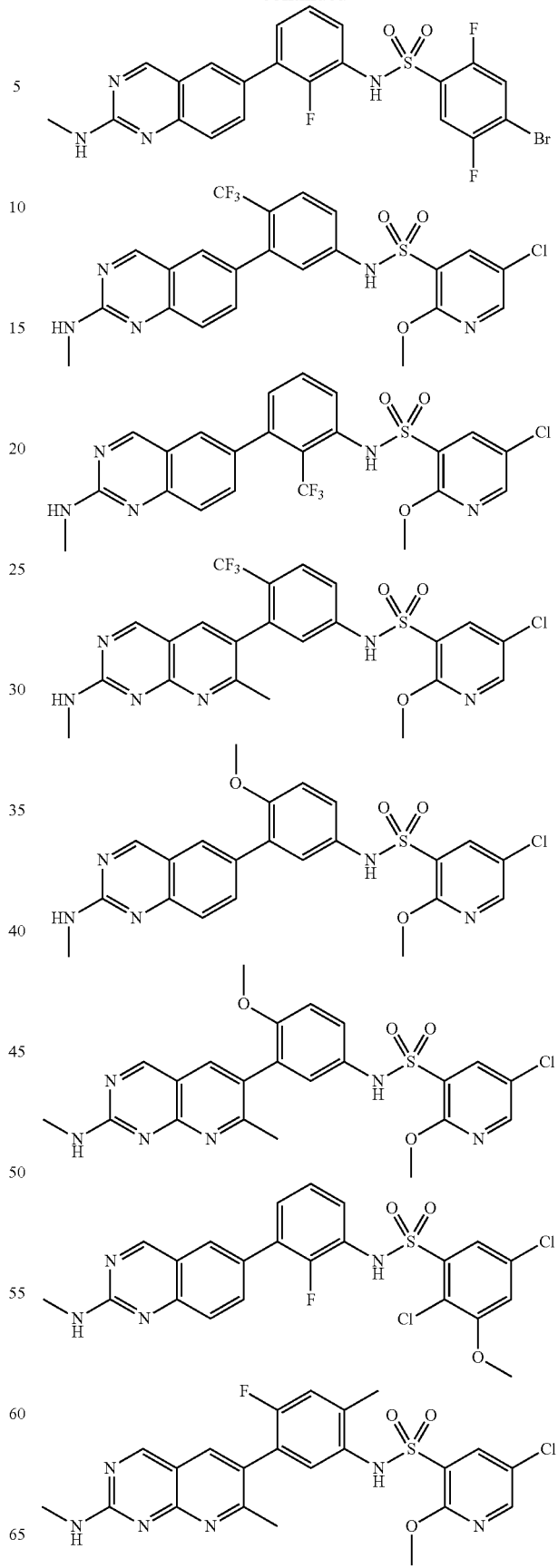

89
-continued
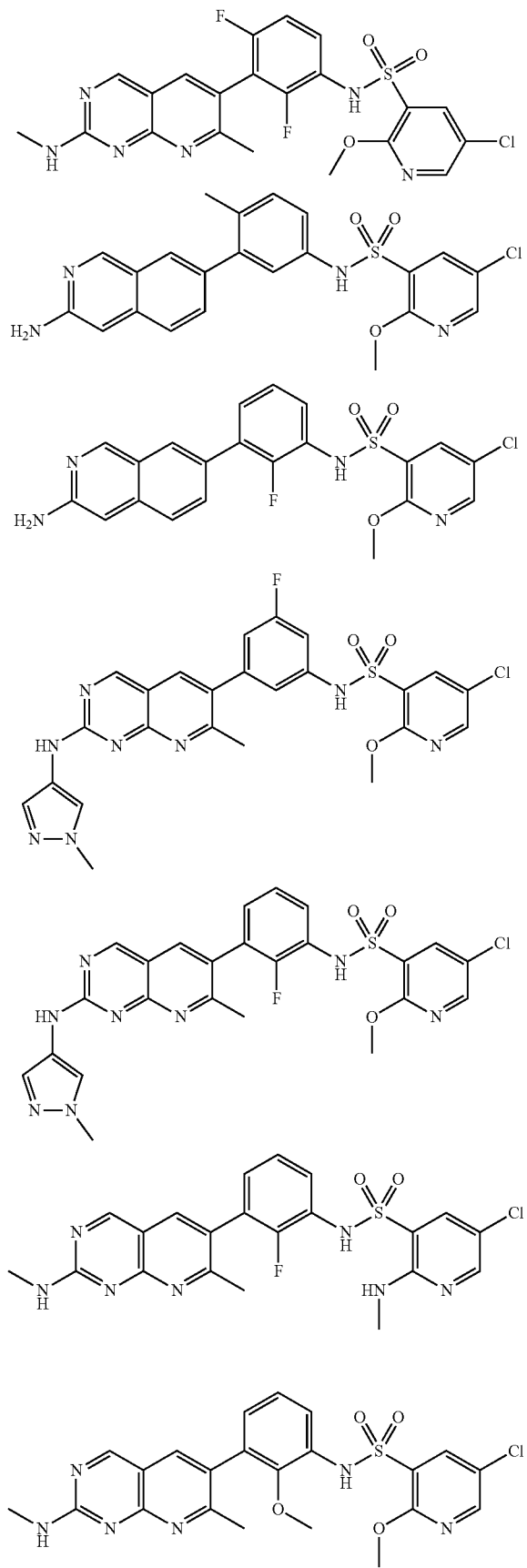
90
-continued
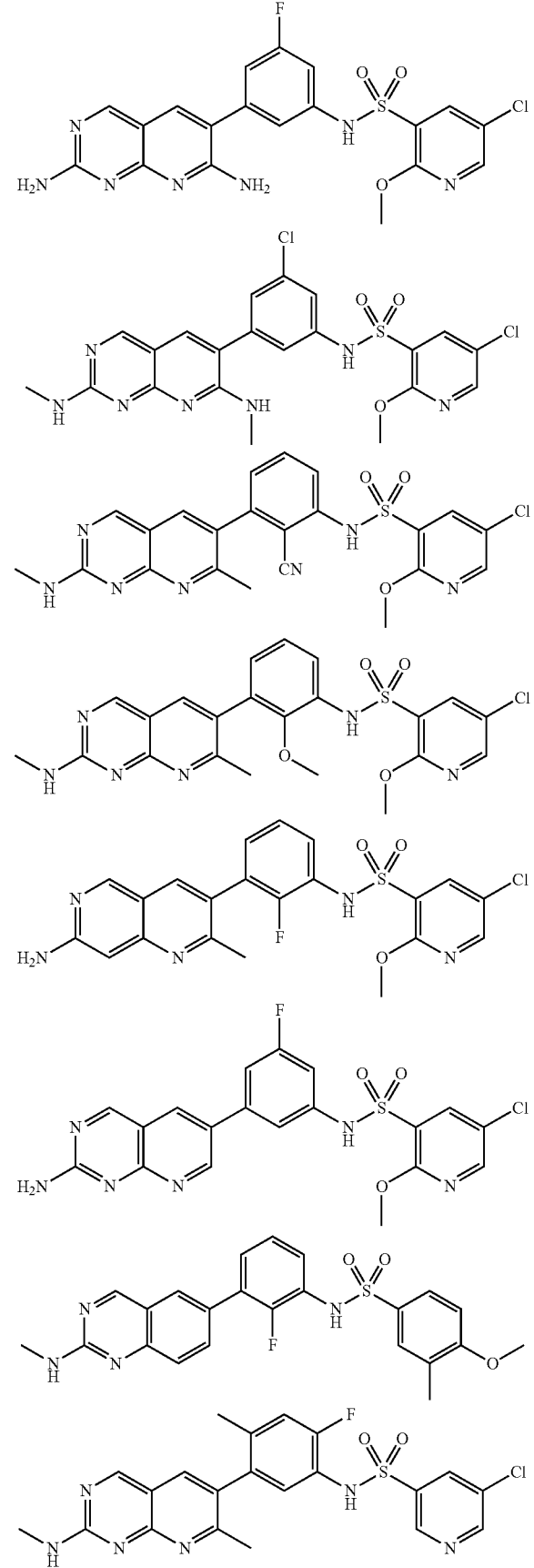

-continued
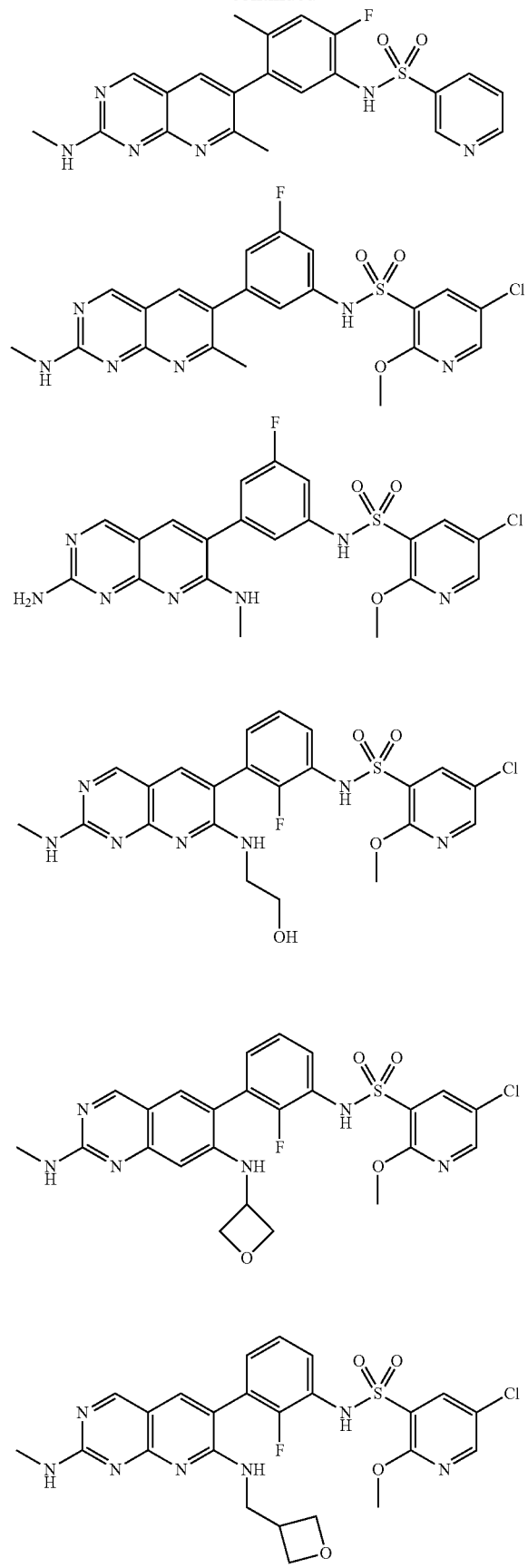
-continued
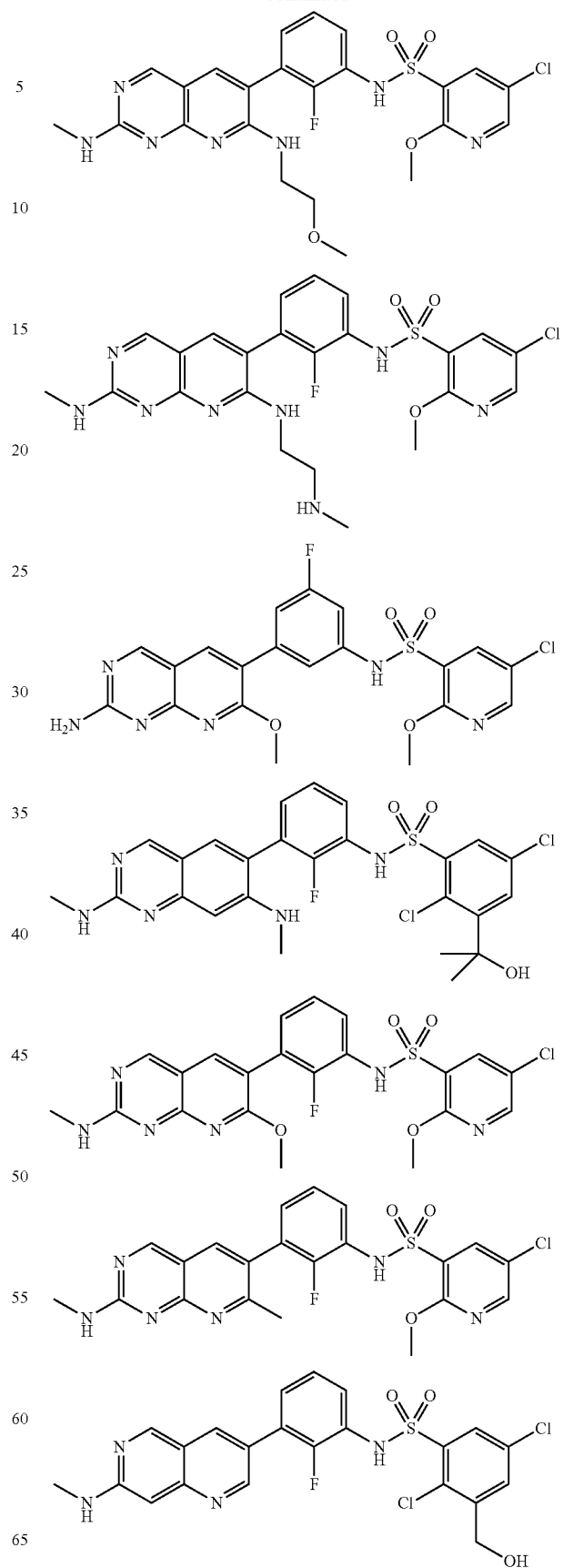

-continued
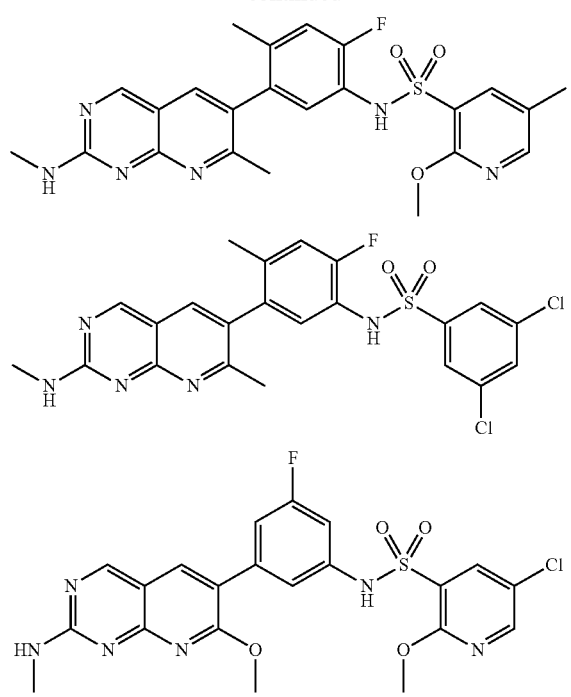
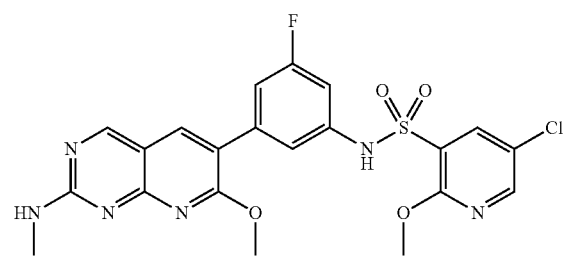
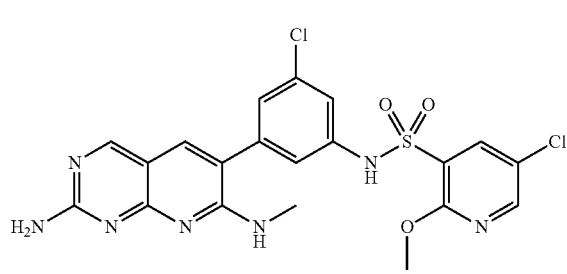
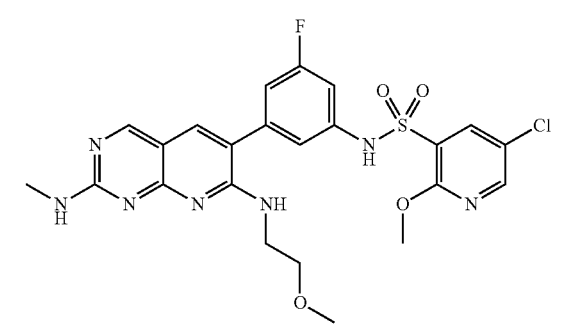
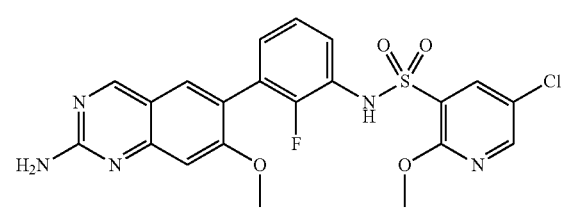
-continued
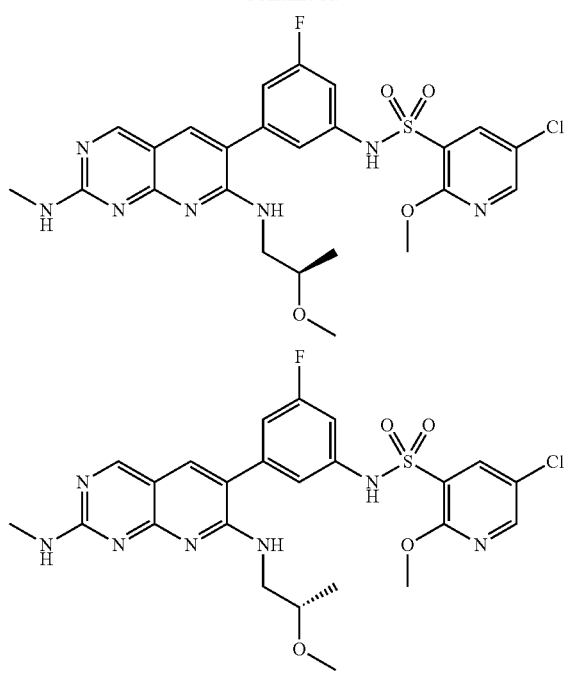
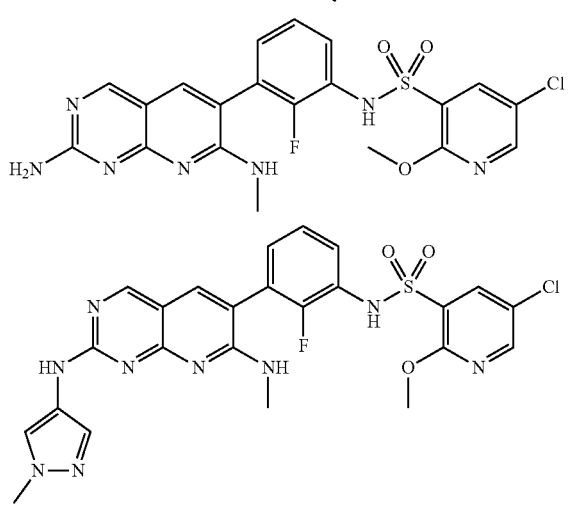
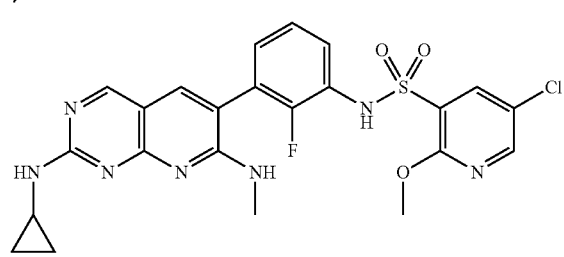
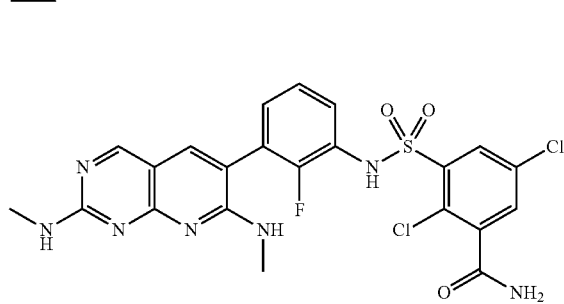

-continued
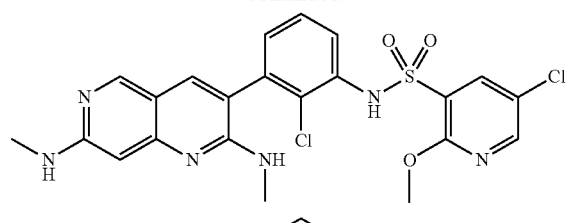
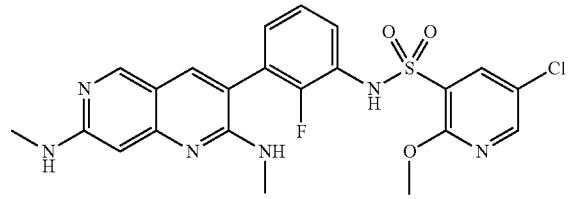
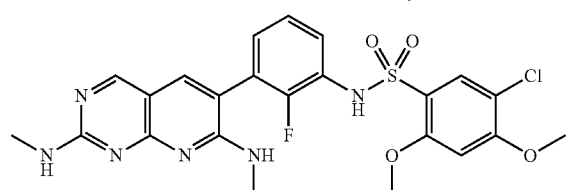
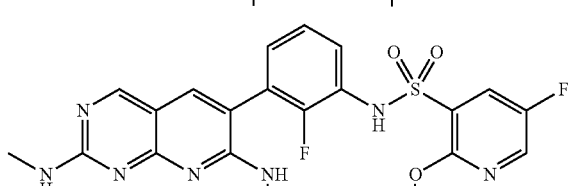
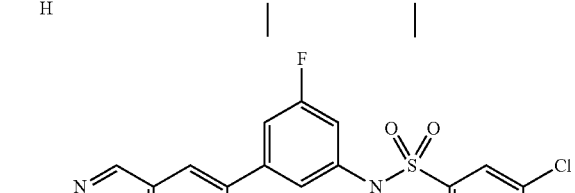
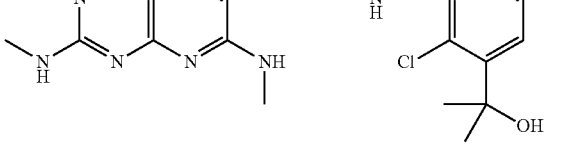
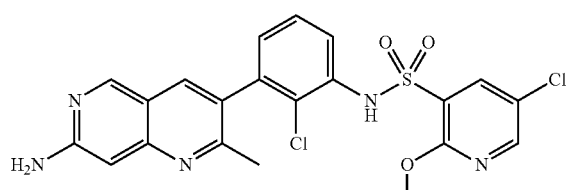
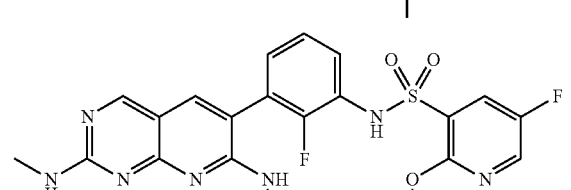
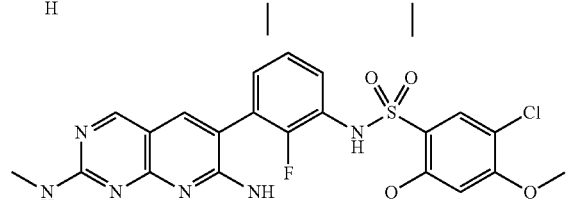
-continued
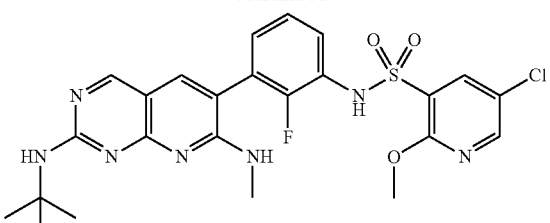
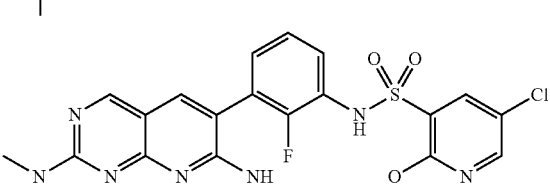
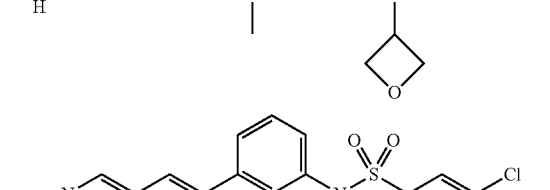
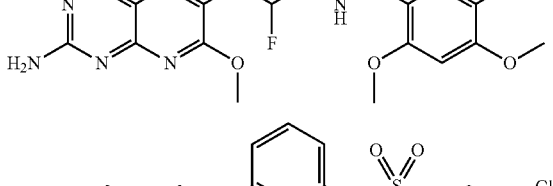
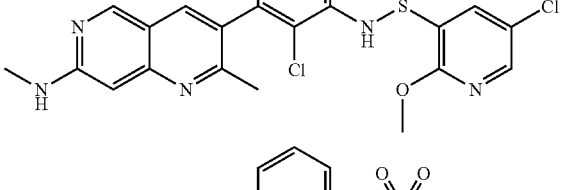
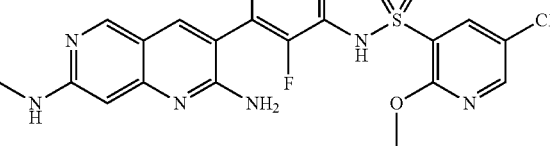
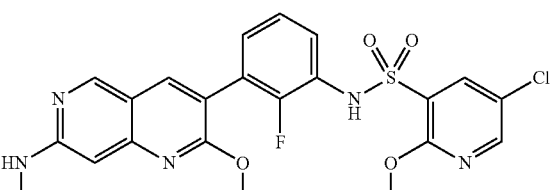
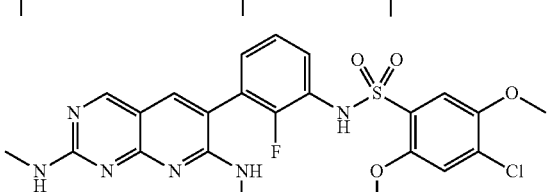
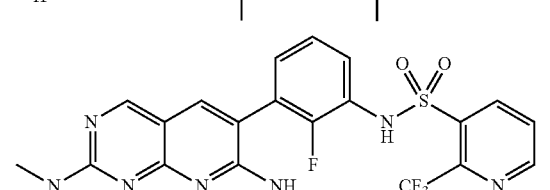

-continued
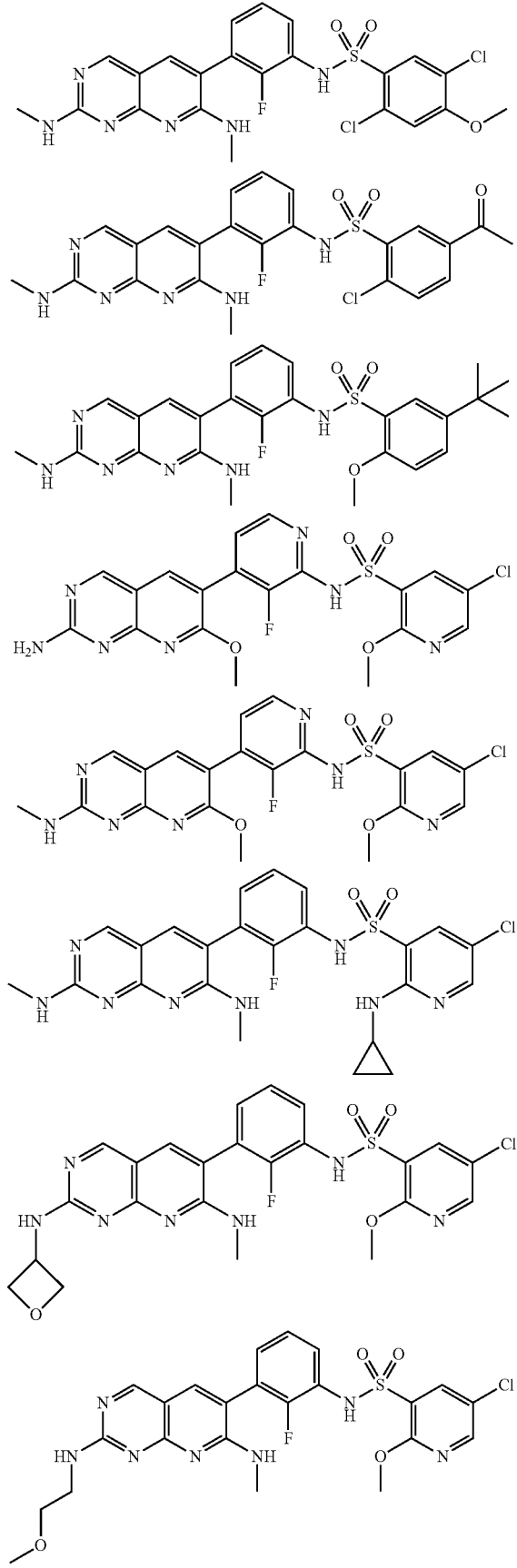
-continued
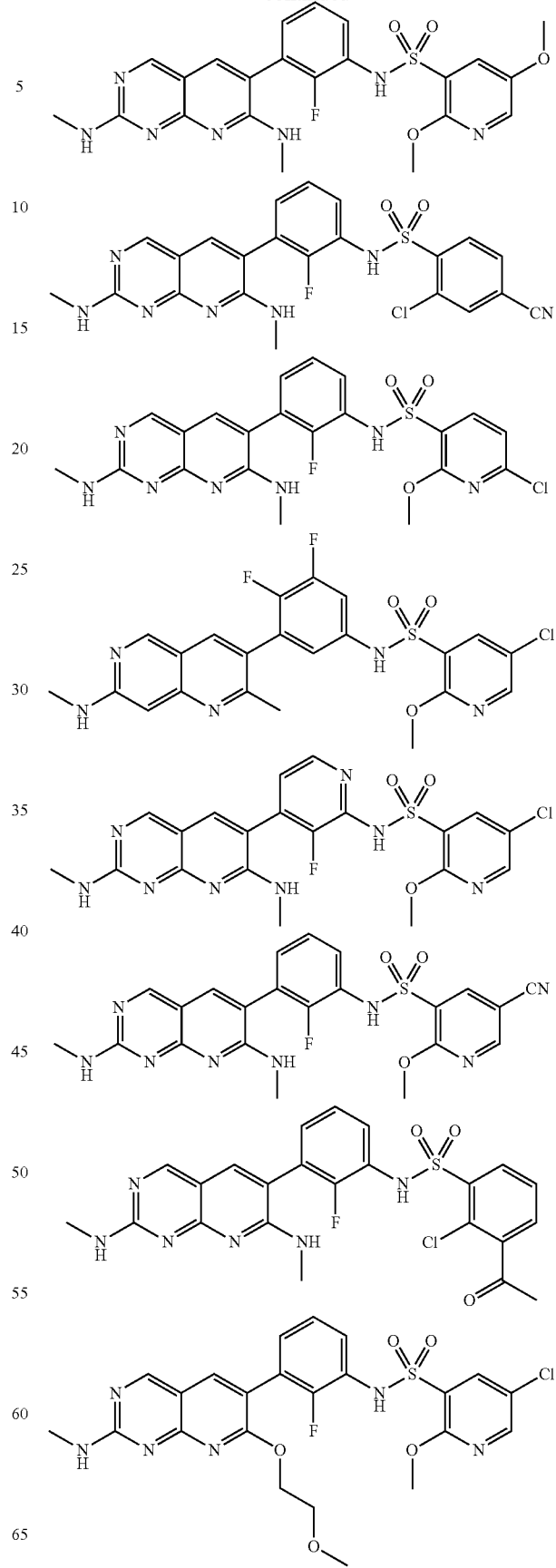

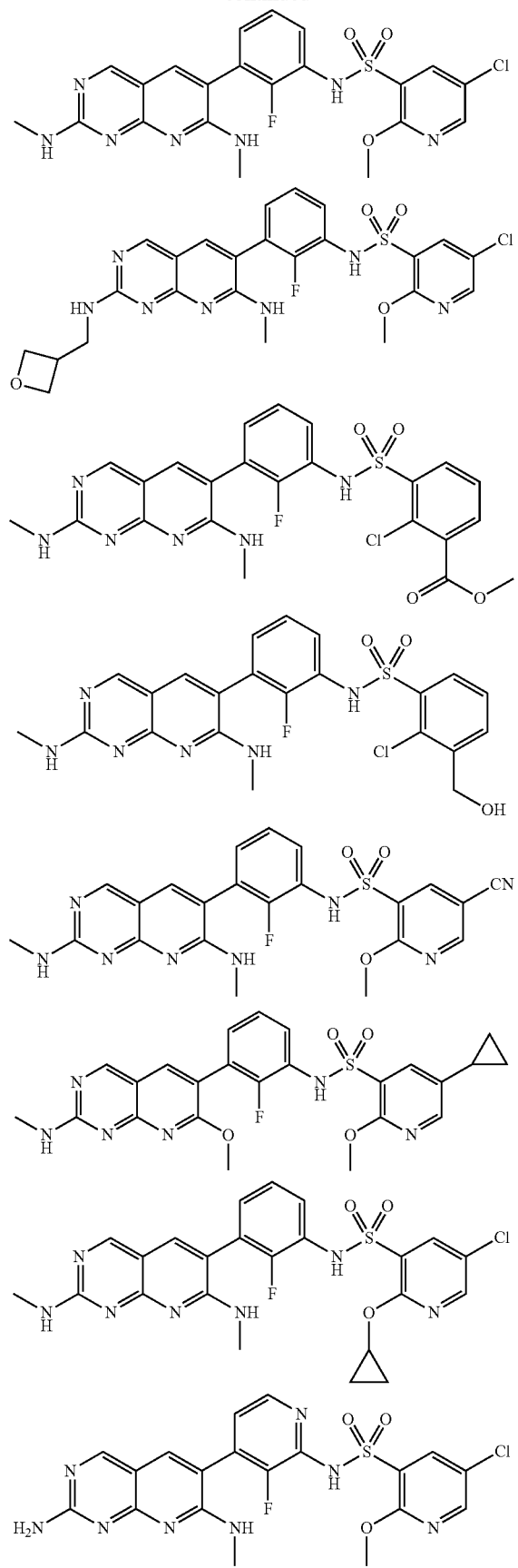
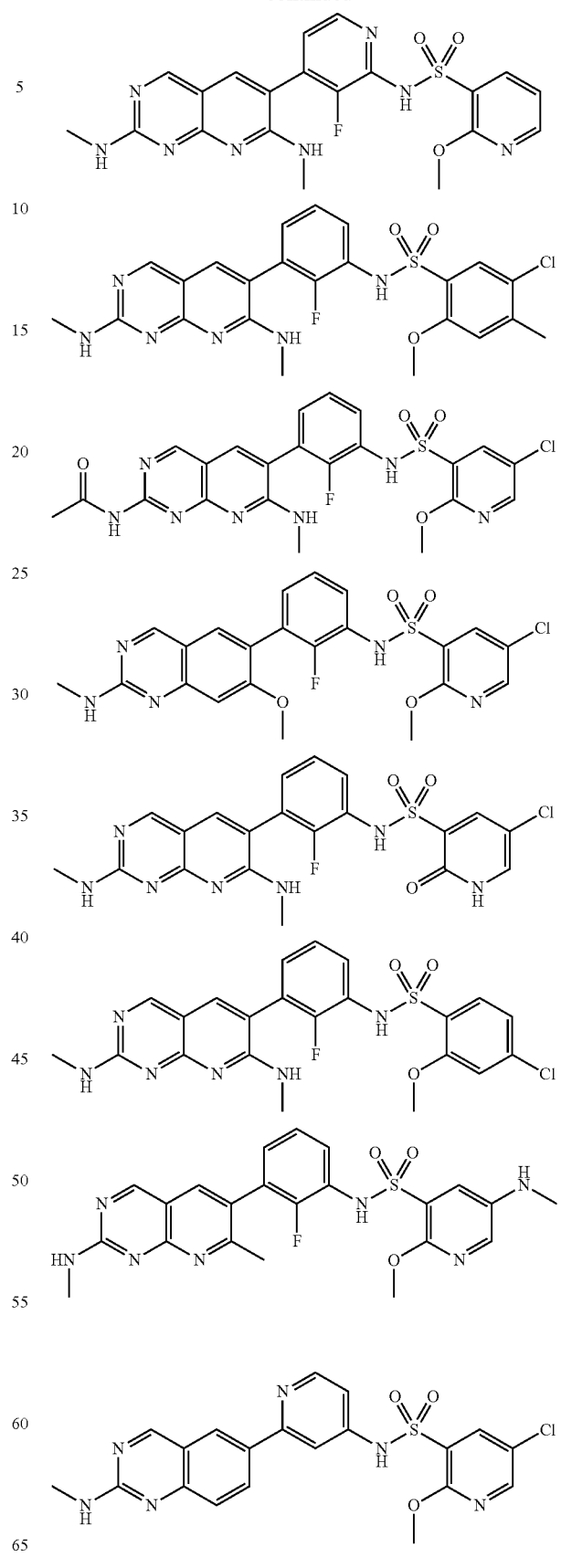

101
-continued
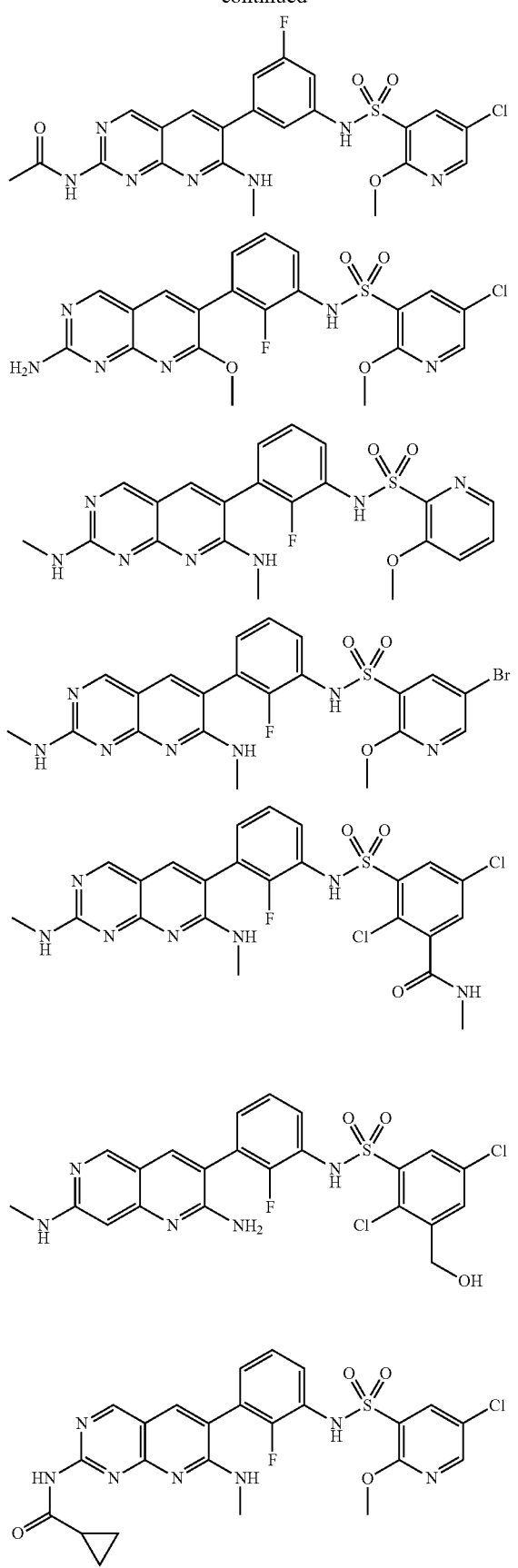
102
-continued
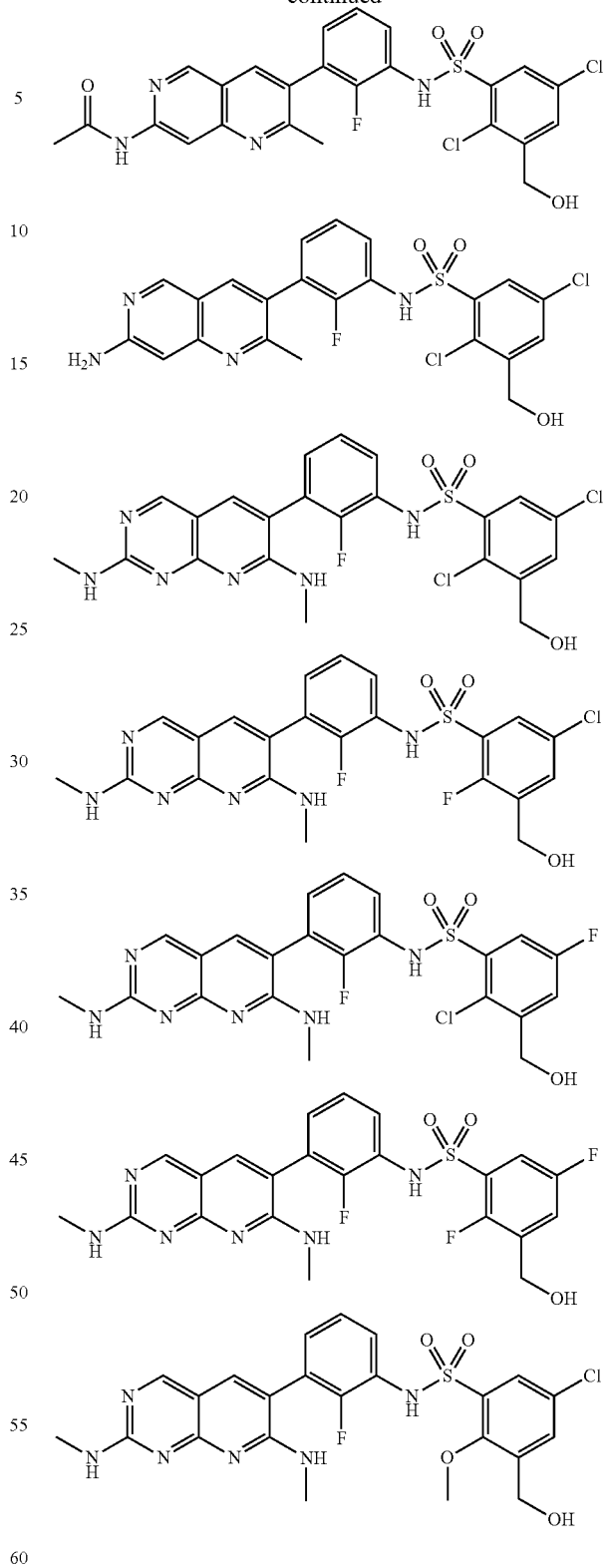
and pharmaceutically acceptable salts, enantiomers, stereoisomers, and tautomers thereof.
Methods of Treatment
Compounds described herein, e.g., compounds of Formula I as defined herein, can act as therapeutic agents for diseases driven by GCN2 or PERK kinase, and are useful in the treatment of diseases and disorders in patients in need thereof, such as cancer. Exemplary cancers include, but are not limited to, colorectal cancer, rectal cancer, anal cancer, familial colorectal cancer, hereditary nonpolyposis colorectal cancer, gastrointestinal stromal tumor, lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell renal cell carcinoma), transitional cell carcinoma of renal pelvis and ureter), uterine cancer (e.g., cervical cancer, uterine body cancer, uterus sarcoma), gestational choriocarcinoma, brain tumor (e.g., medulloblastoma, glioma, pineal astrocytoma, pilocytic astrocytoma, diffuse astrocytoma, anaplastic astrocytoma, hypophyseal adenoma), retinoblastoma, skin cancer (e.g., basal cell carcinoma, malignant melanoma, melanoma), sarcoma (e.g., rhabdomyosarcoma, leiomyosarcoma, soft tissue sarcoma, spindle cell sarcoma, osteosarcoma), fibrosarcoma, malignant bone tumor, urinary bladder cancer, hematologic cancer (e.g., multiple myeloma, leukemia, acute myeloid leukemia (AML), acute lymphoblastic leukemia (ALL), including blast crisis of chronic leukemia), malignant lymphoma, Hodgkin's disease, chronic myeloproliferative disease), cancer of unknown primary nucleus], cancer growth inhibitor, cancer metastasis inhibitor, apoptosis promoter, and for the prophylaxis or treatment of precancerous lesion (e.g., bone marrow myelodysplastic syndrome).

Also described herein, in one embodiment, is a method of treating a disease caused by a dysregulation of an integrated stress response in a patient in need thereof, comprising administering to the patient a therapeutically effective amount of a compound described herein (e.g., a compound of Formula I described herein), or a pharmaceutically acceptable salt thereof, or of a pharmaceutical composition described herein. In some embodiments, the dysregulation of the integrated stress response and/or the unfolded protein response is caused by GCN2 kinase. In some embodiments, the dysregulation of the integrated stress response and/or the unfolded protein response is caused by PERK kinase. In some embodiments, the dysregulation of the integrated stress response is caused by GCN2 kinase. In some embodiments, the dysregulation of the unfolded protein response is caused by PERK kinase. In some embodiments, the dysregulation of the integrated stress response is caused by activation of a kinase selected from the group consisting of PERK kinase and GCN2 kinase. In some embodiments, the dysregulation of the integrated stress response is caused by activation of GCN2 kinase. In some embodiments, the dysregulation of the integrated stress response is caused by activation of PERK kinase.

Also described herein, in one embodiment, is a method of treating a disease caused by a dysregulation of an integrated stress response and/or an unfolded protein response in a patient in need thereof, comprising administering to the patient a therapeutically effective amount of a compound described herein (e.g., a compound of Formula I described herein), or a pharmaceutically acceptable salt thereof, or of a pharmaceutical composition described herein. In some embodiments, the dysregulation of the integrated stress response and/or the unfolded protein response is caused by activation of a kinase selected from the group consisting of PERK kinase and GCN2 kinase. In some embodiments, the dysregulation of the integrated stress response is caused by activation of GCN2 kinase. In some embodiments, the dysregulation of the unfolded protein response is caused by activation of PERK kinase.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting GCN2 kinase and inhibiting PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a cancer in a patient in need thereof, comprising administering to the patient a therapeutically effective amount of a compound described herein (e.g., a compound of Formula I described herein), or a pharmaceutically acceptable salt thereof, or of a pharmaceutical composition described herein. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, and malignant lymphoma. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma.

In an embodiment, described herein is a method of treating amyloidosis in a patient in need thereof, comprising administering to the patient a compound described herein, or pharmaceutically acceptable salt thereof, or pharmaceutical composition described herein. In an embodiment, described herein is a method of treating light chain amyloidosis in a patient in need thereof, comprising administering to the patient a compound described herein, or pharmaceutically acceptable salt thereof, or pharmaceutical composition described herein.

In another embodiment, described herein is a method of treating a disease selected from a GCN2 associated disease and a PERK associated disease, in a patient in need thereof, comprising administering to the patient a therapeutically effective amount of a compound described herein (e.g., a compound of Formula I described herein), or a pharmaceutically acceptable salt thereof, or of a pharmaceutical composition described herein. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, and malignant lymphoma. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis.

In another embodiment, described herein is a method of treating a disease selected from a GCN2 associated disease and a PERK associated disease, in a patient in need thereof, comprising administering to the patient a therapeutically effective amount of a compound described herein (e.g., a compound of Formula I described herein), or a pharmaceutically acceptable salt thereof, and a therapeutically effective amount of one or more therapeutic agents. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, and malignant lymphoma. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, leukemia is acute myeloid leukemia. In some embodiments, leukemia is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis. In some embodiments, the one or more therapeutic agents is selected from the group consisting of L-asparaginase, pegylated asparaginase, a PERK inhibitor, a mTOR inhibitor, an immunomodulatory agent, a MAPK pathway inhibitor, a MEK inhibitor, an ERK inhibitor, and a Ras inhibitor. In some embodiments, the one or more therapeutic agents is selected from the group consisting of an IMiD agent, a proteasome inhibitor, a steroid, an anti-CD38 agent, an anti-CD20 agent, a Bcl-2 inhibitor, a PI3K inhibitor, a Bi-specific antibody, a nucleoside analog, a BTK inhibitor, a DNA alkylating agent, an EZH$_2$ inhibitor, an anthracycline, a topoisomerase inhibitor, a platin, a tyrosine kinase inhibitor, an HDAC inhibitor, a nuclear export inhibitor, an anti-microtubule agent L-asparaginase, pegylated asparaginase, a PERK inhibitor, a mTOR inhibitor, an immunomodulatory agent, a MAPK pathway inhibitor, a MEK inhibitor, an ERK inhibitor, and a Ras inhibitor. In some embodiments, the one or more therapeutic agents is selected from the group consisting of L-asparaginase, pegaspargase, calaspargase pegol—mnkl, bortezomib, carfilzomib, ixazomib, thalidomide, pomalidomide, lenalidomide, dexamethasone, prednisone, daratumumab, daratumumab/hyaluronidase, isatuximab, rituximab, obinutuzumab, venetoclax, idelalisib, copanlisib, duvelisib, umbralisib, gemcitabine, cytarabine, ibrutinib, acalabrutinib, zanubrutinib, bendamustine, cyclophosphamide, tazemetostat, doxorubicin, daunorubicin, etoposide, oxaloplatin, carboplatin, cisplatinbosutinib, dasatinib, imatinib, nilotinib, ponatinib, panobinostat, selinexor, vincristine, JZP-458, eryaspase, PF745 (JZP-341), asparaginase *Erwinia chrysanthemi* (crisantaspase), *Escherichia coli* asparaginase (colaspase), an anti-PD1 agent, an anti-PDL1 agent, and an anti-CTLA4 agent.

In an embodiment, described herein is a compound described herein, or a pharmaceutically acceptable salt thereof, or the pharmaceutical composition described herein, for use in treating a disease caused by a dysregulation of an integrated stress response and/or the unfolded protein response in a patient in need thereof. In some embodiments, the dysregulation of the integrated stress response and/or the unfolded protein response is caused by a kinase selected from the group consisting of PERK kinase and GCN2 kinase. In some embodiments, the dysregulation of the integrated stress response and/or the unfolded protein response is caused by GCN2 kinase. In some embodiments, the dysregulation of the integrated stress response and/or the unfolded protein response is caused by PERK kinase. In some embodiments, the dysregulation of the integrated stress response is caused by GCN2 kinase. In some embodiments, the dysregulation of the unfolded protein response is caused by PERK kinase. In some embodiments, the dysregulation of the integrated stress response is caused by activation of a kinase selected from the group consisting of PERK kinase and GCN2 kinase. In some embodiments, the dysregulation of the integrated stress response is caused by activation of GCN2 kinase. In some embodiments, the dysregulation of the integrated stress response is caused by activation of PERK kinase. In an embodiment, described herein is a compound described herein, or a pharmaceutically acceptable salt thereof, or the pharmaceutical composition described herein, for use in modulating the activity of GCN2 kinase in a patient in need thereof. In an embodiment, described herein is a compound described herein, or a pharmaceutically acceptable salt thereof, or the pharmaceutical composition described herein, for use in activating GCN2 kinase in a patient in need thereof. In an embodiment, described herein is a compound described herein, or a pharmaceutically acceptable salt thereof, or the pharmaceutical composition described herein, for use in modulating the activity of PERK kinase in a patient in need thereof. In an embodiment, described herein is a compound described herein, or a pharmaceutically acceptable salt thereof, or the pharmaceutical composition described herein, for use in activating PERK kinase in a patient in need thereof.

In an embodiment, described herein is a compound described herein, or a pharmaceutically acceptable salt thereof, or the pharmaceutical composition described herein, for use in inhibiting GCN2 kinase and inhibiting PERK kinase in a patient in need thereof. In an embodiment, described herein is a compound described herein, or a pharmaceutically acceptable salt thereof, or the pharmaceutical composition described herein, for use in modulating the activity of GCN2 kinase in a patient in need thereof. In another embodiment, described herein is a compound described herein, or a pharmaceutically acceptable salt thereof, or the pharmaceutical composition described herein, for use in inhibiting the activity of PERK kinase in a patient in need thereof.

In an embodiment, described herein is a compound described herein, or a pharmaceutically acceptable salt thereof, or the pharmaceutical composition described herein, for use in treating a cancer in a patient in need thereof. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma.

In an embodiment, described herein is a compound described herein, or a pharmaceutically acceptable salt thereof, or the pharmaceutical composition described herein, for use in treating amyloidosis in a patient in need thereof. In an embodiment, described herein is a compound described herein, or a pharmaceutically acceptable salt thereof, or the pharmaceutical composition described herein, for use in treating light chain amyloidosis in a patient in need thereof.

In an embodiment, described herein is a compound described herein, or a pharmaceutically acceptable salt thereof, or the pharmaceutical composition described herein, for use in treating a disease selected from a GCN2 associated disease and a PERK associated disease, in a patient in need thereof. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis.

In an embodiment, described herein is a compound described herein, or a pharmaceutically acceptable salt thereof, or the pharmaceutical composition described herein, for use in treating a disease selected from a GCN2 associated disease and a PERK associated disease, in a patient in need thereof. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, leukemia is acute myeloid leukemia. In some embodiments, leukemia is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis. In some embodiments, the one or more therapeutic agents is selected from the group consisting of an IMiD agent, a proteasome inhibitor, a steroid, an anti-CD38 agent, an anti-CD20 agent, a Bcl-2 inhibitor, a PI3K inhibitor, a Bi-specific antibody, a nucleoside analog, a BTK inhibitor, a DNA alkylating agent, an EZH$_2$ inhibitor, an anthracycline, a topoisomerase inhibitor, a platin, a tyrosine kinase inhibitor, an HDAC inhibitor, a nuclear export inhibitor, an anti-microtubule agent, L-asparaginase, pegylated asparaginase, a PERK inhibitor, a mTOR inhibitor, an immunomodulatory agent, a MAPK pathway inhibitor, a MEK inhibitor, an ERK inhibitor, and a Ras inhibitor. In some embodiments, the one or more therapeutic agents is selected from the group consisting of bortezomib, carfilzomib, ixazomib, thalidomide, pomalidomide, lenalidomide, dexamethasone, prednisone, daratumumab, daratumumab/hyaluronidase, isatuximab, rituximab, obinutuzumab, venetoclax, idelalisib, copanlisib, duvelisib, umbralisib, gemcitabine, cytarabine, ibrutinib, acalabrutinib, zanubrutinib, bendamustine, cyclophosphamide, tazemetostat, doxorubicin, daunorubicin, etoposide, oxaloplatin, carboplatin, cisplatinbosutinib, dasatinib, imatinib, nilotinib, ponatinib, panobinostat, selinexor, vincristine, L-asparaginase, pegaspargase, calaspargase pegol-mnkl, JZP-458, eryaspase, PF745 (JZP-341), asparaginase *Erwinia chrysanthemi* (crisantaspase), *Escherichia coli* asparaginase (colaspase), anti-PD1 anti-PDL1, and anti-CTLA4.

The compounds provided herein may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound provided herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result is achieved.

Combination Therapy

Compounds described herein, e.g., a compound of Formula I as defined herein, can be administered in combination with one or more additional therapeutic agents to treat a disorder described herein, such as a cancer described herein. For example, provided in the present disclosure is a pharmaceutical composition comprising a compound described herein, e.g., a compound of Formula I as defined herein, one or more additional therapeutic agents, and a pharmaceutically acceptable excipient. In some embodiments, a compound of Formula I as defined herein, and one additional therapeutic agent is administered. In some embodiments, a compound of Formula I as defined herein, and two additional therapeutic agents are administered. In some embodiments, a compound of Formula I as defined herein, and three additional therapeutic agents are administered. Combination therapy can be achieved by administering two or more therapeutic agents, each of which is formulated and administered separately. For example, a compound of Formula I as defined herein, and an additional therapeutic agent can be formulated and administered separately. Combination therapy can also be achieved by administering two or more therapeutic agents in a single formulation, for example a pharmaceutical composition comprising a compound of Formula I as one therapeutic agent and one or more additional therapeutic agents such as a chemotherapeutic agent. For example, a compound of Formula I as defined herein, and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Combination therapy can also include two or more administrations of one or more of the agents used in the combination using different routes of administration. Each of the one or more of the agents may be independently administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

In some embodiments, the compounds of Formula I as described herein, are combined with asparaginase (ASNase, L-asparaginase) or its derivatives. In some embodiments, asparaginase is obtained from *Erwinia chrysanthemi* and is known as crisantaspase or asparaginase *Erwinia chrysanthemi*. Asparaginase *Erwinia chrysanthemi* is sold under the trademarks Erwinaze® or Erwinase®. In some embodiments, asparaginase is obtained from *Escherichia coli* and is known as colaspase. Colaspase is sold under the trademarks Elspar®, Leunase®, Kidrolase®, or Spectrila® (recombinant *E. coli* aparaginase). Pegylated derivatives of colaspase are pegaspargase, sold under the trademark Oncaspar®, and calaspargase pegol—mnkl, sold under the trademark Asparlas®. Other asparaginase products currently in preclinical or clinical development include JZP-458 (recombinant *Erwinia* asparaginase), PF745 (JZP-341), eryaspase (GRASPA®), and Xoncane.

In some embodiments, the compounds of Formula I as defined herein, are combined with an immunomodulatory agent. In some embodiments, the immunomodulatory enhances the adaptive immune response. In some embodiments, the immunomodulatory enhances the activity of antigen-presenting cells. In some embodiments, the immunomodulatory agent enhances the anti-tumor activity of myeloid cells including macrophages. In some embodiments, the immunomodulatory enhances the anti-tumor activity of Natural Killer cells. In some embodiments, the immunomodulatory agent enhances the activity of effector T Cells, including cytotoxic T Cells.

In some embodiments, the one or more additional therapeutic agents that may be administered in combination with a compound provided herein can be a MAPK pathway inhibitor. Such MAPK pathway inhibitors include, for example, MEK inhibitors, ERK inhibitors, and Ras inhibitors.

Exemplary MEK inhibitors include, but are not limited to, trametinib, selumetinib, cobimetinib, binimetinib, and pharmaceutically acceptable salts thereof. Exemplary ERK inhibitors include, but are not limited to, include, but are not limited to, ulixertinib, SCH772984, LY3214996, ravoxertinib, VX-11e, ASN-007, GDC-0994, MK-8353, ASTX-029, LTT462, KO-947, and pharmaceutically acceptable salts thereof. Exemplary Ras inhibitors include, but are not limited to, AMG-510, MRTX849, ARS-1620, ARS-3248, LY3499446, and pharmaceutically acceptable salts thereof.

In some embodiments, the additional therapeutic agents can be immunomodulatory agents including but not limited to anti-PD-1 or anti-PDL-1 therapeutics including pembrolizumab, nivolumab, pidilizumab, cemiplimab, atezolizumab, durvalumab, BMS-936559, or avelumab. In some embodiments, the additional therapeutic agents can be anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or RO7009789, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles. In some embodiments, the additional therapeutic agents can be anti-CTLA4 agents including ipilimumab, tremelimumab. In some embodiments, the additional therapeutic agents can be hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone. In some embodiments, the additional therapeutic agents can be immunotherapeutic agents including targeted therapeutic agents, cancer vaccines, and CAR-T cell therapy.

The compounds of Formula I as described herein may be administered in combination with other therapeutic agents known to treat cancers. Such other therapeutic agents include radiation therapy, anti-tubulin agents, DNA alkylating agents, DNA synthesis-inhibiting agents, DNA intercalating agents, anti-estrogen agents, anti-androgens, steroids, anti-EGFR agents, kinase inhibitors, mTOR inhibitors, PI3 kinase inhibitors, cyclin-dependent kinase inhibitors, CD4/CD6 kinase inhibitors, topoisomerase inhibitors, Histone Deacetylase (HDAC) inhibitors, DNA methylation inhibitors, anti-HER2 agents, anti-angiogenic agents, proteasome inhibitors, PARP (poly ADP ribose polymerase) inhibitors, cell cycle regulating kinase inhibitors, thalidomide, lenalidomide, pomalidomide, bortezomib, carfilzomib, ixazomib, daratumumab, daratumumab/hyaluronidase, isatuximab, dexamethasone, and antibody-drug-conjugates (ADCs).

In an embodiment, the additional therapeutic agents can be chemotherapeutic agents including but not limited to an anti-tubulin agents (for example, paclitaxel, paclitaxel protein-bound particles for injectable suspension including nab-paclitaxel, eribulin, docetaxel, ixabepilone, vincristine, auristatins, or maytansinoids), vinorelbine, DNA-alkylating agents (including cisplatin, carboplatin, oxaliplatin, cyclophosphamide, ifosfamide, temozolomide), DNA intercalating agents or DNA topoisomerase inhibitors (including anthracyclines such as doxorubicin, pegylated liposomal doxorubicin, daunorubicin, idarubicin, mitoxantrone, or epirubicin, camptothecins such as topotecan, irinotecan, or exatecan), 5-fluorouracil, capecitabine, cytarabine, decitabine, 5-aza cytadine, gemcitabine and methotrexate.

In some embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, ripretinib, sunitinib, pazopanib, sorafenib, regorafenib, sunitinib, axitinib, dasatinib, imatinib, nilotinib, idelalisib, ibrutinib, BLU-667, Loxo 292, larotrectinib, and quizartinib, In some embodiments, the additional therapeutic agents can be anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, talazoparib, and rucaparib, topoisomerase I inhibitors including but not limited to irinotecan, camptothecin, exatecan, and topotecan, topoisomerase II inhibitors including but not limited to anthracyclines, etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNep and 5-aza-2'-deoxycytidine, proteasome inhibitors including but not limited to bortezomib and carfilzomib, biological agents including but not limited to trastuzumab, ado-trastuzumab, pertuzumab, cetuximab, and panitumumab.

In some embodiments, the additional therapeutic agents can be anti-angiogenic agents including bevacizumab, aflibercept, and AMG386.

In some embodiments, the additional therapeutic agents can be antibody-drug-conjugates (ADCs) including DM1, DM4, MMAE, MMAF, or camptothecin payloads, brentuximab vedotin and trastuzumab emtansine, radiotherapy, therapeutic vaccines including but not limited to sipuleucel-T.

In some embodiments, the additional therapeutic agent can be an autophagy inhibitor including ULK inhibitors, VPS34 inhibitors, PIKfyve inhibitors, PPT1 inhibitors, or lysosomal blocking agents. In some embodiments, the additional therapeutic agent can be DCC-3116, SAR405, SB02024, hydroxychloroquinine, chloroquine, apilimod, MRT403, and LYS05.

In some embodiments, the additional therapeutic agent is selected from a luteinizing hormone-releasing hormone (LHRH) analog, including goserelin and leuprolide.

In some embodiments, the additional therapeutic agent is selected from the group consisting of selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, AZD 2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, alanosine (Sdx 102), talampanel, atrasentan, XR 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl] benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, 3-[5-(methylsulfonylpiperadinemethyl)-indolylj-quinolone, vatalanib, AG-013736, AVE-0005, the acetate salt of [D-Ser(tBu) 6, Azgly 10] (pyro-Glu-His-Trp-Ser-Tyr-D-Ser(tBu)-Leu-Arg-Pro-Azgly-NH$_2$ acetate [C$_{59}$H$_{84}$N$_{18}$O$_{14}$—(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714; TAK-165, HKI-272, erlotinib, lapatanib, canertinib, ABX-EGF antibody, erbitux, EKB-569, PKI-166, GW-572016, ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, ipilumumab, and mixtures thereof.

Pharmaceutical Compositions and Kits

Another aspect of this disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which contains one or more of the compounds described herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound provided herein, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another embodiment, provided are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5.

Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives described herein.

Advantageously, provided herein are kits for use by a e.g., a consumer in need of treatment of cancer. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and disclosures of synthetic procedures in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

The following abbreviation are used in this disclosure and have the following definitions: "AcOH' is acetic acid, "ADP" is adenosine diphosphate, "AgNO$_3$" is silver nitrate, "ASNase" is Asparaginase, "Boc" is t-butylcarbonate, "CDI" is carbodiimidazole, "conc." is concentrated, "Cs$_2$CO$_3$" is cesium carbonate, "CuI" is copper (I) iodide, "DBU" is 1,8-diazabicyclo[5.4.0]undec-7-ene, "DCC" is N,N'-Dicyclohexylcarbodiimide, "DCE" is dichloroethane, "DCM" is dichloromethane, "DIAD" is diisopropyl azodicarboxylate, "DIEA" is N,N-diisopropylethylamine, "DMA" is N,N-dimethylacetamide, "DMAP" is 4-(dimethylamino)pyridine, "DMF" is N,N-dimethylformamide, "dppf" is 1,1'-bis(diphenylphosphino)ferrocene, "DMSO" is dimethylsulfoxide, "EDTA" is ethylenediaminetetraacetic acid, "ESI" is electrospray ionization, "EtOAc" is ethyl acetate, "EtOH" is ethanol, "GST" is glutathione S-transferase, "h" is hour or hours, "HBTU" is (2-(1H-benzotriazol-1-yl)-1,1,3,3-tetramethyluronium hexafluorophosphate, "H$_2$" is hydrogen gas, "HCl" is hydrochloric acid, "Hex" is hexane, "H$_2$O" is water, "HOBt" is Hydroxybenzotriazole "IC$_{50}$" is half maximal inhibitory concentration, "K$_2$CO$_3$" is potassium carbonate, "KOAc" is potassium acetate, "K$_3$PO$_4$" is potassium phosphate, "NaBH$_4$" is sodium borohydride, "LAH" is lithium aluminum hydride, "LiOH" is lithium hydroxide, "MeCN" is acetonitrile, "MeOH" is methanol, "Me$_4$tBuXPhos" is di-tert-butyl(2',4',6'-triisopropyl-3,4,5,6-tetramethyl-[1,1'-biphenyl]-2-yl)

phosphine, "MgSO$_4$" is magnesium sulfate, "MHz" is megahertz, "min" is minute or minutes, "MnO$_2$" is manganese (IV) oxide, "MS" is mass spectrometry, "NADH" is nicotinamide adenine dinucleotide, "Na" is sodium, "NaH" is sodium hydride, "NaHCO$_3$" is sodium bicarbonate, "NaNO$_2$" is sodium nitrite, "NaOMe" is sodium methoxide, "Na$_2$SO$_4$" is sodium sulfate, "NBS" is N-bromosuccinimide, "NCS" is N-chlorosuccinimide, "NH$_4$Cl" is ammonium chloride, "NH$_2$OH" is hydroxylamine, "NMP" is N-methyl-2-pyrrolidone, "NMR" is nuclear magnetic resonance, "PBS" is phosphate buffered saline, "Pd/C" is palladium on carbon, "Pd$_2$(dba)$_3$" is tris(dibenzylideneacetone)dipalladium(0), "Pd(OAc)$_2$" is palladium (II) acetate, "Pd(PPh$_3$)$_4$" is tetrakis(triphenylphosphine)palladium (0), "Pd(dppf)Cl$_2$" is 1,1-bis(diphenylphosphino)ferrocene-palladium(II)dichloride, "prep-HPLC" is preparative high performance liquid chromatography, "PCl$_3$" is phosphorus trichloride, "Ph$_3$P" is triphenylphosphine, "PhPOCl$_2$" is phenylphosphonic dichloride, "PMB" is paramethoxybenzyl, "POCl$_3$" is phosphorus oxychloride, "PyBOP" is benzotriazol-1-yl-oxytripyrrolidinophosphonium hexafluorophosphate, "rt" is room temperature which is also known as "ambient temp," which will be understood to consist of a range of normal laboratory temperatures ranging from 15-25° C., "satd." is saturated, "SDS" is sodium dodecyl sulfate, "SFC" is supercritical fluid chromatography, "S$_N$Ar" is nucleophilic aromatic substitution, "SOCl$_2$" is thionyl chloride, "T$_3$P" is n-propanephosphonic acid anhydride, "TEA" is triethylamine, "TFA" is trifluoroacetic acid, "THF" is tetrahydrofuran, "Xantphos" is 4,5-bis(diphenylphosphino)-9,9-dimethylxanthene, "X-Phos" is 2-dicyclohexylphosphino-2',4',6'-triisopropylbiphenyl and "ZnCl$_2$" is zinc chloride.

In the Examples below and corresponding Figures, "Compound 16" refers to the compound depicted as Example 16 in Table I below.

General Chemistry

Exemplary compounds described herein are available by the general synthetic methods illustrated in the Schemes below, intermediate preparations, and the accompanying Examples.

Synthetic Schemes

Scheme 1

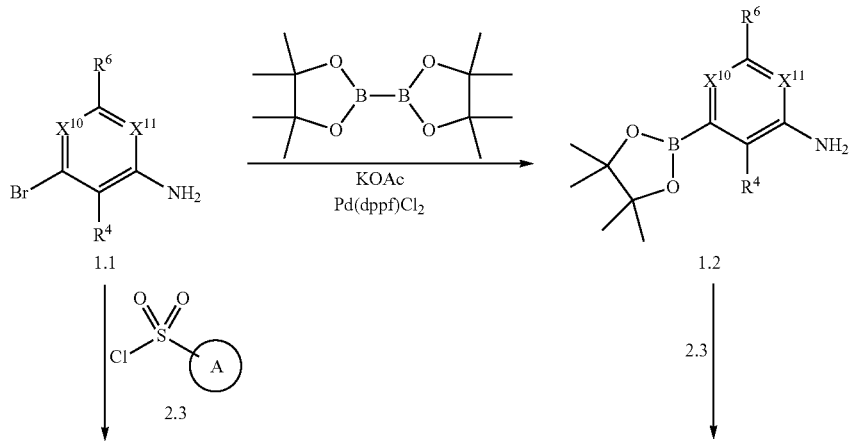

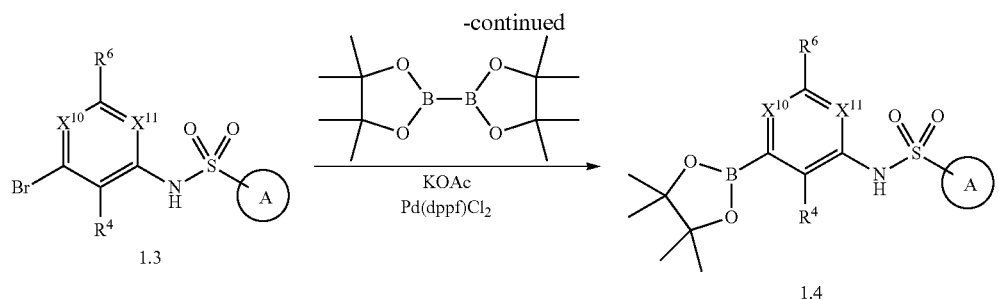

Scheme 1 illustrates an exemplary preparation of boronates 1.4. Compounds 1.1 (commercially available, synthesized as described in WO2013134298 or synthesized by those skilled in the art) react with bis(pinacolato)diboron by borylation reaction known to those skilled in the art (palladium-mediated reaction conducted using palladium catalysts such as Pd(dppf)Cl$_2$, a suitable base such as KOAc in a suitable solvent such as 1,4-dioxane at elevated temperature) to obtain compounds 1.2 which are reacted with sulfonyl chlorides 2.3 (see scheme 2) to give compounds 1.4. Alternatively, compounds 1.1 react with sulfonyl chlorides 2.3 to afford the sulfonamides 1.3 which are converted to the boronates 1.4 under the borylation reaction conditions known to those skilled in the art.

2.2a by a Pd catalyzed coupling reaction (for example, using Pd$_2$(dba)$_3$, XantPhos, phenylmethanthiol in the presence of a base, such as DIEA in a solvent such as toluene, and at elevated temperature). A smooth oxidation of thio-ethers 2.2a (e.g., by combination of NCS and dilute HCl, 1,3-dichloro-5,5-dimethylhydantoin) affords the corresponding sulfonyl chlorides 2.3 according to general reaction conditions reported in *Synthesis,* 2006, 24, 4131-4134 and *Bioorg. Med. Chem.,* 2017, 25, 3447-3460. Alternatively, sulfonyl chlorides 2.3 can be prepared from amines 2.1b (ring A: substituted aryl, five or six-membered heteroaryl, commer-

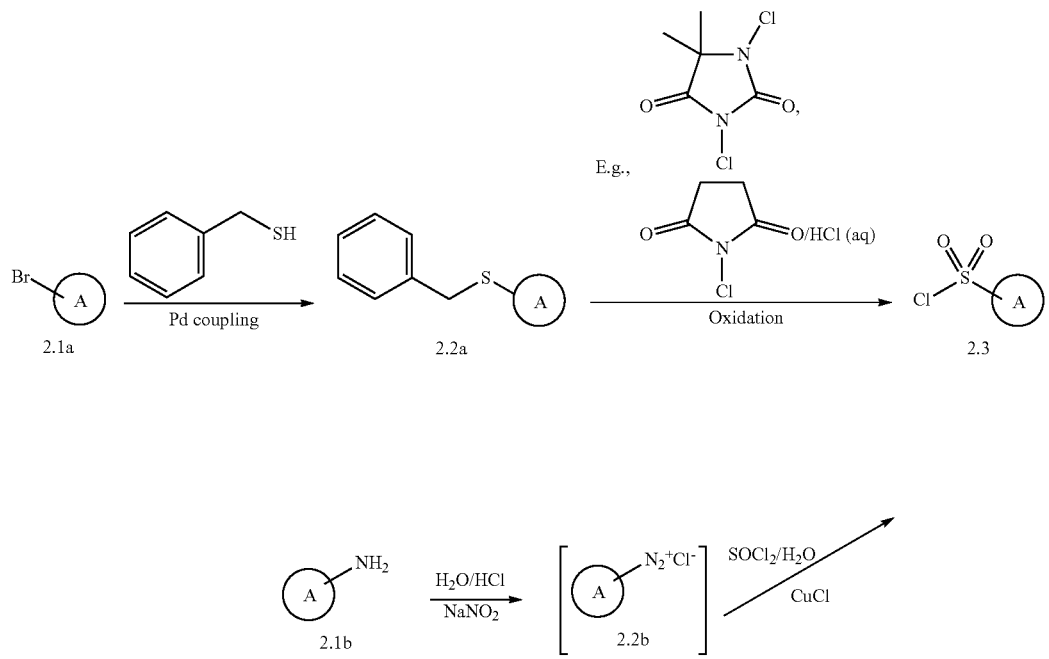

Scheme 2 illustrates an exemplary preparation of sulfonyl chlorides 2.3. Bromides 2.1a (ring A: substituted aryl, five or six-membered heteroaryl, commercially available or synthesized by those skilled in the art) are converted to thio-ethers cially available or synthesized by those skilled in the art) by diazotization, followed by Cu-mediated chlorination of the resulting intermediate (according to general reaction conditions reported in *Org. Proc. Res. Dev.,* 2009, 5, 875-879).

Scheme 3

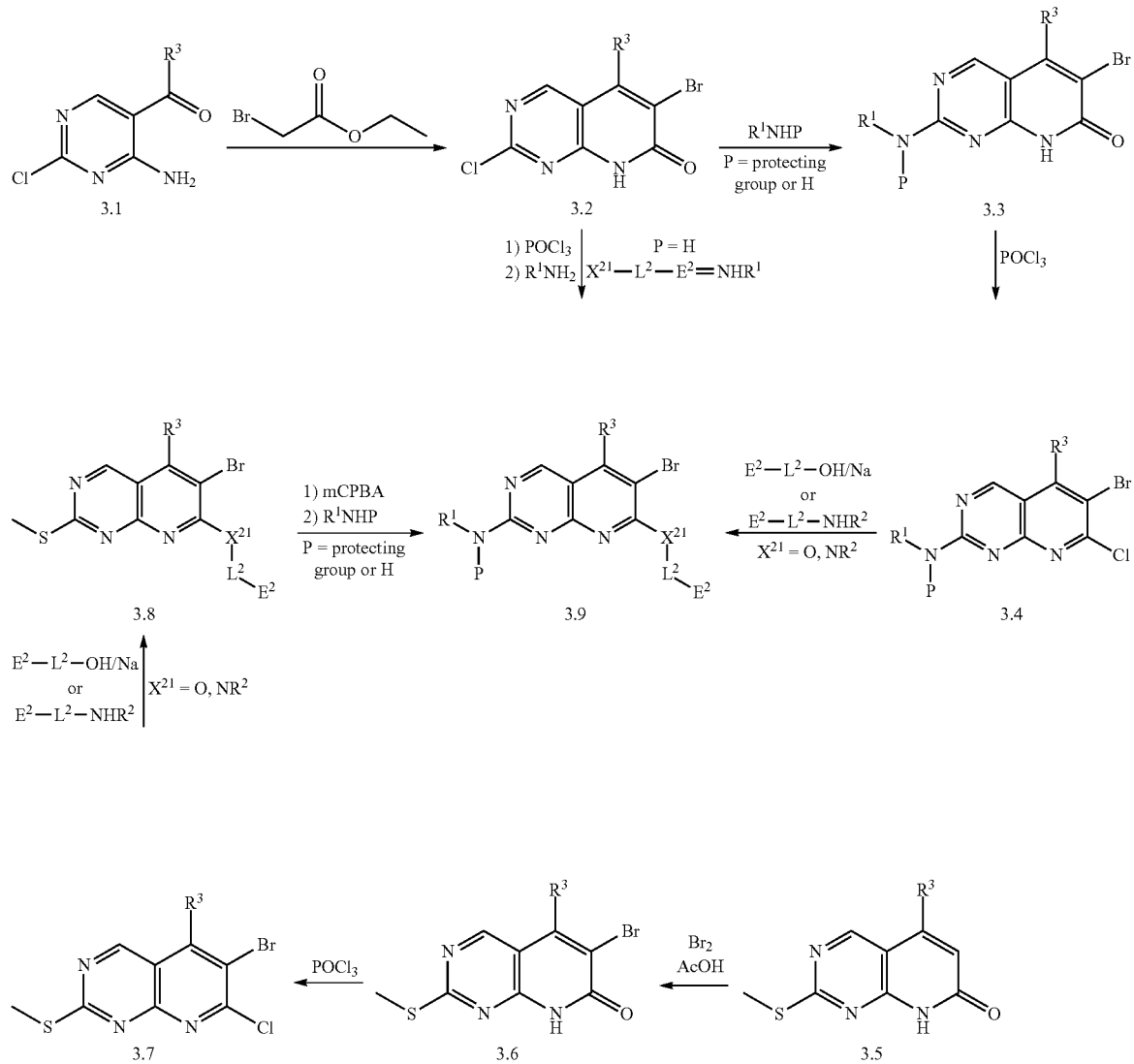

Scheme 3 illustrates an exemplary preparation of intermediates 3.9 ($X^{21}$=O, $NR^2$). Compounds 3.1 (commercially available or synthesized by those skilled in the art) react with ethyl 2-bromoacetate in the presence of a base such as piperidine to afford the pyridopyrimidinones 3.2. Compounds 3.2 react with amines $R^1$NHP (P=protecting group or H) in the presence of base such as DIEA in a polar aprotic solvent such NMP at elevated temperature to afford 3.3. Compounds 3.3 react with $POCl_3$ to afford 3.4 which are converted to the intermediates 3.9 ($X^{21}$=O, $NR^2$) by reaction with either alkoxides ($E^2$-$L^2$-OH/Na) or amines ($E^2$-$L^2$-$NHR^2$). In another embodiment, pyridopyrimidinones 3.2 react with $POCl_3$, followed by substitution reaction of the resulting intermediate with amines ($R^1NH_2$) to provide intermediates 3.9 ($X^{21}$-$L^2$-$E^2$=$NHR^1$). Alternatively, intermediates 3.9 can be prepared from compounds 3.5 according to general reaction conditions reported in WO2018153373, CN105481858, and CN105968108. Bromination of 3.5 with bromine in AcOH affords bromides 3.6 which are converted to the chlorides 3.7 by treatment with $POCl_3$. Intermediates 3.7 are then converted to compounds 3.8 ($X^{21}$=O, $NR^2$) by reaction with alkoxides ($E^2$-$L^2$-OH/Na) or amines ($E^2$-$L^2$-$NHR^2$). Conversion of compounds 3.8 to the intermediates 3.9 is conducted in a two-step process including: (i) Thioether oxidation in the presence of an oxidant such as mCPBA in a suitable solvent such as DCM at rt to obtain the corresponding sulfoxides and (ii) condensation of the sulfoxides with amines $R^1$NHP (P=protecting group or H).

Scheme 4

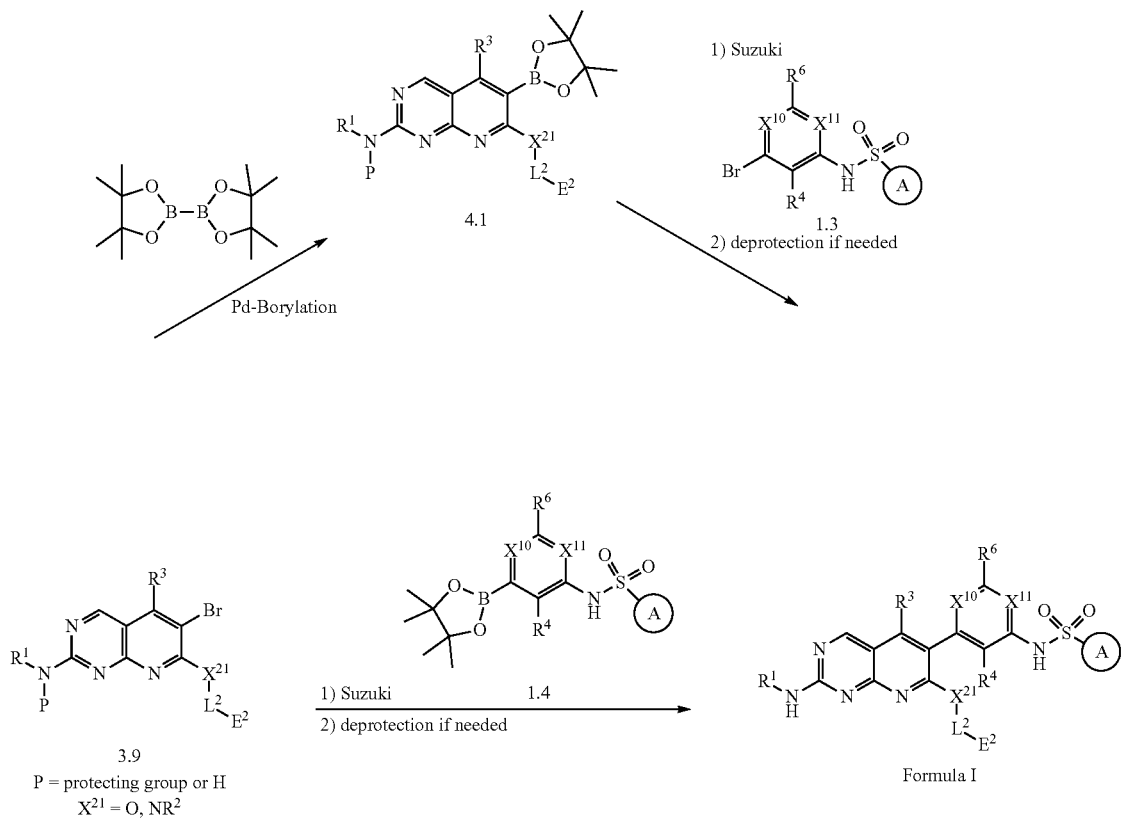

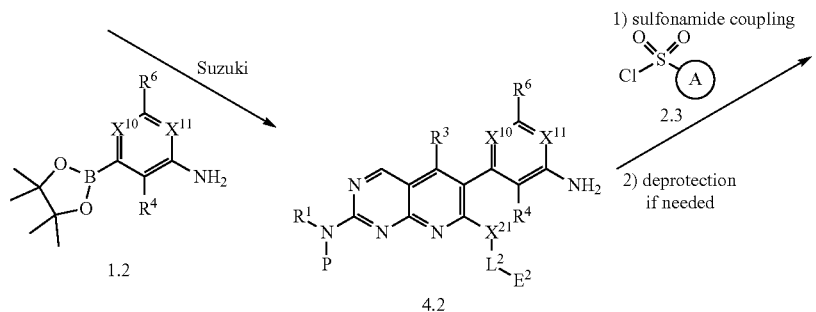

Scheme 4 illustrates an exemplary preparation of compounds of Formula I. Condensation of intermediates 3.9 (prepared as described in Scheme 3, $X^{21}$=O, $NR^2$) with boronates 1.4 in the presence of a Pd catalyst such as $Pd(PPh_3)_4$ or $Pd(dppf)Cl_2$ affords compounds of Formula I. Alternatively, 3.9 reacts with bis(pinacolato)diboron under palladium-mediated borylation reaction conditions to afford the boronate intermediates 4.1. The boronates 4.1 react with bromides 1.3 to afford compounds of Formula I by Suzuki reaction known to those skill in the art. In another embodiment, 3.9 react with boronates 1.2 under Pd catalyzed coupling conditions (Suzuki reaction) to provide compounds 4.2. Anilines 4.2 react with sulfonyl chlorides 2.3 in the presence of base such as pyridine to afford compounds of Formula I. In instances, where compounds of Formula I contain a nitrogen protecting group P, such as Boc or PMB, the protecting group can be removed under acidic conditions (TFA or HCl in 1,4-dioxane) to afford the corresponding amines (compounds of Formula I).

Scheme 5

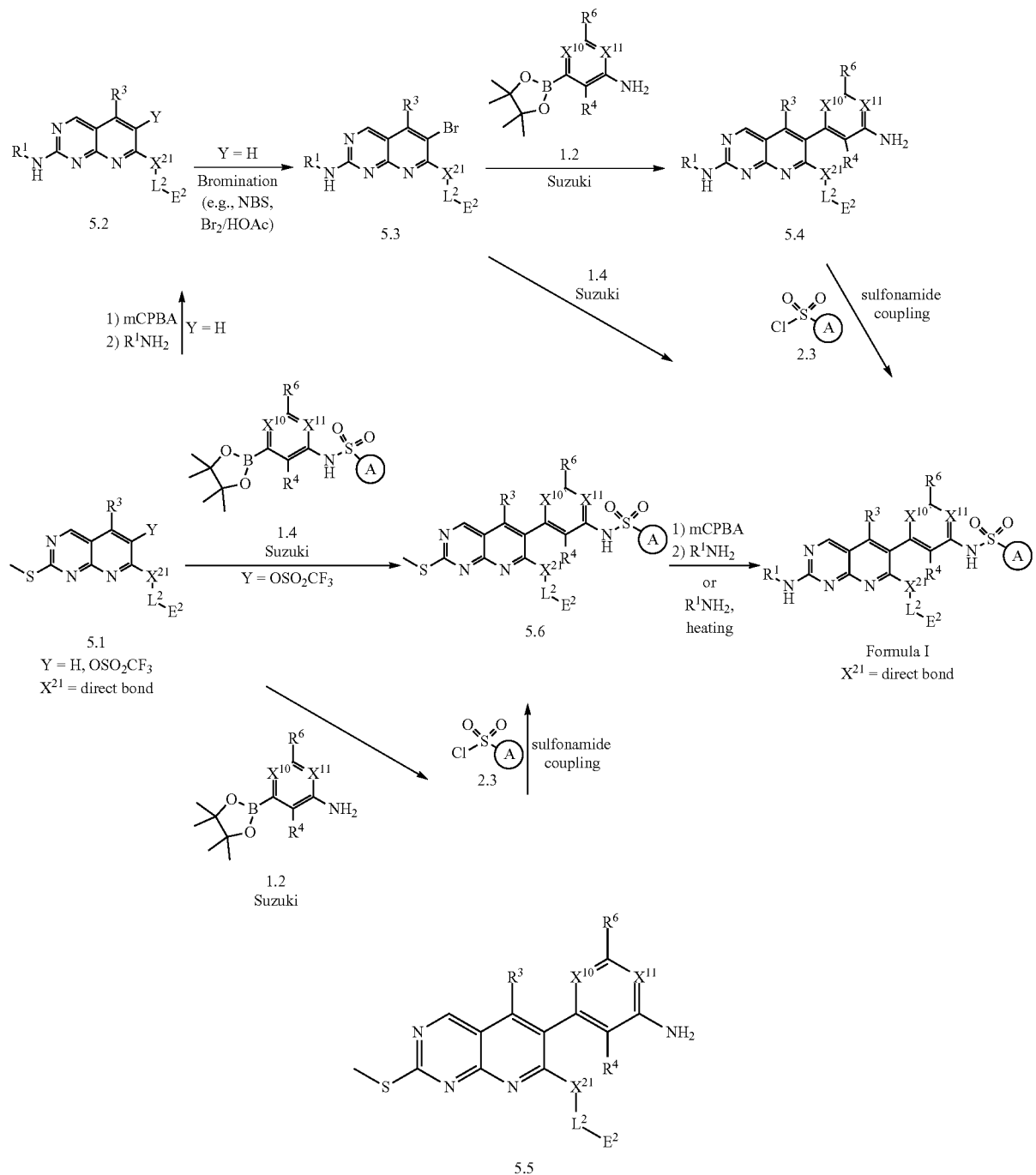

Scheme 5 illustrates an exemplary preparation of compounds of Formula I. Suzuki reaction of 5.1 (Y=OSO$_2$CF$_3$, X$^{21}$=direct bond, synthesized as described in WO2013134243, WO2013029084 and *J. Med. Chem.*, 2015, 58, 4165-4179) with boronates 1.2 in the presence of a Pd catalyst such as Pd(PPh$_3$)$_4$ or Pd(dppf)Cl$_2$ affords anilines 5.5. In a similar manner, compounds 5.1 (Y=OSO$_2$CF$_3$, X$^{21}$=direct bond) react with boronates 1.4 under Pd catalyzed coupling conditions (Suzuki reaction) to provide compounds 5.6. Alternatively, 5.6 can be prepared by sulfonamide coupling reaction of anilines 5.5 with sulfonyl chlorides 2.3. Conversion of compounds 5.6 to compounds of Formula I is conducted in a two-step process including: (i) thioether oxidation in the presence of an oxidant such as mCPBA in a suitable solvent such as DCM at rt to obtain the corresponding sulfoxides and (ii) condensation of the sulfoxides with amines R$^1$NH$_2$. Alternatively, compounds of Formula I can be obtained by direct substitution reaction of 5.6 with amines R$^1$NH$_2$ at elevated temperature.

In another embodiment, oxidation of compounds 5.1 (Y=H, X$^{21}$=direct bond, commercially available or synthesized as described in WO2013134243, WO2013029084 and *J. Med. Chem.*, 2015, 58, 4165-4179) with mCPBA, followed by substitution reaction of the resulting intermediate with amines $R^1NH_2$, typically performed in an aprotic solvent at temperatures ranging from rt to 150° C., affords compounds 5.2. Bromination of 5.2 (e.g., with NBS or $Br_2$/HOAc) affords bromides 5.3 ($X^{21}$=direct bond) according to general reaction conditions reported in WO2013134243, WO2013029084 and *J. Med. Chem.*, 2015, 58, 4165-4179. Pd-catalyzed coupling reaction (Suzuki reaction) of compounds 5.3 with boronates 1.2 in the presence of a Pd catalyst such as $Pd(PPh_3)_4$ or $Pd(dppf)Cl_2$ affords compounds 5.4 which are reacted with sulfonyl chlorides 2.3 to obtain the corresponding sulfonamides (compounds of Formula I). Alternatively, compounds of Formula I can be directly prepared from 5.3 with boronates 1.4 by Suzuki reaction.

Scheme 6

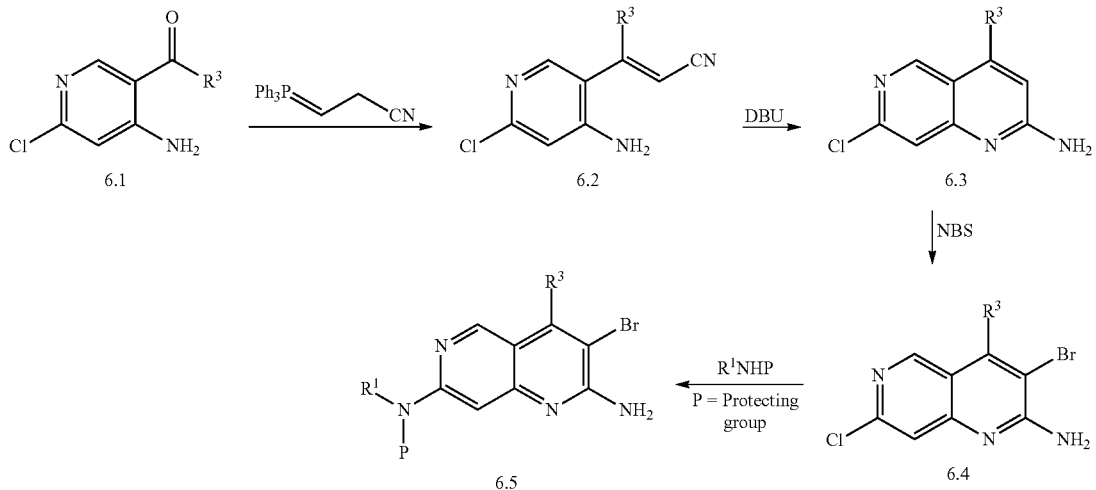

Scheme 6 illustrates an exemplary preparation of intermediates 6.5. Compounds 6.1 (commercially available or synthesized by those skilled in the art) react with 3-(triphenyl-15-phosphanylidene)propanenitrile under Wittig reaction conditions to those skilled in the art to afford compounds 6.2. DBU-promoted cyclization of compounds 6.2 at elevated temperature under microwave irradiation affords the 1,6-naphthyridin-2-amines 6.3. Bromination of 6.3 with NBS affords intermediates 6.4 which are converted to compounds 6.5 by substitution reaction with amines $R^1NHP$ at elevated temperature.

Scheme 7

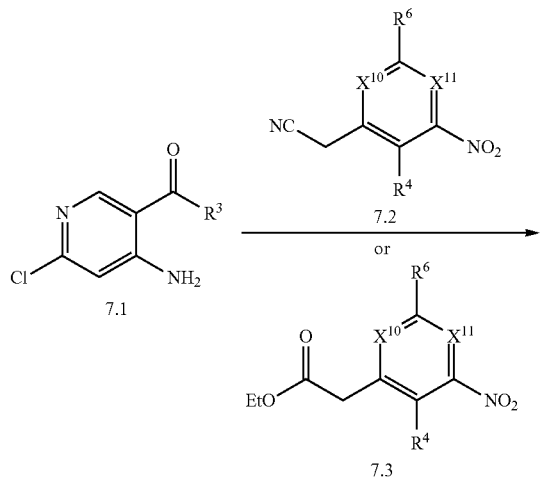

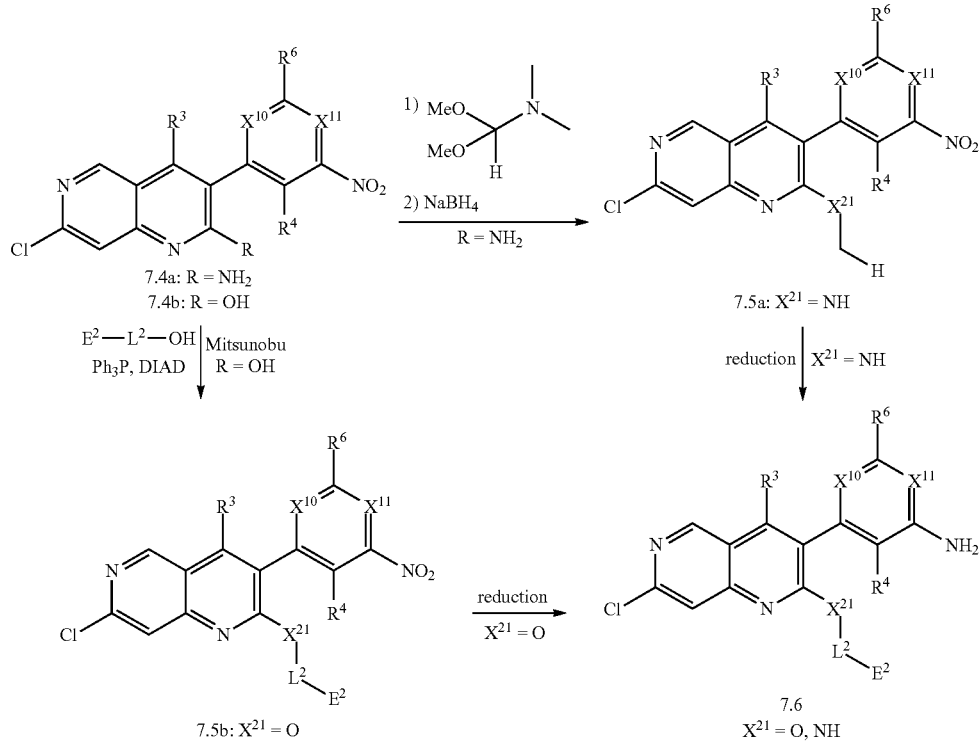

Scheme 7 illustrates an exemplary preparation of intermediates 7.6 ($X^{21}$=O, NH). Compounds 7.1 (commercially available or synthesized by those skilled in the art) react with phenylacetonitriles 7.2 (commercially available or synthesized by those skilled in the art) in the presence of a suitable base such as sodium alkoxide and in a protic solvent such as 2-ethoxyethanol at elevated temperature to obtain 7.4a (R=$NH_2$). Intermediates 7.4a (R=$NH_2$) react with DMF-dimethyl acetal, followed by $NaBH_4$ reduction to afford 7.5a ($X^{21}$=NH) according to general reaction conditions reported in *Synlett*, 2001, 5, 643-645. The reduction of the nitro substituent of compounds 7.5a under mild reducing conditions such as zinc or iron metal with ammonium chloride affords the aniline derivatives 7.6. In another embodiment, compounds 7.1 react with esters 7.3 (commercially available or synthesized by those skilled in the art) in the presence of a base such as piperidine, in a protic solvent such as EtOH at elevated temperature to afford 7.4b (R=OH). Intermediates 7.4b react with alcohols ($E^2$-$L^2$-OH) under standard Mitsunobu conditions (conducted for example in the presence of $Ph_3P$ and DIAD) to provide the ethers 7.5b ($X^{21}$=O), which are converted to the compounds 7.6 via reduction of the nitro functional group of 7.5b to the corresponding anilines in the presence of zinc or iron with ammonium chloride.

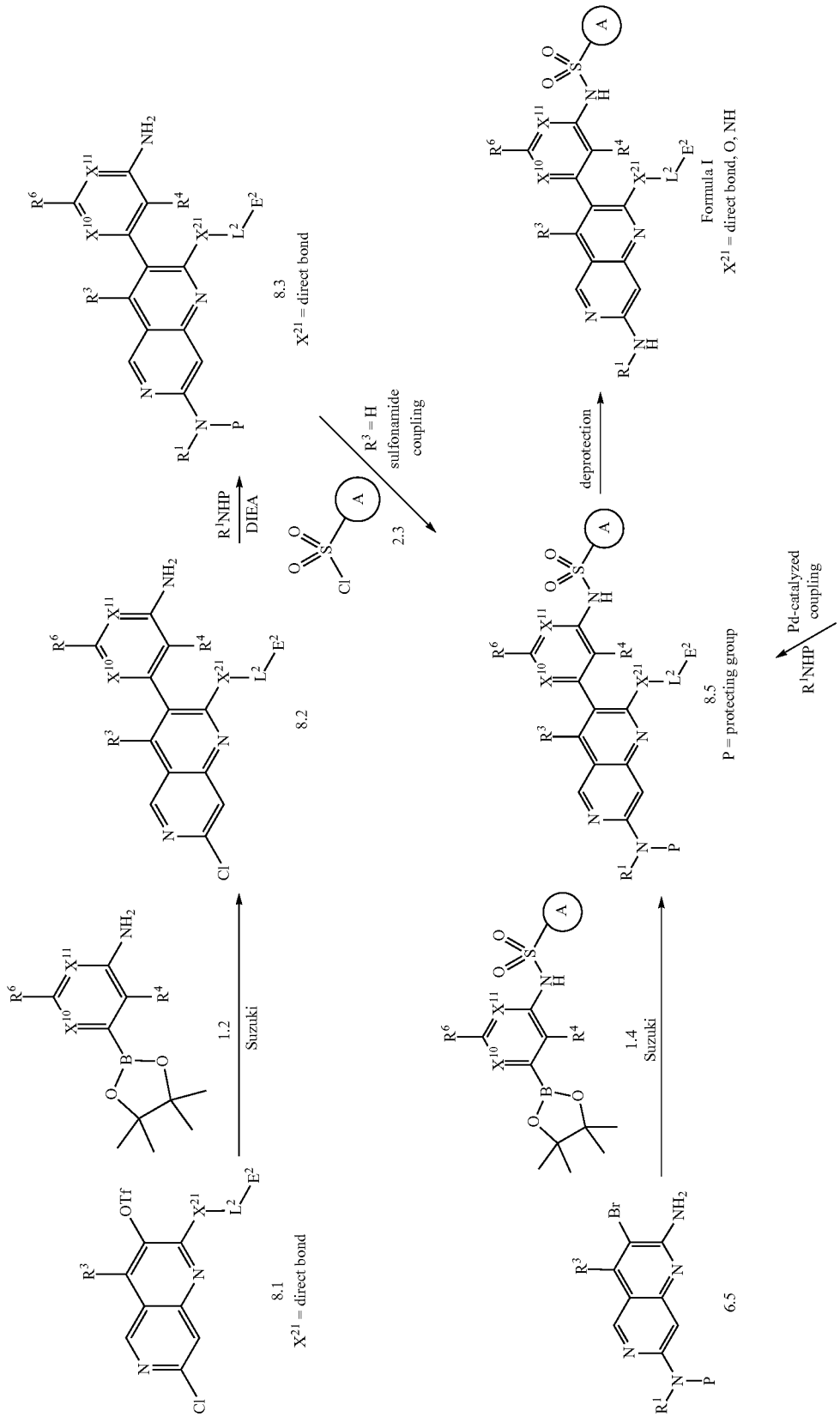

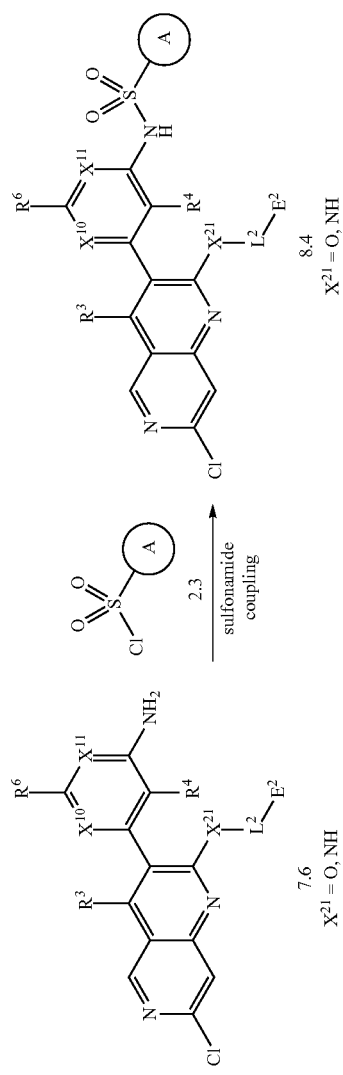

Scheme 8 illustrates an exemplary preparation of compounds of Formula I. Anilines 8.3 are prepared in 2 steps from triflates 8.1 ($X^{21}$=direct bond) according to general reaction conditions reported in WO2013134298 and WO2018229629. Suzuki reaction of triflates 8.1 (synthesized as described in *J. Med. Chem.*, 2015, 58, 4165-4179) with boronates 1.2 affords 8.2. Chlorides 8.2 react with $R^1$NHP (P=protecting group) in the presence of a base such as DIEA at elevated temperature to afford compounds 8.3, which are converted to sulfonamides 8.5 by reaction with sulfonyl chlorides 2.3. In another embodiment, compounds 8.5 are prepared by Suzuki coupling reaction of bromides 6.5 (see preparation of intermediates 6.5 described in scheme 6) with boronates 1.4. Alternatively, anilines 7.6 ($X^{21}$=O, NH, see preparation of intermediates 7.6 described in scheme 7) react with sulfonyl chlorides 2.3 to afford sulfonamides 8.4, which are converted to compounds 8.5 by reaction with amines $R^1$NHP (P=protecting group) in the presence of a palladium catalyst such as $Pd_2(dba)_3$ or $Pd(OAc)_2$, and a metal coordinating group such as XantPhos, or tert-butyl XPhos, in the presence of a base such as $Cs_2CO_3$, in a suitable solvent such as 1,4-dioxane to afford intermediates 8.5. Deprotection of 8.5 provide compounds of Formula I. In instances, where compounds contain a nitrogen protecting group P, such as Boc or PMB, the protecting group can be removed under acidic conditions (TFA or HCl in 1,4-dioxane) to afford the corresponding amines (compounds of Formula I).

Scheme 9
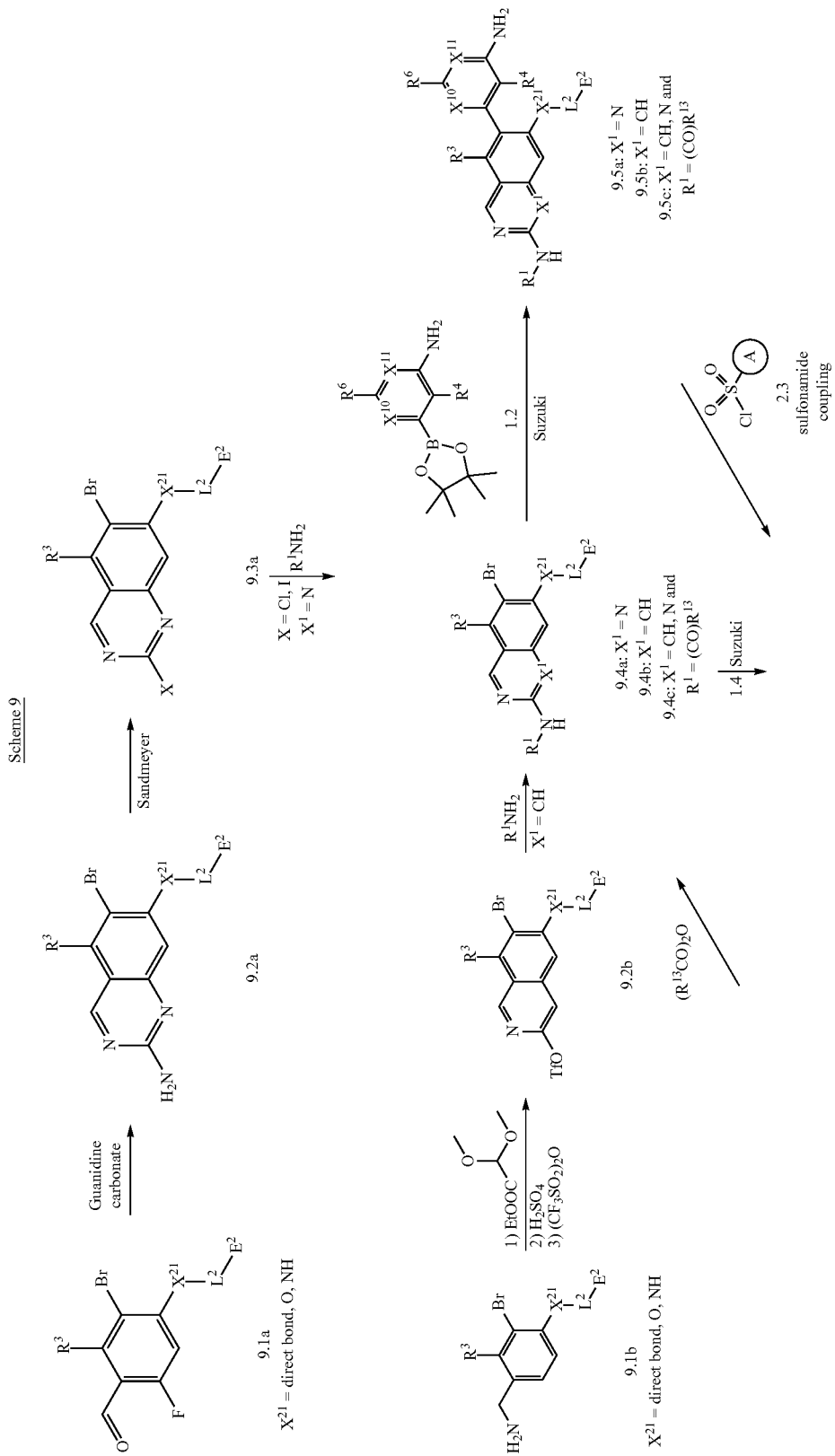

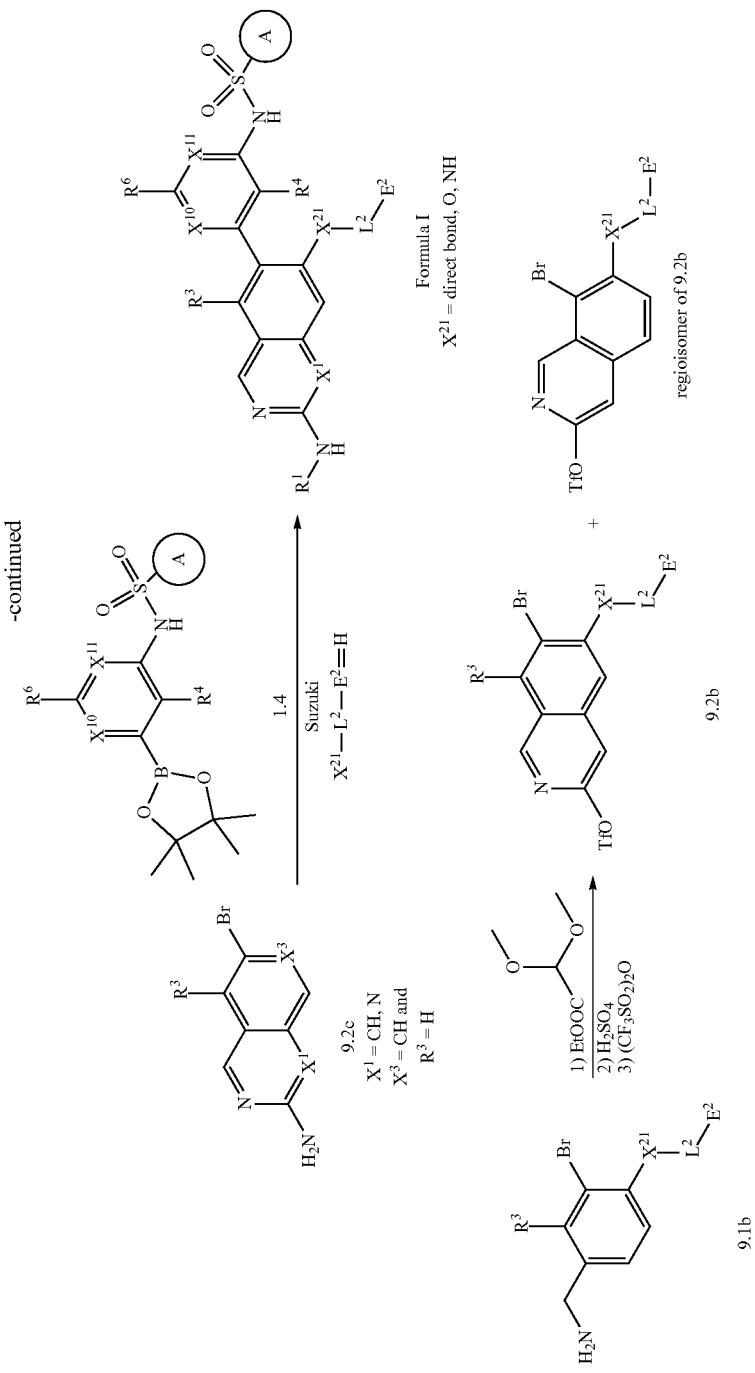

Scheme 9 illustrates an exemplary preparation of compounds of Formula I. Aldehydes 9.1a (commercially available or synthesized by those skilled in the art, $X^{21}$=direct bond, O, NH) react with guanidine carbonate in the presence of a base such as DIEA, in a polar solvent such as NMP at elevated temperature to afford 6-bromoquinazolin-2-amines 9.2a. Compounds 9.2a convert to 9.3a (X=Cl, I) using Sandmeyer reaction conditions known to those skilled in the art (for example, X=I: isoamyl nitrite, CuI and $CH_2I_2$). $S_NAr$ reaction of 9.3a (X=Cl or I) with amines $R^1NH_2$ at elevated temperature affords 9.4a ($X^1$=N, according to general reaction conditions reported in WO2018046739, WO2006039718 US20090197862 and *J. Med. Chem.*, 2006, 49, 5671-5686). In another embodiment, primary amines 9.1b (commercially available or synthesized by those skilled in the art, $X^{21}$=direct bond, O, NH) react with ethyl 2,2-dimethoxyacetate in the presence of a base such as DIEA at elevated temperature, followed by acid-mediated cyclization and triflation with trifluoromethyl sulfonic anhydride to afford triflates 9.2b. When $R^3$ is H, any resulting regioisomers of 9.2b can be separated by a suitable method such as SFC purification, crystallization or chromatography. Triflates 9.2b reacted with amines $R^1NH_2$ via $S_NAr$ reaction at elevated temperature to afford 9.4b ($X^1$=CH) according to general reaction conditions reported in *ACS Med. Chem. Lett*, 2015, 6, 31-36. Commercially available 9.2c ($X^1$=N, $X^3$=CH and $R^3$=H: 6-bromoquinazolin-2-amine and $X^1$=CH, $X^3$=CH and $R^3$=H: 7-bromoisoquinolin-3-amine) reacts with an acid anhydride (($R^{13}$(CO))$_2$O) at elevated temperature to afford acetamides 9.4c ($X^1$=N or CH; $R^1$=(CO)$R^{13}$). Palladium-catalyzed coupling of 9.4a, 9.4b and 9.4c with boronates 1.2 under Suzuki reaction conditions affords the intermediates 9.5a, 9.5b and 9.5c, respectively. Coupling of amines 9.5a, 9.5b and 9.5c with sulfonyl chlorides 2.3 under reaction conditions known to those skilled in the art affords compounds of Formula I. Alternatively, compounds of Formula I can be prepared from 9.2c, 9.4a, 9.4b and 9.4c with boronates 1.4 by palladium-catalyzed coupling reaction (Suzuki reaction).

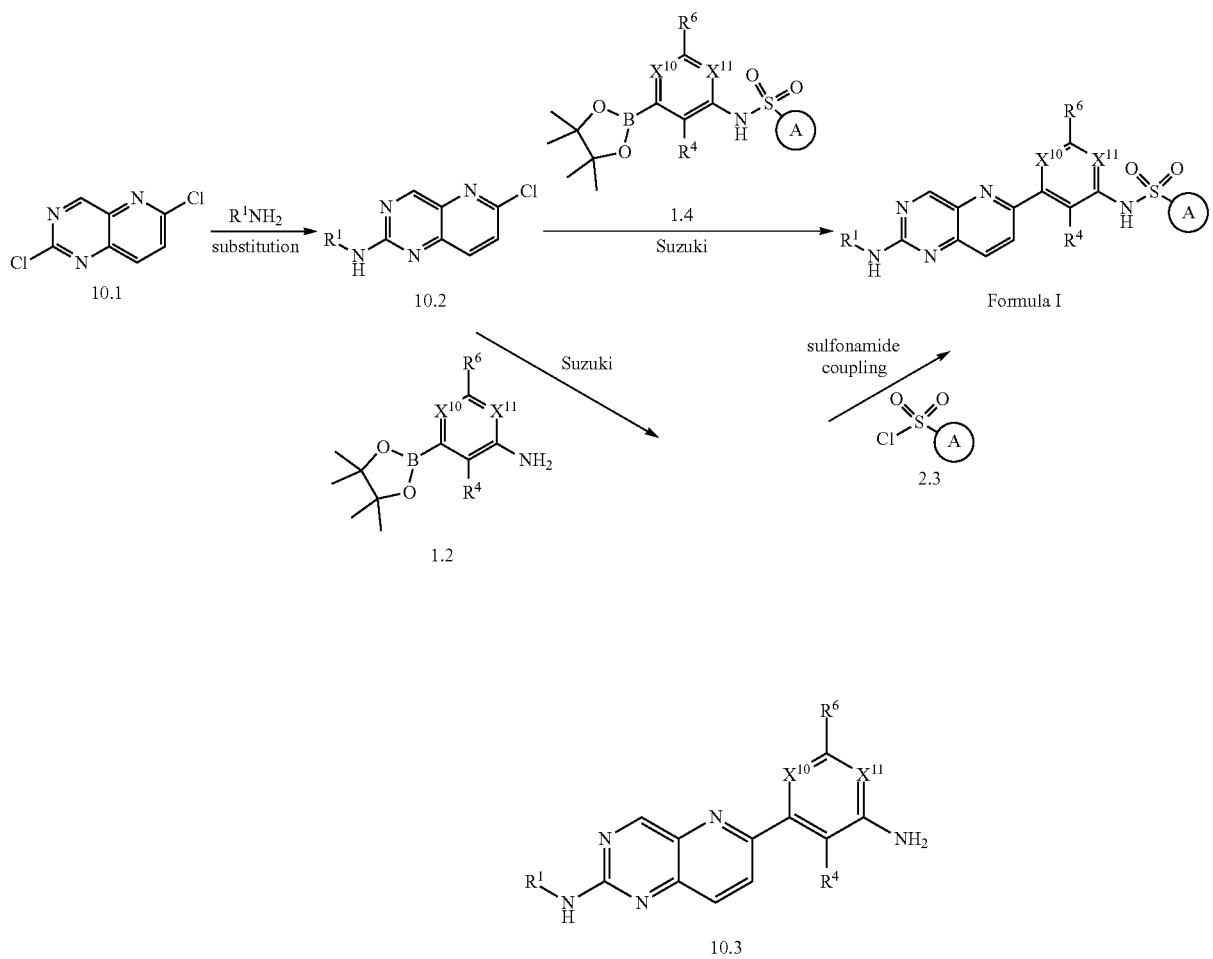

Compounds of Formula I may be prepared as described in Scheme 10. Commercially available 2,6-dichloropyrido[3,2-d]pyrimidine (10.1) reacts with amines $R^1NH_2$ (commercially available or synthesized by those skilled in the art) in the presence of a base such as DIEA to afford intermediates 10.2. Palladium-catalyzed coupling reaction (Suzuki reaction) of chlorides 10.2 with boronates 1.2 affords anilines 10.3. Anilines 10.3 react with sulfonyl chlorides 2.3 to provide compounds of Formula I. Alternatively, compounds of Formula I can be directly prepared from chlorides 10.2 with boronates 1.4 under Suzuki reaction conditions.

Scheme 11

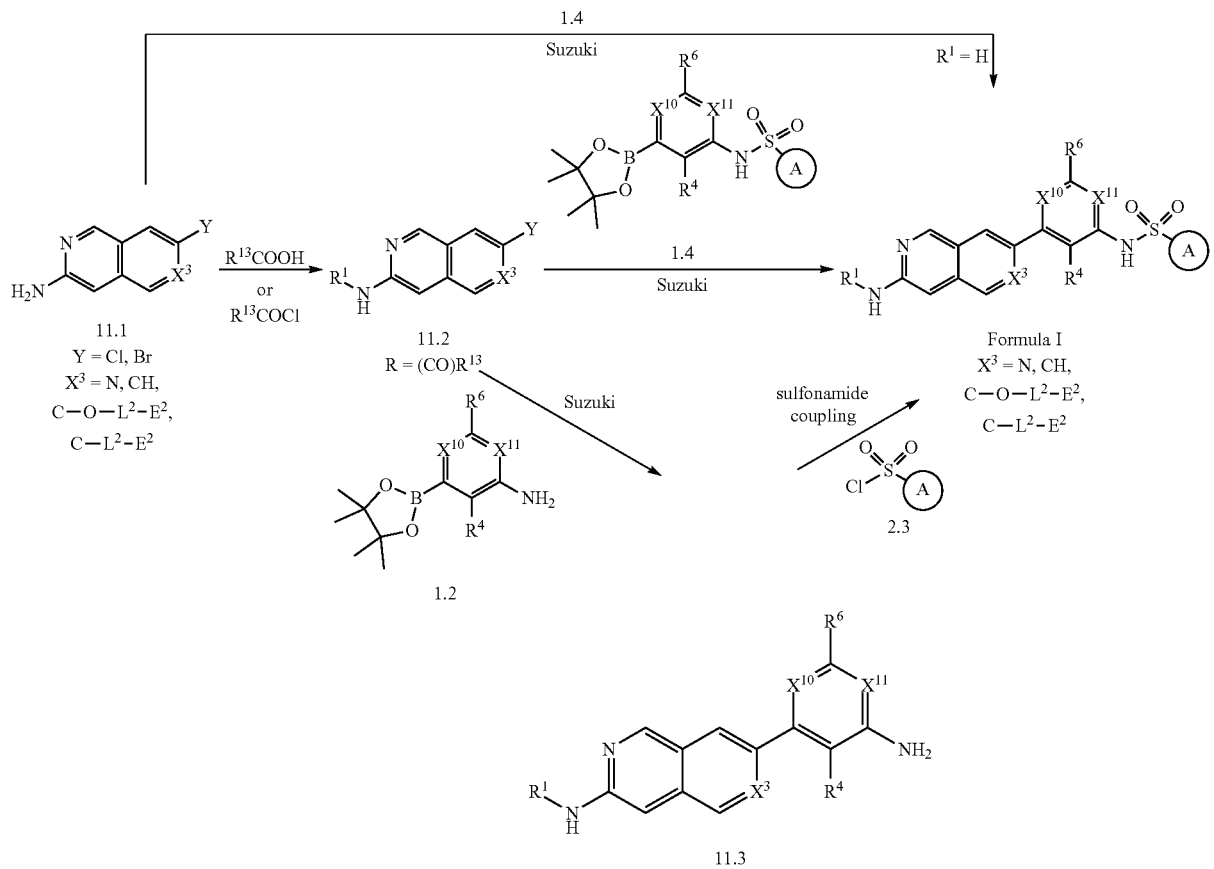

Compounds of Formula I may be prepared as described in Scheme 11. Amines 11.1 (commercially available or synthesized by those skilled in the art) react with boronates 1.4 under palladium-mediated Suzuki coupling conditions to afford compounds of Formula I ($R^1$=H). In another embodiment, amines 11.1 react with carboxylic acids $R^{13}$COOH under amide coupling conditions (for example, HATU and DMAP in the presence of DIEA) or acyl chlorides $R^{13}$COCl in the presence of base such as pyridine to afford 11.2. Intermediates 11.2 react with boronates 1.2 under Suzuki reaction conditions to afford compounds 11.3, which are converted to compounds of Formula I via reaction with sulfonyl chlorides 2.3. Alternatively, compounds of Formula I can be directly prepared from 11.2 with boronates 1.4 under Suzuki reaction conditions.

Scheme 12

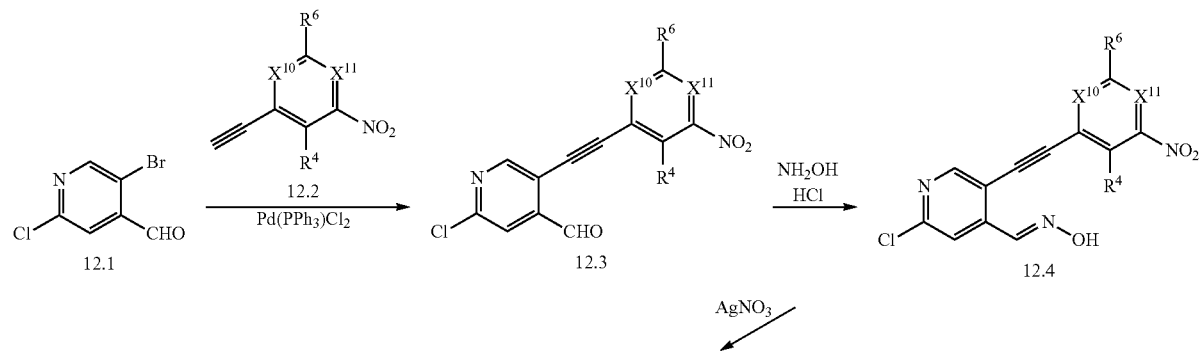

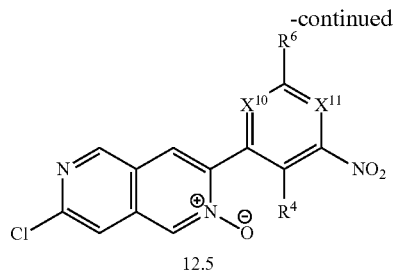

Intermediates of formula 12.5 may be prepared as described in Scheme 12. Commercially available 5-bromo-2-chloroisonicotinaldehyde (12.1) reacts with 3-nitrophenylacetylenes 12.2 (commercially available or synthesized by those skilled in the art) under Pd/Cu-catalyzed Sonogashira cross-coupling reaction conditions (for example, in the presence of a palladium catalyst such as Pd(PPh$_3$)$_2$Cl$_2$, in the presence of a Cu (I) catalyst such as CuCl or CuI, in the presence of a base such as triethylamine, in a suitable solvent such as DMF/THF at temperatures ranging from rt to 120° C.) to afford the acetylenes 12.3. Intermediates 12.3 react with hydroxylamine hydrochloride in the presence of a suitable base such as NaOAc to afford oximes 12.4. N-oxides 12.5 are prepared by electrophilic metal-catalyzed cyclization of 12.4 with AgNO$_3$ according to synthetic procedure reported in US20190270742.

Compounds of Formula I may be prepared as described in Scheme 13. Copper-catalyzed direct amination of N-oxides 12.5 (see preparation of 12.5 illustrated in Scheme 12) reacts with amines E$^2$-L$^2$-NHR$^2$ in the presence of a catalyst such as CuI in an aprotic solvent such as toluene at elevated temperature (according to general reaction conditions reported in *J. Org. Chem.*, 2017, 82, 8933-8942) to afford 13.1 (X$^{21}$=NR$^2$). Conversion of N-oxides 13.1 to compounds 13.2 is conducted in the presence of PCl$_3$ according to synthetic procedures reported in US20190270742. Nitro reduction of 13.2 under mild reducing conditions (reaction conducted in the presence of a metal such as zinc or iron with ammonium chloride) affords anilines 13.3, which are converted to the corresponding sulfonamides 13.4 by reaction with sulfonyl chlorides 2.3. Finally, Pd-catalyzed coupling reaction known to those skill in the art (Buchwald reaction) of 13.4 with R$^1$NH$_2$ affords compounds of Formula I.

Scheme 13

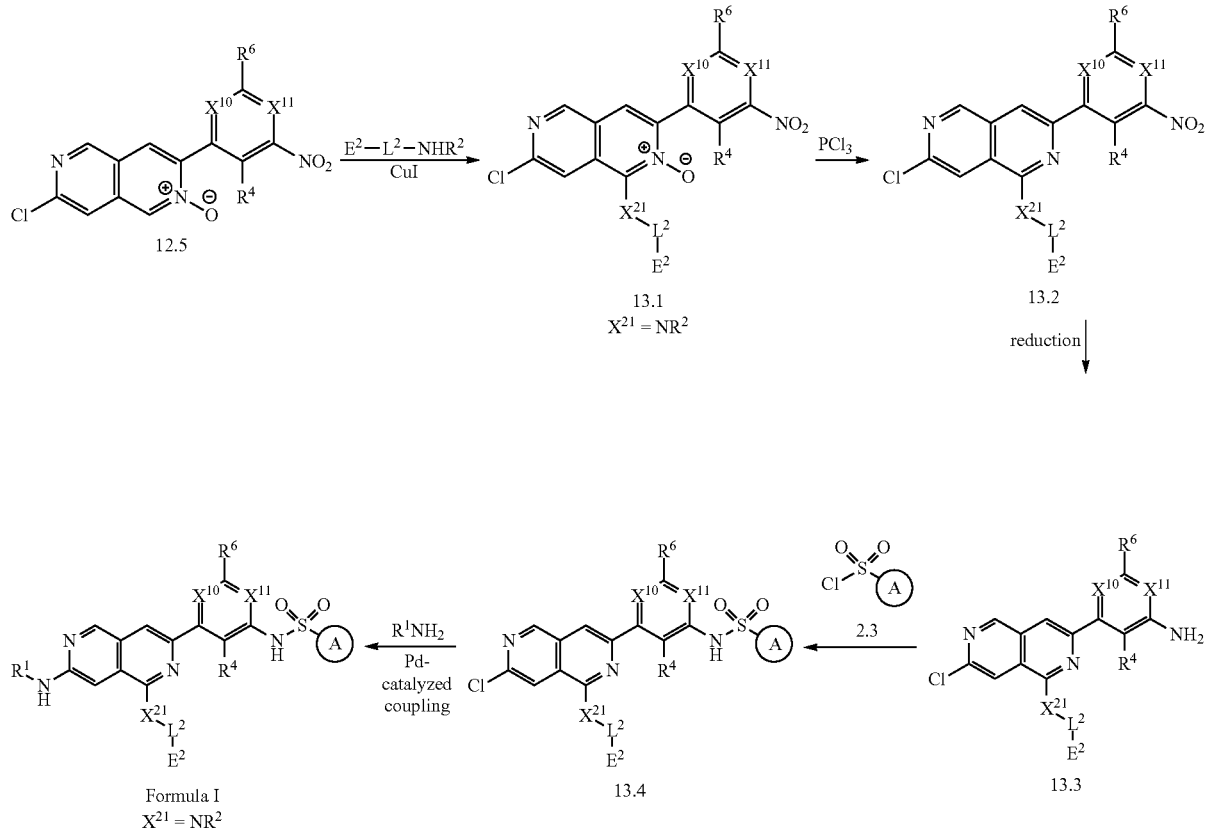

Scheme 14

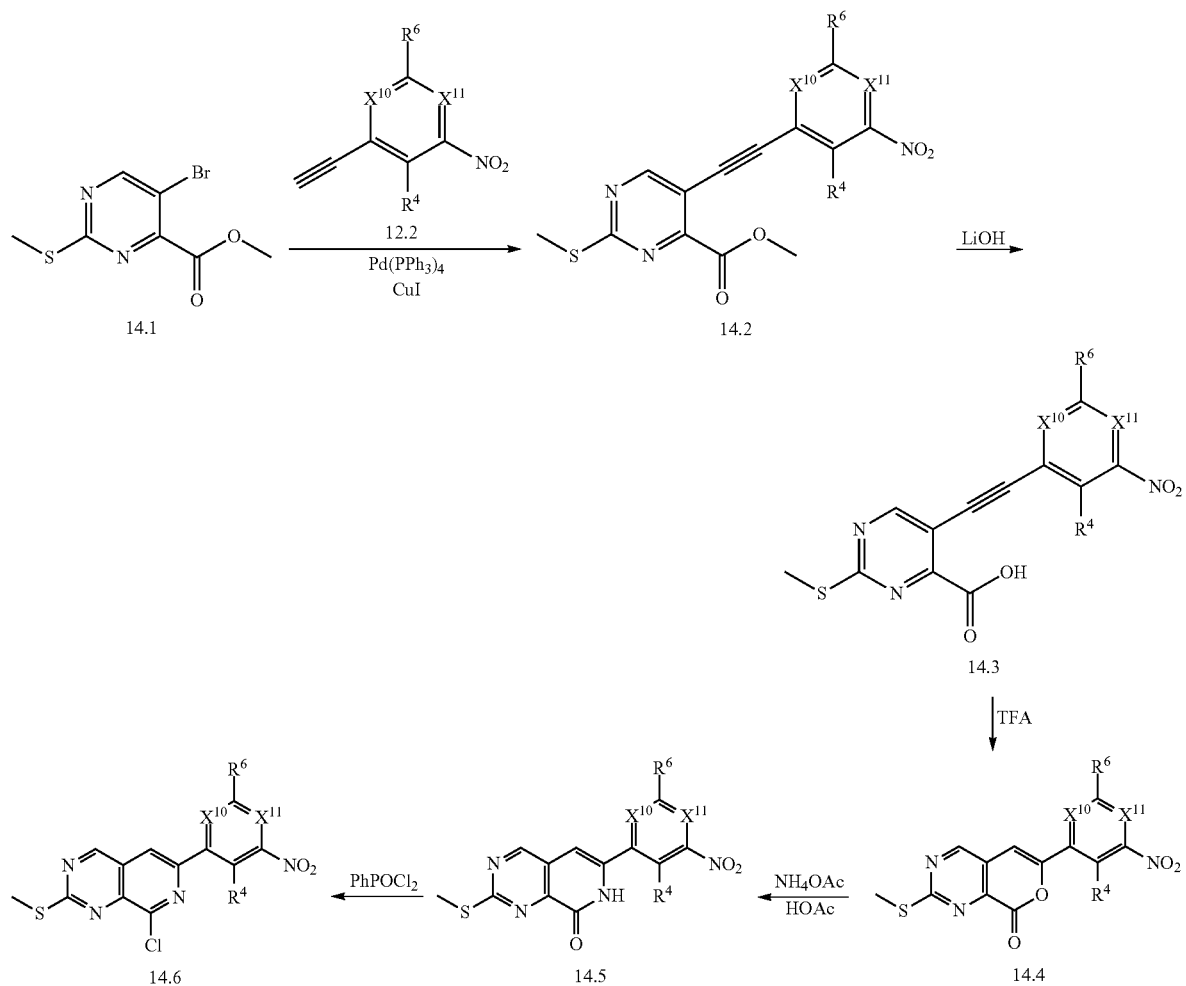

Intermediates of formula 14.6 may be prepared as described in Scheme 14. Commercially available methyl 5-bromo-2-(methylthio)pyrimidine-4-carboxylate (14.1) reacts with 3-nitrophenylacetylenes 12.2 (commercially available or synthesized by those skilled in the art) under Pd/Cu-catalyzed conditions known to those skill in the art (Sonogashira Reaction) to afford 14.2. Hydrolysis of esters 14.2 with LiOH (aq) affords the corresponding acids 14.3. Acid-promoted intramolecular cyclization of acids 14.3 affords 14.4 according to general reaction conditions reported in *Org. Lett.*, 2006, 8, 5517-5520. Intermediates 14.4 are converted to 14.5 under $NH_4OAc$ in glacial acetic acid at elevated temperature. Compounds 14.5 react with $PhPOCl_2$ to afford intermediates 14.6 according to general reaction conditions reported in WO2018113584.

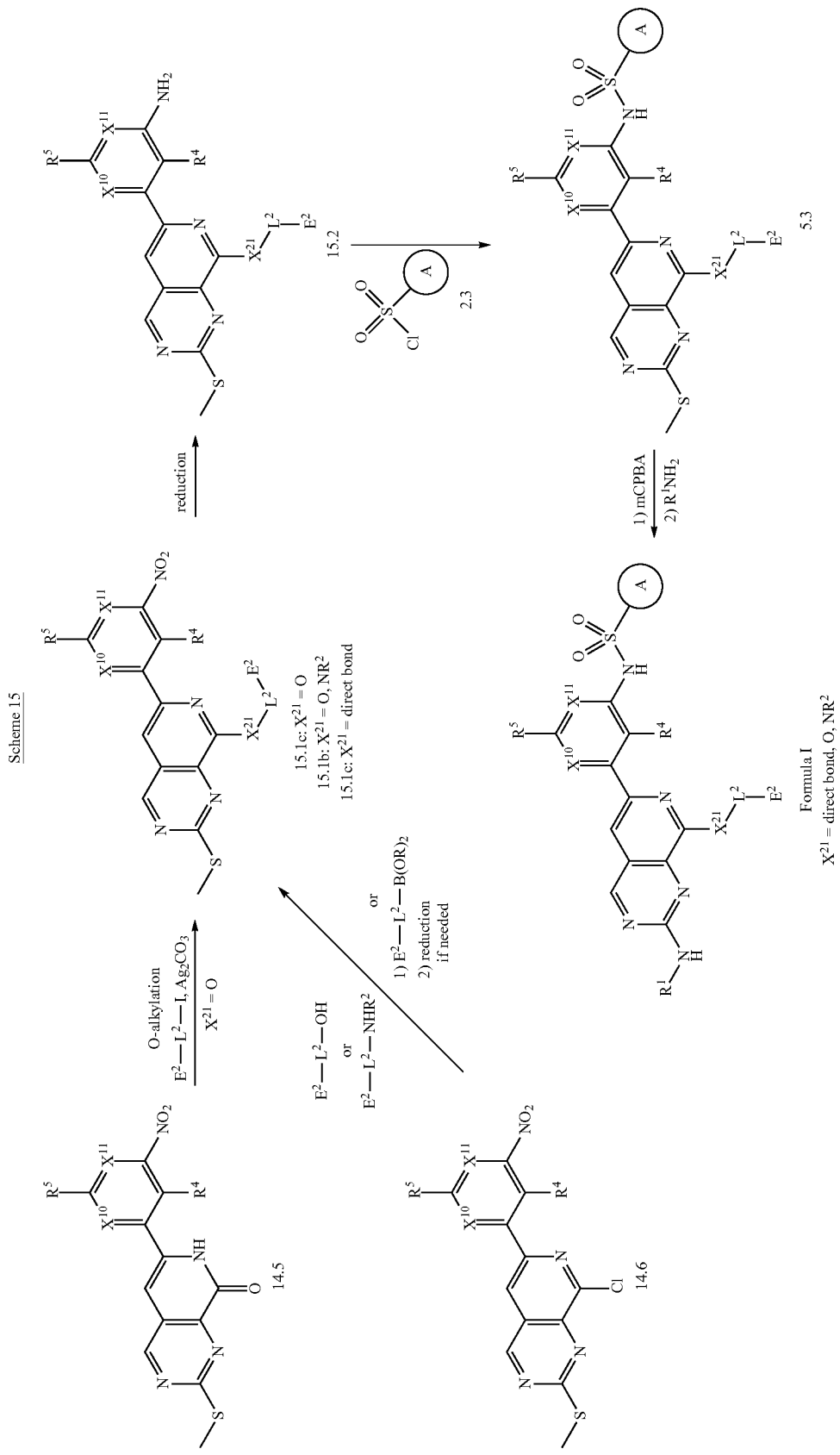
Scheme 15

Compounds of Formula I may be prepared as described in Scheme 15. O-alkylation of 14.5 (see preparation of 14.5 illustrated in Scheme 14) with alkylating reagents $E^2L^2$-I in the presence of $Ag_2CO_3$ affords 15.1a ($X^{21}$=O) according to general reaction conditions reported in WO2018113584. Alternatively, chlorides 14.6 react with alcohols ($E^2$-$L^2$-OH) or amines ($E^2$-$L^2$-$NHR^2$) by substitution reaction in the presence of a base such as DIEA, in polar aprotic solvents such as NMP at elevated temperature to afford 15.1b ($X^{21}$=O, $NR^2$) according to general reaction conditions reported in WO2014037750. Alternatively, chlorides 14.6 (prepared in scheme 14) react with boronic acids or boronates $E^2$-$L^2$-$B(OR)_2$ (commercially available or synthesized by those skilled in the art) under Pd-catalyzed coupling conditions (Suzuki reaction) to afford 15.1c ($X^{21}$=direct bond). Nitro reduction of 15.1a, 15.1b and 15.1c under by palladium catalyzed hydrogenation or mild reducing conditions (zinc or iron metal with ammonium chloride) affords anilines 15.2. When 15.1c contains double or triple bonds at the $L^2$-$E^2$, these moieties along with the nitro group can be fully reduced under palladium catalyzed hydrogenation conditions to afford 15.2. Anilines 15.2 react with sulfonyl chlorides 2.3 to obtain sulfonamides 15.3 under sulfonamide coupling conditions known to those skilled in the art. Finally, compounds of Formula I can be prepared by oxidation of 15.3 with mCPBA, followed by $S_NAr$ reaction of the resulting intermediate with amines $R^1NH_2$.

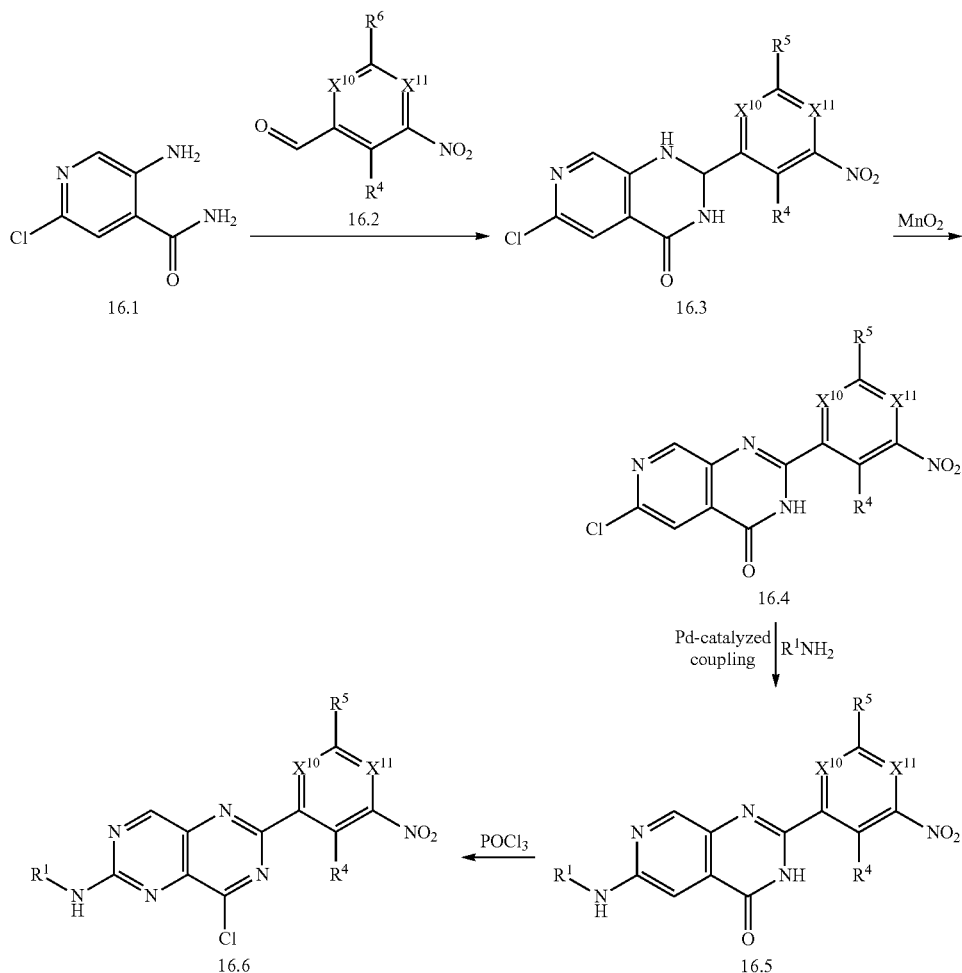

Scheme 16

Intermediates of formula 16.6 may be prepared as described in Scheme 16. Commercially available 5-amino-2-chloroisonicotinamide (16.1) reacts with 3-nitro-aldehydes 16.2 (commercially available or synthesized by those skilled in the art) to afford 16.3. Oxidation of 16.3 with an oxidant such as $MnO_2$ affords 16.4 according to general reaction conditions reported in WO2018113584. Intermediates 16.4 react with amines $R^1NH_2$ under Pd-catalyzed coupling reaction known to those skill in the art (Buchwald reaction) to afford 16.5 which can be reacted with $POCl_3$ to afford intermediates chlorides 16.6.

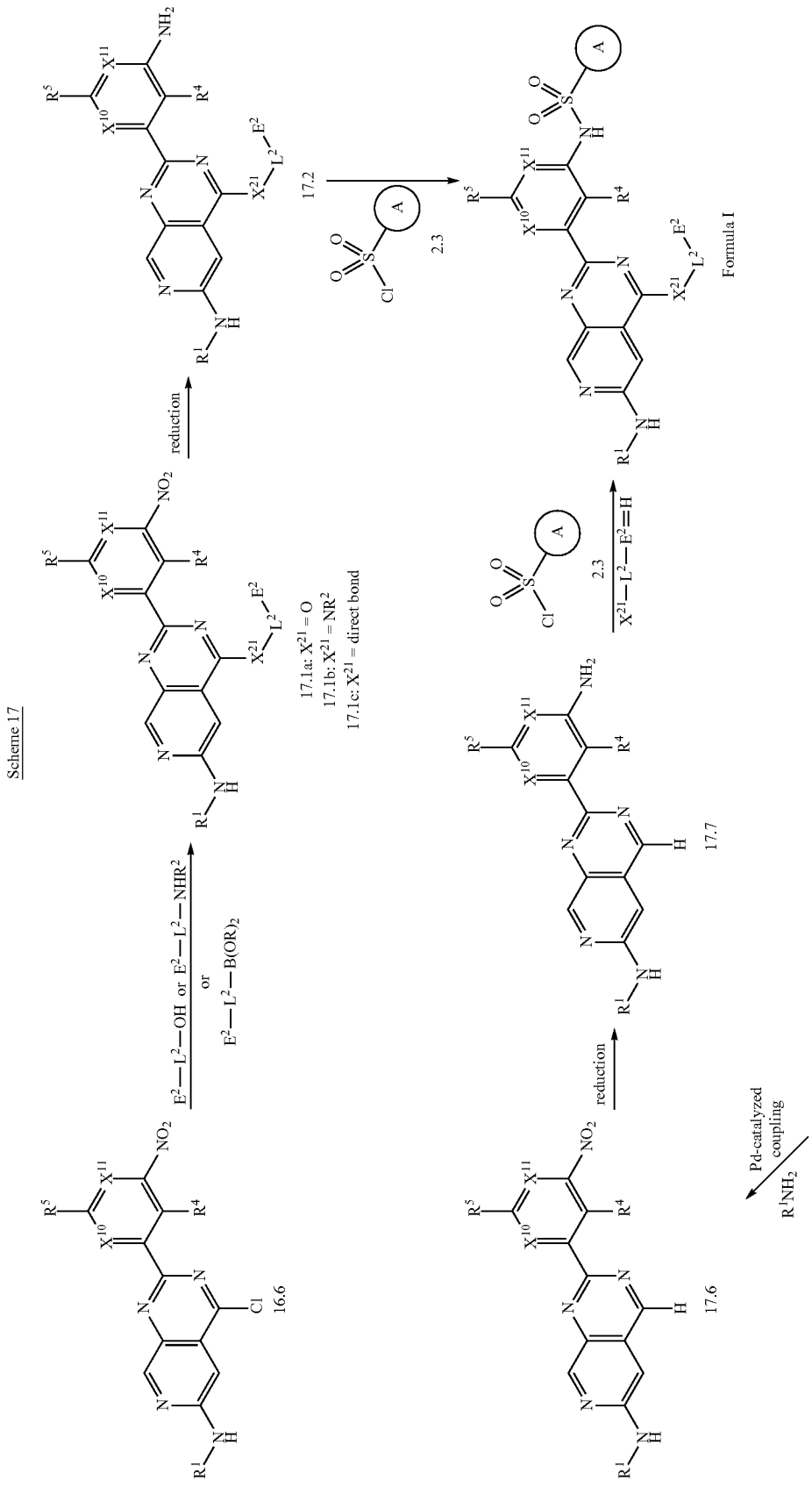

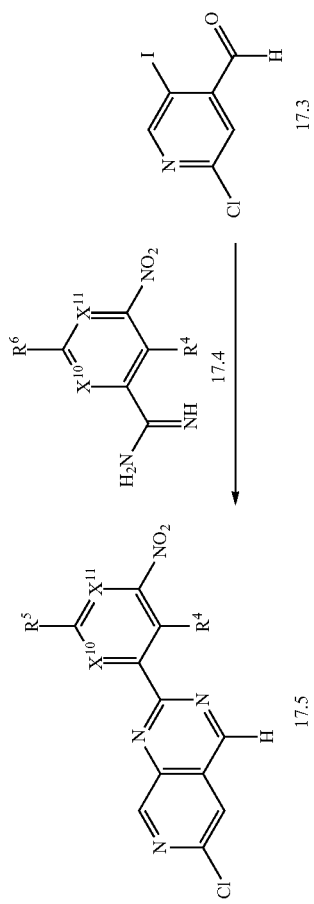

Compounds of Formula I may be prepared as described in Scheme 17. Chlorides 16.6 (prepared as described in Scheme 16) react with alcohols (E²-L²-OH) or amines (E²-L²-NHR²) by substitution reaction to afford 17.1a (X²¹=O) or 17.b (X²¹=NR²). Alternatively, 17.1c (X²¹=direct bond) can be prepared from 16.6 by Pd-coupling reaction (Suzuki reaction) with either boronic acids or boronates (E²-L²-B(OR)₂). Nitro-reduction of 17.1a, 17.1b and 17.1c via palladium catalyzed hydrogenation or mild reducing conditions (zinc or iron metal with ammonium chloride) affords anilines 17.2. When 17.1c contains double or triple bonds at the L²-E², these moieties along with the nitro group can be fully reduced under palladium catalyzed hydrogenation conditions to afford 17.2. Finally, anilines 17.2 react with sulfonyl chlorides 2.3 under sulfonamide coupling conditions to afford compounds of Formula I. In another embodiment, ligand-free copper-catalyzed Ullmann reaction of commercially available 2-chloro-5-iodoisonicotinaldehyde (17.3) with various benzimidamides 17.4 (commercially available or synthesized by those skilled in the art) affords 17.5 (X²¹-L²-E²=H) according to general reaction conditions reported in *Tetrahedron Lett.*, 2010, 51, 785-760. Pyridopyrimidines 17.5 react with amines R¹NH₂ by Pd-catalyzed coupling reaction known to those skill in the art (Buchwald reaction) to afford 17.6. Nitro-reduction of 17.6 via palladium catalyzed hydrogenation or mild reducing conditions (zinc or iron metal with ammonium chloride) affords anilines 17.7. Sulfonamide coupling reaction of anilines 17.7 with sulfonyl chlorides 2.3 affords compounds of Formula I.

Preparation of Intermediates and Final Compounds.

Using the synthetic procedures and methods described herein and methods known to those skilled in the art, the following compounds were made:

General Method A: Borylation

Example A1

2-fluoro-4-methyl-5-(4,4,5,5-tetramethyl-1,3,2-dioxaborolan-2-yl)aniline

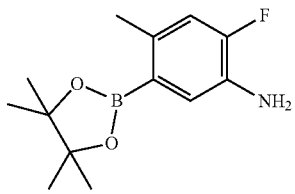 [SMILES: Cc1cc(F)c(N)cc1B1OC(C)(C)C(C)(C)O1]

A mixture of potassium acetate (14.4 g, 147 mmol), 5-bromo-2-fluoro-4-methylaniline (10.0 g, 49 mmol), and 4,4,4',4',5,5,5',5'-octamethyl-2,2'-bi(1,3,2-dioxaborolane) (17.4 g, 69 mmol) in 1,4-dioxane (150 mL) was degassed with Ar for 10 min. PdCl₂(dppf) (1.79 g, 2.5 mmol) was added and the reaction mixture was heated at 110° C. for 6 h. The reaction was cooled to rt and filtered through a pad of celite. The filtrate was removed under reduced pressure and the residue was purified by silica gel column chromatography (0 to 50% EtOAc/hexanes and 1% EtOAc/DCM) to obtain 2-fluoro-4-methyl-5-(4,4,5,5-tetramethyl-1,3,2-dioxaborolan-2-yl)aniline (6.2 g, 50% yield) as a tan solid. ¹H NMR (500 MHz, DMSO-d₆): δ 7.12 (d, J=10.4 Hz, 1H), 6.78 (d, J=12.8 Hz, 1H), 4.86 (s, 2H), 2.29 (s, 3H), 1.26 (s, 12H); MS (ESI) m/z: 252.2 (M+H⁺).

Using the General Method A above, the following Intermediates of Table A were prepared.

TABLE A

| Ex No | Product | Yield (%) | ¹H NMR (400 or 500 MHz, DMSO-d₆): δ | MS (m/z: M + H⁺) |
|---|---|---|---|---|
| A2 | | 96 | No Data | 234.2 |
| A3 | | 61 | 6.85 (m, 1H), 6.78 (m, 1H), 6.65 (m, 1H), 4.90 (brs, 2H), 1.27 (s, 12H). | 238.1 |
| A4 | | 62 | 7.13 (d, J = 9.8 Hz, 1H), 6.94 (m, 2H), 6.82 (t, J = 6.3 Hz, 1H), 5.09 (s, 2H), 1.24 (s, 12H). | 238.1 |

TABLE A-continued

| Ex No | Product | Yield (%) | $^1$H NMR (400 or 500 MHz, DMSO-d$_6$): δ | MS (m/z: M + H$^+$) |
|---|---|---|---|---|
| A5 | (3-amino-5-fluorophenyl pinacol boronate) | 88 | 6.77 (d, J = 2.0 Hz, 1H), 6.42 (m, 2H), 5.42 (s, 2H), 1.27 (s, 12H). | 238.2 |
| A6 | (3-amino-2-fluorophenyl pinacol boronate) | 78 | 6.86 (m, 2H), 6.76 (d, J = 6.8 Hz, 1H), 5.02 (s, 2H), 1.28 (s, 12H). | 238.2 |
| A7 | (3-amino-2,5-difluorophenyl pinacol boronate) | crude | No Data | 256.2 |
| A8 | (3-amino-4,5-difluorophenyl pinacol boronate) | 36 | 6.59 (m, 2H), 5.20 (brs, 2H), 1.28 (s, 12H). | 256.1 |
| A9 | (3-amino-2,4-difluorophenyl pinacol boronate) | 33 | No Data | 256.2 |
| A10 | (5-amino-2,4-difluorophenyl pinacol boronate) | 93 | 7.09 (m, 1H), 6.94 (m, 1H), 5.00 (s, 2H), 1.28 (s, 12H). | 256.2 |
| A11 | (3-amino-4-fluorophenyl pinacol boronate) | crude | 7.1.3 (d, J = 9.8 Hz, 1H), 6.94 (m, 1H), 6.82 (m, 1H), 5.09 (s, 2H), 1.24 (s, 12H). | 238.1 |

TABLE A-continued

| Ex No | Product | Yield (%) | $^1$H NMR (400 or 500 MHz, DMSO-$d_6$): δ | MS (m/z: M + H$^+$) |
|---|---|---|---|---|
| A12 | (2,4-difluoro-3-aminophenyl pinacol boronate) | 61 | 6.88 (t, J = 8.8 Hz, 1H), 6.77 (m, 1H), 5.10 (brs, 2H), 1.28 (s, 12H). | 256.0 |
| A13 | (4-fluoro-3-methyl-5-aminophenyl pinacol boronate) | 65 | 6.74 (d, J = 2.4 Hz, 1H), 6.37 (dd, J = 2.4 and 12.4 Hz, 1H), 5.10 (brs, 2H), 2.18 (d, J = 2.0 Hz, 3H), 1.28 (s, 12H). | 252.1 |
| A14 | (4-fluoro-2-methyl-5-aminophenyl pinacol boronate) | 40 | 6.88 (d, J = 7.8 Hz, 1H), 6.71 (m, 1H), 4.7 (brs, 2H), 2.05 (s, 3H), 1.26 (s, 12H). | 252.3 |
| A15 | (2-methoxy-3-aminophenyl pinacol boronate) | 81 | 6.80 (d, J = 4.6 Hz, 2H), 6.75 (m, 1H), 4.80 (s, 2H), 3.65 (s, 3H), 1.29 (s, 12H). | 250.2 |
| A16 | (4-methoxy-3-aminophenyl pinacol boronate) | 38 | 6.84 (d, J = 2.8 Hz, 1H), 6.66 (d, J = 8.8 Hz, 1H), 6.61 (m, 1H), 4.6 (brs, 2H), 3.59 (s, 3H), 1.25 (s, 12H). | 250.1 |
| A17 | (2-methyl-3-aminophenyl pinacol boronate) | 76 | 6.86 (m, 2H), 6.71 (m, 1H), 4.7 (brs, 2H), 2.20 (s, 3H), 1.28 (s, 12H). | 234.2 |
| A18 | (4-trifluoromethyl-3-aminophenyl pinacol boronate) | 60 | 7.31 (d, J = 8.4 Hz, 1H), 6.83 (d, J = 2.4 Hz, 1H), 6.64 (dd, J = 1.6 and 8.4 Hz, 1H), 5.80 (brs, 2H), 1.28 (s, 12H). | 288.1 |

TABLE A-continued

| Ex No | Product | Yield (%) | $^1$H NMR (400 or 500 MHz, DMSO-$d_6$): δ | MS (m/z: M + H$^+$) |
|---|---|---|---|---|
| A19 | | 62 | 7.22 (t, J = 8.0 Hz, 1H), 6.84 (d, J = 8.0 Hz, 1H), 6.57 (d, J = 6.8 Hz, 1H), 5.50 (brs, 2H), 1.27 (s, 12H). | 287.8 |
| A20 | | 46 | 6.99 (d, J = 8.8 Hz, 1H), 6.87 (d, J = 2.8 Hz, 1H), 6.60 (dd, J = 3.2 and 8.8 Hz, 1H), 5.20 (brs, 2H), 1.28 (s, 12H). | 254.0 |
| A21 | | 43 | 6.99 (t, J = 7.6 Hz, 1H), 6.86 (d, J = 6.4 Hz, 1H), 6.77 (d, J = 6.8 Hz, 1H), 5.25 (brs, 2H), 1.28 (s, 12H). | 254.1 |
| A22 | | 78 | 7.29 (m, 1H), 6.92 (m, 2H), 5.93 (s, 2H), 1.30 (s, 12H). | 245.2 |
| A23 | | 42 | 6.85 (d, J = 1.2 Hz, 1H), 6.69 (s, 1H), 6.67 (m, 1H), 5.41 (brs, 2H), 1.27 (s, 12H) | No Data |

General Method B: Condensation

Example B1

7-methyl-2-(methylthio)pyrido [2,3-d]pyrimidine

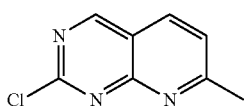

A solution of 4-amino-2-(methylthio)pyrimidine-5-carbaldehyde (3.0 g, 18 mmol) in acetone (50 mL) was treated with $K_2CO_3$ (3.1 g, 22 mmol). The reaction was heated to 65° C. overnight. The reaction was filtered while hot, the filtrate was cooled to rt and the solvent was evaporated. The residue was recrystallized from water. The solids were filtered and rinsed with hexanes (20 mL) to obtain 7-methyl-2-(methylthio)pyrido[2,3-d]pyrimidine (3.1 g, 93% yield) as a yellow solid. $^1$H NMR (400 MHz, DMSO-$d_6$): δ 9.40 (s, 1H), 8.42 (d, J=8.2 Hz, 1H), 7.55 (d, J=8.2 Hz, 1H), 2.71 (s, 3H), 2.63 (s, 3H).

General Method C: Substitution

Example B2

N,7-dimethylpyrido[2,3-d]pyrimidin-2-amine

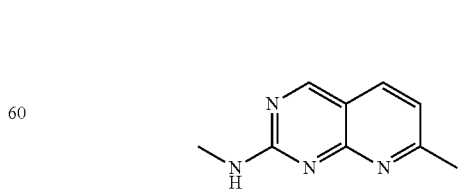

A solution of 7-methyl-2-(methylthio)pyrido[2,3-d]pyrimidine (B1, 1.00 g, 0.52 mmol) in N-methylamine (33% in ethanol, 8 mL) was heated in a sealed tube at 80° C.

overnight. The reaction was cooled to rt and then concentrated under reduced pressure to obtain N,7-dimethylpyrido[2,3-d]pyrimidin-2-amine (0.62 g, 68% yield) as an orange solid. The material was used without further purification for the next reaction. MS (ESI) m/z: 175.2 (M+H$^+$).

General Method D: Halogenation (Br or I)

Example B3

6-bromo-N,7-dimethylpyrido[2,3-d]pyrimidin-2-amine

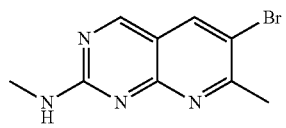

A solution of N,7-dimethylpyrido[2,3-d]pyrimidin-2-amine (B2, 0.62 g, 0.36 mmol) in DCM (7.5 mL) was added NBS (0.67 g, 0.38 mmol) portion wise at rt. The reaction mixture was stirred at rt overnight. The reaction mixture was cooled to 0° C. and stirred for 15 min. The solids were filtered and rinsed with cold DCM (15 mL) to obtain 6-bromo-N,7-dimethylpyrido[2,3-d]pyrimidin-2-amine (0.48 g, 53% yield). $^1$H NMR (500 MHz, DMSO-d$_6$): δ 9.07 (s, 1H), 8.47 (s, 1H), 7.84 (s, 1H), 2.90 (d, J=4.7 Hz, 3H), 2.68 (s, 3H); MS (ESI) m/z: 253.0 (M+H$^+$) and 255.0.

General Method E: Condensation

Example B4

7-methyl-2-(methylthio)pyrido[2,3-d]pyrimidin-6-ol

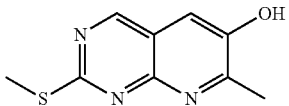

A suspension of 4-amino-2-(methylthio)pyrimidine-5-carbaldehyde (45 g, 266 mmol) in water (600 mL) was treated with NaOH (21 g, 530 mmol). 1-Hydroxypropan-2-one (23 g, 319 mmol) was added and then the reaction mixture was heated to 55° C. for 4 h. The reaction was cooled to 0° C. and conc-HCl was added dropwise to pH ~3-4 under the same conditions. The reaction was stirred at 0° C. for 30 min, then the solids were filtered to obtain 7-methyl-2-(methylthio)pyrido[2,3-d]pyrimidin-6-ol (51 g, 93% yield) as a yellow solid. $^1$H NMR (500 MHz, DMSO-d$_6$): δ 10.8 (s, 1H), 9.28 (s, 1H), 7.53 (s, 1H), 2.57 (s, 3H), 2.56 (s, 3H); MS (ESI) m/z: 208.2 (M+H$^+$).

General Method F: Activation

Example B5

7-methyl-2-(methylthio)pyrido[2,3-d]pyrimidin-6-yl trifluoromethanesulfonate

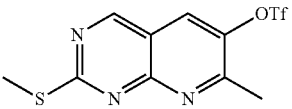 [SMILES: CSc1ncc2cc(OS(=O)(=O)C(F)(F)F)c(C)nc2n1]

A suspension of 7-methyl-2-(methylthio)pyrido[2,3-d]pyrimidin-6-ol (B4, 20 g, 97 mmol) and DIEA (37 g, 290 mmol) in DCM (500 mL) was stirred at 0° C. A solution of 1,1,1-trifluoro-N-phenyl-N-((trifluoromethyl)sulfonyl)methanesulfonamide (34 g, 97 mmol) in DCM (130 mL) was added slowly. The reaction mixture was slowly warmed to rt over 3 h. The reaction mixture was quenched with sat'd NaHCO$_3$ (aq, 500 mL) and then the solution was filtered through a pad of celite. The filtrate was extracted with DCM (3×100 mL) and the combined organics were washed with water (2×20 mL), dried over anhydrous Na$_2$SO$_4$, filtered and concentrated under reduced pressure. The crude was suspended in hexanes and the solids were filtered to obtain 7-methyl-2-(methylthio)pyrido[2,3-d]pyrimidin-6-yltrifluoromethanesulfonate (23 g, 70% yield) as a yellow-brown solid. $^1$H NMR (500 MHz, DMSO-d$_6$): δ 9.55 (s, 1H), 8.77 (s, 1H), 2.75 (s, 3H), 2.65 (s, 3H); MS (ESI) m/z: 340.0 (M+H$^+$).

General Method G: Oxidation and Substitution

Example B6

7-methyl-2-((1-methyl-1H-pyrazol-4-yl)amino)pyrido[2,3-d]pyrimidin-6-yl trifluoromethanesulfonate

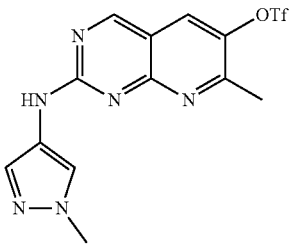 [SMILES: Cc1nc2nc(Nc3cnn(C)c3)ncc2cc1OS(=O)(=O)C(F)(F)F]

A solution of 7-methyl-2-(methylthio)pyrido[2,3-d]pyrimidin-6-yl trifluoromethanesulfonate (B5, 1.0 g, 2.9 mmol) in THF (50 mL) was cooled to 0° C. mCPBA (0.51 g, 2.9 mmol) was added portion-wise and the reaction mixture was stirred under the same conditions for 1 h. 1-Methyl-1H-pyrazol-4-amine (0.29 g, 2.9 mmol) and DIEA (1.0 mL, 5.9 mmol) were added and the reaction mixture was stirred at rt overnight. The reaction was quenched with water (50 mL) and extracted with DCM (3×50 mL). The combined organic extracts were washed with sat'd NaHCO$_3$ (2×50 mL), brine (2×50 mL), then dried over anhydrous Na$_2$SO$_4$ and concentrated under reduced pressure to obtain 7-methyl-2-((1-methyl-1H-pyrazol-4-yl)amino)pyrido[2,3-d]pyrimidin-6-yl trifluoromethanesulfonate (0.81 g, 71% yield) as a brown solid. NMR (500 MHz, DMSO-d$_6$): δ 10.3 (s, 1H), 9.33 (s, 1H), 8.49 (s, 1H), 8.20 (s, 1H), 7.64 (s, 1H), 3.88 (s, 3H), 2.67 (s, 3H); MS (ESI) m/z: 389.0 (M+H$^+$).

General Method H: Condensation Under tris(((trifluoromethyl)sulfonyl)oxy)ytterbium as a Catalyst

Example B7

3-bromo-7-chloro-1,6-naphthyridine

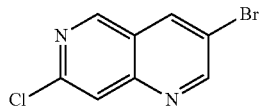 [SMILES: Clc1cc2ncc(Br)cc2cn1]

A mixture of 4-amino-6-chloronicotinaldehyde (2.2 g, 14 mmol) and 2-bromo-1,1-dimethoxyethane (3.3 mL, 28 mmol) in DCE (50 mL) was treated with tris(((trifluoromethyl)sulfonyl)oxy)ytterbium (0.55 g, 0.89 mmol). The reaction mixture was heated at 100° C. for 12 h. The reaction mixture was cooled to rt and concentrated under reduced pressure. The crude was purified by silica gel column chromatography (0 to 100% EtOAc/hexanes) to afford 3-bromo-7-chloro-1,6-naphthyridine (2.7 g, 79% yield) as a yellow solid. MS (ESI) m/z: 243.0 (M+H$^+$) and 245.0.

General Method I: Wittig Reaction and Cyclization

Example B8 cl 7-chloro-1,6-naphthyridin-2-amine

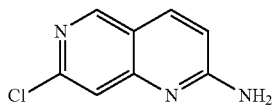 [SMILES: Nc1ccc2cnc(Cl)cc2n1]

A solution of 4-amino-6-chloronicotinaldehyde (0.5 g, 3.2 mmol) and (triphenylphosphoranylidene)acetonitrile (0.97 g, 3.2 mmol) in THF (5 mL) was stirred at rt overnight. The reaction mixture was concentrated and the solid residue was suspended in EtOAc (5 mL). The solids were filtered to obtain (E)-3-(4-amino-6-chloropyridin-3-yl)acrylonitrile (0.51 g, 89% yield). A mixture of (E)-3-(4-amino-6-chloropyridin-3-yl)acrylonitrile (0.51 g, 2.9 mmol) and DBU (0.85 mL, 5.7 mmol) was heated to 170° C. for 5 h in microwave. The reaction mixture was cooled to rt and quenched with sat'd NaHCO$_3$ (aq, 10 mL). The solution was extracted with EtOAc (3×10 mL). The combined organics were washed with brine, dried over anhydrous Na$_2$SO$_4$, filtered and concentrated under reduced pressure to afford 7-chloro-1,6-naphthyridin-2-amine (0.24 g, 47% yield). MS (ESI) m/z: 180.0 (M+H$^+$).

General Method J: Amide Coupling

Example B9

N-(6-bromoquinazolin-2-yl)acetamide

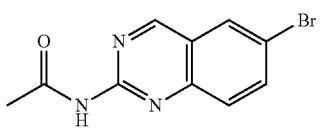

A solution of 6-bromoquinazolin-2-amine (0.20 g, 0.89 mmol) in acetic anhydride (5 mL) was heated to 140° C. for 45 min. The reaction mixture was cooled to rt and the solids were filtered, washed with water and dried under vacuum overnight to obtain N-(6-bromoquinazolin-2-yl)acetamide (0.09 g, 38% yield). MS (ESI) m/z: 266.0 (M+H$^+$) and 268.0.

General Method K: Reaction with POCl$_3$

Example B12

6-bromo-2-chloropyrido[2,3-d]pyrimidine

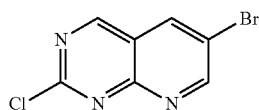 [SMILES: Clc1ncc2cc(Br)cnc2n1]

6-Bromopyrido[2,3-d]pyrimidin-2-ol (B11, 5.0 g, 22 mmol) was treated with POCl$_3$ (31 mL) and the reaction was heated to 100° C. overnight. The reaction was cooled to rt and concentrated under reduced pressure. Ice (~200-300 g) was added to the remaining residue and the solution was extracted with EtOAc (3×250 mL). The combined organics were washed with sat'd NaHCO$_3$(aq, 100 mL). The organic layer was dried over anhydrous Na$_2$SO$_4$, filtered, and concentrated under reduced pressure to afford 6-bromo-2-chloropyrido[2,3-d]pyrimidine (4.5 g, 83% yield) as a yellow solid. MS (ESI) m/z: 244.0 (M+H$^+$) and 246.0.

Using the General Methods B-K above, the following Intermediates of Table B were prepared.

TABLE B

| Ex No | SM | Product | Method | Yield (%) | $^1$H NMR (400 or 500 MHz, DMSO-d$_6$): δ | MS (m/z: M + H$^+$) |
|---|---|---|---|---|---|---|
| B10 | (structure) | (structure) | C & D | crude | 12.3 (brs, 1H), 8.55 (brs, 1H), 8.25 (brs, 1H), 7.80 (brs, 1H), 2.86 (brs, 3H). | 255.0 257.0 |
| B11 | (structure) | (structure) | B | 89 | No Data | 226.0 228.0 |

TABLE B-continued

| Ex No | SM | Product | Method | Yield (%) | ¹H NMR (400 or 500 MHz, DMSO-d$_6$): δ | MS (m/z: M + H⁺) |
|---|---|---|---|---|---|---|
| B13 | B12 | (structure) | C | 82 | 9.13 (s, 1H), 8.90 (t, J = 2.8 Hz, 1H), 8.52 (t, J = 2.6 Hz, 1H), 2.89 (m, 3H). | 239.0 241.0 |
| B14 | B10 | (structure) | K | 93 | 9.18 (s, 1H), 8.68 (s, 1H), 8.19 (brm, 1H), 2.89 (d, J = 4.4 Hz, 3H). | 275.0 |
| B15 | B14 | (structure) | C | 94 | 8.61 (s, 1H), 8.12 (s, 1H), 7.34 (s, 1H), 7.25 (s, 1H), 2.95 (d, J = 4.5 Hz, 3H), 2.85 (d, J = 4.7 Hz, 3H). | 268.0 270.0 |
| B16 | B14 | (structure) | C | 99 | 8.62 (s, 1H), 8.15 (s, 1H), 7.36 (s, 1H), 7.20 (brs, 2H), 2.85 (m, 3H). | 254.0 256.0 |
| B17 | B14 | (structure) | C | crude | No Data | 298.0 300.0 |
| B18 | B14 | (structure) | C | 29 | No Data | 310.0 312.0 |
| B19 | B14 | (structure) | C | 73 | No Data | 324.0 326.0 |
| B20 | B14 | (structure) | C | 88 | No Data | 311.0 313.0 |

TABLE B-continued
| Ex No | SM | Product | Method | Yield (%) | ¹H NMR (400 or 500 MHz, DMSO-d₆): δ | MS (m/z: M + H⁺) |
|---|---|---|---|---|---|---|
| B21 | B11 | 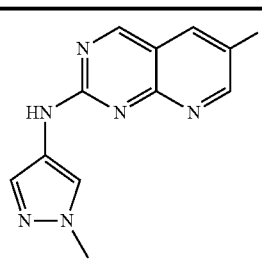 | C | 83 | No Data | 305.0 307.0 |
| B22 | 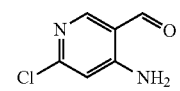 | 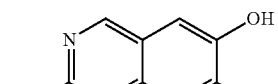 | B | 88 | 10.9 (s, 1H), 9.02 (s, 1H), 7.78 (s, 1H), 7.55 (s, 1H), 2.55 (s, 3H). | 195.1 |
| B23 | B22 | 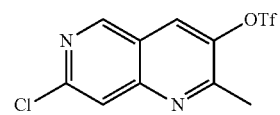 [SMILES: Cc1nc2cc(Cl)ncc2cc1OS(=O)(=O)C(F)(F)F] | F | 90 | No Data | 327.0 |
| B24 | 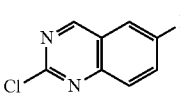 | 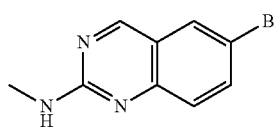 | C | 77 | No Data | 238.0 240.0 |
| B25 | 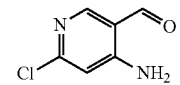 | 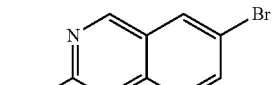 | B | 58 | 9.63 (d, J = 0.8 Hz, 1H), 9.24 (d, J = 2.4 Hz, 1H), 9.00 (dd, J = 0.9 and 2.4 Hz, 1H), 8.14 (s, 1H). | 242.8 245.0 |
| B26 | B25 | 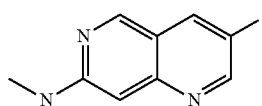 | C | 61 | No Data | 238.0 240.0 |
| B27 | 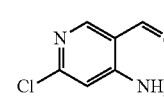 and 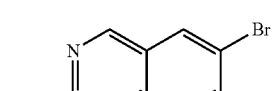 | 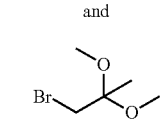 | H | 61 | 9.22 (s, 1H), 8.94 (s, 1H), 8.01 (s, 1H), 2.82 (s, 3H). | 257.0 258.8 |
| B28 | B27 |  | C | 18 | No Data | 358.0 360.0 |
| B29 | B27 | 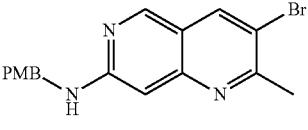 | C | 23 | 8.94 (s, 1H), 8.51 (s, 1H), 7.17 (d, J = 8.3 Hz, 2H), 6.87 (d, J = 8.3 Hz, 2H), 6.71 (s, 1H), 4.86 (s, 2H), 3.71 (s, 3H), 3.09 (s, 3H), 2.67 (s, 3H). | 372.0 374.0 |
| B30 | B8 |  | D | 69 | No Data | 258.0 260.0 262.0 |

TABLE B-continued
| Ex No | SM | Product | Method | Yield (%) | $^1$H NMR (400 or 500 MHz, DMSO-d$_6$): δ | MS (m/z: M + H$^+$) |
|---|---|---|---|---|---|---|
| B31 | B30 | 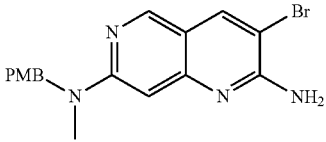 | C | 14 | No Data | 373.0 375.0 |
| B32 | B14 | 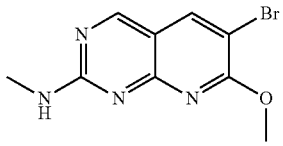 | C | 57 | No Data | 269.0 271.0 |
| B33 | B25 | 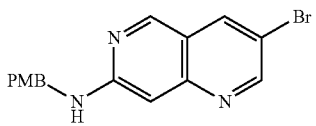 | C | 50 | No Data | 344.0 346.0 |
| B34 | B10 | 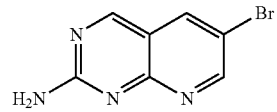 | C | 92 | 9.17 (s, 1H), 8.91 (d, J = 2.7 Hz, 1H), 8.52 (d, J = 2.7 Hz, 1H), 7.44 (s, 2H). | 225.0 227.0 |
| B35 | B14 | 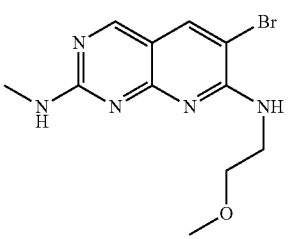 [SMILES: CNc1ncc2cc(Br)c(NCCOC)nc2n1] | C | 79 | No Data | 312.2 314.2 |
| B36 | B5 | 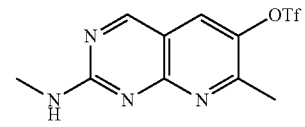 [SMILES: CNc1ncc2cc(OS(=O)(=O)C(F)(F)F)c(C)nc2n1] | G | 77 | 9.20 (s, 1H), 8.40 (s, 1H), 8.0 (brs, 1H), 2.90 (d, J = 4.8 Hz, 3H), 2.61 (s, 3H). | 323.2 |
| B37 | 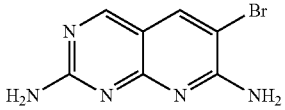 | 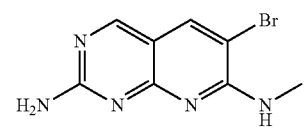 | C & D | 36 | No Data | 239.9 |
| B38 | 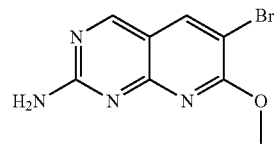 | 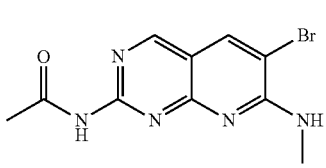 [SMILES: CNc1nc2nc(NC(C)=O)ncc2cc1Br] | K, C & D | 53 | 8.62 (s, 1H), 8.10 (s, 1H), 7.2 (brs, 1H), 6.8 (brs, 2H), 2.91 (d, J = 4.8 Hz, 3H). | 254.1 |
| B39 |  |  | K, C & D | 52 | 9.09 (s, 1H), 8.59 (s, 1H), 7.7 (brs, 2H), 4.06 (s, 3H). | 255.2 257.2 |
| B40 | B38 |  | J | 27 | 12.4 (brs, 1H), 8.6 (brs, 1H), 7.92 (d, J = 9.2 Hz, 1H), 6.65 (d, J = 10.8 Hz, 1H), 3.11 (s, 3H), 1.79 (s, 3H). | 295.9 |

TABLE B-continued

| Ex No | SM | Product | Method | Yield (%) | $^1$H NMR (400 or 500 MHz, DMSO-$d_6$): δ | MS (m/z: M + H$^+$) |
|---|---|---|---|---|---|---|
| B41 | 4-bromo-2-fluoro-5-methoxybenzaldehyde; Guanidine carbonate | 6-bromo-7-methoxyquinazolin-2-amine | B | 63 | 8.92 (s, 1H), 8.06 (s, 1H), 6.89 (s, 1H), 6.84 (brs, 2H), 3.94 (s, 3H). | 254.2 |
| B42 | 2-chloro-5-iodopyrimidin-4-amine; ethyl acrylate | 2-chloropyrido[2,3-d]pyrimidin-7(8H)-one | I | 54 | 12.7 (s, 1H), 8.95 (s, 1H), 7.98 (d, J = 9.6 Hz, 1H), 6.65 (d, J = 9.2 Hz, 1H). | 179.9 |
| B43 | B42 | 7-chloro-N-methylpyrido[2,3-d]pyrimidin-2-amine | K | 62 | 9.75 (s, 1H), 8.77 (d, J = 8.4 Hz, 1H), 7.93 (d, J = 8.8 Hz, 1H). | 200.2 |
| B44 | B43 |  | C | 67 | 8.53 (s, 1H), 7.62 (m, 2H), 7.05 (br s, 1H), 6.45 (d, J = 8.8 Hz, 1H), 3.56 (m, 2H), 3.50 (m, 2H), 3.29 (s, 3H), 2.84 (d, J = 4.4 Hz, 3H). | 233.9 |
| B45 | B43 |  | C | 49 | 8.53 (s, 1H), 7.61 (d, J = 8.8 Hz, 1H), 7.53 (brs, 1H), 7.05 (brs, 1H), 6.50 (d, J = 8.8 Hz, 1H), 3.48-3.55 (m, 2H), 3.40 (m, 1H), 3.28 (s, 3H), 2.84 (d, J = 4.4 Hz, 3H), 1.18 (d, J = 6.0 Hz, 3H). | 248.0 |
| B46 | B43 |  | C | 64 | 8.53 (s, 1H), 7.61 (d, J = 8.4 Hz, 1H), 7.52 (brs, 1H), 7.03 (brs, 1H), 6.50 (d, J = 8.4 Hz, 1H), 3.48-3.57 (m, 2H), 3.40 (m, 1H), 3.29 (s, 3H), 2.84 (d, J = 4.8 Hz, 3H), 1.12 (d, J = 6.0 Hz, 3H). | 248.1 |
| B47 | B44 |  | D | 37 | No Data | 311.9 |
| B48 | B45 |  | D | 60 | 8.61 (s, 1H), 8.15 (s, 1H), 7.35 (brs, 1H), 6.80 (brs, 1H), 3.64 (m, 1H), 3.47-3.60 (m, 2H), 3.25 (s, 3H), 2.84 (s, 3H), 1.11 (d, J = 5.6 Hz, 3H). | 326.0 |

TABLE B-continued

| Ex No | SM | Product | Method | Yield (%) | ¹H NMR (400 or 500 MHz, DMSO-d$_6$): δ | MS (m/z: M + H⁺) |
|---|---|---|---|---|---|---|
| B49 | B46 | (structure) | D | 62 | 8.61 (s, 1H), 8.15 (s, 1H), 7.36 (brs, 1H), 6.79 (brs, 1H), 3.64 (m, 1H), 3.52 (m, 2H), 3.29 (s, 3H), 2.84 (s, 3H), 1.11 (d, J = 5.6 Hz, 3H). | 325.9 |
| B50 | (structure) PMBCl Pyridinium tribromide | (structure) | C & D | 76 | 12.17 (1H, s), 8.52 (1H, s), 8.39 (1H, s), 7.20 (2H, d, J = 8.4 Hz), 6.90-6.92 (2H, m), 6.40 (1H, s), 4.76 (2H, s), 3.73 (3H, s), 3.13 (3H, s). | 387.2 389.2 |
| B51 | B50 BOP CH$_3$NH$_2$ | (structure) | F & C | 76 | 8.52 (s, 1H), 8.17 (s, 1H), 7.13 (d, J = 8.4 Hz, 2H), 7.01 (q, J = 4.6 Hz, 1H), 6.86 (d, J = 8.4 Hz, 2H), 6.36 (s, 1H), 4.80 (s, 2H), 3.70 (s, 3H), 3.02 (s, 3H), 2.92 (d, J = 4.6 Hz, 3H). | 387.2 389.2 |
| B52 | B50 BOP PMBNH$_2$ | (structure) | F & C | 78 | No Data | 493.2 495.2 |
| B53 | B50 | (structure) | K | 95 | No Data | 392.0 |
| B54 | B53 NaOCH$_3$ | (structure) | C | 67 | No Data | 388.0 390.0 |
| B55 | B43 | (structure) | C | 52 | 8.97 (s, 1H), 8.05 (d, J = 8.8 Hz, 1H), 7.56 (brs, 1H), 6.67 (d, J = 8.4 Hz, 1H), 4.50 (t, J = 4.8 Hz, 2H), 3.70 (t, J = 4.8 Hz, 2H), 3.32 (s, 3H), 2.87 (d, J = 4.4 Hz, 3H). | 235.0 |
| B56 | B55 | (structure) | D | 61 | 8.99 (s, 1H), 8.45 (s, 1H), 7.75 (brs, 1H), 4.56 (s, 2H), 3.72 (br s, 2H), 3.33 (s, 3H), 2.87 (br s, 3H). | 312.9 |
| B57 | B41 | (structure) | J | 88 | 10.6 (s, 1H), 9.26 (s, 1H), 8.36 (s, 1H), 7.24 (s, 1H), 4.03 (s, 3H), 2.27 (s, 3H). | 296.1 |

TABLE B-continued

| Ex No | SM | Product | Method | Yield (%) | $^1$H NMR (400 or 500 MHz, DMSO-$d_6$): δ | MS (m/z: M + H$^+$) |
|---|---|---|---|---|---|---|
| B58 | B57 MeI K$_2$CO$_3$ | [structure: 6-bromo-7-methoxy-N-methyl-pyrido[2,3-d]pyrimidin-2-amine] | Methylation & hydrolysis | 35 | 8.89 (brs, 1H), 8.06 (s, 1H), 7.40 (brs, 1H), 6.98 (br s, 1H), 3.96 (s, 3H), 2.86 (d, J = 4.8 Hz, 3H). | 268.1 |
| B59 | B38 | [structure: N-(6-bromo-7-(methylamino)pyrido[2,3-d]pyrimidin-2-yl)cyclopropanecarboxamide] | J | 49 | No Data | 322.0 324.0 |

Using the General Method A above, the following Intermediates of Table C were prepared.

TABLE C

| Ex No | Product | Yield (%) | $^1$H NMR (400 or 500 MHz, DMSO-$d_6$): δ | MS (m/z: M + H$^+$) |
|---|---|---|---|---|
| C1 | [structure: 7-chloro-2-methyl-3-(4,4,5,5-tetramethyl-1,3,2-dioxaborolan-2-yl)-1,6-naphthyridine] | 72 | No Data | 305.2 |
| C2 | [structure: N-(4-methoxybenzyl)-N,2-dimethyl-3-(4,4,5,5-tetramethyl-1,3,2-dioxaborolan-2-yl)-1,6-naphthyridin-7-amine] | 10 | No Data | 420.2 |
| C3 | [structure: N,7-dimethyl-6-(4,4,5,5-tetramethyl-1,3,2-dioxaborolan-2-yl)pyrido[2,3-d]pyrimidin-2-amine] | 28 | No Data | 219.0 (boronic acid) |
| C4 | [structure: N-methyl-6-(4,4,5,5-tetramethyl-1,3,2-dioxaborolan-2-yl)quinazolin-2-amine] | 60 | No Data | 286.2 |

TABLE C-continued

| Ex No | Product | Yield (%) | ¹H NMR (400 or 500 MHz, DMSO-d₆): δ | MS (m/z: M + H⁺) |
|---|---|---|---|---|
| C5 | | 87 | 8.57 (s, 1H), 7.86 (s, 1H), 7.24 (brs, 1H), 7.13 (brs, 1H), 2.95 (d, J = 4.7 Hz, 3H), 2.84 (d, J = 4.6 Hz, 3H), 1.21 (s, 12 H). | 234.2 |
| C6 | | crude | No Data | 303.3 |
| C7 | | crude | No Data | 317.0 |
| C8 | | crude | No Data | 301.9 |

General Method L: Suzuki Reaction

Example D1

2,4-difluoro-5-(isoquinolin-7-yl)aniline

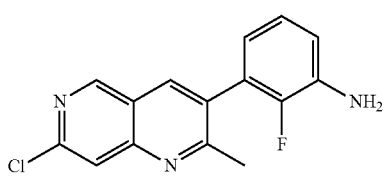 [SMILES: Cc1nc2cc(Cl)ncc2cc1-c1cccc(N)c1F]

A solution of 7-chloro-2-methyl-1,6-naphthyridin-3-yl trifluoromethanesulfonate (B27, 3.0 g, 9.2 mmol), 2-fluoro-3-(4,4,5,5-tetramethyl-1,3,2-dioxaborolan-2-yl)aniline (A6, 2.2 g, 9.2 mmol) and K₂CO₃ (3.81 g, 28 mmol) in 1,4-dioxane (15 mL) and water (2.5 mL) was degassed with Ar for 5 min. PdCl₂(dppf) (0.34 g, 0.46 mmol) was added and the reaction mixture was heated at 80° C. for 1 h. The reaction mixture was cooled to rt and then the solution was filtered through a pad of celite. The filtrate was concentrated under reduced pressure and the crude was purified by silica gel column chromatography (0 to 100% EtOAc/hexanes) to afford 3-(7-chloro-2-methyl-1,6-naphthyridin-3-yl)-2-fluoroaniline (2.0 g, 76% yield) as a brown solid. ¹H NMR (500 MHz, DMSO-d₆): δ 9.27 (s, 1H), 8.45 (s, 1H), 8.02 (s, 1H), 7.03 (t, J=7.7 Hz, 1H), 6.90 (t, J=8.3 Hz, 1H), 6.56 (t, J=6.9 Hz, 1H), 5.35 (s, 2H); MS (ESI) m/z: 288.0 (M+H⁺).

Using the General Method L above, the following Intermediates of Table D were prepared.

TABLE D

| Ex No | SM | Product | Yield (%) | $^1$H NMR (400 or 500 MHz, DMSO-$d_6$): δ | MS (m/z: M + H$^+$) |
|---|---|---|---|---|---|
| D2 | A16 B3 | | 81 | No Data | 296.4 |
| D3 | A6 B5 | | 81 | 9.43 (s, 1H, s), 8.35 (s, 1H, s), 7.02 (t, J = 7.7 Hz, 1H), 6.89 (t, J = 8.3 Hz, 1H), 6.54 (t, J = 6.9 Hz, 1H), 5.35 (s, 2H), 2.65 (s, 3H), 2.56 (s, 3H). | 301.2 |
| D4 | B23 | | 52 | No Data | 270.0 |
| D5 | A4 B23 | | 85 | 9.23 (s, 1H), 8.34 (s, 1H), 7.98 (s, 1H), 7.10 (dd, J = 8.2 and 11.5 Hz, 1H), 6.83 (dd, J = 2.3 and 8.7 Hz, 1H), 6.61 (m, 1H), 5.32 (s, 2H), 2.61 (s, 3H). | 288.1 |
| D6 | A5 B23 | | 43 | No Data | 288.0 |
| D7 | A1 B23 | | 41 | No Data | 302.0 |
| D8 | A10 B23 | | 85 | No Data | 306.0 |
| D9 | A22 B5 | | 77 | 9.45 (s, 1H), 8.39 (s, 1H), 7.43 (t, J = 7.9 Hz, 1H), 6.91 (d, J = 8.5 Hz, 1H), 6.66 (m, 1H), 6.30 (s, 2H), 2.66 (s, 3H), 2.55 (s, 3H). | 308.2 |

TABLE D-continued

| Ex No | SM | Product | Yield (%) | $^1$H NMR (400 or 500 MHz, DMSO-$d_6$): δ | MS (m/z: M + H$^+$) |
|---|---|---|---|---|---|
| D10 | A10 B25 | [6-(4,5-difluoro-2-aminophenyl)-3-chloro-2,7-naphthyridine] | 82 | 9.38 (s, 1H), 9.24 (t, J = 2.1 Hz, 1H), 8.72 (s, 1H), 8.12 (s, 1H), 7.29 (t, J = 10.9 Hz, 1H), 7.05 (m, 1H), 5.25 (s, 2H). | 292.0 |
| D11 | 2-chloro-4-amino-pyrimidine-5-carbaldehyde and 1-(2-bromo-4-fluoro-5-aminophenyl)propan-2-one | [2-chloro-6-(2-bromo-4-fluoro-5-aminophenyl)-7-methyl-pyrido[2,3-d]pyrimidine] Condensation: Method B | Crude | No Data | 366.0 368.0 |
| D12 | A2 B23 | [6-(2-methyl-5-aminophenyl)-3-chloro-2-methyl-1,8-naphthyridine] | 69 | No Data | 284.0 |
| D13 | A4 B3 | [2-(methylamino)-6-(4-fluoro-3-aminophenyl)-7-methyl-pyrido[2,3-d]pyrimidine] | 57 | 9.09 (s, 1H), 7.95 (s, 1H), 7.6 (brs, 1H), 7.06 (m, 1H), 6.78 (dd, J = 2.0 and 8.8 Hz, 1H), 6.54 (m, 1H), 5.2 (brs, 2H), 2.90 (d, J = 4.4 Hz, 3H), 2.49 (s, 3H). | 284.1 |
| D14 | A14 B3 | [2-(methylamino)-6-(4-fluoro-2-methyl-5-aminophenyl)-7-methyl-pyrido[2,3-d]pyrimidine] | 62 | 9.09 (s, 1H), 7.98 (s, 1H), 7.7 (brs, 1H), 6.91 (d, J = 10.4 Hz, 1H), 6.54 (d, J = 7.2 Hz, 1H), 4.8 (brs, 2H), 2.91 (d, J = 4.4 Hz, 3H), 2.42 (s, 3H), 2.11 (s, 3H). | 297.9 |
| D15 | A13 B36 | [2-(methylamino)-6-(3-fluoro-2-methyl-5-aminophenyl)-7-methyl-pyrido[2,3-d]pyrimidine] | 65 | 9.07 (s, 1H), 7.89 (s, 1H), 7.7 (brs, 1H), 6.38 (dd, J = 12.4 Hz & 1.6 Hz, 1H), 6.23 (s, 1H), 5.3 (brs, 2H), 2.90 (d, J = 4.4 Hz, 3H), 2.32 (s, 3H), 1.75 (s, 3H). | 298.0 |
| D16 | A17 B24 | [2-(methylamino)-6-(2-methyl-3-aminophenyl)-quinazoline] | Crude | No Data | 265.1 |

TABLE D-continued

| Ex No | SM | Product | Yield (%) | $^1$H NMR (400 or 500 MHz, DMSO-$d_6$): δ | MS (m/z: M + H$^+$) |
|---|---|---|---|---|---|
| D17 | A12 B36 | | 61 | 9.09 (s, 1H), 8.00 (s, 1H), 7.7 (brs, 1H), 7.01 (m, 1H), 6.53 (m, 1H), 5.4 (brs, 2H), 2.91 (d, J = 4.8 Hz, 3H), 2.41 (s, 3H). | 301.8 |
| D18 | A17 B36 | | 54 | No Data | 280.1 |
| D19 | A2 B36 | | 53 | No Data | 280.1 |
| D20 | A3 B24 | | 66 | 9.15 (s, 1H), 7.90 (s, 1H), 7.7 (m, 1H), 7.53 (d, J = 8.8 Hz, 1H), 7.42 (brs, 1H), 6.97 (m, 1H), 6.73 (dd, J = 3.2 and 7.2 Hz, 1H), 6.56 (m, 1H), 5.0 (brs, 2H), 2.90 (d, J = 4.8 Hz, 3H). | 268.8 |
| D21 | A19 B24 | | 49 | No Data | 319.2 |
| D22 | A8 B24 | | 33 | 9.15 (s, 1H), 7.93 (s, 1H), 7.78 (d, J = 8.4 Hz, 1H), 7.55 (m, 1H), 7.4 (brs, 1H), 6.52 (m, 2H), 5.4 (brs, 2H), 2.90 (d, J = 4.0 Hz, 3H). | 286.8 |
| D23 | A21 B24 | | 33 | No Data | 285.1 |

TABLE D-continued

| Ex No | SM | Product | Yield (%) | $^1$H NMR (400 or 500 MHz, DMSO-$d_6$): δ | MS (m/z: M + H$^+$) |
|---|---|---|---|---|---|
| D24 | A18 B24 | | 41 | 9.11 (s, 1H), 7.67 (s, 1H), 7.57 (d, J = 8.8 Hz, 1H), 7.48 (d, J = 8.8 Hz, 1H), 7.41 (m, 2H), 6.64 (d, J = 8.8 Hz, 1H), 6.51 (s, 1H), 5.9 (brs, 2H), 2.91 (d, J = 4.4 Hz, 3H). | No Data |
| D25 | A20 B36 | | 42 | 9.08 (s, 1H), 7.93 (s, 1H), 7.7 (brs, 1H), 7.18 (d, J = 8.4 Hz, 1H), 6.62 (dd, J = 2.8 and 8.4 Hz, 1H), 6.52 (m, 1H), 5.3 (brs, 2H), 2.91 (d, J = 4.0 Hz, 3H), 2.36 (s, 3H). | No Data |
| D26 | A21 B36 | | 45 | No Data | 300.0 |
| D27 | A20 B24 | | 85 | 9.13 (s, 1H), 7.78 (d, J = 1.6 Hz, 1H), 7.70 (dd, J = 2.0 and 8.8 Hz, 1H), 7.5 (m, 1H), 7.40 (brs, 1H), 7.16 (d, J = 8.4 Hz, 1H), 6.64 (d, J = 2.4 Hz, 1H), 6.57 (dd, J = 2.4 and 8.4 Hz, 1H), 5.3 (brs, 2H), 2.90 (d, J = 4.4 Hz, 3H). | 285.1 |
| D28 | A6 B24 | | 94 | 9.14 (s, 1H), 7.93 (s, 1H), 7.82 (d, J = 8.8 Hz, 1H), 7.53 (d, J = 8.8 Hz, 1H), 7.4 (brs, 1H), 6.96 (t, J = 7.6 Hz, 1H), 6.77 (t, J = 8.0 Hz, 1H), 6.68 (t, J = 7.2 Hz, 1H), 5.2 (brs, 2H), 2.91 (d, J = 4.8 Hz, 3H). | 268.9 |
| D29 | A18 B36 | | 50 | No Data | 334.4 |
| D30 | A16 B24 | | 43 | No Data | 281.3 |

TABLE D-continued
| Ex No | SM | Product | Yield (%) | ¹H NMR (400 or 500 MHz, DMSO-d₆): δ | MS (m/z: M + H⁺) |
|---|---|---|---|---|---|
| D31 | A23 B15 | 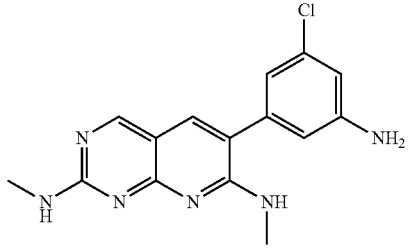 [SMILES: CNc1ncc2cc(-c3cc(N)cc(Cl)c3)c(NC)nc2n1] | 85 | 8.61 (s, 1H), 7.53 (s, 1H), 7.13 (brs, 1H), 6.64 (s, 1H), 6.2 (brs, 1H), 6.5 (m, 2H), 5.41 (brs, 2H), 2.87 (m, 6H). | 315.1 |
| D32 | A6 B23 | 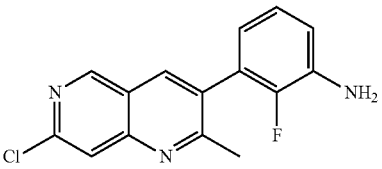 [SMILES: Cc1nc2cc(Cl)ncc2cc1-c1cccc(N)c1F] | 54 | 9.28 (s, 1H), 8.45 (s, 1H), 8.04 (s, 1H), 7.03 (t, J = 7.7 Hz, 1H), 6.90 (t, J = 8.3 Hz, 1H), 6.56 (t, J = 7.0 Hz, 1H), 5.35 (s, 2H), 2.57 (s, 3H). | 288.0 |
| D33 | 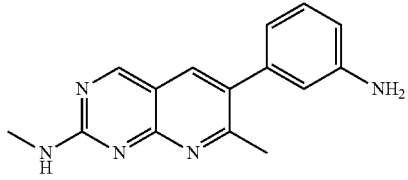<br>B36 | 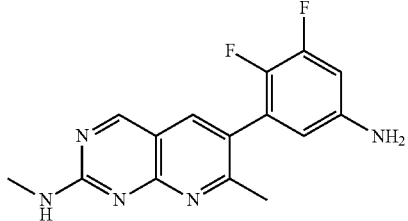 [SMILES: CNc1ncc2cc(-c3cc(N)cc(F)c3F)c(C)nc2n1] | 59 | No Data | 266.3 |
| D34 | A8 B36 | 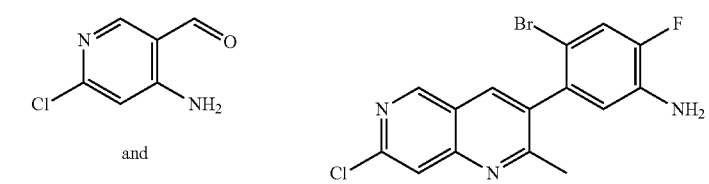 | 33 | No Data | 302.1 |
| D35 | 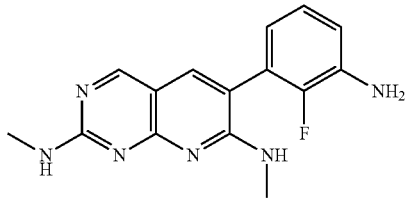<br>and | Condensation: Method B | crude | No Data | 366.1 368.1 |
| D36 | A6 B15 | | crude | No Data | 299.2 |

TABLE D-continued

| Ex No | SM | Product | Yield (%) | ¹H NMR (400 or 500 MHz, DMSO-d₆): δ | MS (m/z: M + H⁺) |
|---|---|---|---|---|---|
| D37 | A23 B38 | (structure) | crude | No Data | 301.1 |
| D38 | A5 B47 | (structure) | 55 | No Data | 343.1 |
| D39 | A5 B48 | (structure) | 80 | 8.64 (s, 1H), 7.59 (s, 1H), 7.17 (brs, 1H), 6.42 (s, 1H), 6.37 (d, J = 11.6 Hz, 1H), 6.31 (d, J = 9.6 Hz, 1H), 6.18 (brs, 1H), 5.61 (brs, 2H), 3.57 (m, 2H), 3.39 (m, 1H), 3.25 (s, 3H), 2.87 (d, J = 4.4 Hz, 3H), 1.09 (d, J = 5.6 Hz, 3H). | 357.1 |
| D40 | A5 B49 | (structure) | 41 | 8.63 (s, 1H), 7.59 (s, 1H), 7.19 (brs, 1H), 6.41 (s, 1H), 6.36 (d, J = 11.6 Hz, 1H), 6.31 (d, J = 8.8 Hz, 1H), 6.18 (brs, 1H), 5.61 (brs, 2H), 3.58 (m, 2H), 3.37 (m, 1H), 3.25 (s, 3H), 2.85 (d, J = 4.8 Hz, 3H), 1.09 (d, J = 5.6 Hz, 3H). | 357.0 |
| D41 | A5 B15 | (structure) | 58 | 8.61 (s, 1H), 7.50 (s, 1H), 7.14 (br s, 1H), 6.58 (brs, 1H), 6.46 (s, 1H), 6.28-6.40 (m, 2H), 5.57 (brs, 2H), 2.89 (d, J = 4.0 Hz, 3H), 2.87 (d, J = 4.8 Hz, 3H). | 298.9 |

TABLE D-continued

| Ex No | SM | Product | Yield (%) | $^1$H NMR (400 or 500 MHz, DMSO-$d_6$): δ | MS (m/z: M + H$^+$) |
|---|---|---|---|---|---|
| D42 | A6 B39 | | 36 | 8.97 (s, 1H), 8.00 (s, 1H), 7.08 (s, 2H), 6.91 (t, J = 7.6 Hz, 1H), 6.79 (t, J = 8.0 Hz, 1H), 6.51 (t, J = 6.4 Hz, 1H), 5.18 (s, 2H), 3.92 (s, 3H). | 285.9 |
| D43 | A6 B38 | | 54 | No Data | 285.1 |

General Method M: Substitution Reaction

Example E1

3-(5-amino-2,4-difluorophenyl)-N-(4-methoxybenzyl)-N,2-dimethyl-1,6-naphthyridin-7-amine

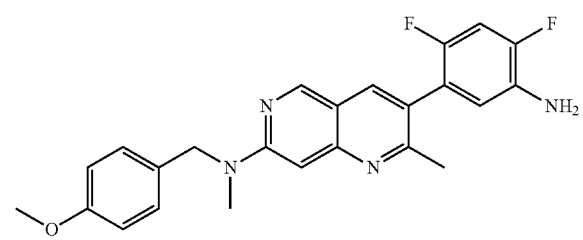 [SMILES: COc1ccc(CN(C)c2cc3nc(C)c(-c4cc(N)c(F)cc4F)cc3cn2)cc1]

A solution of 5-(7-chloro-2-methyl-1,6-naphthyridin-3-yl)-2,4-difluoroaniline (D8, 0.60 g, 2.0 mmol) and 4-methoxy-N-methylbenzylamine (1.2 g, 8.0 mmol) in NMP (7 mL) was treated with DIEA (1.4 mL, 8.0 mmol). The pressure tube was capped tightly and the mixture heated to 185° C. for 3 days. The mixture was cooled to rt and diluted with sat'd NaHCO$_3$ (aq, 20 mL). The solution was extracted with EtOAc (4×20 mL) and the combined organics were washed with 5% LiCl (aq), then brine. The organic layer was dried over anhydrous MgSO$_4$ and concentrated under reduced pressure. The crude was purified by silica gel column chromatographed (5 to 50% EtOAc/hexanes) to obtain 3-(5-amino-2,4-difluorophenyl)-N-(4-methoxybenzyl)-N,2-dimethyl-1,6-naphthyridin-7-amine (0.77 g, 94% yield). MS (ESI) m/z: 421.2 (M+H$^+$).

Using the General Method M above, the following Intermediates of Table E were prepared.

TABLE E

| Ex No | SM | Product | Yield (%) | $^1$H NMR (400 or 500 MHz, DMSO-$d_6$): δ | MS (m/z: M + H$^+$) |
|---|---|---|---|---|---|
| E2 | D10 | | 29 | No Data | 393.2 |
| E3 | D5 | | 68 | 8.95 (s, 1H), 7.95 (s, 1H), 7.15 (d, J = 8.4 Hz, 1H), 7.05 (m, 1H), 6.85 (m, 2H), 6.78 (dd, 2.3 and 8.8 Hz, 1H), 6.71 (s, 1H), 6.54 (m, 1H), 5.24 (s, 2H), 4.85 (s, 2H), 3.69 (s, 3H), 3.08 (s, 3H), 2.47 s, 3H). | 403.2 |

TABLE E-continued

| Ex No | SM | Product | Yield (%) | $^1$H NMR (400 or 500 MHz, DMSO-d$_6$): δ | MS (m/z: M + H$^+$) |
|---|---|---|---|---|---|
| E4 | D6 | (structure) | 70 | No Data | 403.2 |
| E5 | D32 | (structure) | 84 | No Data | 403.2 |
| E6 | D32 | (structure) | 94 | No Data | 389.2 |
| E7 | D8 | (structure) | 88 | No Data | 393.0 |
| E8 | D35 | (structure) | crude | 8.99 (s, 1H), 7.96 (s, 1H), 7.46 (d, J = 10.9 Hz, 1H), 7.20 (d, J = 8.3 Hz, 2H), 6.90 (d, J = 8.4 Hz, 2H), 6.78 (m, 2H), 5.52 (s, 2H), 4.85-4.94 (m, 2H), 3.74 (s, 3H), 3.13 (s, 3H), 2.36 (s, 3H). | 481.2 483.2 |
| E9 | D7 | (structure) | crude | No Data | 417.2 |
| E10 | D12 | (structure) | 51 | No Data | 399.2 |

Preparation of Example E11 by Pd-Catalyzed Reaction: N-(3-(3-amino-2-fluorophenyl)-2-methyl-1,6-naphthyridin-7-yl)acetamide

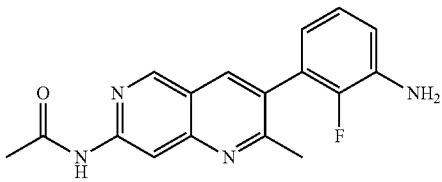 [SMILES: CC(=O)Nc1cc2nc(C)c(-c3cccc(N)c3F)cc2cn1]

A mixture of 3-(7-chloro-2-methyl-1,6-naphthyridin-3-yl)-2-fluoroaniline (D1, 0.29 g, 1.0 mmol), acetamide (0.48 g, 8.1 mol) and $K_3PO_4$ (0.86 g, 4.0 mmol) in 1,4-dioxane (10 mL) was degassed with Ar for 5 min. $Pd_2(dba)_3$ (0.046 g, 0.05 mmol) and 5-(di-tert-butylphosphanyl)-1',3',5'-triphenyl-1'H-1,4'-bipyrazole (0.026 g, 0.05 mmol) were added and the reaction mixture was degassed with Ar for an additional 5 min. The reaction mixture was stirred at 80° C. for 2 h. The reaction mixture was filtered through a pad of celite and concentrated under reduced pressure. The crude was purified by silica gel column chromatography (0 to 100% EtOAc/hexanes) to obtain N-(3-(3-amino-2-fluorophenyl)-2-methyl-1,6-naphthyridin-7-yl)acetamide (0.15 g, 48% yield) as a brown solid. $^1$H NMR (500 MHz, DMSO-$d_6$): δ 10.8 (s, 1H), 9.16 (s, 1H), 8.52 (s, 1H), 8.27 (s, 1H), 7.01 (m, 1H), 6.88 (m, 1H), 6.53 (m, 1H), 5.31 (s, 2H), 2.52 (s, 3H), 2.18 (s, 3H); MS (ESI) m/z: 311.0 (M+H$^+$).

General Method N: Preparation of sulfonyl chlorides

Example F1

5-chloro-2-methoxypyridine-3-sulfonyl chloride

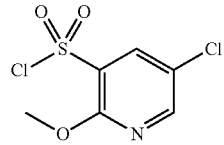

A mixture of 3-bromo-5-chloro-2-methoxypyridine (50 g, 225 mmol), benzylthiol (29 mL, 247 mmol), DIEA (79 mL, 450 mol), and XantPhos (13 g, 22 mmol) in toluene (500 mL) was purged with Ar for 5 min. $Pd_2(dba)_3$ (10 g, 11 mmol) was added and the reaction was sealed under Ar and heated to 90° C. for 3h. The reaction was cooled to rt and concentrated under reduced pressure. The residue was treated with in EtOAc (500 mL). The solution was filtered through a pad of silica gel and washed with EtOAc (500 mL). The filtrate was concentrated under reduced pressure to afford 3-(benzylthio)-5-chloro-2-methoxypyridine (60 g, 100% yield) as an orange solid. $^1$H NMR (500 MHz, DMSO-$d_6$): δ 7.94 (d, J=2.4 Hz, 1H), 7.65 (d, J=2.6 Hz, 1H), 7.41 (d, J=7.9 Hz, 2H), 7.32 (t, J=7.6 Hz, 2H), 7.26 (d, J=8.3 Hz, 1H), 4.27 (s, 2H), 3.89 (s, 3H).

A solution of 3-(benzylthio)-5-chloro-2-methoxypyridine (19.3 g, 73 mol) in acetonitrile (200 mL) was cooled to 0° C. Acetic acid (42 mL, 725 mmol) and distilled water (10 mL) were added followed by addition of 1,3-dichloro-5,5-dimethylimidazolidine-2,4-dione (available chlorine 68%) (41 g, 141 mol). The resulting solution was stirred for 1 h at rt. The reaction mixture was diluted with EtOAc (200 mL) and then the solution was washed with water (2×100 mL). The organic extracts were dried over anhydrous $Na_2SO_4$, filtered, and concentrated under reduced pressure. The crude was purified by silica gel column chromatography (5% EtOAc/hexanes) to afford 5-chloro-2-methoxypyridine-3-sulfonyl chloride (10 g, 57% yield) as a white crystalline solid. $^1$H NMR (500 MHz, DMSO-$d_6$): δ 8.18 (d, J=2.7 Hz, 1H), 7.93 (d, J=2.7 Hz, 1H), 3.87 (s, 3H).

Using the General Method N above, the following Intermediates of Table F were prepared.

TABLE F

| Ex No | Product | Yield (%) | $^1$H NMR (400 or 500 MHz, DMSO-$d_6$): δ | MS (m/z: M + H$^+$) |
|---|---|---|---|---|
| F2 | (structure) | 19 | 8.55 (d, J = 2.6 Hz, 1H), 8.13 (d, J = 2.6 Hz, 1H), 3.20 (s, 3H). | No Data |
| F3 | (structure) | 69 | 7.45 (d, J = 2.0 Hz, 1H), 7.18 (d, J = 2.0 Hz, 1H), 3.86 (s, 3H). | No Data |
| F4 | (structure) | 60 | 8.16 (d, J = 2.4 Hz, 1H), 7.91 (d, J = 2.4 Hz, 1H), 3.85 (s, 3H). | No Data |
| F5 | (structure) | 50 | 8.45 (d, J = 2.4 Hz, 1H), 8.17 (d, J = 2.4 Hz, 1H). | No Data |
| F6 | (structure) | 50 | 8.03 (dd, J = 1.8 and 7.8 Hz, 1H), 7.57 (dd, J = 1.8 and 7.6 Hz, 1H), 7.37 (t, J = 7.7 Hz, 1H), 3.83 (s, 3H). | No Data |
| F7 | (structure) | 35 | 7.91 (d, J = 2.4 Hz, 1H), 7.60 (d, J = 2.4 Hz, 1H), 3.80 (s, 3H), 1.89 (m, 1H), 0.91 (m, 2H), 0.58 (m, 2H). | 247.7 |
| F8 | (structure) | 56 | 8.79 (s, 1H), 8.23 (s, 1H), 3.95 (s, 3H). | No Data |
| F9 | (structure) | 50 | 8.09 (dd, J = 2.0 and 5.2 Hz, 1H), 7.95 (dd, J = 1.6 and 7.2 Hz, 1H), 6.92 (dd, J = 2.4 and 7.2 Hz, 1H), 3.89 (s, 3H). | No Data |

TABLE F-continued

| Ex No | Product | Yield (%) | $^1$H NMR (400 or 500 MHz, DMSO-$d_6$): δ | MS (m/z: M + H$^+$) |
|---|---|---|---|---|
| F10 | 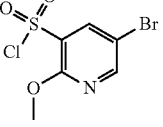 | 65 | 8.24 (d, J = 2.4 Hz, 1H), 8.02 (d, J = 2.4 Hz, 1H), 3.85 (s, 3H). | No Data |
| F11 | 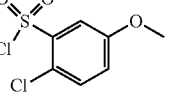 | 67 | 7.42 (d, J = 3.2 Hz, 1H), 7.25 (d, J = 8.8 Hz, 1H), 6.88 (dd, J = 8.8, 3.2 Hz, 1H), 3.74 (s, 3H). | No Data |

Preparation of Example F12: methyl 2,5-dichloro-3-(chlorosulfonyl)benzoate

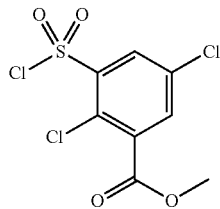 [SMILES: COC(=O)c1cc(Cl)cc(S(=O)(=O)Cl)c1Cl]

A solution of thionyl chloride (12 mL, 164 mmol) in MeOH (45 mL) at 0° C. were stirring for 15 min. 3-Amino-2,5-dichlorobenzoic acid (7.5 g, 36 mmol) was added under the same conditions. The reaction mixture was warmed to rt and stirred for 1 h then heated to refluxed for 5 h. The reaction mixture was concentrated under reduced pressure and the residue was dissolved in EtOAC. The solution was washed with 1 N Na$_2$CO$_3$ solution (aq, 200 mL) and the organic layer was washed with brine (50 mL). The organic layer was dried over anhydrous Na$_2$SO$_4$, filtered, and concentrated under reduce pressure to obtain the crude methyl 3-amino-2,5-dichlorobenzoate (7.0 g, 87% yield) which was proceeded to the next step without further purification. $^1$H NMR (500 MHz, DMSO-$d_6$): δ 6.98 (d, J=2.5 Hz, 1H), 6.88 (d, J=2.5 Hz, 1H), 5.97 (s, 2H), 3.83 (s, 3H); MS (ESI) m/z: 220.0 (M+H$^+$).

Solution A (prep: a solution of sodium nitrite (0.68 g, 9.8 mmol) in water (5.4 mL) was treated with a solution of methyl 3-amino-2,5-dichlorobenzoate (2.0 g, 9.1 mmol) in HCl (18 mL) at −15° C. The solution was stirred under the same conditions for 30 min.) was added dropwise into solution B (prep: thionyl chloride (2.8 mL, 39 mmol) was added dropwise into water (17 mL) under an acetone and ice bath. The mixture was stirred for 16 h at rt. Copper(I) chloride (10 mg, 1 mmol) was added at rt and then the mixture was cooled to −15° C. and stirred for 30 min.) at −15° C. and the reaction mixture was stirred under the same conditions for 2 h. Once the reaction was completed the mixture was diluted with DCM (100 mL). The aqueous phase was extracted with DCM (3×50 mL). The combined organic extracts were dried over MgSO$_4$, filtered, and concentrated under reduced pressure. The crude was purified by silica gel column chromatography (0 to 50% EtOAc/hexanes) to obtain methyl 2,5-dichloro-3-(chlorosulfonyl) benzoate (F12, 2.1 g, 76% yield) as a yellow viscous liquid.

$^1$H NMR (500 MHz, DMSO-$d_6$): δ 8.00 (d, J=2.7 Hz, 1H), 7.72 (d, J=2.7 Hz, 1H), 3.86 (s, 3H).

Preparation of Example F13: 2,5-dichloro-3-((4-methoxybenzyl)carbamoyl)benzenesulfonyl chloride

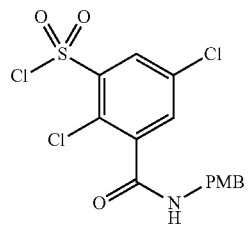

A solution of 3-amino-2,5-dichlorobenzoic acid (3.00 g, 15 mmol) in DMF (10 mL) was added 4-methoxybenzylamine (2.09 mL, 16 mmol). DIEA (5.34 mL, 31 mmol) and HATU (5.81 g, 15 mmol) were added and then the reaction was stirred overnight at rt. The reaction mixture was poured into water and extracted with EtOAc (3×). The combined organic layers were washed with sat'd aqueous NaHCO$_3$ (2×), brine, dried over anhydrous Na$_2$SO$_4$, filtered, and concentrated under reduced pressure. The residue was rinsed with hexanes to afford 3-amino-2,5-dichloro-N-(4-methoxybenzyl)benzamide (2.40 g, 51% yield) as a beige solid. $^1$H NMR (500 MHz, DMSO-$d_6$): δ 8.86 (t, J=6.0 Hz, 1H), 7.26 (d, J=8.4 Hz, 2H), 6.91 (d, J=8.4 Hz, 2H), 6.85 (d, J=2.5 Hz, 1H), 6.55 (d, J=2.5 Hz, 1H), 5.83 (s, 2H), 4.34 (d, J=6.0 Hz, 2H), 3.74 (s, 3H).

Pot A: water (13.7 mL, 760 mmol) was cooled to −15° C. SOCl$_2$ (2.32 mL, 32 mmol) was then added dropwise and the mixture was stirred for 16 h at rt. Copper(I) chloride (0.008 g, 0.08 mmol) was added at rt and the mixture cooled to −15° C. and stirred for 30 min.

Pot B: sodium nitrite (0.55 g, 7.9 mmol) in H$_2$O (4.4 mL, 244 mmol) and 1,4-dioxane (4 mL) was added dropwise to a solution of 3-amino-2,5-dichloro-N-(4-methoxybenzyl) benzamide (2.40 g, 7.4 mmol) in HCl (14.8 mL, 487 mmol) at −15° C. and stirred for 30 min, maintaining temp.

Pot B was then added dropwise to Pot A at −15° C., warmed to rt slowly and stirred rapidly for 1.5 h. (Pot B was rinsed with an additional 4 mL of H$_2$O and added to Pot A). The solids were filtration and the crude was purified by silica gel column chromatography (5-100% EtOAc/hexanes plus 0.5% acetic acid modifier) to obtain 2,5-dichloro-3-((4-methoxybenzyl)carbamoyl)benzenesulfonyl chloride (F13, 1.5 g, 50% yield) as a light orange solid.

Preparation of Example F14: 2-(2,5-dichloro-3-(chlorosulfonyl)phenyl)propan-2-yl Acetate

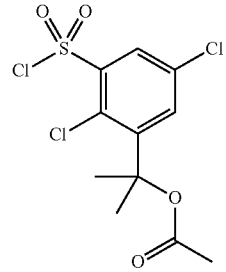 [SMILES: CC(=O)OC(C)(C)c1cc(Cl)cc(S(=O)(=O)Cl)c1Cl]

A solution of 3-amino-2,5-dichlorobenzoic acid (14.0 g, 68.0 mmol) in EtOH (120 mL) was cooled to 0° C. and thionyl chloride (20.0 mL, 169 mmol) was added dropwise. The reaction mixture was further heated at 85° C. for 16 h. The reaction mixture was cooled to rt and concentrated under reduced pressure. The crude was triturated with n-pentane to afford ethyl 3-amino-2,5-dichlorobenzoate (14.0 g, 83% yield) as brown solid. $^1$H NMR (500 MHz, DMSO-d$_6$): δ 6.96 (d, J=2.4 Hz, 1H), 6.85 (d, J=2.4 Hz, 1H), 5.96 (brs, 2H), 4.29 (q, J=7.2 Hz, 2H), 1.29 (t, J=6.8 Hz, 3H).

A solution of ethyl 3-amino-2,5-dichlorobenzoate (12.0 g, 51.0 mmol) in CH$_3$CN (250 mL) was treated with amyl nitrite (9.64 mL, 81.0 mmol). Dibenzyl disulphide (12.6 g, 51.0 mmol) was added at rt and the reaction mixture was heated at 70° C. for 3 h. The reaction mixture was quenched with ice water (100 mL) and extracted with EtOAc (3×). The combined organics were dried over anhydrous Na$_2$SO$_4$, filtered, and concentrated under reduced pressure. The crude was purified by silica gel column chromatography (10 to 20% EtOAc/hexanes) to afford ethyl 3-(benzylthio)-2,5-dichlorobenzoate (10.0 g, 58% yield) as an off white solid. $^1$H NMR (500 MHz, DMSO-d$_6$): δ 7.63 (d, J=2.8 Hz, 1H), 7.56 (d, J=2.4 Hz, 1H), 7.44 (d, J=7.2 Hz, 2H), 7.35 (t, J=7.6 Hz, 2H) 7.28 (d, J=7.2 Hz, 1H), 4.42 (s, 2H), 4.33 (q, J=7.2 Hz, 2H), 1.29 (t, J=6.8 Hz, 3H).

A solution of ethyl 3-(benzylthio)-2,5-dichlorobenzoate (10.0 g, 29.32 mmol) in diethyl ether (20 mL) was stirred at 0° C. under Ar. Methyl magnesium bromide (9.0 g, 76.24 mmol) was added under the same conditions and then the mixture was stirred at rt for 6 h. The reaction mixture was quenched with ice water (50 mL) and extracted with EtOAc (3×). The combined organics were dried over anhydrous Na$_2$SO$_4$, filtered, and concentrated under reduced pressure. The crude was purified by silica gel column chromatography (5 to 10% EtOAc/hexanes) to afford 2-(3-(benzylthio)-2,5-dichlorophenyl)propan-2-ol (6.0 g, 62% yield) as an off white solid. $^1$H NMR (500 MHz, DMSO-d$_6$): δ 7.59 (s, 1H), 7.43 (d, J=7.2 Hz, 2H), 7.35 (m, 3H), 7.28 (m, 1H), 5.49 (s, 1H), 4.33 (s, 2H), 1.58 (s, 6H).

A solution of 2-(3-(benzylthio)-2,5-dichlorophenyl)propan-2-ol (3.0 g, 9.2 mmol), acetic anhydride (2.81 g, 27.6 mmol, 3.0 equiv.), triethyl amine (4.0 ml, 27.6 mmol, 3.0 eq) and dimethyl amino pyridine (2.24 g, 18.4 mmol, 2.0 equiv.) in THF (60 mL) were heated at 80° C. for 24 h. The reaction mixture was cooled to rt and quenched with water (100 mL). The mixture was extracted with EtOAc (3×) and the combined organics were dried over anhydrous Na$_2$SO$_4$, filtered, and concentrated under reduced pressure. The crude was purified by silica gel column chromatography (1 to 2% MeOH/DCM) to afford the 2-(3-(benzylthio)-2,5-dichlorophenyl)propan-2-yl acetate (2.20 g, 65% yield) as a brown solid. $^1$H NMR (500 MHz, DMSO-d$_6$): δ 7.42 (d, J=7.6 Hz, 2H), 7.35 (m, 3H), 7.28 (d, J=7.2 Hz, 1H), 7.25 (s, 1H), 4.33 (s, 2H), 1.98 (s, 3H), 1.72 (s, 6H).

A solution of 2-(3-(benzylthio)-2,5-dichlorophenyl)propan-2-yl acetate (3.0 g, 9.2 mmol) and 1,3-dichloro-5,5-dimethylimidazolidine-2,4-dione (2.35 g, 11.9 mmol) in CH$_3$CN (60 mL) was treated with acetic acid (3.6 g, 59.7 mmol) and water (2.0 mL). The reaction mixture was stirred at rt for 16 h and quenched with sat'd NaHCO$_3$ solution (100 mL). The mixture was extracted with EtOAc (3×) and the combined organics were dried over anhydrous Na$_2$SO$_4$, filtered, and concentrated under reduced pressure to afford 2-(2,5-dichloro-3-(chlorosulfonyl)phenyl)propan-2-yl acetate (F14, 1.5 g, crude) as a white solid which was used for the next reaction without further purification.

Preparation of Example F15:
5-chloro-2,4-dimethoxybenzenesulfonyl Chloride

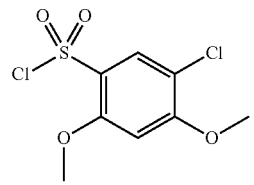

A solution of 1-chloro-2,4-dimethoxybenzene (1.0 g, 5.8 mmol) in CHCl$_3$ (15 mL) under Ar was cooled to 0° C. Chlorosulfonic acid (1.5 mL, 12.9 mmol) was added dropwise at 0° C. and the mixture was further stirred at rt for 3 h. The mixture was quenched with ice water (50 mL) and extracted with EtOAc (2×). The combined organics were dried over anhydrous Na$_2$SO$_4$, filtered, and concentrated under reduced pressure. The crude was further triturated with n-pentane to afford desired 5-chloro-2,4-dimethoxybenzenesulfonyl chloride (F15, 0.9 g, 51% yield) as off white solid. $^1$H NMR (500 MHz, DMSO-d$_6$): δ 7.60 (s, 1H), 6.70 (s, 1H), 3.88 (s, 3H), 3.80 (s, 3H).

Preparation of Example F16:
2,5-dichloro-3-(methylcarbamoyl)benzenesulfonyl Chloride

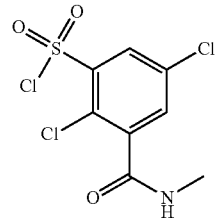 [SMILES: CNC(=O)c1cc(Cl)cc(S(=O)(=O)Cl)c1Cl]

Using General Methods J and N, 2,5-dichloro-3-(methylcarbamoyl)benzenesulfonyl chloride was prepared from methyl 3-bromo-2,5-dichlorobenzoate. $^1$H NMR (500 MHz, DMSO-d$_6$): δ 8.46 (brm, 1H), 7.86 (d, J=2.8 Hz, 1H), 7.41 (d, J=2.8 Hz, 1H), 2.73 (d, J=4.4 Hz, 3H); MS (ESI) m/z: 302.1 (M+H$^+$).

Preparation of Example F17:
2,5-dichloro-3-(chlorosulfonyl)benzyl Acetate

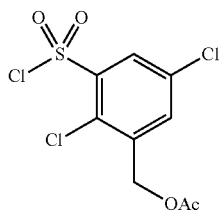 [SMILES: CC(=O)OCc1cc(Cl)cc(S(=O)(=O)Cl)c1Cl]

A solution of ethyl 3-amino-2,5-dichlorobenzoate (14.0 g, 51.0 mmol) in acetonitrile (250 mL) was treated with amyl nitrite (9.64 mL, 81.0 mmol) and dibenzyl disulphide (12.6 g, 51.0 mmol,). The reaction was heated at 70° C. for 3 h and then quenched with ice-cold water (100 mL). The aqueous layer was extracted with EtOAc (3x). The combined organics were dried over anhydrous Na$_2$SO$_4$, filtered, and concentrated under reduced pressure. The crude was purified by silica gel column chromatography (1 to 10% EtOAc/hexanes) to afford ethyl 3-(benzylthio)-2,5-dichlorobenzoate (14.0 g, 58% yield) as an off white solid. $^1$H NMR (400 MHz, DMSO-d$_6$) δ 7.65 (d, J=2.8 Hz, 1H), 7.56 (d, J=2.4 Hz, 1H), 7.43-7.45 (m, 2H), 7.33-7.37 (m, 2H), 7.28 (m, 1H), 4.42 (s, 2H), 4.33 (q, J=7.2 Hz, 2H), 1.31 (t, J=6.8 Hz, 3H).

A solution of ethyl 3-(benzylthio)-2,5-dichlorobenzoate (14.0 g, 9.2 mmol) in THF/EtOH (1:1, 400 mL) was treated with CaCl$_2$ (0.45 g, 0.92 mmol). NaBH$_4$ (6.20 g, 36.8 mmol, 4.0 equiv) was added at 0° C. and the reaction mixture was further heated at 60° C. for 5 h. The reaction was cooled to rt and quenched with NH$_4$Cl solution (50 mL). The solution was extracted with EtOAc (3x) and the combined organics were dried over anhydrous Na$_2$SO$_4$, filtered, and concentrated under reduced pressure. The crude was purified by silica gel column chromatography (1 to 10% EtOAc/hexanes) to afford the (3-(benzylthio)-2,5-dichlorophenyl) methanol (8.0 g, 66% yield) as a brown solid. $^1$H NMR (400 MHz, DMSO-d$_6$) δ 7.42-7.45 (m, 2H), 7.33-7.36 (m, 3H), 7.25-7.32 (m, 2H), 5.57 (t, J=5.6 Hz, 1H), 4.51 (d, J=6.0 Hz, 2H), 4.36 (s, 2H).

A solution of (3-(benzylthio)-2,5-dichlorophenyl)methanol (8.0 g, 2.60 mmol) in THF (60 mL) was treated with acetic anhydride (8.32 g, 8.08 mmol), triethyl amine (13.6 g, 67.1 mmol) and dimethyl amino pyridine (0.90 g, 0.26 mmol). The reaction mixture was heated at 80° C. for 3 h and then cooled to rt. The reaction mixture was quenched with water (300 mL) and extracted with EtOAc (3x). The combined organics were dried over anhydrous Na$_2$SO$_4$, filtered, and concentrated under reduced pressure. The crude was purified by silica gel column chromatography (10 to 20% EtOAc/hexanes) to afford the 3-(benzylthio)-2,5-dichlorobenzyl acetate (8.0 g, 88% yield) as an off-white solid. $^1$H NMR (400 MHz, DMSO-d$_6$) δ 7.44-7.46 (m, 2H), 7.43 (s, 1H), 7.36 (s, 1H), 7.33-7.35 (m, 2H), 7.27 (m, 1H), 5.10 (s, 2H), 4.39 (s, 2H), 2.09 (s, 3H).

A solution of 3-(benzylthio)-2,5-dichlorobenzyl acetate (8.0 g, 2.3 mmol) in AcOH/THF/water (8:1:1, 400.0 mL) was treated with N-chlorosuccinimide (12.0 g, 4.8 mmol). The reaction mixture was stirred at rt for 2 h and then quenched with water (100 mL). The mixture was extracted with EtOAc (3x) and the combined organics were dried over anhydrous Na$_2$SO$_4$, filtered, and concentrated under reduced pressure. The crude was purified by silica gel column chromatography (10 to 20% EtOAc/hexanes) to afford the 2,5-dichloro-3-(chlorosulfonyl)benzyl acetate (F17, 4.2 g, 88% yield) as a white solid. $^1$H NMR (400 MHz, DMSO-d$_6$) δ 7.84 (d, J=2.8 Hz, 1H), 7.52 (d, J=2.8 Hz, 1H), 5.13 (s, 2H), 2.11 (s, 3H).

| F18 | | 74 | 7.60 (m, 1H), 7.50 (m, 1H), 5.08 (s, 2H), 2.07 (s, 3H). | No Data |
|---|---|---|---|---|
| F19 | | 63 | 7.58-7.64 (m, 1H), 7.29-7.35 (m, 1H), 5.13 (s, 2H), 2.11 (s, 3H). | No Data |
| F20 | | 75 | 7.33 (m, 1H), 7.30 (m, 1H), 5.07 (s, 2H), 2.07 (s, 3H). | No Data |
| F21 | | 47 | No Data | 312.0 |

General Method O: Sulfonamide Coupling

Example G1

N-(6-bromoquinazolin-2-yl)acetamide

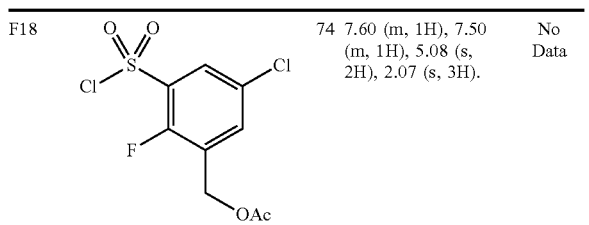

A solution of 2-fluoro-4-methyl-5-(4,4,5,5-tetramethyl-1,3,2-dioxaborolan-2-yl)aniline (A1, 0.2 g, 0.80 mmol) in DCM (3 mL) was cooled to 0° C. Pyridine-3-sulfonyl chloride (0.14 g, 0.80 mmol) was added portion-wise and the reaction mixture was slowly warmed to rt overnight.

The solvent was removed under reduced pressure and the crude was purified by silica gel column chromatography (0 to 10% DCM/MeOH) to obtain N-(2-fluoro-4-methyl-5-(4,4,5,5-tetramethyl-1,3,2-dioxaborolan-2-yl)phenyl)pyridine-3-sulfonamide (0.30 g, 98% yield) as a white solid. $^1$H NMR (500 MHz, DMSO-d$_6$): δ 10.2 (s, 1H), 8.80 (m, 2H), 8.03 (d, J=8.2 Hz, 1H), 7.62 (m, 1H), 7.39 (d, J=9.0 Hz, 1H), 7.03 (d, J=11.6 Hz, 1H), 2.41 (s, 3H), 1.29 (s, 12H); MS (ESI) m/z: 393.2 (M+H$^+$).

Using the General Method O above, the following Intermediates of Table G were prepared.

TABLE G

| Ex No | SM | Product | Yield (%) | ¹H NMR (400 or 500 MHz, DMSO-d₆): δ | MS (m/z: M + H⁺) |
|---|---|---|---|---|---|
| G2 | A1 | | 91 | 10.3 (s, 1H), 8.95 (d, J = 2.3 Hz, 1H), 8.73 (d, J = 2.0 Hz, 1H), 8.14 (t, J = 2.1 Hz, 1H), 7.34 (d, J = 8.9 Hz, 1H), 7.08 (d, J = 11.6 Hz, 1H), 2.42 (s, 3H), 1.28 (s, 12H). | 427.0 |
| G3 | F1 | | 98 | 10.5 (s, 1H), 8.46 (d, J = 2.6 Hz, 1H), 8.14 (d, J = 2.6 Hz, 1H), 7.42 (d, J = 2.2 Hz, 1H), 7.33 (m, 1H), 7.25 (m, 2H), 3.95 (s, 3H), 1.27 (s, 12H). | 425.0 |
| G4 | A1 F1 | | 93 | 10.1 (s, 1H), 8.51 (d, J = 2.6 Hz, 1H), 7.99 (d, J = 2.6 Hz, 1H), 7.43 (d, J = 9.0 Hz, 1H), 7.03 (d, J = 11.6 Hz, 1H), 3.97 (s, 3H), 2.40 (s, 3H), 1.28 (s, 12H). | 457.2 |
| G5 | A10 F1 | | 44 | 10.3 (s, 1H), 8.53 (d, J = 2.6 Hz, 1H), 8.04 (d, J = 2.6 Hz, 1H), 7.50 (m, 1H), 7.25 (m, 1H), 3.96 (s, 3H), 1.30 (s, 12H). | 461.0 |
| G6 | A1 | | 20 | 10.2 (s, 1H), 8.01 (t, J = 1.9 Hz, 1H), 7.65 (d, J = 1.9 Hz, 2H), 7.29 (d, J = 9.0 Hz, 1H), 7.09 (d, J = 11.6 Hz, 1H), 2.42 (s, 3H), 1.28 (s, 12H). | 482.2 (M + 23) |
| G7 | A5 | | 78 | 10.9 (s, 1H), 7.87 (d, J = 2.3 Hz, 1H), 7.63 (dd, J = 2.3 and 8.2 Hz, 1H), 7.44 (d, J = 8.2 Hz, 1H), 7.23 (d, J = 2.0 Hz, 1H), 6.99 (m, 2H), 2.56 (s, 3H), 1.28 (s, 12H). | 448.0 (M + 23) |
| G8 | A1 | | 53 | 10.2 (s, 1H), 7.61 (m, 1H), 7.45 (d, J = 8.0 Hz, 1H), 7.34 (d, J = 9.0 Hz, 1H), 7.01 (d, J = 11.6 Hz, 1H), 2.54 (s, 3H), 2.38 (s, 3H), 1.26 (s, 12H). | 462.2 (M + 23) |

TABLE G-continued
| Ex No | SM | Product | Yield (%) | ¹H NMR (400 or 500 MHz, DMSO-d₆): δ | MS (m/z: M + H⁺) |
|---|---|---|---|---|---|
| G9 | A5 F1 | 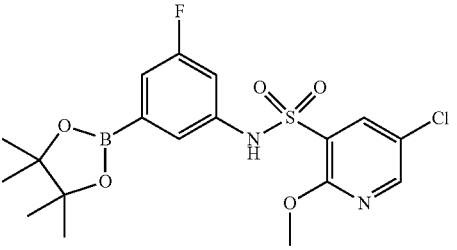 [SMILES: COc1ncc(Cl)cc1S(=O)(=O)Nc1cc(F)cc(B2OC(C)(C)C(C)(C)O2)c1] | 27 | 10.8 (s, 1H), 8.48 (d, J = 2.6 Hz, 1H), 8.22 (d, J = 2.6 Hz, 1H), 7.25 (d, J = 2.0 Hz, 1H), 7.02 (m, 2 H), 3.93 (s, 3H), 1.28 (s, 12H). | 443.0 |
| G10 | A13 F1 | 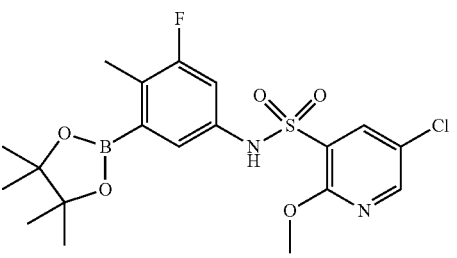 [SMILES: COc1ncc(Cl)cc1S(=O)(=O)Nc1cc(F)c(C)c(B2OC(C)(C)C(C)(C)O2)c1] | 38 | No Data | 457.0 |
| G11 | A2 F1 | 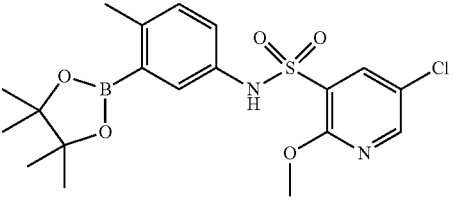 [SMILES: COc1ncc(Cl)cc1S(=O)(=O)Nc1ccc(C)c(B2OC(C)(C)C(C)(C)O2)c1] | 62 | 10.2 (s, 1H), 8.45 (d, J = 2.6 Hz, 1H), 8.08 (d, J = 2.6 Hz, 1H), 7.36 (d, J = 2.4 Hz, 1H), 7.06 (m, 2H), 3.98 (s, 3H), 2.33 (s, 3H), 1.27 (s, 12H). | 439.0 |
| G12 | A3 F1 | 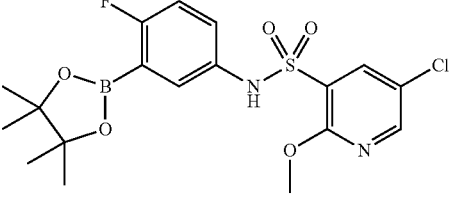 | 56 | 10.4 (s, 1H, s), 8.47 (d, J = 2.6 Hz, 1H), 8.10 (d, J = 2.6 Hz, 1H), 7.36 (m, 1H), 7.24 (m, 1H), 7.07 (t, J = 8.8 Hz, 1H), 3.96 (s, 3H), 1.27 (s, 12H) | 465.0 (M + 23) |
| G13 | A6 F1 | 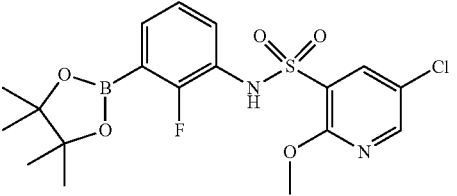 [SMILES: COc1ncc(Cl)cc1S(=O)(=O)Nc1cccc(B2OC(C)(C)C(C)(C)O2)c1F] | 94 | 10.3 (s, 1H), 8.50 (d, J = 2.5 Hz, 1H), 8.06 (d, J = 2.6 Hz, 1H), 7.45 (s, 1H), 7.39 (dd, J = 1.7 and 7.7 Hz, 1H), 7.15 (t, J = 7.7 Hz, 1H), 3.89 (s, 3H), 1.27 (s, 12H). | 443.2 |
| G14 | A9 F1 | 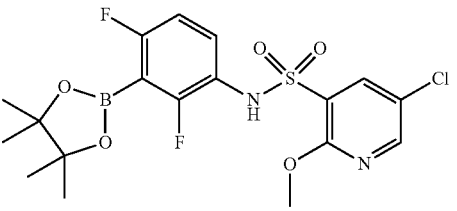 [SMILES: COc1ncc(Cl)cc1S(=O)(=O)Nc1ccc(F)c(B2OC(C)(C)C(C)(C)O2)c1F] | 21 | 10.2 (s, 1H), 8.52 (d, J = 2.6 Hz, 1H), 8.04 (d, J = 2.6 Hz, 1H), 7.37 (d, J = 8.1 Hz, 1H), 7.02 (t, J = 8.5 Hz, 1H), 3.89 (s, 3H), 1.28 (s, 12H). | 441.2 |

TABLE G-continued

| Ex No | SM | Product | Yield (%) | ¹H NMR (400 or 500 MHz, DMSO-d₆): δ | MS (m/z: M + H⁺) |
|---|---|---|---|---|---|
| G15 | A15 F1 | | 82 | No Data | 455.0 |
| G16 | A6 F2 | | 63 | 11.0 (s, 1H), 8.97 (d, J = 2.4 Hz, 1H), 8.42 (d, J = 2.4 Hz, 1H), 7.50 (t, J = 6.0 Hz, 1H), 7.40 (m, 1H), 7.19 (t, J = 7.7 Hz, 1H), 3.18 (s, 3H), 1.28 (s, 12H). | 560 (M + 23) |
| G17 | A6 F12 | | 56 | No Data | 526.0 |
| G18 | A22 F1 | | crude | No Data | 450.0 |
| G19 | A5 F12 | | 70 | No Data | 504.0 |
| G20 | A6 F13 | | 32 | No Data | 609.2 |

TABLE G-continued
| Ex No | SM | Product | Yield (%) | ¹H NMR (400 or 500 MHz, DMSO-d₆): δ | MS (m/z: M + H⁺) |
|---|---|---|---|---|---|
| G21 | A21 F1 | 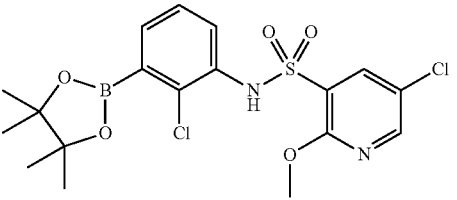 [SMILES: COc1ncc(Cl)cc1S(=O)(=O)Nc1cccc(B2OC(C)(C)C(C)(C)O2)c1Cl] | 64 | 10.2 (s, 1H), 8.51 (d, J = 2.6 Hz, 1H), 8.01 (d, J = 2.6 Hz, 1H), 7.47 (dd, J = 1.7 and 7.3 Hz, 1H), 7.42 (dd, J = 1.7 and 7.9 Hz, 1H), 7.32 (t, J = 7.6 Hz, 1H), 3.87 (s, 3H), 1.28 (s, 12H). | 459.2 |
| G22 | A8 F1 | 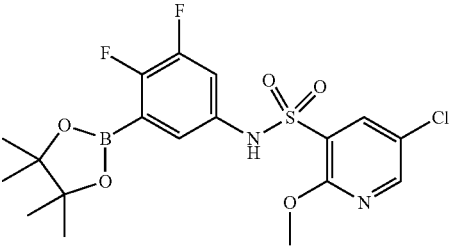 [SMILES: COc1ncc(Cl)cc1S(=O)(=O)Nc1cc(F)c(F)c(B2OC(C)(C)C(C)(C)O2)c1] | 94 | 10.7 (d, J = 2.3 Hz, 1H), 8.50 (m, 1H), 8.19 (d, J = 2.6 Hz, 1H), 7.25 (ddd, J = 11.8, 6.9, 2.7 Hz, 1H), 7.14 (t, J = 3.0 Hz, 1H), 3.94 (s, 3H), 1.28 (s, 12H). | 461.2 |
| G23 | A6 | 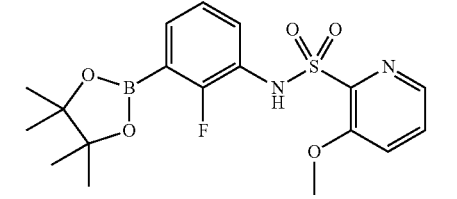 [SMILES: COc1cccnc1S(=O)(=O)Nc1cccc(B2OC(C)(C)C(C)(C)O2)c1F] | 49 | 10.1 (s, 1H), 8.15 (d, J = 4.4 Hz, 1H), 7.76 (dd, J = 1.1 and 8.5 Hz, 1H), 7.65 (dd, J = 4.5 and 8.5 Hz, 1H), 7.30-7.42 (m, 2H), 7.06 (t, J = 7.7 Hz, 1H), 3.88 (s, 3H), 1.28 (s, 12H). | 409.2 |
| G24 | A6 F17 | 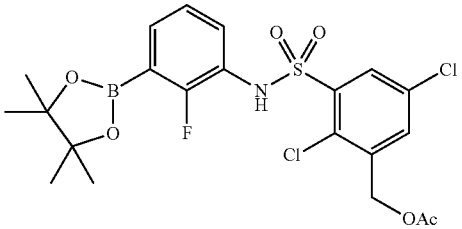 [SMILES: CC(=O)OCc1cc(Cl)cc(S(=O)(=O)Nc2cccc(B3OC(C)(C)C(C)(C)O3)c2F)c1Cl] | 68 | 10.6 (s, 1H), 7.85 (m, 2H), 7.41 (m, 1H), 7.35 (m, 1H), 7.12 (t, J = 7.6 Hz, 1H), 5.13 (s, 2H), 2.12 (s, 3H), 1.26 (s, 12H). | 434.0 (boronic acid) |
| G25 | A6 F18 | 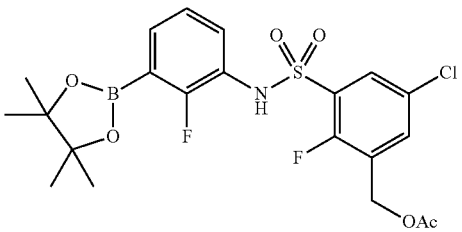 [SMILES: CC(=O)OCc1cc(Cl)cc(S(=O)(=O)Nc2cccc(B3OC(C)(C)C(C)(C)O3)c2F)c1F] | 60 | 7.88 (m, 1H), 7.66 (m, 1H), 7.45-7.51 (m, 1H), 7.38 (m, 1H), 7.15 (m, 1H), 5.14 (s, 2H), 2.07 (s, 3H), 1.26 (s, 12H). NH is missing | No Data |
| G26 | A6 F19 | 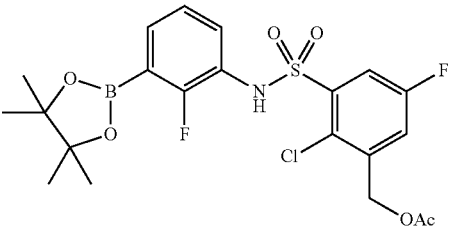 [SMILES: CC(=O)OCc1cc(F)cc(S(=O)(=O)Nc2cccc(B3OC(C)(C)C(C)(C)O3)c2F)c1Cl] | 86 | 10.61 (br s, 1H), 7.70 (m, 1H), 7.55 (t, J = 7.2 Hz, 1H), 7.43 (t, J = 5.6 Hz, 1H), 7.35 (t, J = 7.6 Hz, 1H), 7.13 (t, J = 7.6 Hz, 1H), 5.21 (s, 2H), 2.13 (s, 3H), 1.22 (s, 12H). | No Data |

TABLE G-continued

| Ex No | SM | Product | Yield (%) | $^1$H NMR (400 or 500 MHz, DMSO-$d_6$): δ | MS (m/z: M + H$^+$) |
|---|---|---|---|---|---|
| G27 | A6 F20 | 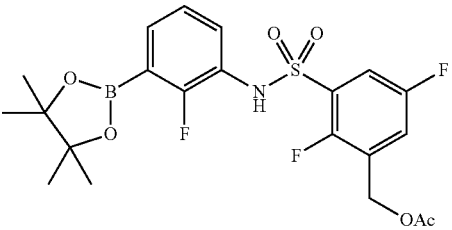 [SMILES: CC(=O)OCc1cc(F)cc(S(=O)(=O)Nc2cccc(B3OC(C)(C)C(C)(C)O3)c2F)c1F] | 86 | 10.58 (br m, 1H), 7.68 (m, 1H), 7.57 (m, 1H), 7.43 (m, 1H), 7.39 (m, 1H), 7.13 (t, J = 4.0 Hz, 1H), 5.08 (s, 2H), 2.08 (s, 3H), 1.23 (s, 12H). | No Data |
| G28 | A6 F21 | 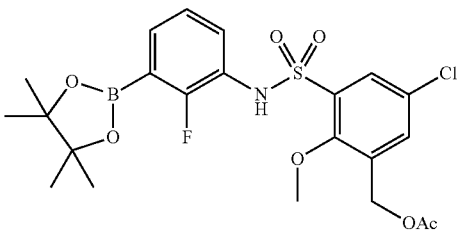 [SMILES: COc1c(COC(C)=O)cc(Cl)cc1S(=O)(=O)Nc1cccc(B2OC(C)(C)C(C)(C)O2)c1F] | 98 | 10.15 (br s, 1H), 7.74 (m, 1H), 7.64 (d, J = 2.8 Hz, 1H), 7.41 (t, J = 5.6 Hz, 1H), 7.33 (t, J = 7.6 Hz, 1H), 7.11 (t, J = 8.0 Hz, 1H), 5.14 (s, 2H), 3.84 (s, 3H), 2.10 (s, 3H), 1.27 (s, 12H). | 512.2 |

Using the General Method O above, the following Intermediates of Table H were prepared.

TABLE H

| Ex No | SM | Product | Yield (%) | $^1$H NMR (400 or 500 MHz, DMSO-$d_6$): δ | MS (m/z: M + H$^+$) |
|---|---|---|---|---|---|
| H1 | 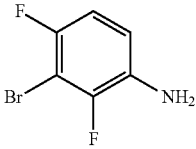 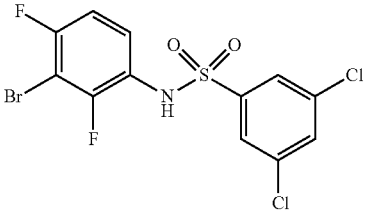 | 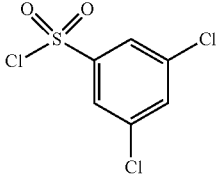 [SMILES: O=S(=O)(Cl)c1cc(Cl)cc(Cl)c1] | 100 | 10.6 (s, 1H), 8.01 (d, J = 2.2 Hz, 1H), 7.66 (d, J = 1.9 Hz, 2H), 7.26 (m, 2H); | 322.2 |
| H2 |  F12 | 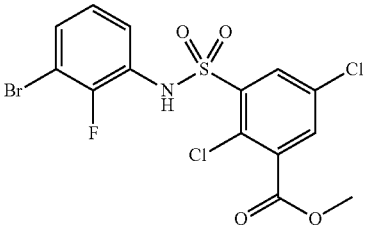 [SMILES: COC(=O)c1cc(Cl)cc(S(=O)(=O)Nc2cccc(Br)c2F)c1Cl] | 59 | No Data | No Data |
| H3 |  F1 | 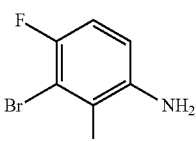 | 57 | 10.5 (s, 1H), 8.53 (d, J = 2.6 Hz, 1H), 8.07 (d, J = 2.6 Hz, 1H, 7.23-7.37 (m, 2H), 3.92 (s, 3H). | 413.0 415.0 |

TABLE H-continued

| Ex No | SM | Product | Yield (%) | ¹H NMR (400 or 500 MHz, DMSO-d₆): δ | MS (m/z: M + H⁺) |
|---|---|---|---|---|---|
| H4 | 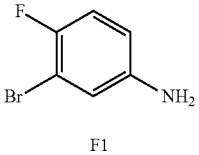 | 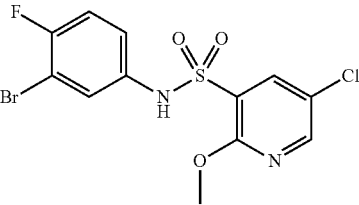 [SMILES: COc1ncc(Cl)cc1S(=O)(=O)Nc1ccc(F)c(Br)c1] | 81 | No Data | 395.0 397.0 |
| H5 | 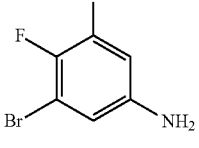 | 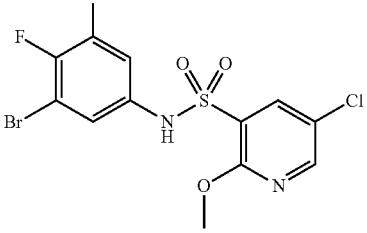 | 93 | 10.9 (s, 1H), 8.52 (d, J = 2.6 Hz, 1H), 8.29 (d, J = 2.6 Hz, 1H), 7.18 (m, 2H), 3.95 (s, 3H). | 412.9 414.9 |
| H6 | 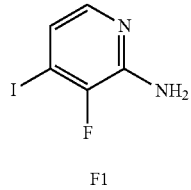 | 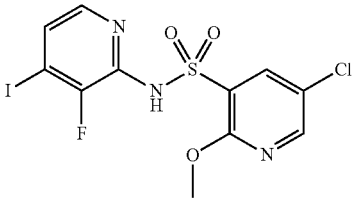 [SMILES: COc1ncc(Cl)cc1S(=O)(=O)Nc1nccc(I)c1F] | 54 | 11.6 (s, 1H), 8.48 (s, 1H), 8.22 (s, 1H), 7.60 (d, J = 3.6 Hz, 1H), 7.49 (brs, 1H), 3.87 (s, 3H). | 443.7 |
| H7 | 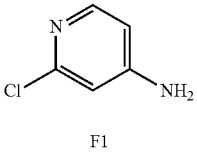 | 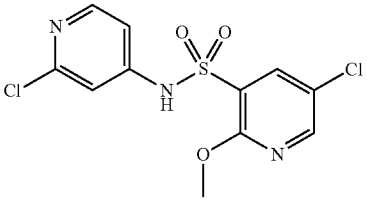 [SMILES: COc1ncc(Cl)cc1S(=O)(=O)Nc1ccnc(Cl)c1] | crude | No Data | 334.0 |

Preparation of Example H8: N-(3-bromo-2-fluorophenyl)-2,5-dichloro-3-(2-hydroxypropan-2-yl)benzenesulfonamide

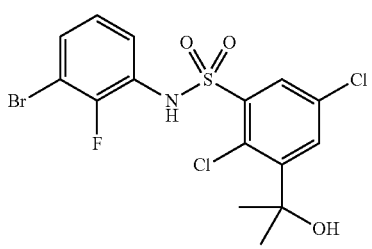 [SMILES: CC(C)(O)c1cc(Cl)cc(S(=O)(=O)Nc2cccc(Br)c2F)c1Cl]

A solution of methyl 3-(N-(3-bromo-2-fluorophenyl)sulfamoyl)-2,5-dichlorobenzoate (H₂, 0.85 g, 1.9 mmol) in THF (10 mL) was stirred at −78° C. Methylmagnesium bromide (3.2 M in THF, 3.8 mL, 12 mmol) was added dropwise at −78° C. The reaction mixture was slowly warmed to rt overnight. The reaction was quenched with sat'd NH₄Cl(aq, 20 mL) and the solution was extracted with EtOAc (3×30 mL). The combined organics were dried over anhydrous Na₂SO₄, filtered, and concentrated under reduced pressure. The crude was purified by silica gel column chromatography (1% EtOAc/DCM) to obtain N-(3-bromo-2-fluorophenyl)-2,5-dichloro-3-(2-hydroxypropan-2-yl) benzenesulfonamide (0.4 g, 47% yield).

General Method P: Suzuki reaction

Example 1

N-(2-fluoro-4-methyl-5-(7-methyl-2-(methylamino)pyrido[2,3-d]pyrimidin-6-yl)phenyl)pyridine-3-sulfonamide

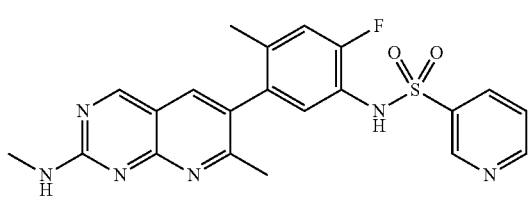 [SMILES: CNc1ncc2cc(-c3cc(NS(=O)(=O)c4cccnc4)c(F)cc3C)c(C)nc2n1]

A mixture of N-(2-fluoro-4-methyl-5-(4,4,5,5-tetramethyl-1,3,2-dioxaborolan-2-yl)phenyl)pyridine-3-sulfonamide (G1, 0.20 g, 0.51 mmol), 6-bromo-N,7-dimethylpyrido[2,3-d]pyrimidin-2-amine (B3, 0.13 g, 0.51 mmol), and K$_2$CO$_3$ (0.21 g, 1.5 mmol) in 1,4-dioxane (2 mL) and water (0.5 mL) was purged with Ar for 10 min. Pd(PPh$_3$)$_4$ (0.059 g, 0.05 mmol) was added and the reaction was heated at 80° C. under microwave for 3 h. The reaction was cooled to rt and filtered through a pad of celite. The filtrate was concentrated under reduced pressure and then the residue was purified by silica gel column chromatography (0 to 10% MeOH/DCM) to obtain N-(2-fluoro-4-methyl-5-(7-methyl-2-(methylamino)pyrido[2,3-d]pyrimidin-6-yl)phenyl)pyridine-3-sulfonamide (0.11 g, 48% yield) as an orange solid. $^1$H NMR (500 MHz, DMSO-d$_6$): δ 10.4 (s, 1H), 9.08 (s, 1H), 8.82 (m, 2H), 8.10 (m, 1H), 7.89 (s, 1H), 7.72 (s, 1H), 7.65 (dd, J=4.9 and 8.1 Hz, 1H), 7.23 (d, J=11.2 Hz, 1H), 6.99 (d, J=8.0 Hz, 1H), 2.93 (d, J=4.7 Hz, 3H), 2.20 (s, 3H), 1.99 (s, 3H); MS (ESI) m/z: 439.2 (M+H$^+$).

General Method Q: Sulfonamide Coupling

Example 2

5-chloro-N-(2-fluoro-3-(7-methyl-2-(methylthio)pyrido[2,3-d]pyrimidin-6-yl)phenyl)-2-methoxypyridine-3-sulfonamide

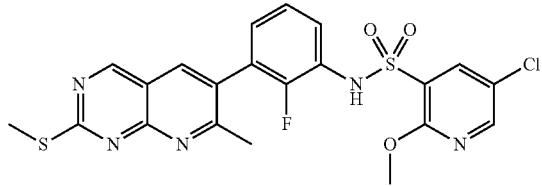

A solution of 2-fluoro-3-(7-methyl-2-(methylthio)pyrido[2,3-d]pyrimidin-6-yl)aniline (D3, 0.50 g, 1.7 mmol) in pyridine (2 mL) was added a solution of 5-chloro-2-methoxypyridine-3-sulfonyl chloride (F1, 0.44 g, 1.8 mmol) in pyridine (2 mL) at 0° C. The reaction mixture was warmed to rt and stirred for 12 h. The reaction mixture was concentrated under reduced pressure. The crude was purified by silica gel column chromatography (0 to 100% EtOAc/hexanes) to afford 5-chloro-N-(2-fluoro-3-(7-methyl-2-(methylthio)pyrido[2,3-d]pyrimidin-6-yl)phenyl)-2-methoxypyridine-3-sulfonamide (0.60 g, 71% yield) as a yellow solid. MS (ESI) m/z: 506.0 (M+H$^+$).

General Method R: Oxidation and Substitution

Example 3

5-chloro-N-(2-fluoro-3-(7-methyl-2-(methylamino)pyrido[2,3-d]pyrimidin-6-yl)phenyl)-2-methoxypyridine-3-sulfonamide

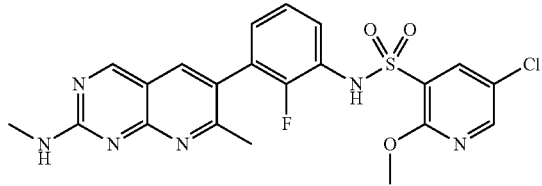

A solution of 5-chloro-N-(2-fluoro-3-(7-methyl-2-(methylthio)pyrido[2,3-d]pyrimidin-6-yl)phenyl)-2-methoxypyridine-3-sulfonamide (2, 0.26 g, 0.52 mmol) in DCM (2 mL) at 0° C. was treated with mCPBA (0.12 g, 0.54 mmol). The reaction stirred for 60 min. The solid was filtered off and rinsed with cold DCM (25 mL). The filtrate was concentrated under reduced pressure. The residue was dissolved in THF (2 mL) and then DIEA (0.17 mL, 0.97 mmol) was added. Methyl amine (33% in EtOH, 0.65 mL, 5.2 mmol) was added and the reaction mixture was slowly warmed to rt over 1 h. The reaction mixture was quenched with sat'd NaHCO$_3$ (aq, 30 mL) and then the solution was extracted with DCM (2×25 mL). The combined organics were dried over anhydrous Na$_2$SO$_4$, filtered, and concentrated under reduced pressure. The crude was purified by reverse phase column chromatography (0 to 100% (0.4% FA) water/CH$_3$CN) to obtain 5-chloro-N-(2-fluoro-3-(7-methyl-2-(methylamino)pyrido[2,3-d]pyrimidin-6-yl)phenyl)-2-methoxypyridine-3-sulfonamide (0.13 g, 53% yield) as a yellow solid. $^1$H NMR (500 MHz, DMSO-d$_6$): δ 10.4 (brs, 1H), 9.09 (s, 1H), 8.34 (s, 1H), 8.00 (m, 3H), 7.72 (s, 1H), 7.30 (s, 1H), 7.06 (m, 1H), 3.88 (s, 3H), 2.92 (d, J=4.8 Hz, 3H), 2.27 (s, 3H); MS (ESI) m/z: 489.0 (M+H$^+$).

General Method S: Reduction with LiAlH$_4$

Example 4

2,5-dichloro-N-(2-fluoro-3-(7-(methylamino)-1,6-naphthyridin-3-yl)phenyl)-3-(hydroxymethyl)benzenesulfonamide

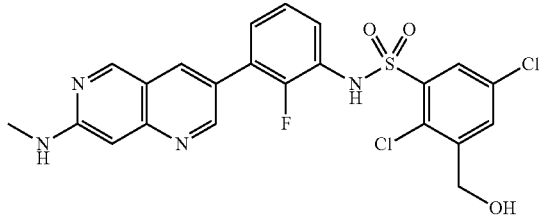 [SMILES: CNc1cc2ncc(-c3cccc(NS(=O)(=O)c4cc(Cl)cc(CO)c4Cl)c3F)cc2cn1]

Methyl 2,5-dichloro-3-(N-(2-fluoro-3-(7-(methylamino)-1,6-naphthyridin-3-yl)phenyl)sulfamoyl)benzoate (0.21 g, 47% yield) was prepared from 3-bromo-N-methyl-1,6-naphthyridin-7-amine (B26, 0.20 g, 0.84 mmol), and methyl 2,5-dichloro-3-(N-(2-fluoro-3-(4,4,5,5-tetramethyl-1,3,2-dioxaborolan-2-yl)phenyl)sulfamoyl)benzoate (G17, 0.42 g, 0.84 mmol) by General Method Q. MS (ESI) m/z: 535.0 (M+H$^+$).

A solution of methyl 2,5-dichloro-3-(N-(2-fluoro-3-(7-(methylamino)-1,6-naphthyridin-3-yl)phenyl)sulfamoyl)benzoate (0.10 g, 0.19 mmol) in THF (2 mL) was treated with LiAlH$_4$ (0.021 g, 0.56 mmol) under Ar. The reaction mixture was stirred at 0° C. for 1 h. The reaction mixture was quenched with EtOAc (1 mL) and MeOH (1 mL) at 0° C. The reaction mixture was warmed to rt and stirred for 2 h. The mixture was filtered through a pad of celite and the filtrate was concentrated under reduced pressure. The crude was purified reverse phase column chromatography (0 to 100% (0.4% FA) water/CH$_3$CN) to afford 2,5-dichloro-N-(2-fluoro-3-(7-(methylamino)-1,6-naphthyridin-3-yl)phenyl)-3-(hydroxymethyl)benzenesulfonamide (0.02 g, 21% yield) as a yellow solid. $^1$H NMR (500 MHz, DMSO-d$_6$): δ 10.8 (s, 1H), 8.98 (s, 1H), 8.82 (s, 1H), 8.30 (s, 1H), 7.83 (m, 2H), 7.51 (t, J=5.6 Hz, 1H), 7.28 (m, 2H), 6.99 (m, 1H), 6.60

(s, 1H), 5.75 (m, 1H), 4.63 (d, J=5.4 Hz, 2H), 2.87 (d, J=4.9 Hz, 3H); MS (ESI) m/z: 507.0 (M+H⁺).
General Method T: Deprotection with TFA Example 5

5-chloro-N-(2,4-difluoro-5-(2-methyl-7-(methylamino)-1,6-naphthyridin-3-yl)phenyl)-2-methoxypyridine-3-sulfonamide

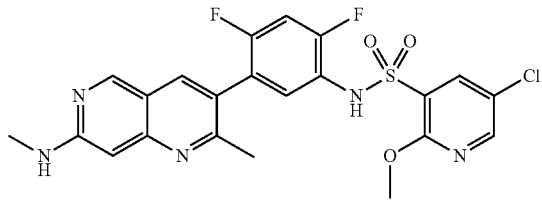 [SMILES: CNc1cc2nc(C)c(-c3cc(NS(=O)(=O)c4cc(Cl)cnc4OC)c(F)cc3F)cc2cn1]

5-chloro-N-(2,4-difluoro-5-(7-((4-methoxybenzyl)(methyl)amino)-2-methyl-1,6-naphthyridin-3-yl)phenyl)-2-methoxypyridine-3-sulfonamide (0.14 g, 93% yield) was prepared by reacting 3-(5-amino-2,4-difluorophenyl)-N-(4-methoxybenzyl)-N,2-dimethyl-1,6-naphthyridin-7-amine (E7, 0.10 g, 0.24 mmol) and 5-chloro-2-methoxypyridine-3-sulfonyl chloride (F1, 0.07 g, 0.29 mmol) by method Q. MS (ESI) m/z: 626.2 (M+H⁺).

A solution of 5-chloro-N-(2,4-difluoro-5-(7-((4-methoxybenzyl)(methyl)amino)-2-methyl-1,6-naphthyridin-3-yl)phenyl)-2-methoxypyridine-3-sulfonamide (0.10 g, 0.16 mmol) in TFA (1.0 mL) was stirred at rt for 1 h. The reaction mixture was concentrated under reduced pressure and the crude was purified via flash column chromatography (0 to 100% EtOAc/hexanes) to obtain 5-chloro-N-(2,4-difluoro-5-(2-methyl-7-(methylamino)-1,6-naphthyridin-3-yl)phenyl)-2-methoxypyridine-3-sulfonamide (0.070 g, 84% yield) as a yellow solid. ¹H NMR (500 MHz, DMSO-d₆): δ 10.5 (s, 1H,), 8.88 (s, 1H), 8.53 (d, J=2.6 Hz, 1H), 8.08 (d, J=2.6 Hz, 1H), 7.99 (s, 1H), 7.47 (t, J=9.8 Hz, 1H), 7.32 (t, J=8.3 Hz, 1H), 6.89 (d, J=5.7 Hz, 1H), 6.54 (s, 1H), 3.96 (s, 3H), 2.86 (d, J=4.9 Hz, 3H), 2.32 (s, 3H); MS (ESI) m/z: 506.0 (M+H⁺).
General Method U: Conversion from SMe to Cl Example 109A 5-chloro-N-(3-(2-chloro-7-(methylamino)pyrido[2,3-d]pyrimidin-6-yl)-2-fluorophenyl)-2-methoxypyridine-3-sulfonamide

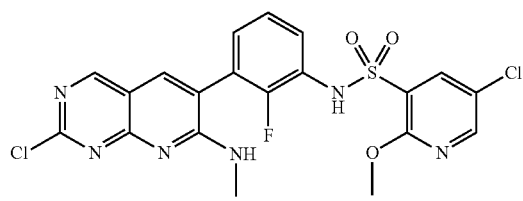 [SMILES: CNc1nc2nc(Cl)ncc2cc1-c1cccc(NS(=O)(=O)c2cc(Cl)cnc2OC)c1F]

A solution of 5-chloro-N-(2-fluoro-3-(7-(methylamino)-2-(methylthio)pyrido[2,3-d]pyrimidin-6-yl)phenyl)-2-methoxypyridine-3-sulfonamide (0.88 g, 1.7 mmol) in CH₃CN (8.5 mL) was cooled to 0° C. for 10 min. A solution of sulfuryl chloride (1.37 mL, 17 mmol) in DCM (8.5 mL) was then added dropwise and the reaction was allowed to warm to rt over 1H. The reaction mixture was quenched with sat'd NaHCO₃ (aq) and then poured into 10% AcOH (aq) (25 mL). The solution was extracted with DCM (3×). The combined organics were dried over anhydrous Na₂SO₄, filtered and concentrated under reduced pressure to obtain 5-chloro-N-(3-(2-chloro-7-(methylamino)pyrido[2,3-d]pyrimidin-6-yl)-2-fluorophenyl)-2-methoxypyridine-3-sulfonamide (0.36 g, 41% yield) as an orange solid. MS (ESI) m/z: 509.0 (M+H⁺).
General Method V: Substitution Example 109

N-(3-(2-amino-7-(methylamino)pyrido[2,3-d]pyrimidin-6-yl)-2-fluorophenyl)-5-chloro-2-methoxypyridine-3-sulfonamide

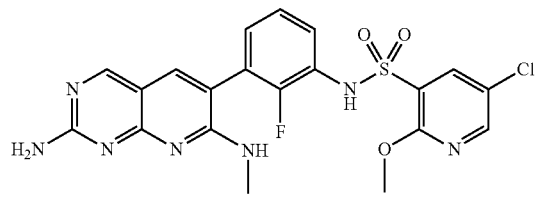 [SMILES: CNc1nc2nc(N)ncc2cc1-c1cccc(NS(=O)(=O)c2cc(Cl)cnc2OC)c1F]

A mixture of 5-chloro-N-(3-(2-chloro-7-(methylamino)pyrido[2,3-d]pyrimidin-6-yl)-2-fluorophenyl)-2-methoxypyridine-3-sulfonamide (109A, 0.25 g, 0.49 mmol) in NH₄OH (30%, 1.27 mL, 9.8 mmol) was sealed and heated to 100° C. for overnight. The reaction mixture was cooled to rt and dissolved into a small amount of DMSO and purified by reverse phase column chromatography (10 to 100% (0.4% FA) water/CH₃CN). The residue was neutralized with sat'd NaHCO₃ (aq) and the solution was extracted with DCM (3×). The combined organics were dried over anhydrous Na₂SO₄, filtered and concentrated N-(3-(2-amino-7-(methylamino)pyrido[2,3-d]pyrimidin-6-yl)-2-fluorophenyl)-5-chloro-2-methoxypyridine-3-sulfonamide (0.14 g, 60% yield) as a pale yellow solid. ¹H NMR (500 MHz, DMSO-d⁶): δ 10.3 (brs, 1H), 8.55 (s, 1H), 8.42 (d, J=2.6 Hz, 1H), 8.02 (d, J=2.6 Hz, 1H), 7.41 (s, 1H), 7.31 (td, J=1.8 and 7.7 Hz, 1H), 7.16 (t, J=7.7 Hz, 1H), 7.11 (m, 1H), 6.62 (s, 2H), 6.39 (q, J=4.5 Hz, 1H), 3.84 (s, 3H), 2.71 (d J=4.5 Hz, 3H); MS (ESI) m/z: 490.0 (M+H⁺).

Preparation of Example 121A: 5-chloro-N-(2-chloro-3-(7-chloro-2-methyl-1,6-naphthyridin-3-yl)phenyl)-2-methoxypyridine-3-sulfonamide

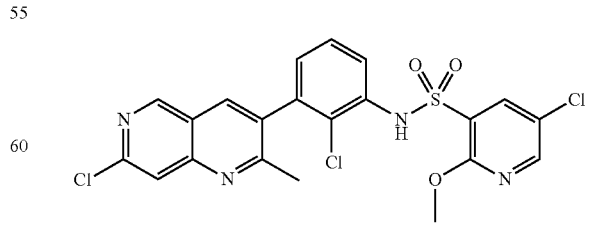

Using the General Method P, 5-chloro-N-(2-chloro-3-(7-chloro-2-methyl-1,6-naphthyridin-3-yl)phenyl)-2-methoxypyridine-3-sulfonamide (1.5 g, 96% yield) was prepared from 7-chloro-2-methyl-1,6-naphthyridin-3-yl trifluoromethanesulfonate (B23) and 5-chloro-N-(2-chloro-3-(4,4,5,5-tetramethyl-1,3,2-dioxaborolan-2-yl)phenyl)-2-methoxypyridine-3-sulfonamide (G21). $^1$H NMR (500 MHz, DMSO-d$^6$): δ 9.24 (s, 1H), 8.31 (s, 1H), 8.20 (s, 1H), 8.01 (d, J=6.6 Hz, 2H), 7.33 (d, J=8.3 Hz, 1H), 7.05 (t, J=7.8 Hz, 1H), 6.57 (d, J=7.3 Hz, 1H), 3.82 (s, 3H), 2.46 (s, 3H).

General Method W: Buchwald Reaction

Example 121B tert-butyl (3-(2-chloro-3-((5-chloro-2-methoxypyridine)-3-sulfonamido)phenyl)-2-methyl-1,6-naphthyridin-7-yl)carbamate

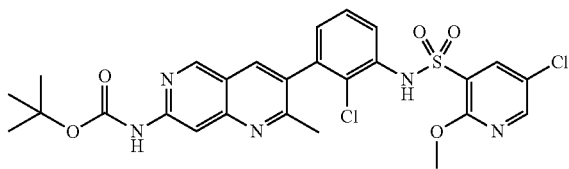 [SMILES: COc1ncc(Cl)cc1S(=O)(=O)Nc1cccc(-c2cc3cnc(NC(=O)OC(C)(C)C)cc3nc2C)c1Cl]

A mixture of 5-chloro-N-(2-chloro-3-(7-chloro-2-methyl-1,6-naphthyridin-3-yl)phenyl)-2-methoxypyridine-3-sulfonamide (121A, 0.50 g, 0.98 mmol), Cs$_2$CO$_3$ (0.96 g, 2.9 mmol) and tert-butyl carbamate (0.17 g, 1.5 mmol) in 1,4-dioxane (5 mL) was degassed with Ar for 3 min. tBuBrettPhos Pd G3 (0.042 g, 0.05 mmol) was added and the mixture was degassed with Ar again for 2 min. The reaction mixture was stirred at 100° C. for 12 h. The reaction mixture was cooled to rt and diluted with EtOAc (20 mL). The mixture was filtered through a pad of celite and washed with EtOAc (10 mL). The filtrate was concentrated under reduced pressure and the residue was purified by silica gel column chromatography (0 to 50% MeOH/DCM) to obtain tert-butyl (3-(2-chloro-3-((5-chloro-2-methoxypyridine)-3-sulfonamido)phenyl)-2-methyl-1,6-naphthyridin-7-yl)carbamate (0.54 g, 93% yield) as a brown solid. MS (ESI) m/z: 590.2 (M+H$^+$).

General Method X: Deprotection with K$_2$CO$_3$

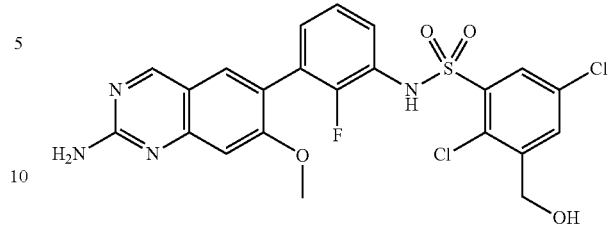

3-(N-(3-(2-amino-7-methoxyquinazolin-6-yl)-2-fluorophenyl)sulfamoyl)-2,5-dichlorobenzyl acetate (0.16 g, 29% yield) was prepared by reacting 2,5-dichloro-3-(N-(2-fluoro-3-(4,4,5,5-tetramethyl-1,3,2-dioxaborolan-2-yl)phenyl)sulfamoyl)benzyl acetate (G24, 0.65 g, 0.012 mmol) and 6-bromo-7-methoxyquinazolin-2-amine (B41, 0.25 g, 0.098 mmol) by method P. $^1$H NMR (400 MHz, DMSO-d$_6$) δ 10.68 (s, 1H), 8.92 (s, 1H), 7.88 (m, 2H), 7.56 (s, 1H), 7.17-7.28 (m, 3H), 6.86 (s, 1H), 6.80 (s, 2H), 5.20 (s, 2H), 3.75 (s, 3H), 2.06 (s, 3H); MS (ESI) m/z: 565.0 (M+H$^+$).

A solution of 3-(N-(3-(2-amino-7-methoxyquinazolin-6-yl)-2-fluorophenyl)sulfamoyl)-2,5-dichlorobenzyl acetate (0.16 g, 0.028 mmol) in MeOH (5.0 mL) was treated with K$_2$CO$_3$ (0.16 g, 0.11 mmol). The reaction mixture was stirred at rt for 4 h and then concentrated under reduced pressure. the crude was acidified with citric acid (pH: 4~5) to get solid precipitate. Solids were filtered and then triturated in CH$_3$CN to afford a N-(3-(2-amino-7-methoxyquinazolin-6-yl)-2-fluorophenyl)-2,5-dichloro-3-(hydroxymethyl)benzenesulfonamide (0.075 g, 57% yield) as an off-white solid. $^1$H NMR (400 MHz, DMSO-d$_6$) δ 10.6 (s, 1H), 8.92 (s, 1H), 7.8 (brs, 1H), 7.80 (d, J=2.4 Hz 1H), 7.78 (brs, 1H), 7.56 (s, 1H), 7.25-7.23 (m, 1H), 7.18 (brs, 1H), 6.85 (s, 1H), 6.79 (s, 2H), 5.73 (t, J=5.6 Hz, 1H), 4.60 (d, J=5.6 Hz, 2H), 3.75 (s, 3H); LCMS (ES) m/z 523.23 (M+H$^+$).

Using the General Methods P-X above, the following compounds (Examples) of Table I were prepared.

TABLE I

| Ex. No | SM | Product | Method | Yield (%) | $^1$H NMR (400 or 500 MHz, DMSO-$d_6$): δ | MS (m/z: M + H$^+$) |
|---|---|---|---|---|---|---|
| 6 | B3 G8 | | P | 33 | 9.00 (s, 1H), 7.77 (s, 1H), 7.64 (s, 1H), 7.58 (s, 1H), 7.52 (dd, J = 2.4 and 8.2 Hz, 1H), 7.37 (d, J = 8.2 Hz, 1H), 7.13 (d, J = 11.3 Hz, 1H), 6.88 (d, J = 8.0 Hz, 1H), 2.85 (d, J = 4.7 Hz, 3H), 2.50 (s, 3H), 2.11 (s, 3H), 1.89 (s, 3H). | 486.2 |
| 7 | E3 F1 | | Q & T | 72 | 10.6 (s, 1H), 9.06 (s, 1H), 8.53 (d, J = 2.6 Hz, 1H), 8.34 (m, 1H), 8.11 (d, J = 2.6 Hz, 1H), 7.42 (d, J = 7.3 Hz, 1H), 7.37 (d, J = 7.6 Hz, 2H), 6.57 (s, 1H), 3.94 (s, 3H), 2.87 (s, 3H), 2.44 (s, 3H). NH missing | 488.0 |
| 8 | B3 G7 | | P | 48 | 9.00 (s, 1H), 7.85 (s, 1H), 7.83 (d, J = 2.3 Hz, 1H), 7.68 (d, J = 5.8 Hz, 1H), 7.57 (m, J = 2.3 and 8.2 Hz, 1H), 7.39 (d, J = 8.2 Hz, 1H), 6.92 (d, J = 9.2 Hz, 1H), 6.82 (m, 2H), 2.85 (t, J = 4.8 Hz, 3H), 2.51 (s, 3H), 2.29 (s, 3H). | 472.0 |
| 9 | B15 G7 | | P | 51 | 8.53 (s, 1H), 8.07 (s, 1H), 7.88 (d, J = 2.3 Hz, 1H), 7.60 (dd, J = 2.3 and 8.2 Hz, 1H), 7.40 (d, J = 8.2 Hz, 1H), 7.35 (s, 1H), 7.15 (s, 1H), 6.85 (m, 1H), 6.82-6.82 (m, 1H), 6.57 (s, 1H), 2.80 (d, J = 4.8 Hz, 3H), 2.77 (d, J = 4.5 Hz, 3H), 2.51 (s, 3H). | 487.2 |

TABLE 1-continued

| # | Structure | Method | IC50 | NMR | MS |
|---|---|---|---|---|---|
| 10 | B15 G4 | P | 23 | 10.3 (s, 1H), 8.61 (s, 1H), 8.51 (d, J = 2.6 Hz, 1H), 8.06 (d, J = 2.6 Hz, 1H), 7.36 (s, 1H), 7.19 (d, J = 11.4 Hz, 1H), 6.96 (d, J = 8.1 Hz, 1H), 6.22 (s, 1H), 3.97 (m, 3H), 2.88 (m, 4H), 2.84 (d, J = 4.6 Hz, 3H), 2.02 (m, 3H). | 518.2 |
| 11 | B15 G9 | P | 52 | 10.9 (s, 1H), 8.61 (s, 1H), 8.53 (d, J = 2.6 Hz, 1H), 8.32 (d, J = 2.6 Hz, 1H), 7.45 (s, 1H), 7.22 (d, J = 2.6 Hz, 1H), 6.98 (m, 3H), 6.60 (s, 1H), 3.98 (s, 3H), 2.88 (d, J = 4.8 Hz, 3H), 2.84 (d, J = 4.6 Hz, 3H). | 504.2 |
| 12 | B3 G5 | P | 25 | 10.5 (s, 1H), 9.11 (s, 1H), 8.51 (d, J = 2.5 Hz, 1H), 8.07 (d, J = 2.6 Hz, 1H), 8.02 (s, 1H), 7.79 (d, J = 5.6 Hz, 1H), 7.45 (t, J = 9.8 Hz, 1H), 7.32 (t, J = 8.3 Hz, 1H), 3.94 (s, 3H), 2.93 (d, J = 4.7 Hz, 3H), 2.34 (s, 3H). | 507.0 |
| 13 | B15 G5 | P | 40 | 8.60 (s, 1H), 8.23 (d, J = 2.5 Hz, 1H), 7.99 (d, J = 2.6 Hz, 1H), 7.40 (d, J = 2.6 Hz, 1H), 7.11 (m, 1H), 7.02 (t, J = 10.3 Hz, 1H), 6.42 (s, 1H), 3.80 (m, 3H), 2.88 (d, J = 4.8 Hz, 3H), 2.84 (d, J = 4.6 Hz, 3H). NH missing | 522.2 |

TABLE 1-continued

| | | Q, S & T | | |
|---|---|---|---|---|
| 14 | E8 F12 | (structure) | 90 | 11.0 (brs, 1H), 9.02 (s, 1H), 8.25 (s, 1H), 7.90 (m, 3H), 7.39 (d, J = 8.0 Hz, 1H), 6.58 (s, 1H), 4.61 (s, 2H), 2.90 (s, 3H), 2.29 (s, 3H). NH and OH missing | 601.0 |
| 15 | B15 G3 | (structure) | 71 | 10.6 (brs, 1H), 8.62 (s, 1H), 8.47 (t, J = 2.6 Hz, 1H), 8.22 (d, J = 2.6 Hz, 1H), 7.41 (s, 1H), 7.33 (t, J = 7.8 Hz, 1H), 7.14 (m, 3H), 7.00 (m, 1H), 6.42 (m, 1H), 3.97 (m, 3H), 2.88 (d, J = 4.8 Hz, 3H), 2.86 (d, J = 4.6 Hz, 3H). | 486.2 |
| 16 | B15 G13 | (structure) | 39 | 10.4 (s, 1H), 8.61 (s, 1H), 8.47 (d, J = 2.6 Hz, 1H), 8.10 (d, J = 2.6 Hz, 1H), 7.48 (s, 1H), 7.36 (t, J = 7.7 Hz, 1H), 7.14-7.24 (m, 3H), 6.44 (s, 1H), 3.91 (s, 3H), 2.88 (d, J = 4.8 Hz, 3H), 2.82 (d, J = 4.5 Hz, 3H), | 504.2 |
| 17 | B3 G4 | (structure) | 87 | 10.4 (s, 1H), 9.08 (s, 1H), 8.51 (d, J = 2.6 Hz, 1H), 8.04 (d, J = 2.6 Hz, 1H), 7.88 (s, 1H), 7.71 (s, 1H), 7.22 (d, J = 11.3 Hz, 1H), 7.04 (d, J = 8.0 Hz, 1H), 3.96 (m, 3H), 2.92 (d, J = 4.7 Hz, 3H), 2.51 (t, J = 2.2 Hz, 3H), 2.18 (s, 3H), 1.98 (s, 3H). | 503.2 |
| 18 | E8 F1 | (structure) | 63 | 10.6 (brs, 1H), 8.84 (s, 1H), 8.33 (m, 1H), 7.98 (s, 1H), 7.81 (s, 1H), 7.51 (brs, 1H), 7.22 (d, J = 8.6 Hz, 1H), 6.80 (d, J = 5.7 Hz, 1H), 6.52 (s, 1H), 3.84 (s, 3H), 2.83 (d, J = 4.9 Hz, 3H), 2.20 (s, 3H). | 568.0 |

| # | Structure | Methods | % | 1H NMR | MS |
|---|---|---|---|---|---|
| 19 | E3, F12 | | Q, S & T | 69 | 10.8 (s, 1H), 8.86 (s, 1H), 7.90 (s, 1H), 7.82 (m, 2H), 7.32 (m, 2H), 7.24 (m, 1H), 6.82 (m, 1H), 6.53 (s, 1H), 5.75 (t, J = 6.1 Hz, 1H), 4.62 (d, J = 5.6 Hz, 2H), 2.85 (d, J = 4.9 Hz, 3H), 2.35 (s, 3H). | 521.0 |
| 20 | D13, F1 | | Q | 22 | 10.5 (s, 1H), 9.09 (s, 1H), 8.51 (d, J = 1.8 Hz, 1H), 8.09 (d, J = 2.0 Hz, 1H), 7.96 (s, 1H), 7.71 (s, 1H), 7.32 (m, 3H), 3.93 (s, 3H), 2.92 (d, J = 3.4 Hz, 3H), 2.40 (s, 3H). | 489.3 |
| 21 | D14, F1 | | Q | 20 | 10.0 (s, 1H), 9.08 (s, 1H), 8.52 (d, J = 2.4 Hz, 1H), 8.02 (d, J = 2.3 Hz, 1H), 7.91 (s, 1H), 7.77 (brs, 1H), 7.24 (d, J = 10.4 Hz, 1H), 6.97 (d, J = 7.3 Hz, 1H), 3.94 (s, 3H), 2.92 (d, J = 4.6 Hz, 3H), 2.28 (s, 3H), 2.19 (s, 3H). | 503.2 |
| 22 | E1, F1 | | Q, S & T | 74 | 10.7 (s, 1H), 8.87 (s, 1H), 7.95 (s, 1H), 7.81 (t, J = 3.4 Hz, 2H), 7.48 (t, J = 9.8 Hz, 1H), 7.25 (t, J = 8.2 Hz, 1H), 6.89 (d, J = 5.6 Hz, 1H), 6.54 (s, 1H), 5.76 (t, J = 5.7 Hz, 1H), 4.62 (d, J = 5.5 Hz, 2H), 2.85 (d, J = 4.9 Hz, 3H), 2.29 (s, 3H). | 539.0 |

TABLE 1-continued

| # | Structure | Route | Ex# | ¹H NMR | MS |
|---|---|---|---|---|---|
| 23 | E4, F1 | Q & T | 41 | 11.0 (s, 1H), 9.01 (s, 1H), 8.53 (d, J = 2.5 Hz, 1H), 8.34 (d, J = 2.6 Hz, 1H), 8.28 (brs, 1H), 7.05 (m, 3H), 6.56 (s, 1H), 3.98 (s, 3H), 2.89 (s, 3H), 2.44 (s, 3H). NH missing | 488.0 |
| 24 | B15, G11 | P | 44 | 10.5 (s, 1H), 8.59 (s, 1H), 8.49 (d, J = 2.6 Hz, 1H), 8.18 (d, J = 2.6 Hz, 1H), 7.30 (s, 1H), 7.20 (d, J = 8.4 Hz, 1H), 7.15 (brs, 1H), 7.09 (dd, J = 2.4 and 8.3 Hz, 1H), 6.88 (d, J = 2.3 Hz, 1H), 6.07 (d, J = 5.5 Hz, 1H), 3.97 (s, 3H), 2.88 (d, J = 4.8 Hz, 3H), 2.83 (d, J = 4.6 Hz, 3H), 1.96 (s, 3H). | 500.0 |
| 25 | E4, F12 | Q, S & T | 43 | 11.3 (s, 1H), 9.00 (m, 1H), 8.32 (m, 1H), 8.06 (d, J = 2.6 Hz, 1H), 7.83 (d, J = 2.5 Hz, 1H), 7.07 (m, 2H), 6.98 (d, J = 10.4 Hz, 1H), 6.55 (s, 1H), 4.60 (s, 2H), 2.90 (s, 3H), 2.43 (s, 3H). NH and OH missing | 521.0 |
| 26 | D15, F1 | Q | 20 | 9.10 (s, 1H), 8.51 (d, J = 2.4 Hz, 1H), 8.24 (d, J = 2.4 Hz, 1H), 7.85 (d, J = 2.4 Hz, 1H), 7.7 (brs, 1H), 6.96 (d, J = 12.6 Hz, 1H), 6.76 (s, 1H), 3.96 (s, 3H), 2.91 (d, J = 4.4 Hz, 3H), 2.10 (s, 3H), 1.82 (s, 3H). | 503.2 |

TABLE 1-continued

| # | Building blocks | Structure | Method | Yield (%) | ¹H NMR | MS |
|---|---|---|---|---|---|---|
| 27 | C3, H3 | (structure) | P | 14 | 10.4 (brs, 1H), 9.02 (s, 1H), 8.42 (d, J = 2.6 Hz, 1H), 8.01 (s, 1H), 7.95 (d, J = 2.6 Hz, 1H), 7.78 (d, J = 5.7 Hz, 1H), 7.35 (m, 1H), 7.17 (t, J = 8.8 Hz, 1H), 3.86 (s, 3H), 2.85 (d, J = 4.7 Hz, 3H), 2.09 (s, 3H). | 507.0 |
| 28 | G11 | (structure) | P | 51 | 10.4 (s, 1H), 8.84 (s, 1H), 8.50 (d, J = 2.6 Hz, 1H), 8.19 (d, J = 2.6 Hz, 1H), 7.57 (m, 2H), 7.31 (dd, J = 1.8 and 8.6 Hz, 1H), 7.18 (d, J = 8.2 Hz, 1H), 7.00 (m, 2H), 6.65 (s, 1H), 6.00 (m, 2H), 3.98 (s, 3H), 2.15 (s, 3H). | 451.0 |
| 29 | G13 | (structure) | P | 40 | 10.4 (s, 1H), 8.86 (s, 1H), 8.50 (d, J = 2.6 Hz, 1H), 8.09 (d, J = 2.6 Hz, 1H), 7.86 (s, 1H), 7.59 (d, J = 8.7 Hz, 1H), 7.48 (d, J = 8.8 Hz, 1H), 7.41 (s, 1H), 7.26 (m, 2H), 6.63 (s, 1H), 6.08 (s, 2H), 3.92 (s, 3H). | 459.0 |
| 30 | B13, G11 | (structure) | P | 23 | 10.5 (s, 1H), 9.19 (s, 1H), 8.71 (d, J = 2.6 Hz, 1H), 8.50 (d, J = 2.6 Hz, 1H), 8.21 (d, J = 2.6 Hz, 1H), 8.12 (d, J = 2.6 Hz, 1H), 7.85 (d, J = 5.6 Hz, 1H), 7.23 (d, J = 8.2 Hz, 1H), 7.06 (m, 2H), 3.97 (s, 3H), 2.94 (d, J = 4.7 Hz, 3H), 2.17 (s, 3H). | 471.0 |
| 31 | E5, F1 | (structure) | Q & T | 61 | 10.5 (s, 1H), 8.99 (s, 1H), 8.52 (d, J = 2.6 Hz, 1H), 8.30 (d, J = 17.3 Hz, 1H), 8.05 (d, J = 2.6 Hz, 1H), 7.42 (m, 1H), 7.32 (m, 2H), 6.54 (s, 1H), 3.95 (s, 3H), 2.88 (s, 3H), 2.23 (s, 3H), NH missing | 488.0 |

TABLE 1-continued

| # | Structure | Route | Yield | ¹H NMR | MS |
|---|---|---|---|---|---|
| 32 | E10 F1 | Q & T | 74 | 10.6 (s, 1H), 9.02 (s, 1H), 8.49 (d, J = 2.6 Hz, 1H), 8.30 (m, 1H), 8.18 (d, J = 2.6 Hz, 1H), 7.26 (d, J = 8.3 Hz, 1H), 7.09 (m, 1H,), 6.99 (d, J = 2.3 Hz, 1H), 6.56 (s, 1H), 3.98 (s, 3H), 2.90 (s, 3H), 2.20 (s, 3H), 1.96 (s, 3H). NH missing | 484.0 |
| 33 | G13 (6-bromo-2-aminoquinazoline shown) | P | 45 | 10.4 (s, 1H), 9.17 (s, 1H), 8.50 (d, J = 2.6 Hz, 1H), 8.09 (d, J = 2.6 Hz, 1H), 7.87 (s, 1H), 7.70-7.73 (m, 1H), 7.49 (d, J = 8.8 Hz, 1H), 7.41 (t, J = 7.1 Hz, 1H), 7.23-7.32 (m, 2H), 7.00 (s, 2H), 3.91 (s, 3H). | 460.0 |
| 34 | B15 G10 | P | 64 | 10.7 (s, 1H), 8.53 (s, 1H), 8.45 (d, J = 2.6 Hz, 1H), 8.20 (d, J = 2.6 Hz, 1H), 7.28 (s, 1H), 7.14 (s, 1H), 6.89 (dd, J = 2.2 and 11.2 Hz, 1H), 6.67 (s, 1H), 6.21 (s, 1H), 3.90 (m, 3H), 2.80 (d, J = 4.7 Hz, 3H), 2.75 (d, J = 4.5 Hz, 3H), 1.78 (s, 3H). | 518.2 |
| 35 | B9 G13 | P | 24 | 10.8 (s, 1H), 10.5 (s, 1H), 9.55 (s, 1H), 8.51 (d, J = 2.6 Hz, 1H), 8.11 (d, J = 2.6 Hz, 1H), 7.98 (d, J = 8.9 Hz, 1H), 7.88 (d, J = 8.8 Hz, 1H), 7.48 (s, 1H), 7.27-7.36 (m, 2H), 3.91 (s, 3H), 2.29 (s, 3H). | 502.0 |
| 36 | B24 G13 | P | 31 | 10.4 (s, 1H), 9.12 (s, 1H), 8.51 (d, J = 2.6 Hz, 1H), 8.10 (d, J = 2.6 Hz, 1H), 7.86 (dd, J = 1.9 and 9.0 Hz, 1H), 7.53 (m, 2H), 7.42 (t, J = 7.3 Hz, 1H), 7.23-7.31 (m, 2H), 3.89 (s, 3H), 2.91 (d, J = 4.7 Hz, 3H). | 474.0 |

| | | | | | |
|---|---|---|---|---|---|
| 37 | B24 G9 | [structure] | P | 75 | 10.9 (s, 1H), 9.14 (s, 1H), 8.50 (d, J = 2.6 Hz, 1H), 8.39 (d, J = 2.6 Hz, 1H), 7.99 (d, J = 2.2 Hz, 1H), 7.87 (dd, J = 2.2 and 8.8 Hz, 1H), 7.54 (m, 2H), 7.29 (m, 2H), 6.90 (m, 1H), 3.95 (s, 3H), 2.91 (d, J = 4.7 Hz, 3H). | 474.0 |
| 38 | B3 G12 | [structure] | P | 44 | 10.6 (brs, 1H), 9.20 (s, 1H), 8.49 (d, J = 2.8 Hz, 1H), 8.19 (d, J = 2.8 Hz, 1H), 7.95 (s, 1H), 7.80 (brs, 1H), 7.27 (t, J = 8.8 Hz, 1H), 7.18 (m, 1H), 7.08 (m, 1H), 3.92 (s, 3H), 2.81 (s, 3H), 2.19 (s, 3H). | 489.1 |
| 39 | B15 G12 | [structure] | P | 44 | 10.5 (s, 1H), 8.55 (s, 1H), 8.44 (d, J = 2.6 Hz, 1H), 8.13 (d, J = 2.6 Hz, 1H), 7.38 (m, 1H), 7.09-7.17 (m, 3H), 6.97 (dd, J = 2.6 and 6.4 Hz, 1H), 6.47 (d, J = 5.5 Hz, 1H), 3.91 (s, 3H), 2.80 (d, J = 4.7 Hz, 3H), 2.76 (d, J = 4.5 Hz, 3H). | 504.0 |
| 42 | B3 G2 | [structure] | P | 5 | 10.5 (s, 1H), 9.00 (s, 1H), 8.86 (d, J = 2.3 Hz, 1H), 8.69 (d, J = 1.9 Hz, 1H), 8.09 (t, J = 2.1 Hz, 1H), 7.82 (s, 1H), 7.64 (d, J = 5.8 Hz, 1H), 7.17 (d, J = 11.2 Hz, 1H), 6.94 (d, J = 8.0 Hz, 1H), 2.85 (d, J = 4.7 Hz, 3H), 2.14 (s, 3H), 1.92 (s, 3H). | 473.0 |

TABLE I-continued

| # | Code | Structure | Method | Yield | ¹H NMR | MS |
|---|---|---|---|---|---|---|
| 43 | B24 G3 | (5-chloro-2-methoxy-N-{3-[2-(methylamino)quinazolin-6-yl]phenyl}pyridine-3-sulfonamide) | P | 45 | 10.6 (brs, 1H), 9.10 (brs, 1H), 8.47 (d, J = 2.4 Hz, 1H), 8.28 (d, J = 2.4 Hz, 1H), 7.94 (s, 1H), 7.85 (dd, J = 2.0 and 8.8 Hz, 1H), 7.55 (d, J = 8.8 Hz, 1H), 7.43 (m, 3H), 7.35 (t, J = 7.6 Hz, 1H), 7.08 (d, J = 8.0 Hz, 1H), 3.97 (s, 3H), 2.91 (d, J = 4.4 Hz, 3H). | 456.2 |
| 44 | C2 H4 | (5-chloro-N-{4-fluoro-3-[2-methyl-7-(methylamino)quinolin-3-yl]phenyl}-2-methoxypyridine-3-sulfonamide) | P & T | 37 | 10.6 (s, 1H), 8.87 (s, 1H), 8.51 (d, J = 2.6 Hz, 1H), 8.21 (d, J = 2.6 Hz, 1H), 7.93 (s, 1H), 7.27 (t, J = 9.1 Hz, 1H), 7.18 (m, 1H), 7.09 (m, 1H), 6.89 (m, 1H), 6.53 (s, 1H), 3.98 (s, 3H), 2.84 (m, 3H), 2.24 (s, 3H). | 488.0 |
| 45 | E5 F12 | (structure with CH₂OH and 2-Cl) | Q, S & T | 54 42 | 10.7 (s, 1H), 8.85 (s, 1H), 7.96 (s, 1H), 7.79 (s, 1H), 7.70 (s, 1H), 7.28 (s, 1H), 7.12 (brs, 1H), 6.84 (d, J = 5.8 Hz, 1H), 6.52 (s, 1H), 5.71 (s, 1H), 4.58 (d, J = 5.6 Hz, 2H), 2.84 (d, J = 4.9 Hz, 3H), 2.22 (s, 3H). NH and OH missing | 521.0 |
| 46 | D17 F1 | (5-chloro-N-{2,6-difluoro-3-[2-methyl-7-(methylamino)-1,8-naphthyridin-3-yl]phenyl}-2-methoxypyridine-3-sulfonamide) | Q | 6 | 10.4 (brs, 1H), 9.08 (s, 1H), 8.49 (s, 1H), 8.03 (d, J = 2.4 Hz, 1H), 8.01 (s, 1H), 7.80 (brs, 1H), 7.38 (s, 1H), 7.26 (s, 1H), 3.94 (s, 3H), 2.90 (s, 3H), 2.22 (s, 3H). | 507.2 |

TABLE 1-continued

| | | | | | |
|---|---|---|---|---|---|
| 47 | D33 F1 | (structure) | Q | 8 | 10.6 (brs, 1H), 9.09 (s, 1H), 8.49 (s, 1H), 8.23 (s, 1H), 7.90 (s, 1H), 7.70 (brs, 1H), 7.36 (s, 1H), 7.13 (m, 3H), 3.97 (s, 3H), 2.91 (s, 3H), 2.33 (s, 3H). | 471.1 |
| 48 | D34 F1 | (structure) | Q | 50 | 10.9 (brs, 1H), 9.09 (s, 1H), 8.52 (d, J = 2.8 Hz, 1H), 8.29 (d, J = 2.4 Hz, 1H), 8.00 (s, 1H), 7.8 (brs, 1H), 7.19 (m, 1H), 6.91 (m, 1H), 3.96 (s, 3H), 2.91 (s, 3H), 2.28 (s, 3H). | 507.2 |
| 49 | C5 H5 | (structure) | P | 28 | 10.8 (s, 1H), 8.54 (s, 1H), 8.46 (d, J = 2.6 Hz, 1H), 8.21 (d, J = 2.6 Hz, 1H), 7.44 (s, 1H), 7.21 (m, 1H), 7.10 (m, 1H), 6.76 (m, 1H), 6.58 (d, J = 5.4 Hz, 1H), 3.91 (s, 3H), 2.80 (d, J = 4.7 Hz, 3H), 2.75 (d, J = 4.5 Hz, 3H). | 522.0 |
| 50 | B24 G16 | (structure) | P | 47 | 10.5 (s, 1H), 9.13 (s, 1H), 8.33 (s, 1H), 7.87 (s, 1H), 7.77 (d, J = 2.6 Hz, 1H), 7.73 (d, J = 8.9 Hz, 1H), 7.53 (m, 3H), 7.23-7.35 (m, 3H), 3.18 (s, 3H), 3.17 (s, 3H). | 473.0 |

TABLE I-continued

| | | | Q | | |
|---|---|---|---|---|---|
| 51 | D18 F1 | [structure] | Q | 12 | 10.0 (brs, 1H), 9.07 (s, 1H), 8.51 (d, J = 2.4 Hz, 1H), 7.96 (d, J = 2.4 Hz, 1H), 7.86 (s, 1H), 7.7 (brs, 1H), 7.23 (t, J = 8.0 Hz, 1H), 7.08 (m, 2H), 3.97 (s, 3H), 2.91 (brs, 3H), 2.18 (s, 3H), 1.86 (s, 3H). | 485.1 |
| 52 | D16 F1 | [structure] | Q | 42 | 9.90 (brs, 1H), 9.11 (s, 1H), 8.52 (d, J = 4.8 Hz, 1H), 8.03 (d, J = 2.0 Hz, 1H), 7.68 (s, 1H), 7.53 (m, 2H), 7.40 (brm, 1H), 7.19 (m, 2H), 7.99 (d, J = 7.6 Hz, 1H), 3.96 (s, 3H), 2.90 (s, 3H), 2.08 (s, 3H). | 470.1 |
| 53 | D19 F1 | [structure] | Q | 23 | 10.4 (brs, 1H), 9.06 (s, 1H), 8.47 (d, J = 2.8 Hz, 1H), 8.14 (d, J = 2.4 Hz, 1H), 7.82 (s, 1H), 7.7 (brs, 1H), 7.21 (d, J = 8.4 Hz, 1H), 7.06 (d, J = 8.0 Hz, 1H), 6.87 (s, 1H), 3.96 (s, 3H), 2.91 (s, 3H), 2.8 (s, 3H), 1.90 (s, 3H). | 485.2 |
| 54 | D20 F1 | [structure] | Q | 41 | 10.6 (brs, 1H), 9.16 (s, 1H), 8.49 (d, J = 2.8 Hz, 1H), 8.22 (d, J = 2.4 Hz, 1H), 7.84 (s, 1H), 7.21 (d, J = 8.8 Hz, 1H), 7.56 (d, J = 8.4 Hz, 1H), 7.50 (brs, 1H), 7.26 (m, 2H), 3.97 (s, 3H), 2.91 (s, 3H). | 474.2 |
| 55 | D22 F1 | [structure] | Q | 41 | 10.8 (brs, 1H), 9.2 (brs, 1H), 8.51 (d, J = 2.40 Hz, 1H), 8.32 (d, J = 2.40 Hz, 1H), 7.87 (s, 1H), 7.72 (d, J = 8.8 Hz, 1H), 7.57 (m, 2H), 7.12 (m, 2H), 3.96 (s, 3H), 2.90 (s, 3H). | 492.1 |

TABLE I-continued

| | | | | | |
|---|---|---|---|---|---|
| 56 | B26 G13 | [structure] | P | 58 | 10.5 (s, 1H), 8.98 (s, 1H), 8.80 (t, J = 2.1 Hz, 1H), 8.51 (m, 1H), 8.30 (s, 1H), 8.10 (d, J = 2.6 Hz, 1H), 7.51 (m, 1H), 7.3 (m, 2H), 7.01 (m, 1H), 6.60 (s, 1H), 3.92 (s, 3H), 2.86 (d, J = 4.9 Hz, 3H). | 474.0 |
| 57 | B15 G19 | [structure] | P & S | 4 | 8.53 (s, 1H), 7.96 (d, J = 2.6 Hz, 1H), 7.72 (s, 1H), 7.35 (s, 1H), 7.15 (s, 1H), 6.81 (s, 3H), 6.53 (d, J = 5.6 Hz, 1H), 5.66 (m, 1H), 4.52 (d, J = 5.6 Hz, 2H), 2.80 (d, J = 4.8 Hz, 3H), 2.76 (d, J = 4.5 Hz, 3H). Nh missing | 537.2 |
| 58 | B26 G9 | [structure] | P | 19 | 11.0 (s, 1H), 8.99 (m, 2H), 8.50 (d, J = 2.6 Hz, 1H), 8.41 (d, J = 2.6 Hz, 1H), 8.38 (d, J = 2.4 Hz, 1H), 7.39 (m, 1H), 7.02 (m, 1H), 6.94 (m, 1H), 6.60 (s, 1H), 3.98 (s, 3H), 2.87 (d, J = 4.9 Hz, 3H). NH missing | 474.0 |
| 59 | B21 G3 | [structure] | P | 10 | 10.1 (s, 1H), 9.28 (s, 1H), 9.04 (s, 1H), 8.37 (d, J = 2.5 Hz, 2H), 8.19 (m, 2H), 7.58 (s, 1H), 7.29-7.39 (m, 4H), 7.04 (d, J = 8.0 Hz, 1H), 3.89 (m, 3H), 3.81 (s, 3H). | 523.1 |

TABLE 1-continued
| | | | | | |
|---|---|---|---|---|---|
| 60 | B26 G12 | 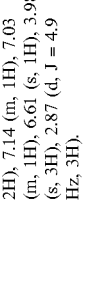 | P | 20 | 10.6 (s, 1H), 9.01 (s, 1H), 8.81 (t, J = 2.1 Hz, 1H), 8.50 (d, J = 2.6 Hz, 1H), 8.28 (s, 1H), 8.25 (d, J = 2.6 Hz, 1H), 7.28-7.36 (m, 2H), 7.14 (m, 1H), 7.03 (m, 1H), 6.61 (s, 1H), 3.98 (s, 3H), 2.87 (d, J = 4.9 Hz, 3H). | 474.0 |
| 61 | B16 G13 | 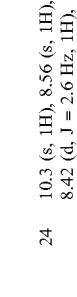 | P | 24 | 10.3 (s, 1H), 8.56 (s, 1H), 8.42 (d, J = 2.6 Hz, 1H), 8.03 (d, J = 2.6 Hz, 1H), 7.49 (s, 1H), 7.27 (m, 1H), 7.13 (m, 3H), 6.41 (brs, 2H), 3.84 (s, 3H), 2.78 (d, J = 4.7 Hz, 3H). | 490.0 |
| 62 | D23 F1 | 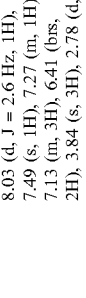 | Q | 41 | 10.3 (brs, 1H), 9.10 (brs, 1H), 8.49 (d, J = 2.4 Hz, 1H), 8.06 (d, J = 2.4 Hz, 1H), 7.76 (d, J = 1.6 Hz, 1H), 7.62 (dd, J = 2.0 and 8.8 Hz, 1H), 7.51 (m, 1H), 7.36 (m, 4H), 3.85 (s, 3H), 2.90 (d, J = 4.4 Hz, 3H). | 490.1 |
| 63 | B16 G9 |  | P | 29 | 10.8 (s, 1H), 8.56 (s, 1H), 8.43 (d, J = 2.6 Hz, 1H), 8.24 (d, J = 2.6 Hz, 1H), 7.47 (s, 1H), 7.18 (s, 1H), 6.93 (s, 1H), 6.86 (m, 2H), 6.53 (brs, 2H), 3.89 (s, 3H), 2.78 (d, J = 4.7 Hz, 3H). | 490.0 |
| 64 | B16 G3 | 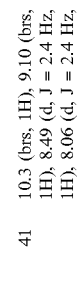 | P | 31 | 10.6 (brs, 1H), 8.57 (s, 1H), 8.40 (d, J = 2.6 Hz, 1H), 8.16 (d, J = 2.6 Hz, 1H), 7.43 (s, 1H), 7.27 (t, J = 7.9 Hz, 1H), 7.11 (m, 2H), 7.05 (t, J = 7.1 Hz, 2H), 6.41 (brs, 2H), 3.88 (s, 3H), 2.78 (d, J = 4.7 Hz, 3H). | 472.0 |

| | | | | | |
|---|---|---|---|---|---|
| 65 | B3 G9 | [structure: 5-chloro-2-methoxy-pyridine-3-sulfonamide linked to 3-fluorophenyl bearing methyl-pyrido-pyrimidine with NHMe] | P | 21 | 10.9 (brs, 1H), 9.10 (m, 1H), 8.51 (d, J = 2.4 Hz, 1H), 8.32 (d, J = 2.4 Hz, 1H), 7.94 (s, 1H), 7.7 (brs, 1H), 7.02 (d, J = 9.2 Hz, 1H), 6.95 (m, 2H), 3.96 (s, 3H), 2.90 (d, J = 4.4 Hz, 3H), 2.35 (s, 3H). | 490.0 |
| 66 | B32 G13 | [structure: analogous with 2-fluoro-3-methoxyphenyl] | P | 46 | 10.4 (s, 1H), 8.95 (s, 1H), 8.52 (d, J = 2.6 Hz, 1H), 8.08 (d, J = 2.6 Hz, 1H), 8.00 (s, 1H), 7.69 (s, 1H), 7.35 (t, J = 7.5 Hz, 1H), 7.24 (m, 2H), 3.91 (s, 3H), 3.87 (s, 3H), 2.91 (d, J = 4.7 Hz, 3H). | 505.0 |
| 67 | D26 F1 | [structure: analogous with 2-chlorophenyl] | Q | 25 | 10.4 (s, 1H), 9.08 (s, 1H), 8.49 (d, J = 2.0 Hz, 1H), 7.97 (d, J = 2.4 Hz, 1H), 7.92 (s, 1H), 7.70 (brs, 1H), 7.44 (m, 2H), 7.29 (s, 1H), 3.90 (s, 3H), 2.91 (d, J = 4.0 Hz, 3H), 2.15 (s, 3H). | 505.1 |
| 68 | D25 F1 | [structure: analogous with 3-chloro-5-phenyl] | Q | 5 | 10.8 (brs, 1H), 9.08 (s, 1H), 8.51 (d, J = 2.4 Hz, 1H), 8.22 (d, J = 2.4 Hz, 1H), 7.89 (s, 1H), 7.6 (brs, 1H), 7.50 (d, J = 8.8 Hz, 1H), 7.19 (dd, J = 2.4 and 8.8 Hz, 1H), 7.09 (d, J = 2.4 Hz, 1H), 3.95 (s, 3H), 2.92 (d, J = 3.6 Hz, 3H), 2.16 (s, 3H). | 505.2 |

TABLE 1-continued
| | | | | | |
|---|---|---|---|---|---|
| 69 | D27 F1 | 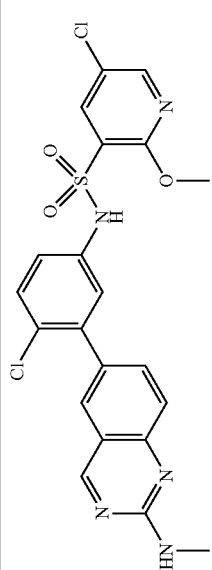 | 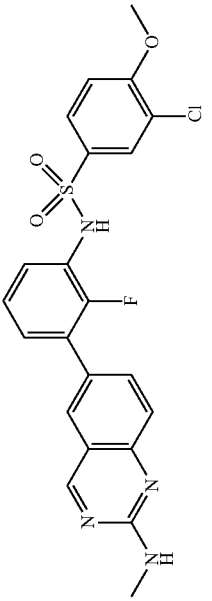 | Q | 47 | 10.8 (brs, 1H), 9.13 (s, 1H), 8.51 (d, J = 2.4 Hz, 1H), 8.26 (d, J = 2.4 Hz, 1H), 7.70 (d, J = 1.2 Hz, 1H), 7.62 (dd, J = 2.0 and 10.8 Hz, 1H), 7.5 (brs, 1H), 7.46 (d, J = 8.4 Hz, 2H), 7.18 (d, J = 2.4 Hz, 1H), 7.13 (dd, J = 2.8 and 8.8 Hz, 1H), 3.95 (s, 3H), 2.91 (d, J = 4.4 Hz, 3H). | 490.1 |
| 70 | D28 | | | Q | 45 | 10.2 (brs, 1H), 9.11 (s, 1H), 7.84 (s, 1H), 7.75 (d, J = 2.0 Hz, 1H), 7.69 (m, 2H), 7.53 (d, J = 8.0 Hz, 1H), 7.5 (brs, 1H), 7.40 (m, 1H), 7.32 (d, J = 8.4 Hz, 1H), 7.25 (m, 2H), 3.90 (s, 3H), 2.91 (d, J = 4.8 Hz, 3H). | 473.1 |
| 71 | D28 | | | Q | 25 | 10.6 (brs, 1H), 9.10 (s, 1H), 8.15 (d, J = 8.4 Hz, 1H), 8.03 (s, 1H), 7.90 (d, J = 8.4 Hz, 1H), 7.79 (s, 1H), 7.65 (d, J = 8.8 Hz, 1H), 7.47 (m, 3H), 7.26 (m, 2H), 2.91 (d, J = 4.4 Hz, 3H). | 555.1 557.1 |
| 72 | D28 | | | Q | 26 | 10.8 (brs, 1H), 9.13 (s, 1H), 8.10 (m, 1H), 7.85 (s, 1H), 7.70 (m, 2H), 7.50 (brm, 1H), 7.45 (m, 2H), 7.25 (m, 2H), 2.91 (d, J = 4.4 Hz, 3H). | 523.1 525.1 |

TABLE 1-continued

| # | Code | Structure | Method | Yield | ¹H NMR | MS |
|---|------|-----------|--------|-------|--------|-----|
| 73 | C5 H3 | (structure) | P | 6 | 10.3 (s, 1H), 8.53 (s, 1H), 8.31 (s, 1H), 7.97 (d, J = 2.6 Hz, 1H), 7.47 (s, 1H), 7.27 (s, 1H), 7.17 (brs, 1H), 6.99 (brs, 1H), 6.52 (brs, 1H), 3.81 (m, 3H), 2.80 (s, 3H), 2.75 (s, 3H). | 522.2 |
| 74 | C5 H8 | (structure) | P | 17 | 10.6 (s, 1H), 8.51 (s, 1H), 8.01 (d, J = 2.7 Hz, 1H), 7.81 (d, J = 2.7 Hz, 1H), 7.36 (s, 1H), 7.25 (t, J = 7.6 Hz, 1H), 7.12 (m, 3H), 6.39 (m, 1H), 5.60 (s, 1H), 2.80 (d, J = 4.8 Hz, 3H), 2.75 (d, J = 4.5 Hz, 3H), 1.52 (s, 6H). | 565.2 |
| 75 | B3 G6 | (structure) | P | 36 | 9.00 (s, 1H), 7.93 (s, 1H), 7.81 (s, 1H), 7.64 (s, 1H), 7.59 (s, 2H), 7.19 (d, J = 11.3 Hz, 1H), 6.89 (d, J = 7.9 Hz, 1H), 2.85 (d, J = 4.7 Hz, 3H), 2.14 (s, 3H), 1.92 (s, 3H). NH missing | 506.0 |
| 76 | D24 F1 | (structure) | Q | 17 | 11.2 (brs, 1H), 9.11 (s, 1H), 8.52 (d, J = 2.4 Hz, 1H), 8.31 (d, J = 2.4 Hz, 1H), 7.72 (d, J = 8.8 Hz, 1H), 7.62 (s, 1H), 7.50 (m, 3H), 7.30 (d, J = 8.8 Hz, 1H), 7.10 (s, 1H), 3.92 (s, 3H), 2.91 (d, J = 4.4 Hz, 3H). | 524.2 |

TABLE 1-continued

| | | | | | |
|---|---|---|---|---|---|
| 77 | B28 G13 | [structure] | P & T | 18 | 10.4 (brs, 1H), 8.74 (s, 1H), 8.43 (d, J = 2.6 Hz, 1H), 7.95 (d, J = 2.6 Hz, 1H), 7.87 (s, 1H), 7.31 (m, 1H), 7.19 (m, 2H), 6.57 (s, 1H), 6.27 (s, 2H), 3.87 (s, 3H), 2.03 (s, 3H). | 474.0 |
| 78 | B29 G16 | [structure] | P | 22 | 10.5 (s, 1H), 8.85 (s, 1H), 8.33 (d, J = 2.5 Hz, 1H), 7.96 (s, 1H), 7.68 (d, J = 2.6 Hz, 1H), 7.41 (td, J = 2.1 and 7.6 Hz, 1H), 7.28 (m, 2H), 6.87 (d, J = 5.6 Hz, 1H), 6.72 (q, J = 4.7 Hz, 1H), 6.53 (s, 1H), 2.90 (d, J = 4.6 Hz, 3H), 2.85 (d, J = 4.9 Hz, 3H), 2.14 (s, 3H). | 487.0 |
| 79 | D21 F1 | [structure] | Q | 3 | 10.3 (brs, 1H), 9.12 (s, 1H), 8.49 (s, 1H), 8.06 (d, J = 2.4 Hz, 1H), 7.66 (s, 1H), 7.6 (brs, 1H), 7.50 (m, 2H), 7.40 (s, 1H), 7.26 (d, J = 8.0 Hz, 2H), 3.87 (s, 3H), 2.91 (d, J = 4.8 Hz, 3H). | 524.2 |
| 80 | D29 F1 | [structure] | Q | 12 | 11.2 (brs, 1H), 9.08 (s, 1H), 8.50 (d, J = 2.8 Hz, 1H), 8.28 (d, J = 2.4 Hz, 1H), 7.91 (s, 1H), 7.76 (d, J = 8.4 Hz, 1H), 7.6 (brs, 1H), 7.33 (d, J = 8.4 Hz, 1H), 7.07 (s, 1H), 3.93 (s, 3H), 2.92 (d, J = 3.6 Hz, 3H), 2.07 (s, 3H). | 539.2 |

TABLE 1-continued

| | | | | | | |
|---|---|---|---|---|---|---|
| 81 | D30<br>F1 | *(structure)* | Q | 24 | 10.2 (brs, 1H), 9.11 (s, 1H), 8.48 (d, J = 2.8 Hz, 1H), 8.13 (d, J = 2.4 Hz, 1H), 7.71 (d, J = 2.0 Hz, 1H), 7.67 (dd, J = 2.0 and 8.4 Hz, 1H), 7.48 (d, J = 8.8 Hz, 1H), 7.4 (brs, 1H), 7.08 (d, J = 2.0 Hz, 1H), 7.03 (m, 2H), 4.00 (s, 3H), 3.71 (s, 3H), 2.91 (d, J = 4.4 Hz, 3H). | 486.2 |
| 82 | D2<br>F1 | *(structure)* | Q | 9 | 10.3 (brs, 1H), 9.07 (s, 1H), 8.49 (d, J = 2.4 Hz, 1H), 8.09 (d, J = 2.4 Hz, 1H), 7.74 (s, 1H), 7.7 (brs, 1H), 7.12 (dd, J = 2.4 and 8.8 Hz, 1H), 7.02 (d, J = 9.2 Hz, 1H), 6.89 (d, J = 2.4 Hz, 1H), 3.98 (s, 3H), 3.65 (s, 3H), 2.91 (d, J = 4.0 Hz, 3H), 2.17 (s, 3H). | 501.2 |
| 83 | D28<br>F3 | *(structure)* | Q | 10 | 11.9 (brs, 1H), 10.67 (s, 1H), 7.88 (s, 1H), 7.72 (d, J = 8.8 Hz, 1H), 7.55 (m, 2H), 7.47 (d, J = 2.4 Hz, 2H), 7.4 (brs, 1H), 7.23 (m, 2H), 3.94 (s, 3H), 2.90 (d, J = 4.8 Hz, 3H). | 507.2 |
| 84 | E11<br>F1 | *(structure)* | Q | 92 | 10.8 (s, 1H), 10.5 (s, 1H), 9.15 (s, 1H), 8.52 (m, 2H), 8.25 (s, 1H), 8.04 (d, J = 2.6 Hz, 1H), 7.44 (m, 1H), 7.31 (m, 2H), 3.95 (s, 3H), 2.23 (s, 3H), 2.18 (s, 3H). | 516.0 |

TABLE I-continued

| | | | | | |
|---|---|---|---|---|---|
| 85 | B33 G13 | [structure] | P & T | 10 | 10.4 (brs, 1H), 8.87 (s, 1H), 8.71 (s, 1H), 8.42 (t, J = 2.3 Hz, 1H), 8.21 (s, 1H), 8.02 (d, J = 2.6 Hz, 1H), 7.38 (s, 1H), 7.24 (m, 1H), 7.19 (s, 1H), 6.66 (s, 1H), 6.39 (s, 2H), 3.84 (s, 3H). | 460.0 |
| 86 | B34 G9 | [structure] | P | 33 | 11.0 (brs, 1H), 9.26 (s, 1H), 9.08 (d, J = 2.7 Hz, 1H), 8.49 (d, J = 2.6 Hz, 1H), 8.39 (d, J = 2.6 Hz, 2H), 7.41 (s, 2H), 7.36 (d, J = 10.0 Hz, 1H), 7.30 (s, 1H), 6.95 (d, J = 10.3 Hz, 1H), 3.97 (s, 3H). | 461.0 |
| 87 | B6 G9 | [structure] | P | 57 | 10.9 (brs, 1H), 10.0 (s, 1H), 9.14 (s, 1H), 8.44 (d, J = 2.6 Hz, 1H), 8.26 (d, J = 2.6 Hz, 1H), 8.15 (s, 1H), 7.95 (s, 1H), 7.55 (s, 1H), 6.89–6.97 (m, 3H), 3.89 (m, 3H), 3.81 (s, 3H), 2.34 (s, 3H) | 555.2 |

TABLE 1-continued

| # | ID | Structure | Method | Yield (%) | NMR | MS |
|---|---|---|---|---|---|---|
| 88 | B6 G13 | (structure) | P | 61 | 10.4 (s, 1H), 10.0 (s, 1H), 9.14 (s, 1H), 8.44 (d, J = 2.6 Hz, 1H), 8.15 (s, 1H), 8.01 (s, 1H), 7.96 (d, J = 2.6 Hz, 1H), 7.55 (s, 1H), 7.33 (m, 1H), 7.22 (m, 2H), 3.88 (m, 3H), 3.81 (s, 3H), 2.13 (s, 3H) | 555.2 |
| 89 | B5 G15 | (structure) | P & R | 26 | 9.90 (s, 1H), 9.07 (s, 1H), 8.51 (d, J = 2.6 Hz, 1H), 7.98 (m, 2H), 7.71 (s, 1H), 7.38 (dd, J = 1.7 and 8.0 Hz, 1H), 7.20 (t, J = 7.8 Hz, 1H), 7.13 (d, J = 7.6 Hz, 1H), 4.00 (s, 3H), 3.09 (s, 3H), 2.91 (d, J = 4.7 Hz, 3H), 2.07 (s, 3H). | 501.0 |
| 90 | B36 G16 | (structure) | P | 61 | 10.5 (s, 1H), 9.08 (s, 1H), 8.33 (d, J = 2.5 Hz, 1H), 7.98 (s, 1H), 7.77 (m, 1H), 7.69 (d, J = 2.5 Hz, 1H), 7.42 (m, 1H), 7.30 (t, J = 7.8 Hz, 1H), 7.25 (t, J = 6.9 Hz, 1H), 6.73 (d, J = 5.4 Hz, 3H), 2.92 (d, J = 4.5 Hz, 3H), 2.90 (d, J = 4.6 Hz, 3H), 2.16 (s, 3H). | 488.2 |
| 91 | D28 | (structure) | Q | 78 | 10.1 (brs, 1H), 9.11 (s, 1H), 7.84 (s, 1H), 7.69 (d, J = 8.8 Hz, 1H), 7.59 (dd, J = 2.4 and 8.4 Hz, 1H), 7.53 (m, 2H), 7.5 (brs, 1H), 7.35 (m, 1H), 7.23 (m, 2H), 7.08 (d, J = 8.8 Hz, 1H), 3.84 (s, 3H), 2.90 (d, J = 4.8 Hz, 3H), 2.15 (s, 3H). | 453.1 |

| | | | | | |
|---|---|---|---|---|---|
| 92 | B37 G9 | [structure] | P | 7 | 10.9 (brs, 1H), 8.63 (s, 1H), 8.46 (brs, 1H), 8.27 (brs, 1H), 7.52 (s, 1H), 6.94 (brs, 1H), 6.89 (m, 2H), 6.7 (s, 2H), 6.5 (brs, 2H), 3.94 (s, 3H). | 476.1 |
| 93 | B39 G9 | [structure] | P | 6 | 10.8 (s, 1H), 8.97 (s, 1H), 8.50 (s, 1H), 8.30 (s, 1H), 8.04 (d, 1H), 7.15 (m, 3H), 7.08 (d, J = 8.8 Hz, 1H), 6.91 (d, J = 10.0 Hz, 1H), 3.97 (s, 3H), 3.94 (s, 3H). | 491.0 |
| 94 | D31 F1 | [structure] | Q | 7 | 10.9 (brs, 1H), 8.60 (brs, 1H), 8.49 (d, J = 2.0 Hz, 1H), 8.26 (d, J = 2.0 Hz, 1H), 7.45 (s, 1H), 7.2 (brs, 1H), 7.15 (s, 1H), 7.05 (m, 2H), 6.57 (d, J = 4.0 Hz, 1H), 3.96 (s, 3H), 2.87 (d, J = 4.4 Hz, 3H), 2.82 (d, J = 4.8 Hz, 3H) | 520.1 |
| 95 | D9 F1 | [structure] | Q & R | 27 | 9.11 (s, 1H), 8.28 (s, 1H), 8.05 (d, J = 2.6 Hz, 1H), 8.01 (s, 1H), 7.74 (s, 1H), 7.33 (s, 2H), 6.67 (brs, 1H), 3.83 (s, 3H), 2.93 (d, J = 4.7 Hz, 3H), 2.39 (s, 3H). | 496.1 |

| | | | | |
|---|---|---|---|---|
| 96 | B38 G9 | [structure] | P | 12 | 10.9 (brs, 1H), 8.61 (s, 1H), 8.51 (d, J = 2.8 Hz, 1H), 8.30 (d, J = 2.4 Hz, 1H), 7.44 (s, 1H), 6.93 (m, 3H), 6.70 (brs, 2H), 6.60 (brs, 1H), 3.97 (s, 3H), 2.82 (d, J = 4.0 Hz, 3H). | 490.0 |
| 97 | B17 G13 | [structure] | P | 46 | 10.3 (s, 1H), 8.55 (s, 1H), 8.42 (d, J = 2.6 Hz, 1H), 8.04 (d, J = 2.6 Hz, 1H), 7.44 (s, 1H), 7.30 (t, J = 7.7 Hz, 1H), 7.13-7.19 (m, 3H), 6.22 (s, 1H), 4.74 (s, 3H), 3.84-3.84 (m, 3H), 3.37-3.40 (m, 4H), 2.80 (d, J = 4.7 Hz, 3H). | 534.2 |
| 98 | B18 G13 | [structure] | P | 23 | 10.01 (brs, 1H), 8.49 (brs, 1H), 8.37 (d, J = 2.5 Hz, 1H), 8.00 (d, J = 2.5 Hz, 1H), 7.59 (brs, 1H), 7.26 (t, J = 7.2 Hz, 2H), 7.13 (t, J = 7.9 Hz, 1H), 4.74 (brm, 1H), 4.25 (s, 2H), 3.85 (m, 3H), 3.50 (d, J = 10.1 Hz, 1H), 3.42 (s, 3H), 2.86 (d, J = 4.8 Hz, 3H)-two NHs missing: high temp NMR (at 70° C). | 546.2 |
| 99 | B19 G13 | [structure] | P | 26 | Complicated NMR due to atropisomers | 560.2 |

| | | | | | |
|---|---|---|---|---|---|
| 100 | B35 G13 | [structure] | P | 27 | 10.3 (s, 1H), 8.56 (d, J = 7.6 Hz, 1H), 8.42 (d, J = 2.6 Hz, 1H), 8.03 (d, J = 2.6 Hz, 1H), 7.45 (s, 1H), 7.30 (t, J = 7.7 Hz, 1H), 7.18 (t, J = 7.8 Hz, 2H), 7.12 (t, J = 7.1 Hz, 1H), 6.21 (brs, 1H), 3.84 (s, 3H), 3.46 (s, 2H), 3.35 (t, J = 6.2 Hz, 2H), 3.16 (s, 3H), 2.80 (d, J = 4.7 Hz, 3H). | 548.2 |
| 101 | B20 G13 | [structure] | P | 36 | 8.64 (brs, 1H), 8.25 (d, J = 2.6 Hz, 1H), 8.05 (d, J = 2.6 Hz, 1H), 7.58 (s, 1H), 7.27 (brs, 1H), 7.19 (t, J = 8.2 Hz, 1H), 6.92 (t, J = 8.2 Hz, 1H), 6.64 (bm, 1H), 6.59 (brs, 1H), 3.85 (s, 3H), 3.69 (bm, 2H), 3.06 (bm, 2H), 2.86 (d, J = 4.7 Hz, 3H), 2.57 (s, 3H), two NHs missing | 547.2 |
| 102 | D36 F12 | [structure] | Q | 18 | 10.8 (brs, 1H), 8.53 (s, 1H), 8.03 (t, J = 6.0 Hz, 2H), 7.41 (s, 1H), 7.27 (t, J = 7.6 Hz, 1H), 7.15 (m, 3H), 6.44 (s, 1H), 3.81 (s, 3H), 2.80 (d, J = 4.7 Hz, 3H), 2.75 (d, J = 4.5 Hz, 3H). | 565.0 |
| 103 | B32 G9 | [structure] | P | 20 | 10.8 (brs, 1H), 9.05 (s, 1H), 8.51 (d, J = 2.8 Hz, 1H), 8.31 (d, J = 2.4 Hz, 1H), 8.05 (s, 1H), 7.7 (brs, 1H), 7.19 (s, 1H), 7.10 (d, J = 9.2 Hz, 1H), 6.92 (m, 1H), 3.97 (s, 3H), 3.96 (s, 3H), 2.91 (d, J = 4.4 Hz, 3H). | 504.9 |

TABLE 1-continued

| | | | | | |
|---|---|---|---|---|---|
| 104 | D37 F1 | [structure] | Q | 31 | 10.9 (s, 1H), 8.61 (s, 1H), 8.52 (s, 1H), 8.29 (s, 1H), 7.45 (s, 1H), 7.16 (s, 1H), 7.12 (s, 1H), 7.06 (s, 1H), 6.7 (s, 2H), 6.6 (m, 1H), 3.97 (s, 3H), 2.81 (d, J = 3.6 Hz, 3H). | 505.8 |
| 105 | D38 F1 | [structure] | Q | 32 | 10.9 (brs, 1H), 8.62 (s, 1H), 8.52 (d, J = 2.4 Hz, 1H), 8.32 (d, J = 2.4 Hz, 1H), 7.48 (s, 1H), 7.3 (brs, 1H), 6.95 (m, 3H), 6.5 (brs, 1H), 3.96 (s, 3H), 3.54 (m, 2H), 3.45 (m, 2H), 3.24 (s, 3H), 2.85 (brs, 3H). | 548.0 |
| 106 | B41 G13 | [structure] | P | 16 | 10.3 (brs, 1H), 8.92 (s, 1H), 8.50 (d, J = 2.4 Hz, 1H), 8.06 (d, J = 2.8 Hz, 1H), 7.56 (s, 1H), 7.32 (m, 1H), 7.19 (m, 2H), 6.85 (s, 1H), 6.79 (brs, 2H), 3.90 (s, 3H), 3.74 (s, 3H). | 489.9 |

| # | Structure | Ref | | NMR | MS |
|---|---|---|---|---|---|
| 107 | (structure with 5-chloro-2-methoxypyridine-3-sulfonamide linked to fluoro-phenyl-pyrido[2,3-d]pyrimidine with methylamino and (S)-2-methoxypropylamino groups) | D39 F1 | Q | 28 | 11.0 (brs, 1H), 8.62 (s, 1H), 8.51 (d, J = 2.0 Hz, 1H), 8.33 (d, J = 2.4 Hz, 1H), 7.49 (s, 1H), 7.24 (brs, 1H), 6.94-6.02 (m, 3H), 6.27 (brs, 1H), 3.96 (s, 3H), 3.55 (m, 1H), 3.46 (m, 1H), 3.36 (m, 1H), 3.22 (s, 3H), 2.86 (d, J = 4.0 Hz, 3H), 1.07 (d, J = 6.0 Hz, 3H). | 561.9 |
| 108 | (structure with 5-chloro-2-methoxypyridine-3-sulfonamide linked to fluoro-phenyl-pyrido[2,3-d]pyrimidine with methylamino and (R)-2-methoxypropylamino groups) | D40 F1 | Q | 46 | 11.0 (brs, 1H), 8.63 (s, 1H), 8.51 (d, J = 2.4 Hz, 1H), 8.32 (d, J = 2.4 Hz, 1H), 7.49 (s, 1H), 7.24 (br s, 1H), 6.97 (m, 3H), 6.26 (brs, 1H), 3.96 (s, 3H), 3.56 (m, 1H), 3.47 (m, 1H), 3.38 (m, 1H), 3.22 (s, 3H), 2.87 (d, J = 4.0 Hz, 3H), 1.07 (d, J = 6.0 Hz, 3H). | 562.1 |
| 110 | (structure with 5-chloro-2-methoxypyridine-3-sulfonamide linked to fluoro-phenyl-pyrido[2,3-d]pyrimidine with (1-methyl-1H-pyrazol-4-yl)amino group) | 109A | V | 53 | 10.3 (s, 1H), 9.45 (s, 1H), 8.66 (s, 1H), 8.42 (d, J = 2.6 Hz, 1H), 8.03 (d, J = 2.6 Hz, 1H), 7.97 (br s, 1H), 7.49 (brs, 1H), 7.48 (s, 1H), 7.32 (td, J = 1.9 and 7.7 Hz, 1H), 7.19 (t, J = 7.7 Hz, 1H), 714 (m, 1H), 6.51 (bm, 1H), 3.84 (s, 3H), 3.77 (s, 3H), 2.79 (d, J = 4.5 Hz, 3H) | 570.2 |

109A: 1-methyl-1H-pyrazol-4-amine

TABLE 1-continued
| | | | | | | |
|---|---|---|---|---|---|---|
| 111 | 109A  | 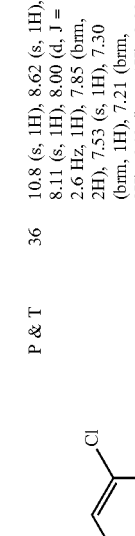 | V | 24 | 10.4 (s, 1H), 8.62 (s, 1H), 8.44 (s, 1H), 8.08 (s, 1H), 7.49 (m, 2H), 7.41 (s, 1H), 7.34 (s, 1H), 7.24 (s, 1H), 6.43 (s, 1H), 3.89 (s, 3H), 2.83 (m, 4H), 0.71 (m, 2H), 0.50 (m, 2H). | 530.2 |
| 112 | B15 G20 | 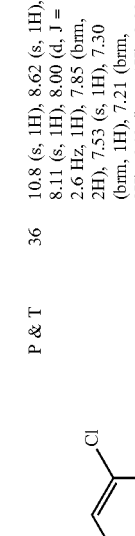 | P & T | 36 | 10.8 (s, 1H), 8.62 (s, 1H), 8.11 (s, 1H), 8.00 (d, J = 2.6 Hz, 1H), 7.85 (brm, 2H), 7.53 (s, 1H), 7.30 (brm, 1H), 7.21 (brm, 3H), 6.49 (brm, 1H), 2.88 (d, J = 4.8 Hz, 3H), 2.85 (d, J = 4.5 Hz, 3H). | 550.0 |
| 113 | B51 G21 | 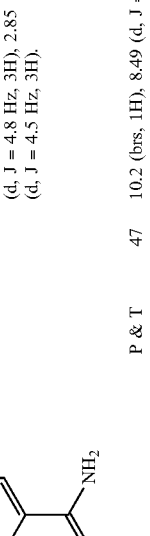 | P & T | 47 | 10.2 (brs, 1H), 8.49 (d, J = 2.6 Hz, 1H), 8.41 (s, 1H), 8.07 (d, J = 2.6 Hz, 1H), 7.43 (m, 3H), 7.23 (dd, J = 1.9 and 7.2 Hz, 1H), 6.42 (m, 1H), 6.22 (s, 1H), 5.98 (brm, 1H), 3.89 (s, 3H), 2.80 (d, J = 4.7 Hz, 6H). | 519.0 |
| 114 | B51 G13 |  | P & T | 60 | 10.4 (s, 1H), 8.48 (d, J = 2.5 Hz, 1H), 8.40 (s, 1H), 8.09 (d, J = 2.6 Hz, 1H), 7.47 (s, 1H), 7.36 (dt, J = 1.9 and 7.6 Hz, 1H), 7.24 (t, J = 7.8 Hz, 1H), 7.19 (m, 1H), 6.42 (m, 1H), 6.20 (s, 3H), 3.91 (s, 3H), 2.79 (d, J = 4.8 Hz, 6H). | 503.2 |

| | | | | | |
|---|---|---|---|---|---|
| 115 | 109A EtNH2 | [structure with ethyl amine] | V | 38 | 10.3 (s, 1H), 8.55 (s, 1H), 8.42 (d, J = 2.6 Hz, 1H), 8.03 (d, J = 2.6 Hz, 1H), 7.42 (s, 1H), 7.31 (dt, J = 1.9 and 7.7 Hz, 1H), 7.28 (s, 1H), 7.18 (t, J = 7.9 Hz, 1H), 7.12 (m, 1H), 6.46 (brs, 1H), 3.84 (s, 3H), 3.31 (m, 2H), 2.75 (d, J = 4.6 Hz, 3H), 1.09 (t, J = 7.1 Hz, 3H). | 518.2 |
| 116 | 109A NH2-CH2-CF3 | [structure with trifluoroethyl amine] | V | 16 | 10.3 (s, 1H), 8.64 (s, 1H), 8.42 (d, J = 2.6 Hz, 1H), 8.03 (d, J = 2.6 Hz, 1H), 7.75 (s, 1H), 7.48 (s, 1H), 7.32 (td, J = 1.7 and 7.6 Hz, 1H), 7.18 (t, J = 7.9 Hz, 1H), 7.12 (t, J = 6.9 Hz, 1H), 6.55 (s, 1H), 4.13-4.20 (m, 2H), 3.84 (s, 3H), 2.75 (d, J = 4.5 Hz, 3H). | 572.2 |
| 117 | 109A NH2-iPr | [structure with isopropyl amine] | V | 25 | 10.3 (s, 1H), 8.53 (s, 1H), 8.42 (d, J = 2.6 Hz, 1H), 8.02 (d, J = 2.6 Hz, 1H), 7.38 (s, 1H), 7.30 (dt, J = 1.8 and 7.6 Hz, 1H), 7.17 (t, J = 7.9 Hz, 1H), 7.11 (t, J = 6.9 Hz, 1H), 7.02 (brs, 1H), 6.36 (brs, 1H), 4.11 (m, 1H), 3.84 (s, 3H), 2.73 (d, J = 4.5 Hz, 3H), 1.11 (d, J = 6.5 Hz, 6H). | 532.2 |
| 118 | 109A NH2-cyclobutyl | [structure with cyclobutyl amine] | V | 23 | 10.3 (s, 1H), 8.53 (s, 1H), 8.42 (d, J = 2.6 Hz, 1H), 8.02 (d, J = 2.6 Hz, 1H), 7.48 (brs, 1H), 7.39 (s, 1H), 7.30 (dt, J = 1.7 and 7.6 Hz, 1H), 7.17 (t, J = 7.9 Hz, 1H), 7.10 (m, 1H), 6.39 (s, 1H), 4.45 (m, 1H), 3.84 (s, 3H), 2.74 (d, J = 4.5 Hz, 3H), 2.20 (m, 2H), 1.93 (m, 2H), 1.58 (m, 2H). | 544.2 |

TABLE 1-continued

| # | Structure | Amine | Letter | IC50 | NMR | MS |
|---|---|---|---|---|---|---|
| 119 | (5-chloro-2-methoxy-N-{2-fluoro-3-[2-(cyclopentylamino)pyrido[2,3-d]pyrimidin-6-yl]phenyl}pyridine-3-sulfonamide) | 109A (cyclopentylamine) | V | 32 | 10.3 (s, 1H), 8.53 (s, 1H), 8.42 (d, J = 2.6 Hz, 1H), 8.02 (d, J = 2.6 Hz, 1H), 7.38 (s, 1H), 7.30 (dt, J = 1.8 and 7.6 Hz, 1H), 7.18 (m, 2H), 7.11 (t, J = 7.0 Hz, 1H), 6.36 (s, 1H), 4.24 (m, 1H), 3.84 (s, 3H), 2.73 (d, J = 4.5 Hz, 3H), 1.85 (m, 2H), 1.63 (m, 2H), 1.41-1.50 (m, 4H). | 558.2 |
| 120 | | D41 F14 | Q | 10 | 11.14 (brs, 1H), 8.59 (brs, 1H), 8.09 (d, J = 2.4 Hz, 1H), 8.05 (d, J = 2.8 Hz, 1H), 7.39 (s, 1H), 7.22 (brs, 1H), 6.94 (m, 3H), 6.62 (brm, 1H), 5.69 (s, 1H), 2.86 (d, J = 4.4 Hz, 3H), 2.83 (d, J = 4.4 Hz, 3H), 1.58 (s, 6H). | 565.1 |
| 121 | | 121B | T | 20 | 10.3 (brs, 1H), 8.79 (s, 1H), 8.50 (d, J = 2.6 Hz, 1H), 8.05 (d, J = 2.6 Hz, 1H), 7.87 (s, 1H), 7.45 (m, 2H), 7.30 (t, J = 4.7 Hz, 1H), 6.64 (s, 1H), 6.30 (s, 2H), 3.91 (s, 3H), 2.10 (s, 3H). | 490.0 |
| 122 | | D36 F4 | Q | 57 | 10.4 (brs, 1H), 8.60 (brs, 1H), 8.45 (d, J = 2.8 Hz, 1H), 8.03 (dd, J = 2.8 and 7.2 Hz, 1H), 7.47 (s, 1H), 7.36 (td, J = 1.6 and 7.6 Hz, 1H), 7.16-7.25 (m, 3H), 6.43 (brs, 1H), 3.89 (s, 3H), 2.87 (d, J = 4.4 Hz, 3H), 2.81 (d, J = 4.4 Hz, 3H). | 488.2 |

TABLE 1-continued

| | | | | | |
|---|---|---|---|---|---|
| 123 | D36 F15 | [structure] | Q | 16 | 9.92 (brs, 1H), 8.60 (s, 1H), 7.65 (s, 1H), 7.46 (s, 1H), 7.35 (t, J = 6.4 Hz, 1H), 7.19 (t, J = 7.6 Hz, 1H), 7.10 (brm, 1H), 6.87 (s, 1H), 6.69 (brm, 2H), 6.44 (m, 1H), 3.95 (s, 3H), 3.85 (s, 3H), 2.80 (d, J = 4.0 Hz, 3H). | 519.1 |
| 124 | 109A [structure] | [structure] | V | 28 | 10.4 (brs, 1H), 8.54 (s, 1H), 8.39 (d, J = 2.6 Hz, 1H), 8.02 (d, J = 2.6 Hz, 1H), 7.39 (s, 1H), 7.29 (t, J = 7.8 Hz, 1H), 7.14 (t, J = 7.9 Hz, 1H), 7.05 (m, 1H), 6.73 (s, 1H), 6.33 (d, J = 5.5 Hz, 1H), 3.83 (s, 3H), 2.74 (d, J = 4.5 Hz, 3H), 1.37 (s, 9H). | 546.2 |
| 125 | D36 F5 [structure] | [structure] | Q & V | 6 | 10.5 (brs, 1H), 8.59 (brs, 1H), 8.42 (brs, 1H), 8.17 (d, J = 2.4 Hz, 1H), 7.49 (s, 1H), 7.44 (t, J = 7.6 Hz, 1H), 7.16-7.24 (brm, 3H), 6.47 (brm, 1H), 5.55 (m, 1H), 4.78 (m, 2H), 4.47 (m, 2H), 2.86 (d, J = 4.4 Hz, 3H), 2.80 (d, J = 4.0 Hz, 3H). | 546.1 |
| 126 | D42 F15 | [structure] | Q | 22 | 9.89 (br s, 1H), 8.96 (s, 1H), 7.99 (s, 1H), 7.60 (s, 1H), 7.32 (br m, 1H), 7.16 (m, 3H), 6.90 (s, 1H), 3.96 (s, 3H), 3.86 (s, 3H), 3.84 (s, 3H). Note: one NH proton was not observed. | 519.9 |

TABLE 1-continued
| | | | | | |
|---|---|---|---|---|---|
| 127 | 121A <br> —NH₂ | 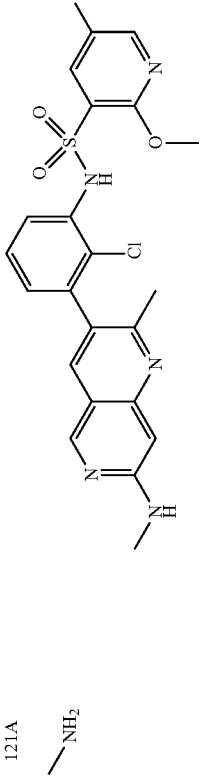 | V | 28 | 10.4 (s, 1H), 8.85 (s, 1H), 8.51 (d, J = 2.6 Hz, 1H), 7.98 (d, J = 2.6 Hz, 1H), 7.90 (s, 1H), 7.45-7.46 (m, 2H), 7.32 (t, J = 4.7 Hz, 1H), 6.86 (s, 1H), 6.52 (s, 1H), 3.92 (s, 3H), 2.84 (d, J = 4.9 Hz, 3H), 2.12 (s, 3H). | 504.0 |
| 128 | B52 G13 | 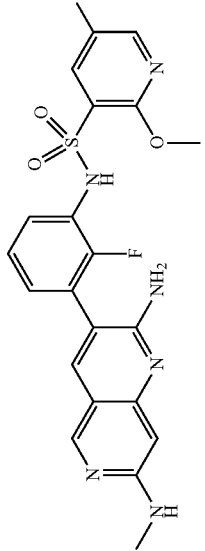 | P & T | 11 | 10.5 (s, 1H), 8.50 (d, J = 2.5 Hz, 1H), 8.45 (s, 1H), 8.10 (d, J = 2.5 Hz, 1H), 7.57 (s, 1H), 7.33 (td, J = 2.6 and 7.3 Hz, 1H), 7.22 (m, 2H), 6.51 (q, J = 5.3 Hz, 1H), 6.21 (brs, 2H), 2.79 (d, J = 4.8 Hz, 3H). | 489.2 |
| 129 | B54 G13 | 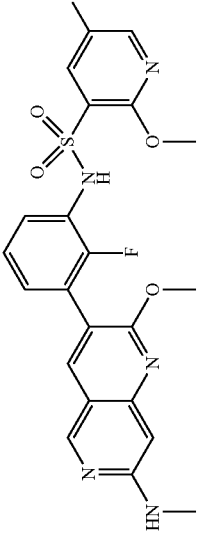 | P | 63 | 10.4 (s, 1H), 8.72 (s, 1H), 8.53 (d, J = 2.5 Hz, 1H), 8.08 (d, J = 2.6 Hz, 1H), 7.98 (s, 1H), 7.34 (td, J = 1.9 and 7.6 Hz, 1H), 7.28 (m, 1H), 7.22 (t, J = 7.8 Hz, 1H), 6.87 (q, J = 5.3 Hz, 1H), 6.42 (s, 1H), 3.91 (s, 3H), 3.84 (s, 3H), 2.84 (d, J = 4.8 Hz, 3H). | 504.0 |
| 130 | D36 F15 | 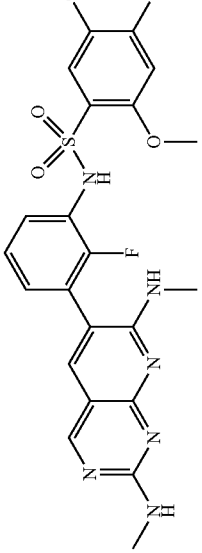 | Q | 20 | 9.99 (s, 1H), 8.53 (s, 1H), 7.40 (d, J = 3.5 Hz, 1H), 7.29 (m, 2H), 7.17 (t, J = 7.9 Hz, 1H), 7.12 (t, J = 7.0 Hz, 1H), 7.05 (t, J = 7.9 Hz, 1H), 6.37 (s, 1H), 3.76 (s, 3H), 3.70 (s, 3H), 2.80 (d, J = 4.8 Hz, 3H), 2.75 (d, J = 4.5 Hz, 3H) | 533.0 |
| 131 | D36 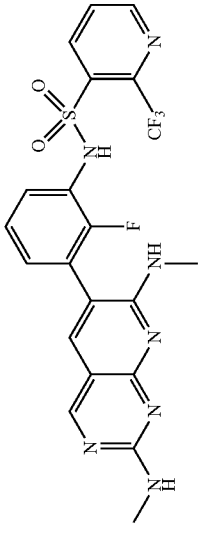 | | Q | 10 | 10.8 (s, 1H), 8.93 (d, J = 4.7 Hz, 1H), 8.59 (s, 1H), 8.44 (d, J = 8.1 Hz, 1H), 7.92 (m, 2H), 7.45 (s, 2H), 7.32 (m, 2H), 7.27-7.17 (m, 4H), 6.47 (s, 1H), 2.86 (d, J = 4.7 Hz, 3H), 2.82 (d, J = 4.5 Hz, 3H). | 508.2 |

TABLE 1-continued

| | | | | | |
|---|---|---|---|---|---|
| 132 | D36 (2,5-dichloro-4-methoxyphenylsulfonyl chloride) | (structure) | Q | 18 | 10.6 (s, 1H), 8.58 (s, 1H), 7.91 (s, 1H), 7.46 (s, 1H), 7.42 (s, 1H), 7.29 (t, J = 7.2 Hz, 1H), 7.23 (m, 1H), 7.15 (m, 1H), 7.07 (s, 1H), 6.46 (s, 1H), 3.94 (s, 3H), 2.86 (d, J = 4.8 Hz, 3H), 2.82 (d, J = 4.5 Hz, 3H). | 537.2 |
| 133 | D36 (3-acetyl-6-chlorophenylsulfonyl chloride) | (structure) | Q | 32 | 10.7 (s, 1H), 8.59 (s, 1H), 8.42 (d, J = 2.1 Hz, 1H), 8.19 (dd, J = 2.2 and 8.3 Hz, 1H), 7.84 (d, J = 8.2 Hz, 1H), 7.46 (s, 1H), 7.34 (td, J = 1.8 and 7.7 Hz, 1H), 7.25 (s, 1H), 7.21 (t, J = 7.8 Hz, 1H), 7.16 (t, J = 7.0 Hz, 1H), 6.46 (s, 1H), 2.86 (d, J = 4.8 Hz, 3H), 2.79 (d, J = 4.5 Hz, 3H), 2.60 (s, 3H). | 515.2 |
| 134 | D36 (5-tert-butyl-2-methoxyphenylsulfonyl chloride) | (structure) | Q | 32 | 9.92 (s, 1H), 8.59 (s, 1H), 7.70 (d, J = 2.5 Hz, 1H), 7.62 (dd, J = 2.6 and 8.7 Hz, 1H), 7.42 (s, 1H), 7.37 (td, J = 1.7 and 7.8 Hz, 1H), 7.24 (s, 1H), 7.16 (t, J = 7.9 Hz, 1H), 7.11 (d, J = 8.8 Hz, 1H), 7.07 (m, 1H), 6.44 (s, 1H), 3.74 (s, 3H), 2.86 (d, J = 4.8 Hz, 3H), 2.83 (d, J = 4.6 Hz, 3H), 1.22 (s, 9H). | 525.2 |
| 135 | C6 H6 | (structure) | P | 11 | 8.99 (s, 1H), 8.43 (d, J = 2.0 Hz, 1H), 8.22 (d, J = 2.4 Hz, 1H), 8.17 (s, 1H), 7.97 (brd, J = 4.8 Hz, 1H), 7.14 (brs, 1H), 6.99 (s, 2H), 3.98 (s, 3H), 3.92 (s, 3H), at high Temp. Note: one NH proton was not observed. | 492.0 |

TABLE 1-continued

| | Structure | Amine | Method | Ex. | ¹H NMR | MS |
|---|---|---|---|---|---|---|
| 136 | | C7 H6 | P | 5 | 8.98 (s, 1H), 8.41 (brs, 1H), 8.22 (d, J = 2.0 Hz, 1H), 8.15 (s, 1H), 7.94 (brm, 1H), 7.46 (brm, 1H), 7.07 (brs, 1H), 3.99 (s, 3H), 3.92 (s, 3H), 2.97 (d, J = 4.4 Hz, 3H). at high Temp. Note: one NH proton was not observed. | 506.0 |
| 137 | 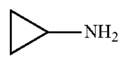 | D36 F5 cyclopropylamine | Q & V | 32 | 10.3 (brs, 1H), 8.60 (s, 1H), 8.32 (d, J = 2.4 Hz, 1H), 7.79 (d, J = 2.4 Hz, 1H), 7.43 (s, 1H), 7.35 (brt, J = 7.2 Hz, 1H), 7.23 (t, J = 7.6 Hz, 1H), 7.15 (brt, J = 6.8 Hz, 1H), 6.90 (brm, 1H), 6.68 (brm, 1H), 6.16 (brm, 1H), 2.92 (d, J = 4.4 Hz, 3H), 2.89 (d, J = 4.4 Hz, 3H), 2.81 (m, 1H), 0.72 (m, 2H), 0.44 (m, 2H), at high Temp. | 529.1 |
| 138 | 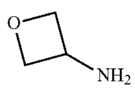 | 109A oxetan-3-amine | V | 33 | 8.58 (s, 1H), 8.27 (brs, 1H), 7.98 (m, 2H), 7.44 (m, 2H), 7.19 (brs, 1H), 6.97 (brs, 1H), 6.39 (brs, 1H), 5.00 (m, 1H), 4.75 (t, J = 6.6 Hz, 2H), 4.48 (m, 2H), 3.78 (m, 4H), 2.76 (d, J = 4.5 Hz, 3H). | 546.2 |
| 139 | 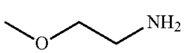 | 109A 2-methoxyethylamine | V | 73 | 10.4 (brs, 1H), 8.54 (s, 1H), 8.41 (d, J = 2.6 Hz, 1H), 8.02 (d, J = 2.6 Hz, 1H), 7.41 (s, 1H), 7.30 (t, J = 7.7 Hz, 1H), 7.16 (t, J = 8.6 Hz, 2H), 7.09 (s, 1H), 6.43 (s, 1H), 3.83 (s, 3H), 3.44 (brm, 4H), 3.21 (m, 3H), 2.73 (d, J = 4.5 Hz, 3H). | 548.2 |

TABLE 1-continued

| | | | | | |
|---|---|---|---|---|---|
| 140 | D36 (2,5-dimethoxybenzenesulfonyl chloride) | (structure) | Q | 39 | 9.94 (s, 1H), 8.60 (s, 1H), 7.47 (s, 1H), 7.34 (td, J = 1.7 and 7.8 Hz, 1H), 7.25 (m, 2H), 7.09 (m, 1H), 6.44 (s, 1H), 3.74 (s, 3H), 3.72 (s, 3H), 2.86 (d, J = 4.8 Hz, 3H), 2.82 (d, J = 4.6 Hz, 3H). | 499.2 |
| 141 | D36 (4-cyano-2-chlorobenzenesulfonyl chloride) | (structure) | Q | 17 | 10.9 (s, 1H), 8.60 (s, 1H), 8.33 (d, J = 1.7 Hz, 1H), 8.07 (d, J = 8.1 Hz, 1H), 8.00 (dd, J = 1.6 and 8.3 Hz, 1H), 7.45 (s, 1H), 7.34-7.15 (m, 4H), 6.47 (s, 1H), 2.86 (d, J = 4.7 Hz, 3H), 2.82 (d, J = 4.5 Hz, 3H). | 498.0 |
| 142 | D36 (6-chloro-2-methoxypyridine-3-sulfonyl chloride) | (structure) | Q | 29 | 10.4 (s, 1H), 8.60 (s, 1H), 8.09 (d, J = 7.9 Hz, 1H), 7.45 (s, 1H), 7.35 (td, J = 1.8 and 7.7 Hz, 1H), 7.28-7.20 (m, 3H), 7.16 (m, 1H), 6.44 (s, 1H), 3.91 (s, 3H), 2.86 (d, J = 4.8 Hz, 3H), 2.82 (d, J = 4.5 Hz, 3H). | 504.2 |
| 143 | B23 G22 CH₃NH₂ | (structure) | P & V | 9 | 10.9 (s, 1H), 8.87 (s, 1H), 8.53 (d, J = 2.6 Hz, 1H), 8.31 (d, J = 2.5 Hz, 1H), 7.99 (s, 1H), 7.20 (m, 1H), 6.95 (m, 2H), 6.53 (s, 1H), 3.97 (s, 3H), 2.85 (d, J = 4.9 Hz, 3H), 2.26 (s, 3H). | 506.2 |

TABLE 1-continued

| | | | | | NMR | MS |
|---|---|---|---|---|---|---|
| 144 | ![structure] C5 H6 | ![structure] | ![structure] | P | 9 | 11.6 (brs, 1H), 8.63 (s, 1H), 8.40 (d, J = 2.0 Hz, 1H), 8.24 (d, J = 2.4 Hz, 1H), 7.92 (d, J = 5.6 Hz, 1H), 7.66 (s, 1H), 6.96 (brm, 2H), 6.58 (brm, 1H), 3.93 (s, 3H), 2.92 (d, J = 4.8 Hz, 3H), 2.91 (d, J = 5.6 Hz, 3H). at high Temp. | 505.2 |
| 145 | D36 | | | Q | 29 | 10.2 (s, 1H), 8.52 (s, 1H), 8.04 (dd, J = 2.2 and 8.7 Hz, 1H), 8.01 (d, J = 2.1 Hz, 1H), 7.40 (s, 1H), 7.32 (d, J = 8.7 Hz, 1H), 7.28 (m, 1H), 7.15 (m, 2H), 7.07 (m, 1H), 6.38 (s, 1H), 3.83 (s, 3H), 2.79 (d, J = 4.8 Hz, 3H), 2.73 (d, J = 4.5 Hz, 3H). | 494.2 |
| 146 | D36 | | | Q | 10 | 10.7 (s, 1H), 8.59 (s, 1H), 8.07 (d, J = 7.9 Hz, 1H), 7.82 (d, J = 7.6 Hz, 1H), 7.59 (t, J = 7.8 Hz, 1H), 7.45 (s, 1H), 7.35–7.20 (m, 2H), 7.17 (m, 1H), 7.11 (brs, 1H), 6.46 (brs, 1H), 2.86 (d, J = 4.8 Hz, 3H), 2.82 (d, J = 4.6 Hz, 3H), 2.56 (s, 3H). | 515.0 |
| 147 | B56 G13 | | | P | 12 | 10.1 (brs, 1H), 8.94 (s, 1H), 8.45 (d, J = 2.4 Hz, 1H), 8.07 (d, J = 2.4 Hz, 1H), 7.96 (s, 1H), 7.27–7.36 (m, 3H), 7.20 (m, 1H), 4.52 (t, J = 4.8 Hz, 2H), 3.93 (s, 3H), 3.60 (t, J = 5.2 Hz, 2H), 3.20 (s, 3H), 2.95 (d, J = 4.4 Hz, 3H). at high Temp. | 549.2 |

TABLE 1-continued
| | | | | | |
|---|---|---|---|---|---|
| 148 | D36 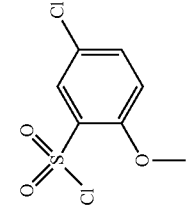 | 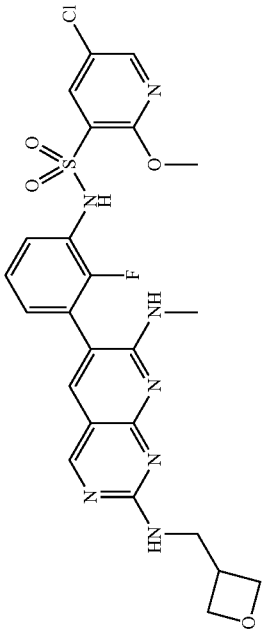 | Q | 10 | 10.1 (s, 1H), 8.60 (s, 1H), 7.67 (m, 2H), 7.47 (s, 1H), 7.34 (m, 1H), 7.17-7.28 (m, 3H), 7.14 (brm, 1H), 6.44 (brs, 1H), 3.80 (s, 3H), 2.86 (d, J = 4.4 Hz, 3H), 2.82 (d, J = 4.0 Hz, 3H). | 503.2 |
| 149 | 109A 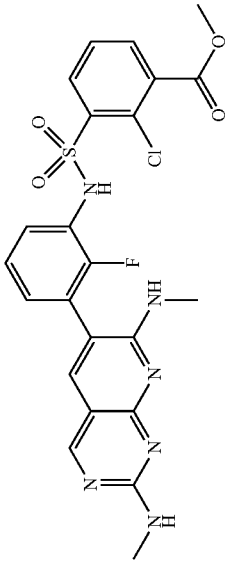 | | V | 6 | 8.87 (s, 1H), 8.26 (d, J = 2.6 Hz, 1H), 8.20 (s, 1H), 8.04 (d, J = 2.6 Hz, 1H), 7.82 (s, 1H), 7.73 (m, 1H), 7.24 (t, J = 8.1 Hz, 1H), 6.97 (t, J = 7.9 Hz, 1H), 6.61 (m, 1H), .79 (d, J = 13.5 Hz, 1H), 4.01 (m, 1H), 3.83 (s, 3H), 3.62-3.51 (m, 3H), 3.31 (m, 1H), 2.97 (d, J = 4.6 Hz, 3H), 2.32 (s, 1H). | 560.2 |
| 150 | D36 F6 | | Q | 64 | 10.7 (s, 1H), 8.59 (s, 1H), 8.13 (dd, J = 1.6 and 8.0 Hz, 1H), 7.95 (d, J = 7.7 Hz, 1H), 7.61 (t, J = 7.8 Hz, 1H), 7.45 (s, 1H), 7.32-7.22 (m, 2H), 7.18 (m, 1H), 7.14 (brs, 1H), 6.46 (brs, 1H), 3.87 (s, 3H), 2.86 (d, J = 4.7 Hz, 3H), 2.82 (d, J = 4.6 Hz, 3H). | 531.0 |
| 151 | 150 | 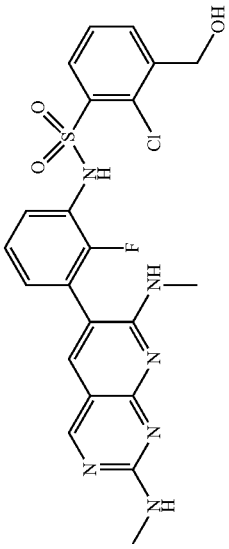 | S | 7 | 10.5 (s, 1H), 8.52 (s, 1H), 7.83 (d, J = 7.9 Hz, 1H), 7.75 (d, J = 7.8 Hz, 1H), 7.47 (t, J = 7.8 Hz, 1H), 7.40 (s, 1H), 7.25-7.16 (m, 2H), 7.11 (t, J = 7.9 Hz, 1H), 7.06 (m, 1H), 6.42 (s, 1H), 5.54 (m, 1H), 4.54 (d, J = 5.5 Hz, 2H), 2.80 (d, J = 4.7 Hz, 3H), 2.76 (d, J = 4.5 Hz, 3H). | 503.2 |

TABLE 1-continued
| | | | | | |
|---|---|---|---|---|---|
| 152 | D36 F8 | 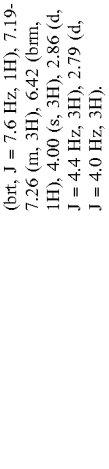 | Q | 15 | 10.4 (s, 1H), 8.91 (d, J = 1.6 Hz, 1H), 8.59 (brs, 1H), 8.45 (d, J = 1.6 Hz, 1H), 7.47 (s, 1H), 7.38 (brt, J = 7.6 Hz, 1H), 7.19-7.26 (m, 3H), 6.42 (brm, 1H), 4.00 (s, 3H), 2.86 (d, J = 4.4 Hz, 3H), 2.79 (d, J = 4.0 Hz, 3H). | 495.3 |
| 153 | D36 F7 | 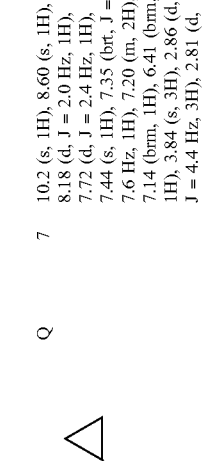 | Q | 7 | 10.2 (s, 1H), 8.60 (s, 1H), 8.18 (d, J = 2.0 Hz, 1H), 7.72 (d, J = 2.4 Hz, 1H), 7.44 (s, 1H), 7.35 (brt, J = 7.6 Hz, 1H), 7.20 (m, 2H), 7.14 (brm, 1H), 6.41 (brm, 1H), 3.84 (s, 3H), 2.86 (d, J = 4.4 Hz, 3H), 2.81 (d, J = 4.4 Hz, 3H), 1.97 (m, 1H), 0.93 (m, 2H), 0.64 (m, 2H). | 510.3 |
| 154 | D36 F5 <br> ![OH cyclopropyl] | 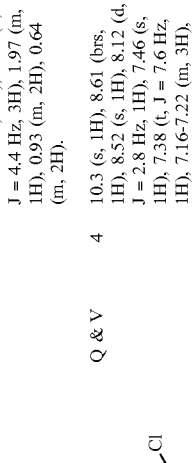 | Q & V | 4 | 10.3 (s, 1H), 8.61 (brs, 1H), 8.52 (s, 1H), 8.12 (d, J = 2.8 Hz, 1H), 7.46 (s, 1H), 7.38 (t, J = 7.6 Hz, 1H), 7.16-7.22 (m, 3H), 6.45 (brm, 1H), 4.33 (m, 1H), 2.86 (d, J = 4.4 Hz, 3H), 2.80 (d, J = 4.0 Hz, 3H), 0.62 (m, 2H), 0.65 (m, 2H). | 530.3 |
| 155 | C8 H6 | 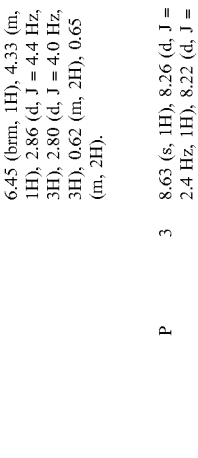 | P | 3 | 8.63 (s, 1H), 8.26 (d, J = 2.4 Hz, 1H), 8.22 (d, J = 2.4 Hz, 1H), 7.76 (d, J = 5.2 Hz, 1H), 7.60 (s, 1H), 6.62 (br m, 1H), 6.42 (brs, 2H), 3.90 (s, 3H), 2.90 (d, J = 4.4 Hz, 3H). two NH protons not observed. at high Temp. | 491.2 |

TABLE 1-continued
| | | | | | |
|---|---|---|---|---|---|
| 156 | D36 F9 | 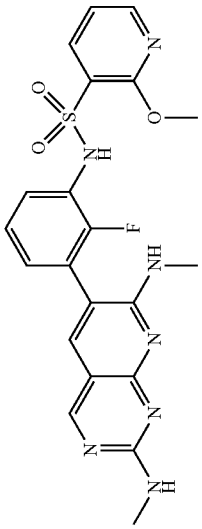 | Q | 10 | 10.2 (s, 1H), 8.60 (s, 1H), 8.38 (brd, J = 4.0 Hz, 1H), 8.09 (dd, J = 7.6, 2.0 Hz, 1H), 7.44 (s, 1H), 7.33 (brt, J = 7.2 Hz, 1H), 7.27 (m, 2H), 7.11-7.18 (m, 2H), 6.37 (brm, 1H), 3.90 (s, 3H), 2.85 (d, J = 4.8 Hz, 3H), 2.81 (d, J = 4.4 Hz, 3H). | 470.3 |
| 157 | D36 | 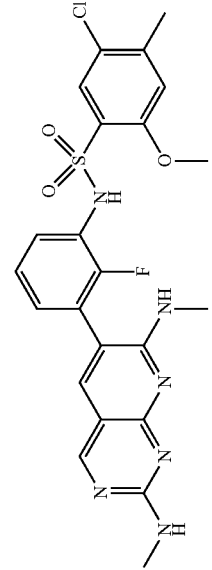 | Q | 13 | 10.0 (s, 1H), 8.59 (s, 1H), 7.63 (s, 1H), 7.47 (s, 1H), 7.34 (br t, J = 7.6 Hz, 1H), 7.25 (s, 1H), 7.19 (m, 2H), 7.12 (m, 1H), 6.43 (brm, 1H), 3.79 (s, 3H), 2.86 (d, J = 4.4 Hz, 3H), 2.81 (d, J = 4.0 Hz, 3H), 2.36 (s, 3H). | 517.2 |
| 158 | B40 G13 | 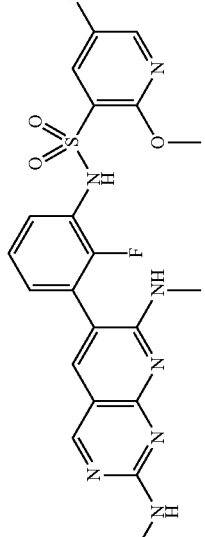 | P | 39 | 10.5 (s, 1H), 10.4 (brs, 1H), 8.92 (s, 1H), 8.48 (d, J = 2.0 Hz, 1H), 8.10 (d, J = 2.4 Hz, 1H), 7.72 (s, 1H), 7.41 (t, J = 7.2 Hz, 1H), 7.26 (m, 2H), 6.89 (br m, 1H), 3.90 (s, 3H), 2.83 (d, J = 4.8 Hz, 3H), 2.25 (s, 3H). | 532.3 |
| 159 | B58 G13 | 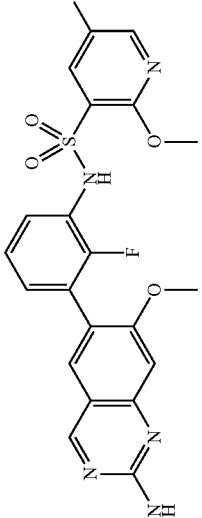 | P | 57 | 10.32 (s, 1H), 8.91 (br s, 1H), 8.50 (d, J = 2.4 Hz, 1H), 8.06 (d, J = 2.8 Hz, 1H), 7.55 (s, 1H), 7.31 (m, 2H), 7.19 (br m, 2H), 6.94 (br s, 1H), 3.90 (s, 3H), 3.76 (s, 3H), 2.88 (d, J = 4.8 Hz, 3H). | 504.3 |
| 160 | 16 | 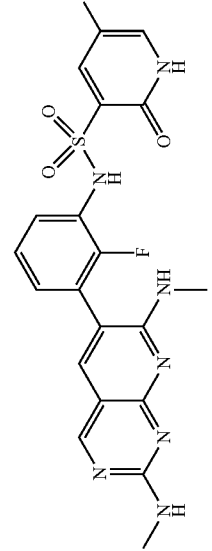 | De—Me with BBr₃ | 36 | 12.80 (br s, 1H), 9.92 (br s, 1H), 8.60 (br s, 1H), 8.02 (d, J = 2.8 Hz, 1H), 7.96 (d, J = 3.2 Hz, 1H), 7.51 (s, 1H), 7.37 (td, J = 8.0, 1.6 Hz, 1H), 7.15-7.24 (m, 3H), 6.41 (br m, 1H), 2.86 (d, J = 4.8 Hz, 3H), 2.84 (d, J = 4.4 Hz, 3H). | 490.2 |

TABLE I-continued
| | | | | | |
|---|---|---|---|---|---|
| 161 | D36 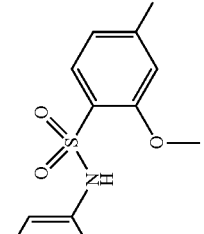 | 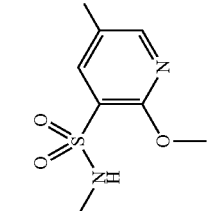 | Q | 8 | 10.01 (s, 1H), 8.60 (br s, 1H), 7.70 (d, J = 8.4 Hz, 1H), 7.44 (s, 1H), 7.32 (m, 2H), 7.18 (m, 2H), 7.11 (m, 2H), 6.38 (br m, 1H), 3.83 (s, 3H), 2.86 (d, J = 4.8 Hz, 3H), 2.82 (d, J = 4.4 Hz, 3H). | 503.2 |
| 162 | B23 G13 —NH₂ | 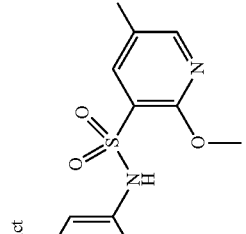 | P & V | 12 | 9.96 (brs, 1H), 8.77 (s, 1H), 7.88 (s, 1H), 7.57 (d, J = 2.9 Hz, 1H), 7.24-7.30 (m, 2H), 7.12-7.17 (m, 2H), 6.77 (d, J = 5.6 Hz, 1H), 6.45 (s, 1H), 5.66 (d, J = 6.0 Hz, 1H), 3.74 (s, 3H), 2.77 (d, J = 5.0 Hz, 3H), 2.56 (d, J = 4.7 Hz, 3H), 2.07 (s, 3H). | 483.2 |
| 163 | C4 H7 | 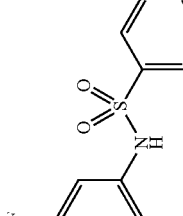 side product | P | 20 | 9.20 (s, 1H), 8.45 (brs, 1H), 8.29 (s, 1H), 8.03-8.23 (m, 2H), 7.37-7.73 (m, 4H), 7.07 (d, J = 5.2 Hz, 1H), 3.90 (s, 3H), 2.91 (d, J = 4.7 Hz, 3H). sulfonamide NH not observed. | 457.0 |
| 164 | B40 G9 | 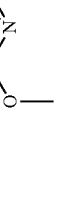 | P | 4 | 11.0 (brs, 1H), 10.5 (s, 1H), 8.92 (s, 1H), 8.50 (s, 1H), 8.30 (s, 1H), 7.67 (s, 1H), 6.90-7.00 (m, 4H), 3.96 (s, 3H), 2.86 (d, J = 4.4 Hz, 3H), 2.24 (s, 3H). | 532.3 |

| | | | | |
|---|---|---|---|---|
| 165 | B39 G13 | [structure] | P | 10 | 10.4 (s, 1H), 8.96 (s, 1H), 8.51 (d, J = 2.4 Hz, 1H), 8.06 (d, J = 2.8 Hz, 1H), 7.99 (s, 1H), 7.34 (td, J = 2.0 and 8.0 Hz, 1H), 7.19-7.25 (m, 2H), 7.15 (brs, 2H), 3.90 (s, 3H), 3.83 (s, 3H). | 491.2 |
| 166 | B15 G23 | [structure] | P | 34 | 10.3 (s, 1H), 8.61 (s, 1H), 8.18 (dd, J = 1.2 and 4.6 Hz, 1H), 7.77 (d, J = 8.6 Hz, 1H), 7.67 (dd, J = 4.5 and 8.5 Hz, 1H), 7.52 (s, 1H), 7.33 (td, J = 1.8 and 7.8 Hz, 1H), 7.24 (s, 1H), 7.14 (t, J = 7.9 Hz, 1H), 7.07 (m, 1H), 6.51 (s, 1H), 3.90 (s, 3H), 2.87 (d, J = 4.8 Hz, 3H), 2.84 (d, J = 4.6 Hz, 3H). | 470.2 |
| 167 | B41 G24 | [structure] | P & X | 30 | 10.3 (brs, 1H), 8.91 (s, 1H), 7.84 (d, J = 2.4 Hz, 1H), 7.79 (d, J = 2.4 Hz, 1H), 7.54 (s, 1H), 7.23-7.28 (m, 2H), 7.10-7.21 (m, 2H), 6.89 (s, 1H), 6.50 (brs, 2H), 5.49 (t, J = 5.6 Hz, 1H), 4.62 (d, J = 4.0 Hz, 2H), 3.79 (s, 3H), at high Temp. | 523.2 |
| 168 | D36 F11 | [structure] | Q | 9 | 10.6 (brs, 1H), 8.60 (brs, 1H), 7.57 (d, J = 8.8 Hz, 1H), 7.47 (s, 1H), 7.45 (d, J = 2.8 Hz, 1H), 7.31 (brt, J = 6.8 Hz, 1H), 7.10-7.28 (m, 4H), 6.45 (brm, 1H), 3.78 (s, 3H), 2.87 (d, J = 4.4 Hz, 3H), 2.82 (d, J = 4.4 Hz, 3H). | 503.3 |

TABLE 1-continued

| | | | | | |
|---|---|---|---|---|---|
| 169 | D36 F10 | [structure] | Q | 22 | 10.4 (s, 1H), 8.60 (brs, 1H), 8.55 (d, J = 2.0 Hz, 1H), 8.16 (d, J = 2.4 Hz, 1H), 7.46 (s, 1H), 7.37 (t, J = 7.6 Hz, 1H), 7.18-7.25 (m, 3H), 6.45 (brs, 1H), 3.89 (s, 3H), 2.86 (d, J = 4.4 Hz, 3H), 2.80 (d, J = 4.4 Hz, 3H). | 548.3 550.3 |
| 170 | D36 F16 | [structure] | Q | 2 | 8.62 (s, 1H), 8.32 (br m, 1H), 8.01 (d, J = 2.4 Hz, 1H), 7.68 (brs, 1H), 7.49 (s, 1H), 7.31 (t, J = 7.6 Hz, 1H), 7.16 (t, J = 7.6 Hz, 1H), 7.07 (brm, 1H), 6.86 (brm, 1H), 6.14 (brm, 1H), 2.92 (d, J = 4.8 Hz, 3H), 2.90 (d, J = 4.8 Hz, 3H), 2.78 (d, J = 4.4 Hz, 3H). NH proton was not observed. at high Temp. | 564.3 |
| 171 | B31 G17 | [structure] | P, T & S | 15 | 10.8 (s, 1H), 8.45 (d, J = 0.7 Hz, 1H), 7.85 (d, J = 2.7 Hz, 1H), 7.79 (d, J = 2.6 Hz, 1H), 7.59 (s, 1H), 7.30 (m, 1H), 7.20 (m, 2H), 6.53 (q, J = 4.9 Hz, 1H), 6.27 (s, 2H), 6.14 (s, 1H), 5.74 (t, J = 5.7 Hz, 1H), 4.61 (d, J = 5.4 Hz, 2H), 2.79 (d, J = 4.9 Hz, 3H). | 523.0 |
| 172 | B59 G13 | [structure] | P | 1 | 10.8 (s, 1H), 10.4 (s, 1H), 8.93 (s, 1H), 8.48 (m, J = 2.3 Hz, 1H), 8.11 (d, J = 2.6 Hz, 1H), 7.73 (s, 1H), 7.41 (td, J = 1.9 and 7.7 Hz, 1H), 7.19-7.30 (m, 2H), 6.90 (d, J = 4.7 Hz, 1H), 3.90 (s, 3H), 2.84 (d, J = 4.5 Hz, 3H), 2.18-2.27 (m, 1H), 0.79-0.87 (m, 4H). | 558.0 |

TABLE 1-continued

| | | | | | |
|---|---|---|---|---|---|
| 173 | E11 F17 | [structure] | Q & X | 60 | 10.5 (s, 1H), 10.4 (brs, 1H), 9.11 (s, 1H), 8.47 (s, 1H), 8.20 (s, 1H), 7.79 (d, J = 2.4 Hz, 1H), 7.40 (m, 1H), 7.29 (m, 2H), 5.50 (br t, J = 4.4 Hz, 1H), 4.62 (d, J = 4.8 Hz, 2H), 2.31 (s, 3H), 2.18 (s, 3H). at high Temp. | 549.3 |
| 174 | 173 | [structure] | X (at 60° C). | 82 | 10.4 (brs, 1H), 7.90 (s, 1H), 7.82 (d, J = 2.4 Hz, 1H), 7.74 (d, J = 2.0 Hz, 1H), 7.33 (t, J = 7.2 Hz, 1H), 7.17 (t, J = 8.0 Hz, 1H), 7.10 (brm, 1H), 6.69 (s, 1H), 6.04 (brs, 2H), 5.46 (br t, J = 4.4 Hz, 1H), 4.61 (d, J = 4.8 Hz, 2H), 2.23 (s, 3H). at high Temp. | 505.1 |
| 175 | B15 G24 | [structure] | P & X | 31 | 10.7 (s, 1H), 8.60 (s, 1H), 7.87 (d, J = 2.6 Hz, 1H), 7.79 (d, J = 2.6 Hz, 1H), 7.49 (s, 1H), 7.32 (td, J = 1.8 and 7.7 Hz, 3H), 7.10-7.27 (m, 3H), 6.49 (s, 1H), 5.74 (t, J = 5.7 Hz, 1H), 4.60 (d, J = 5.7 Hz, 2H), 2.88 (d, J = 4.8 Hz, 3H), 2.83 (d, J = 4.6 Hz, 3H). | 537.0 |
| 176 | B15 G25 | [structure] | P & X | 19 | 10.8 (brs, 1H), 8.59 (brs, 1H), 7.74 (brm, 1H), 7.65 (brm, 1H), 7.46 (s, 1H), 7.33 (m, 1H), 7.22 (brm, 3H), 6.49 (brs, 1H), 5.60 (t, J = 6.0 Hz, 1H), 4.55 (d, J = 5.6 Hz, 2H), 2.86 (d, J = 4.4 Hz, 3H), 2.82 (d, J = 4.4 Hz, 3H). | 521.4 |

TABLE 1-continued

| | | | | | |
|---|---|---|---|---|---|
| 177 | B15 G26 | [structure] | P & X | 60 | 10.7 (brs, 1H), 8.60 (brs, 1H), 7.68 (dd, J = 3.2 and 8.0 Hz, 1H), 7.58 (brd, J = 9.6 Hz, 1H), 7.48 (s, 1H), 7.29 (brt, J = 7.6 Hz, 1H), 7.18 (brm, 3H), 6.44 (brs, 1H), 5.72 (t, J = 5.2 Hz, 1H), 4.59 (d, J = 5.6 Hz, 2H), 2.86 (d, J = 4.8 Hz, 3H), 2.83 (d, J = 4.4 Hz, 3H). | 521.4 |
| 178 | B15 G27 | [structure] | P & X | 78 | 10.7 (brs, 1H), 8.60 (brs, 1H), 7.56 (brm, 1H), 7.47 (m, 1H), 7.46 (s, 1H), 7.34 (brt, J = 6.0 Hz, 1H), 7.24 (m, 3H), 6.46 (brs, 1H), 5.59 (t, J = 5.6 Hz, 1H), 4.56 (d, J = 5.6 Hz, 2H), 2.87 (d, J = 4.4 Hz, 3H), 2.82 (d, J = 4.0 Hz, 3H). | 505.4 |
| 179 | B15 G28 | [structure] | P & X | 22 | 10.3 (s, 1H), 8.59 (brs, 1H), 7.72 (d, J = 2.8 Hz, 1H), 7.64 (d, J = 2.8 Hz, 1H), 7.48 (s, 1H), 7.31 (td, J = 1.6 and 8.0 Hz, 1H), 7.20 (m, 2H), 7.14 (brt, J = 6.4 Hz, 1H), 6.46 (brm, 1H), 5.52 (t, J = 5.6 Hz, 1H), 4.57 (d, J = 5.6 Hz, 2H), 3.79 (s, 3H), 2.86 (d, J = 4.8 Hz, 3H), 2.84 (d, J = 4.4 Hz, 3H). | 533.1 |

Example 180

Biochemical Assay for GCN2

Activity of GCN2 kinase was determined using a TR-FRET kinase activity assay (e.g. Riddle et al. Analytical Biochemistry (2006) 356(1) 108-116). Assays were conducted in 384-well plates (13 μL assay volume) using 2 nM GCN2 (Carna Biosciences), 130 nM GFP-EIf2α (Invitrogen), 0.2 mg/mL E. coli tRNA (sigma) and 1 mM ATP in kinase buffer (Invitrogen). Inhibition of GCN2 was measured by adding serial diluted test compound (final assay concentration of 0.5% DMSO) followed by a 3-hour incubation. Tb-peIF2α (pSer52) antibody (Invitrogen) (2 nM final assay concentration) in kinase buffer containing ETDA (final assay concentration of 20 mM) was added. After a 60 min incubation at room temperature, TR-FRET was monitored using an excitation wavelength of 340 nm and emission wavelengths of 490 nm and 520 nm. The emission ratio (520/490) at each compound concentration of was converted to percent inhibition using controls (i.e. reaction with no test compound and reaction with a known inhibitor) and $IC_{50}$ values were calculated by fitting a four-parameter sigmoidal curve to the data using Prism (GraphPad software).

```
- GCN2 protein sequence (residues
1-1649; G556E with a N-terminal GST tag)
                                      SEQ ID NO: 1
MAPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLEVLFQGPLGAMGSGIQRPTSTSSLVMAGG

RGAPGRGRDEPPESYPQRQDHELQALEAIYGADFQDLRPDACGPVKEPPE

INLVLYPQGLTGEEVYVKVDLRVKCPPTYPDVVPEIELKNAKGLSNESVN

LLKSRLEELAKKHCGEVMIFELAYHVQSFLSEHNKPPPKSFHEEMLERRA

QEEQQRLLEAKRKEEQEQREILHEIQRRKEEIKEEKKRKEMAKQERLEIA

SLSNQDHTSKKDPGGHRTAAILHGGSPDFVGNGKHRANSSGRSRREROYS

VCNSEDSPGSCEILYFNMGSPDQLMVHKGKCIGDEQLGKLVYNALETATG

GFVLLYEWVLQWQKKMGPFLTSQEKEKIDKCKKQIQGTETEFNSLVKLSH

PNVVRYLAMNLKEQDDSIVVDILVEHISGVSLAAHLSHSGPIPVHQLRRY

TAQLLSGLDYLHSNSVVHKVLSASNVLVDAEGTVKITDYSISKRLADICK

EDVFEQTRVRFSDNALPYKTGKKGDVWRLGLLLLSLSQGQECGEYPVTIP

SDLPADFQDFLKKCVCLDDKERWSPQQLLKHSFINPQPKMPLVEQSPEDS

GGQDYVETVIPSNRLPSAAFFSETQRQFSRYFIEFEELQLLGKGAFGAVI

KVQNKLDGCCYAVKRIPINPASRQFRRIKGEVTLLSRLHHENIVRYYNAW

IERHERPAGPGTPPPDSGPLAKDDRAARGQPASDTDGLDSVEAAAPPPIL

SSSVEWSTSGERSASARFPATGPGSSDDEDDDEDEHGGVFSQSFLPASDS

ESDIIFDNEDENSKSQNQDEDCNEKNGCHESEPSVTTEAVHYLYIQMEYC

EKSTLRDTIDQGLYRDTVRLWRLFREILDGLAYIHEKGMIHRDLKPVNIF

LDSDDHVKIGDFGLATDHLAFSADSKQDDQTGDLIKSDPSGHLTGMVGTA

LYVSPEVQGSTKSAYNQKVDLFSLGIIFFEMSYHPMVTASERIFVLNQLR

DPTSPKFPEDFDDGEHAKQKSVISWLLNHDPAKRPTATELLKSELLPPPQ

MEESELHEVLHHTLTNVDGKAYRTMMAQIFSQRISPAIDYTYDSDILKGN

FSIRTAKMQQHVCETIIRIFKRHGAVQLCTPLLLPRNRQIYEHNEAALFM

DHSGMLVMLPFDLRIPFARYVARNNILNLKRYCIERVFRPRKLDRFHPKE

LLECAFDIVTSTTNSFLPTAEIIYTIYEIIQEFPALQERNYSIYLNHTML

LKAILLHCGIPEDKLSQVYIILYDAVTEKLTRREVEAKFCNLSLSSNSLC

RLYKFIEQKGDLQDLMPTINSLIKQKTGIAQLVKYGLKDLEEVVGLLKKL

GIKLQVLINLGLVYKVQQHNGIIFQFVAFIKRRQRAVPEILAAGGRYDLL

IPQFRGPQALGPVPTAIGVSIAIDKISAAVLNMEESVTISSCDLLVVSVG

QMSMSRAINLTQKLWTAGITAEIMYDWSQSQEELQEYCRHHEITYVALVS

DKEGSHVKVKSFEKERQTEKRVLETELVDHVLQKLRTKVTDERNGREASD

NLAVQNLKGSFSNASGLFEIHGATVVPIVSVLAPEKLSASTRRRYETQVQ

TRLQTSLANLHQKSSEIEILAVDLPKETILQFLSLEWDADEQAFNTTVKQ

LLSRLPKQRYLKLVCDEIYNIKVEKKVSVLFLYSYRDDYYRILF
```

Example 181

Biochemical Assay for PERK

Activity of PERK kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 μL final volume) using 10 nM PERK (from Beryllium), 0.25 mg/mL Myelin Basic Protein substrate, 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.004% (w/v) BSA, and 0.004% Triton X-100). Inhibition of PERK was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated using software routines in Prism (GraphPad software).

```
- PERK protein sequence (residues
563-1115; Sequence ID: NM 004836)
                                      SEQ ID NO: 2
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLVPRGSKYDSVSGEANDSSWNDIKNSGYIS

RYLTDFEPIQCLGRGGFGVVFEAKNKVDDCNYAIKRIRLPNRELAREKVM

REVKALAKLEHPGIVRYFNAWLEAPPEKWQEKMDEIWLKDESTDWPLSSP
```

-continued

SPMDAPSVKIRRMDPFSTKEHIEIIAPSPQRSRSFSVGISCDQTSSSESQ
FSPLEFSGMDHEDISESVDAAYNLQDSCLTDCDVEDGTMDGNDEGHSFEL
CPSEASPYVRSRERTSSSIVFEDSGCDNASSKEEPKTNRLHIGNHCANKL
TAFKPTSSKSSSEATLSISPPRPTTLSLDLTKNTTEKLQPSSPKVYLYIQ
MQLCRKENLKDWMNGRCTIEERERSVCLHIFLQIAEAVEFLHSKGLMHRD
LKPSNIFFTMDDVVKVGDFGLVTAMDQDEEEQTVLTPMPAYARHTGQVGT
KLYMSPEQIHGNSYSHKVDIFSLGLILFELLYPFSTQMERVRTLTDVRNL
KFPPLFTQKYPCEYVMVQDMLSPSPMERPEAINIIENAVFEDLDFPGKTV
LRQRSRSLSSSGTKHSRQSNNSHSPLPSN

TABLE 1

Inhibition of biochemical activity of GCN2 and PERK kinases by exemplary compounds.

| Example No | GCN2 IC$_{50}$ (nM) | PERK IC$_{50}$ (nM) |
|---|---|---|
| 1 | ++++ | ++++ |
| 3 | + | + |
| 4 | + | + |
| 5 | ++ | +++ |
| 6 | ++ | ++ |
| 7 | +++ | ++ |
| 8 | + | + |
| 9 | + | + |
| 10 | +++ | ++++ |
| 11 | + | ++ |
| 12 | +++ | ++++ |
| 13 | +++ | ++++ |
| 14 | + | ++ |
| 15 | + | ++ |
| 16 | + | ++ |
| 17 | +++ | ++ |
| 18 | +++ | ++++ |
| 19 | + | + |
| 20 | ++++ | ++++ |
| 21 | ++++ | ++++ |
| 22 | + | + |
| 23 | + | + |
| 24 | ++ | ++ |
| 25 | + | + |
| 26 | + | + |
| 27 | + | + |
| 28 | ++++ | ++ |
| 29 | ++ | + |
| 30 | + | ++ |
| 31 | + | + |
| 32 | + | + |
| 33 | + | + |
| 34 | + | ++ |
| 35 | + | ++ |
| 36 | + | + |
| 37 | ++++ | |
| 38 | + | ++ |
| 39 | + | ++ |
| 42 | ++++ | ++++ |
| 43 | ++++ | ++++ |
| 44 | + | + |
| 45 | + | + |
| 46 | ++ | ++++ |
| 47 | + | ++ |
| 48 | + | ++ |
| 49 | + | ++ |
| 50 | + | + |
| 51 | + | ++ |
| 52 | ++ | ++ |
| 53 | + | ++ |
| 54 | +++ | ++ |
| 55 | +++ | ++ |
| 56 | ++ | + |
| 57 | + | + |
| 58 | ++++ | ++++ |
| 59 | + | ++ |
| 60 | ++ | +++ |
| 61 | + | + |
| 62 | + | + |
| 63 | + | + |
| 64 | + | ++ |
| 65 | + | ++ |
| 66 | + | + |
| 67 | + | + |
| 68 | + | + |
| 69 | ++ | + |
| 70 | ++++ | ++ |
| 71 | ++++ | ++++ |
| 72 | ++ | ++ |
| 73 | ++ | ++ |
| 74 | ++ | ++ |
| 75 | +++ | ++ |
| 76 | ++++ | ++++ |
| 77 | + | + |
| 78 | + | + |
| 79 | ++ | ++ |
| 80 | +++ | ++++ |
| 81 | ++++ | ++++ |
| 82 | ++++ | ++++ |
| 83 | ++ | + |
| 84 | + | + |
| 85 | + | + |
| 86 | ++++ | ++++ |
| 87 | + | + |
| 88 | + | + |
| 89 | ++ | + |
| 90 | + | + |
| 91 | ++++ | ++ |
| 92 | + | + |
| 93 | + | ++ |
| 94 | +++ | ++++ |
| 95 | + | ++ |
| 96 | + | ++ |
| 97 | + | ++ |
| 98 | ++ | +++ |
| 99 | ++ | ++ |
| 100 | + | ++ |
| 101 | ++ | ++++ |
| 102 | + | ++ |
| 103 | ++ | ++ |
| 104 | ++++ | ++++ |
| 105 | ++ | ++++ |
| 106 | + | + |
| 107 | +++ | ++++ |
| 108 | +++ | ++++ |
| 109 | + | ++ |
| 110 | + | + |
| 111 | + | ++ |
| 112 | ++++ | ++++ |
| 113 | ++ | ++ |
| 114 | + | + |
| 115 | + | + |
| 116 | + | ++ |
| 117 | + | ++ |
| 118 | + | ++ |
| 119 | + | ++ |
| 120 | ++++ | |
| 121 | + | + |
| 122 | + | ++ |
| 123 | ++++ | ++++ |
| 124 | ++ | |
| 125 | ++ | +++ |
| 126 | ++++ | +++ |
| 127 | + | + |
| 128 | + | + |
| 129 | + | + |
| 130 | +++ | |

TABLE 1-continued

Inhibition of biochemical activity of GCN2 and
PERK kinases by exemplary compounds.

| Example No | GCN2 IC$_{50}$ (nM) | PERK IC$_{50}$ (nM) |
|---|---|---|
| 131 | ++ | |
| 132 | + | + |
| 133 | ++ | ++ |
| 134 | ++++ | |
| 135 | + | ++ |
| 136 | + | ++ |
| 137 | + | ++ |
| 138 | ++ | |
| 139 | ++ | |
| 140 | ++ | |
| 141 | ++++ | |
| 142 | ++ | ++ |
| 143 | + | + |
| 144 | ++ | ++ |
| 145 | ++ | +++ |
| 146 | ++ | |
| 147 | + | ++ |
| 148 | + | + |
| 149 | +++ | |
| 150 | +++ | |
| 151 | + | ++ |
| 152 | ++ | |
| 153 | + | ++ |
| 154 | ++ | ++ |
| 155 | ++ | ++ |
| 156 | ++ | +++ |
| 157 | + | |
| 158 | + | ++ |
| 159 | + | + |
| 160 | +++ | ++++ |
| 161 | ++ | ++ |
| 162 | + | ++ |
| 163 | ++++ | ++++ |
| 164 | + | ++ |
| 165 | + | + |
| 166 | ++++ | ++++ |
| 167 | + | + |
| 168 | + | + |
| 169 | + | ++ |
| 170 | ++++ | ++++ |
| 171 | + | + |
| 172 | ++ | |
| 173 | + | + |
| 174 | + | + |
| 175 | + | + |
| 176 | + | + |
| 177 | + | ++ |
| 178 | + | ++ |
| 179 | + | + |

For Table 1,
"+" refers to an IC$_{50}$ less than or equal to 100 nM;
"++" refers to an IC$_{50}$ greater than 100 nM and less than or equal to 500 nM;
"+++" refers to an IC$_{50}$ greater than 500 nM and less than or equal to 1000 nM; and
"++++" refers to an IC$_{50}$ greater than 1000 nM and less than or equal to 10000 nM.

Example 182

CCRF-CEM ASNase Cell Proliferation Assay, a Phenotypic Assay for Cellular Inhibition of GCN2

CCRF-CEM leukemia cells (catalog #CCL-116) were obtained from the American Type Culture Collect (ATTC, Manassas, VA). Cells were grown in RPMI-1640 medium supplemented with 10% heat-inactivated fetal bovine serum (Invitrogen, Carlsbad, CA) and 1% Penicillin/Streptomycin/L-Glutamine at 37° C., 5% CO$_2$, and 95% humidity. Cells were expanded until reaching one million cells per mL at which time they are subcultured or harvested for assay use. Ten thousand cells per well in 200 µL RPMI-1640 supplemented with 10% heat-inactivated fetal bovine serum and 1% Penicillin/Streptomycin were dispensed into a 96-well black clear bottom plate. A serial dilution of test compound and 1 mU/mL ASNase was added in triplicate and plates were incubated for 72 h at 37° C., 5% CO$_2$, and 95% humidity. At the end of the incubation, 40 µL of a 440 mM solution of resazurin (Sigma, St. Louis, MO) in PBS was added to each well of the plate and plates were incubated for an additional 6 h at 37° C., 5% CO$_2$, and 95% humidity. Plates were read on a Synergy2 or equivalent reader (Biotek, Winooski VT) using an excitation of 540 nm and an emission of 600 nm. Data was analyzed using GraphPad Prism software (GraphPad, San Diego, CA) to calculate IC$_{50}$ values.

Example 183

HCT116 Amino Acid Starved (-AA) Phospho-GCN2 and ATF4 Assay

HCT116 colorectal cancer cells (catalog #CCL-247) were obtained from the American Type Culture Collect (ATTC, Manassas, VA). Briefly, cells were grown in RPMI 1640 supplemented with 10% heat inactivated fetal bovine serum (Invitrogen, Carlsbad, CA) and 1% Penicillin/Streptomycin/L-Glutamine at 37° C., 5% CO$_2$, and 95% humidity. Cells were expanded until reaching 70-95% confluency at which point they were subcultured or harvested for assay use. Cells were seeded in 12-well culture plate at five hundred thousand cells per well in 1 mL complete growth medium and incubated overnight at 37° C., 5% CO$_2$, and 95% humidity. The next day each well was replaced with 1 mL Earle's Balanced Salt Solution (EBSS, Invitrogen, Carlsbad, CA) supplemented with 10% Dialyzed Fetal Bovine Serum, 5.5 mM Glucose, 1% Penicillin/Streptomycin and 1% Vitamin solution (thermo #11120052). A serial dilution of test compound was dispensed into well. Plates were incubated for 4 h at 37° C., 5% CO$_2$, and 95% humidity. At the end of the incubation, cells were washed with PBS supplemented with 1× Halt protease inhibitor, 1× Halt phosphatase inhibitor, 1× Sigma phosphatase inhibitor cocktail 2 and 1×EDTA and then lysed with M-PER Mammalian Protein Extraction Reagent supplemented with 3× of the inhibitor mix as described above. Cell lysates were sonicated with water bath sonicator (Qsonica, Newtown, CT) and supernatants were boiled with SDS buffer and reducing agent. Western blot was performed on each lysate to quantify phospho-GCN2 (Thr899), total GCN2, ATF4 and beta-Actin. Membranes were imaged with LI-COR Odyssey CLx Imaging System (LI-COR, Lincoln, NE). Data were analyzed using GraphPad Prism software (GraphPad, San Diego, CA) to calculate IC$_{50}$ values.

Example 184

CCRF-CEM TG ATF4 ELISA, a Phenotypic Assay for Cellular Inhibition of PERK Preactivated by Thapsigargin (TG)

CCRF-CEM leukemia cells (catalog #CCL-116) were obtained from the American Type Culture Collection (ATTC, Manassas, VA). Briefly, cells were grown in RPMI-1640 medium supplemented with 10% heat-inactivated fetal bovine serum (Invitrogen, Carlsbad, CA) and 1% Penicillin/Streptomycin/L-Glutamine at 37° C., 5% CO$_2$, and 95% humidity. Cells were expanded until reaching one million cells per mL at which time they were subcultured or harvested for assay use. One million five hundred thousand cells per well in 1 mL complete growth medium were dispensed into 12-well plates and incubated overnight. A serial dilution of test compound was added and cells were incubated at 37° C., 5% $CO_2$, and 95% for three hours, then 1 μM thapsigargin was added and cells were incubated for an additional hour at 37° C., 5% $CO_2$, and 95%. Cells were lysed then ATF4 levels were measured using an ELISA assay (Proteintech, Rosemont, IL). Absorbance was measured at 450 nM and 544 nM using a Synergy2 or equivalent reader (Biotek, Winooski VT). Data was analyzed using PRISM software (Graphpad, San Diego, CA) to calculate $IC_{50}$ values.

TABLE 2

Inhibition of proliferation of ASNase treated CCRF-CEM cells, Phospho-GCN2 and ATF4 in amino acid starved HCT116, and ATF4 in Thapsigargin stimulated CCRF-CEM cells by exemplary compounds..

| Example No | CCRF-CEM ASNase Cell Proliferation | HCT116-AA pGCN2 Western Blot | HCT116-AA ATF4 Western Blot | CCRF-CEM Thapsigargin ATF4 ELISA |
|---|---|---|---|---|
| 3 | + | + | + | |
| 4 | ++++ | | | + |
| 8 | ++ | + | ++ | ++++ |
| 9 | +++ | + | ++ | ++++ |
| 11 | ++ | + | + | ++++ |
| 14 | ++++ | ++ | +++ | ++++ |
| 15 | ++ | + | ++ | |
| 16 | + | + | + | ++++ |
| 17 | ++++ | ++ | ++++ | ++++ |
| 19 | ++ | + | + | ++++ |
| 22 | + | + | + | ++++ |
| 23 | ++ | + | + | ++++ |
| 25 | + | + | + | ++++ |
| 26 | + | + | + | ++++ |
| 27 | + | + | + | ++++ |
| 30 | + | + | + | ++++ |
| 31 | + | + | + | ++++ |
| 33 | ++ | + | + | ++++ |
| 35 | + | + | + | ++++ |
| 36 | + | + | + | ++++ |
| 38 | ++ | + | ++ | ++++ |
| 39 | ++ | + | ++ | ++++ |
| 44 | + | + | + | ++++ |
| 45 | + | + | + | ++ |
| 48 | ++ | + | + | ++++ |
| 49 | + | + | ++ | ++++ |
| 50 | + | + | + | ++++ |
| 51 | + | + | + | ++++ |
| 53 | + | + | + | ++++ |
| 56 | + | + | + | +++ |
| 57 | + | + | + | ++++ |
| 59 | + | + | + | ++++ |
| 61 | + | + | + | ++ |
| 62 | + | + | ++ | ++++ |
| 63 | + | + | + | ++++ |
| 64 | + | + | + | ++++ |
| 65 | ++ | + | ++ | ++++ |
| 66 | + | + | + | ++++ |
| 67 | + | + | + | ++++ |
| 68 | + | + | + | ++++ |
| 74 | + | + | + | ++++ |
| 77 | + | + | + | ++ |
| 78 | + | + | + | +++ |
| 84 | + | + | + | ++ |
| 85 | + | + | + | ++++ |
| 87 | + | + | + | ++++ |
| 88 | + | + | + | ++ |
| 89 | ++ | + | ++ | ++++ |
| 90 | + | + | + | ++++ |
| 92 | + | + | + | ++++ |

TABLE 2-continued

Inhibition of proliferation of ASNase treated CCRF-CEM cells, Phospho-GCN2 and ATF4 in amino acid starved HCT116, and ATF4 in Thapsigargin stimulated CCRF-CEM cells by exemplary compounds..

| Example No | CCRF-CEM ASNase Cell Proliferation | HCT116-AA pGCN2 Western Blot | HCT116-AA ATF4 Western Blot | CCRF-CEM Thapsigargin ATF4 ELISA |
|---|---|---|---|---|
| 93 | ++ | + | ++ | ++++ |
| 95 | ++ | + | ++ | ++++ |
| 96 | ++ | + | ++ | ++++ |
| 97 | + | + | ++ | ++++ |
| 100 | + | + | + | ++++ |
| 102 | + | + | + | ++++ |
| 106 | + | + | + | ++ |
| 109 | + | + | + | +++ |
| 110 | + | + | + | ++ |
| 111 | ++ | ++ | + | ++++ |
| 113 | + | + | ++ | +++ |
| 114 | + | + | ++ | ++++ |
| 115 | + | + | + | ++++ |
| 117 | ++ | ++ | ++ | ++++ |
| 121 | + | + | + | ++ |
| 127 | + | + | + | +++ |
| 128 | + | + | + | + |
| 129 | + | + | + | ++++ |
| 132 | + | + | + | +++ |
| 135 | +++ | ++ | ++++ | ++++ |
| 136 | ++ | + | ++ | ++++ |
| 137 | + | + | + | ++++ |
| 143 | + | + | + | ++++ |
| 148 | + | + | + | ++++ |
| 151 | + | + | + | ++ |
| 158 | + | + | + | ++++ |
| 159 | + | | | +++ |
| 162 | + | | | |
| 164 | ++ | | | ++++ |
| 165 | + | | | ++++ |
| 167 | + | | | + |
| 168 | ++ | | | ++++ |
| 171 | + | | | + |
| 173 | + | | | ++ |
| 174 | + | | | + |
| 175 | + | | | ++ |
| 176 | + | | | ++++ |
| 177 | + | | | ++ |
| 178 | + | | | ++++ |
| 179 | + | | | ++ |

For Table 2,
"+" refers to an $IC_{50}$ less than or equal to 100 nM;
"++" refers to an $IC_{50}$ greater than 100 nM and less than or equal to 500 nM;
"+++" refers to an $IC_{50}$ greater than 500 nM and less than or equal to 1000 nM; and
"++++" refers to an $IC_{50}$ greater than 1000 nM and less than or equal to 10000 nM.

Example 185

H929 ATF4 ELISA ASSAY

H929 multiple myeloma cells (catalog #CRL-9068) were obtained from the American Type Culture Collection (ATTC, Manassas, VA). Briefly, cells were grown in RPMI-1640 medium supplemented with 20% heat-inactivated fetal bovine serum (catalog #A3840002, ThermoFisher Scientific, Waltham, MA), 1% Penicillin/Streptomycin/L-Glutamine (catalog #10378016, ThermoFisher Scientific, Waltham, MA), and 0.05 mM 2-mercaptoethanol (catalog #21985-023, ThermoFisher Scientific, Waltham, MA) at 37° C., 5% $CO_2$, and 95% humidity. Cells were expanded until reaching one million five hundred thousand cells per mL at which time they were subcultured or harvested for assay use. One million five hundred thousand cells per well in 1 mL complete growth medium were dispensed into 12-well plates and incubated overnight. A serial dilution of test compound was added, and cells were incubated at 37° C., 5% $CO_2$, and 95% for four hours. Cells were lysed then ATF4 levels were measured using an ELISA assay (Proteintech, Rosemont, IL). Absorbance is measured at 450 nM and 544 nM using a Synergy2 or equivalent reader (Biotek, Winooski VT). Data were analyzed using PRISM software (Graphpad, San Diego, CA) to calculate fold stimulation of cellular ATF4 relative to vehicle treated control.

TABLE 3

Stimulation of ATF4 in H929 Multiple Myeloma cells by exemplary compounds.

| Example No | H929 NS ATF4 ELISA |
|---|---|
| 16 | +++ |
| 25 | ++ |
| 31 | ++ |
| 49 | + |
| 79 | +++ |
| 86 | +++ |
| 109 | +++ |
| 110 | ++ |
| 128 | +++ |
| 151 | ++ |
| 174 | +++ |
| 175 | +++ |
| 179 | +++ |

For Table 3,
"+" refers to an ATF4 stim less than or equal to 5-fold;
"++" refers to an ATF4 stim greater than 5 fold and less than or equal to 10 fold;
"+++" refers to an ATF4 stim greater than 10 fold and less than or equal to 20 fold.

Compound 16 unexpectedly exhibited stimulation of ATF4 in H929 multiple myeloma cells (in the absence of thapsigargin) across a concentration range of 123 nM to 10 µM. A graph of the stimulation of cellular ATF4 in H929 multiple myeloma cells induced by Compound 16 is shown in FIG. 1.

Example 186

Detection of PERK Oligomerization Using NanoBRET

Constructs for BRET were built using the NanoBRET™ Flexi® PPI Starter System (Promega, Madison, WI). The full-length PERK ORF was obtained from Genscript (Piscataway, NJ). HEK-293 cells (catalog #CRL-1573) were obtained from the American Type Culture Collection (ATTC, Manassas, VA). Cells were grown in MEM medium supplemented with 10% heat-inactivated fetal bovine serum (Invitrogen, Carlsbad, CA) and 1% Penicillin/Streptomycin/ L-Glutamine at 37° C., 5% $CO_2$, and 95% humidity. For BRET assays, cells were seeded at a density of 40,000 cells/mL in culture medium in 6-well plates and allowed to attach and recover. Cells were transfected with C-terminally tagged PERK-NLuc and C-terminally tagged PERK-Halo using Lipofectamine LTX (Thermo, Waltham, MA) and allowed to express proteins overnight at 37° C., 5% $CO_2$, and 95% humidity. Cells were then detached from culture dishes using 0.05% trypsin-EDTA, collected, and diluted in assay medium consisting of Opti-MEM® I Reduced Serum Medium supplemented with 4% FBS (Thermo) to 22,000 cells/mL. Cells were dispensed into 96-well cell culture plates and HaloTag® NanoBRET™ 618 Ligand (Promega) was added to a final concentration of 100 nM. Compound or DMSO was added to the cells, and plates were incubated 4 to 24 h at 37° C., 5% $CO_2$, and 95% humidity. NanoBRET™ Nano-Glo® Substrate was added to the cells, and cells were shaken for 30 sec. Donor (460 nM) and acceptor (618) emissions were measured on a Synergy Neo2 Multi-Mode Reader (BioTek, Winooski, VT) within 10 min of substrate addition. Data was reported as BRET ratio (Acceptor/Donor).

Figure 2:
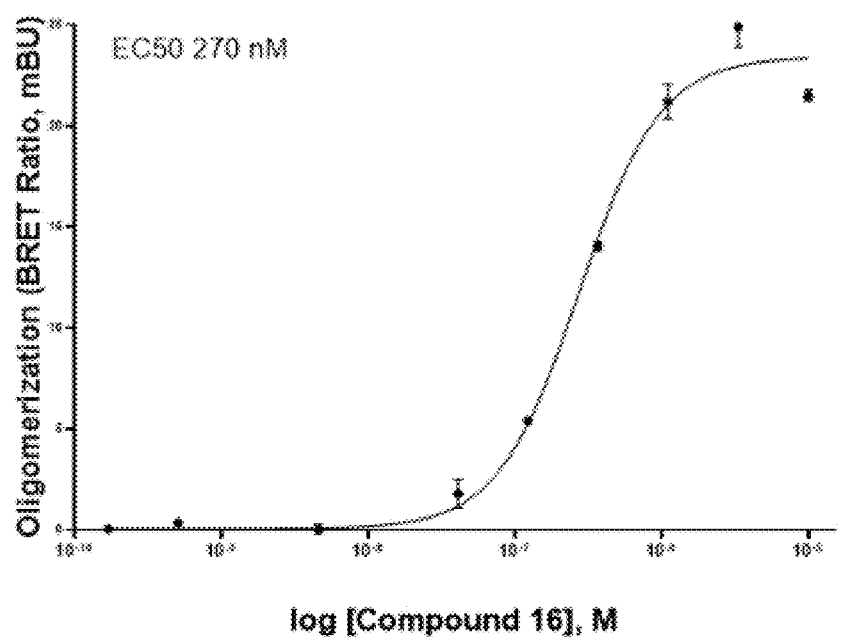
FIG. 2 depicts a plot of PERK oligomer stimulation by Compound 16 in an HEK293T NanoBRET based assay.

Compound 16 unexpectedly exhibited stimulation of the formation of PERK oligomers, with an $EC_{50}$ of 270 nM. A graph of the stimulation PERK oligomers induced by Compound 16 is shown in FIG. 2.

Example 187

Stimulation of Multiple Myeloma UPR/ISR Signaling Pathway Proteins ATF4 and CHOP H929 multiple myeloma cells (catalog #CRL-9068) were obtained from the American Type Culture Collection (ATTC, Manassas, VA), grown in RPMI 1640 supplemented with 20% heat inactivated fetal bovine serum (Invitrogen, Carlsbad, CA), 1% Penicillin/Streptomycin/L-Glutamine and 0.05 mM 2-mercaptoethanol at 37° C., 5% $CO_2$, and 95% humidity and maintained at 1-2 million cells per mL. Cells were seeded in 6 well plates at 4 million cells per well in 2 mL complete growth medium and treated with a serial dilution of test compounds for 4 h at 37° C., 5% $CO_2$, and 95% humidity. At the end of the incubation, cells are washed with PBS supplemented with 1× Halt protease inhibitor, 1× Halt phosphatase inhibitor, 1× Sigma phosphatase inhibitor cocktail 2 and 1×EDTA and then lysed with M-PER Mammalian Protein Extraction Reagent supplemented with 3× of the inhibitor mix as described above. Cell lysates were sonicated with water bath sonicator (Qsonica, Newtown, CT) and supernatants were boiled with SDS buffer and reducing agent. Western blot was performed to quantify ATF4, CHOP and beta-Actin (Cell Signaling Technology, Danvers, MA). Membranes were imaged with LI-COR Odyssey CLx Imaging System (LI-COR, Lincoln, NE).

Figure 3:
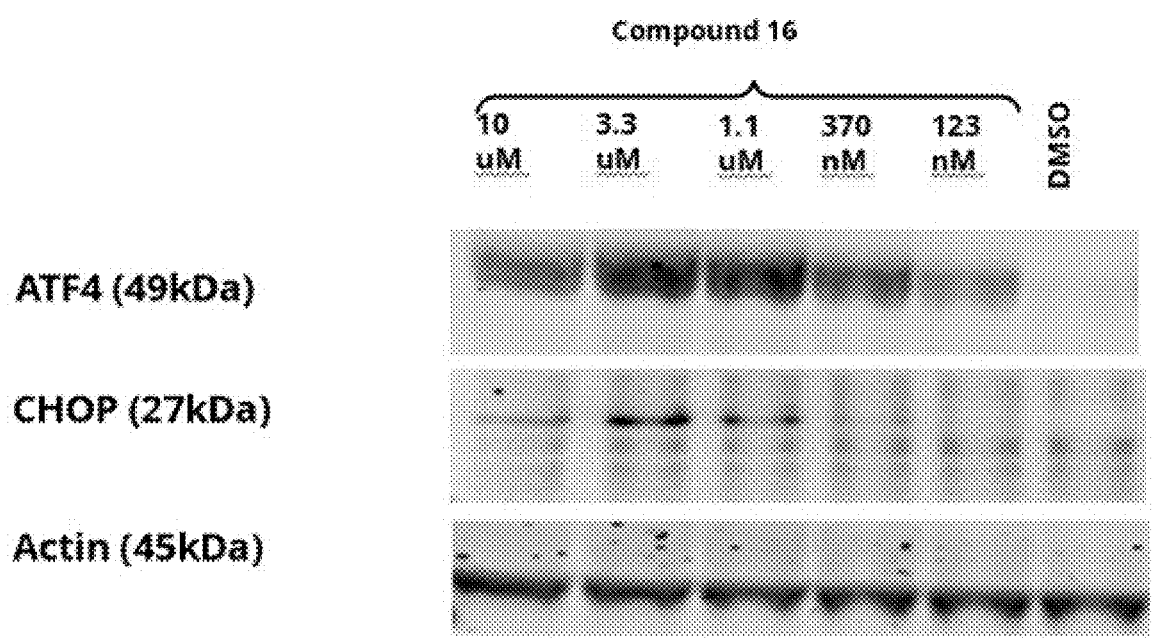
FIG. 3 depicts stimulation PERK downstream signaling proteins ATF4 and CHOP with actin as a loading control. The figure shows that Compound 16 increases expression of the PERK signaling pathway in H929 multiple myeloma cells as detected Western blot analysis.

Compound 16 unexpectedly exhibited stimulation of the PERK pathway in H929 multiple myeloma cells. A figure of the stimulation PERK downstream signaling proteins ATF4 and CHOP (Actin as a loading control) is shown in FIG. 3. ATF4 is stimulated across a concentration range of 123 nM to 10 µM. CHOP is stimulated across a concentration range of 1.1 to 10 µM.

Example 188

Stimulation of Multiple Myeloma UPR/ISR Target Genes Using Quantitative RT-PCR

H929 multiple myeloma cells (catalog #CRL-9068) multiple myeloma cells were obtained from the American Type Culture Collection (ATTC, Manassas, VA). Cells were grown in RPMI-1640 medium supplemented with 20% heat-inactivated fetal bovine serum (catalog #A3840002, ThermoFisher Scientific, Waltham, MA), 1% Penicillin/ Streptomycin/L-Glutamine (catalog #10378016, ThermoFisher Scientific, Waltham, MA), and 0.05 mM 2-mercaptoethanol (catalog #21985-023, ThermoFisher Scientific, Waltham, MA) at 37° C., 5% $CO_2$, and 95% humidity. Cells were expanded until reaching 70-95% confluency at which point they were subcultured or harvested for assay use. Cells were seeded in 6-well culture plate at $3.0 \times 10^6$ cells per well in 2 mL complete growth medium and incubated with indicated concentrations of Compound 16 at 37° C., 5% $CO_2$, and 95% humidity for 4 h or 24 h time. At the end of the incubation, cells were washed with PBS (Sigma) and RNA was extracted using RNeasy® Plus Kits (Qiagen, Germantown, MD). cDNA was synthesized using the High-Capacity cDNA Reverse Transcription Kit (Applied Biosciences, Beverly Hills, CA), and quantitative PCR was performed on a QuantStudio 3 (Applied Biosciences) using TaqMan Assays (Table A, Thermo) and TaqMan Fast Advanced Master Mix (Thermo) according to manufacturer's specifications.

TABLE A

TaqMan Probes

| Gene Of Interest | Assay ID |
|---|---|
| ATF4 | Hs00909569_g1 |
| DDIT3 (CHOP) | Hs00358796_g1 |
| GPT2 | Hs00370287_m1 |
| GUSB (Endogenous Control) | Hs00939627_m1 |
| PPP1R15A (GADD34) | Hs00169585_m1 |
| VEGFA | Hs00900055_m1 |

Figure 4:
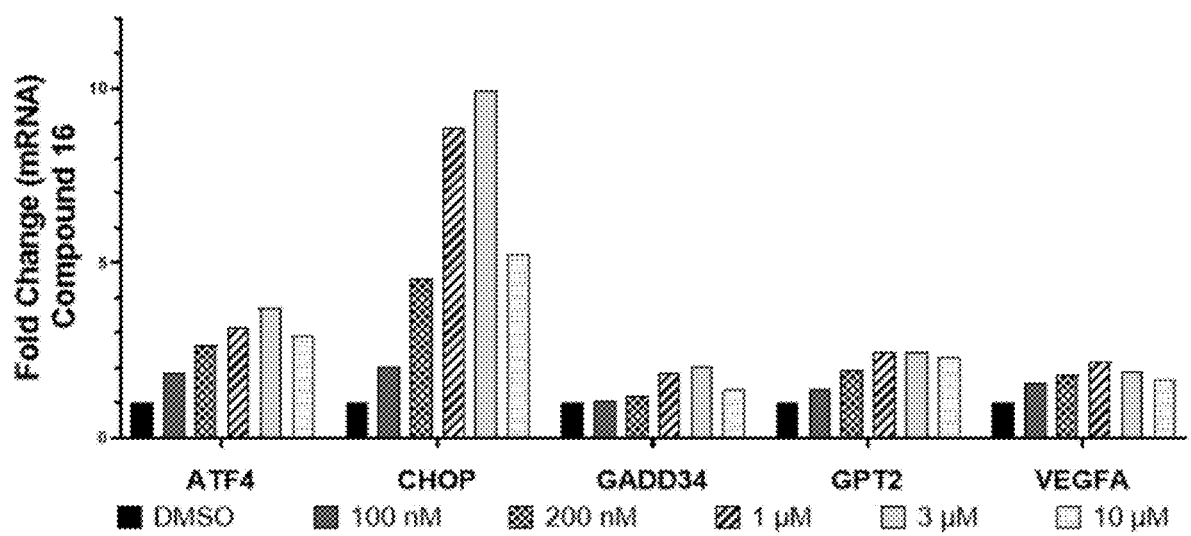
FIG. 4 depicts fold increases (compared to DMSO control) in expression of PERK pathway target genes ATF4, CHOP, GADD34, GPT2, and VEGFA by Compound 16 in H929 multiple myeloma cells using qRT-PCR analysis.

Compound 16 unexpectedly induced the expression of PERK UPR/ISR target genes in H929 multiple myeloma cells. A figure illustrating the fold increases (compared to DMSO control) of ATF4, CHOP, GADD34, GPT2, and VEGFA is shown in FIG. 4. Target genes were increased across a concentration range of 100 nM to 10 µM.

Example 189

Stimulation of Multiple Myeloma Apoptosis Signaling Pathway

H929 multiple myeloma cells (catalog #CRL-9068) were obtained from the American Type Culture Collection (ATTC, Manassas, VA), grown in RPMI 1640 supplemented with 20% heat inactivated fetal bovine serum (Invitrogen, Carlsbad, CA), 1% Penicillin/Streptomycin/L-Glutamine and 0.05 mM 2-mercaptoethanol at 37° C., 5% $CO_2$, and 95% humidity and maintained at 1-2 million cells per mL. RPMI8226 (catalog #CCL-155) were obtained from the American Type Culture Collection (ATTC, Manassas, VA), grown in RPMI 1640 supplemented with 10% heat inactivated fetal bovine serum (Invitrogen, Carlsbad, CA) and 1% Penicillin/Streptomycin/L-Glutamine at 37° C., 5% $CO_2$, and 95% humidity and maintained at 0.1-1 million cells per mL. Cells were seeded in 6 well plates at 4 million cells per well in 2 mL complete growth medium and treated with a serial dilution of test compounds combined with either 100 nM Dexamethasone (Selleckchem, Houston, TX) or equal volume of DMSO for 24 h at 37° C., 5% $CO_2$, and 95% humidity. At the end of the incubation, cells are washed with PBS supplemented with 1× Halt protease inhibitor, 1× Halt phosphatase inhibitor, 1× Sigma phosphatase inhibitor cocktail 2 and 1×EDTA and then lysed with M-PER Mammalian Protein Extraction Reagent supplemented with 3× of the inhibitor mix as described above. Cell lysates were sonicated with water bath sonicator (Qsonica, Newtown, CT) and supernatants were boiled with SDS buffer and reducing agent. Western blot was performed to quantify cleaved-Caspase 3, cleaved-Caspase 7, PARP, and beta-Actin (Cell Signaling Technology, Danvers, MA). Membranes were imaged with LI-COR Odyssey CLx Imaging System (LI-COR, Lincoln, NE).

Figure 5:
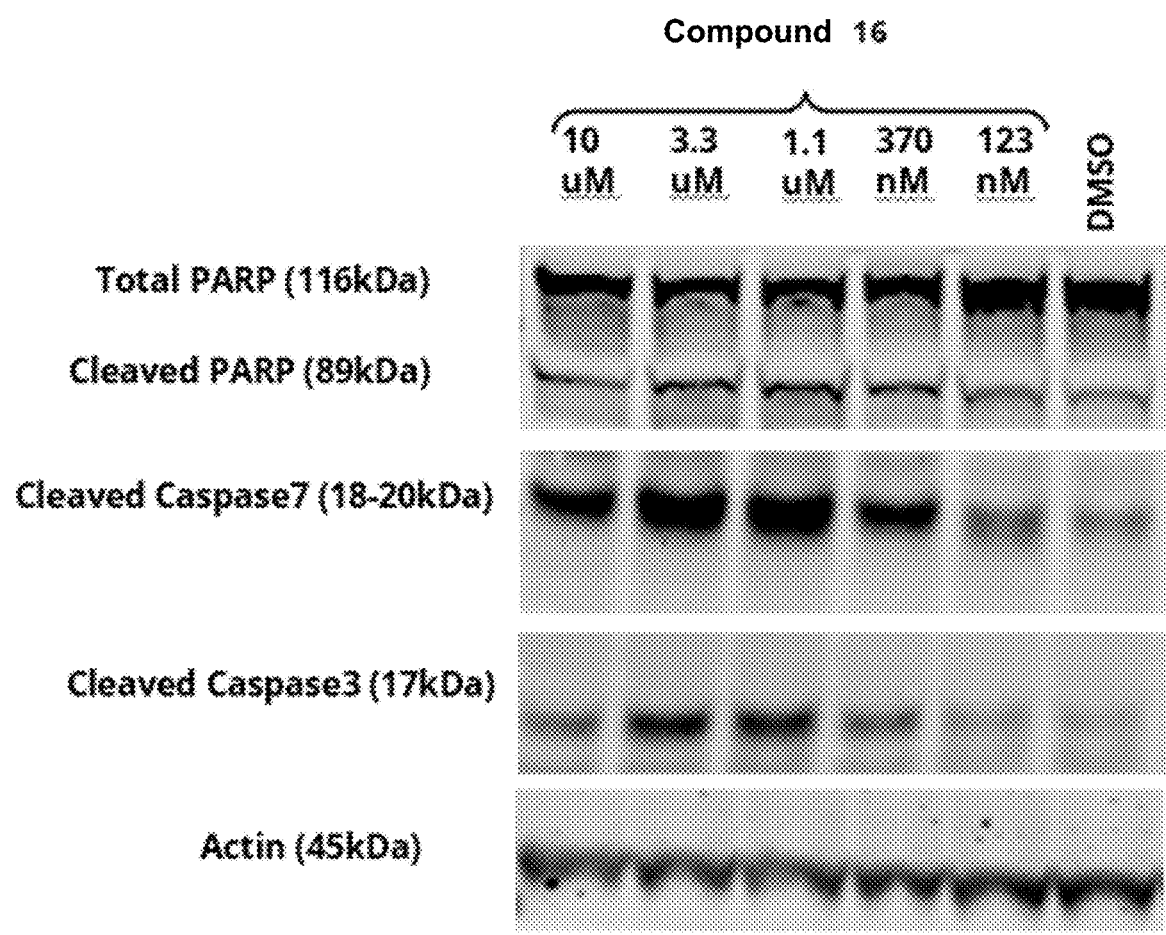
FIG. 5 illustrates effects of Compound 16 as a single agent on apoptotic pathway readouts in H929 multiple myeloma cells using Western blot analysis, including cleaved PARP, cleaved Caspase 7, and cleaved Caspase 3.

Compound 16 unexpectedly induced the expression of proapoptotic proteins in H929 multiple myeloma cells. A figure illustrating cleaved PARP, cleaved Caspase 7, and cleaved Caspase 3 is shown in FIG. 5. Apoptotic proteins were increased across a concentration range of 123 nM to 10 µM.

Example 190

Inhibition of Multiple Myeloma and B-Cell Lymphoma Cell Proliferation

H929, RPMI8226, GA-10, and DoHH-2 cells (catalog #CRL-9068) were obtained from the American Type Culture Collection (ATTC, Manassas, VA). H929 Cells were maintained in RPMI-1640 medium supplemented with 20% heat-inactivated fetal bovine serum (catalog #A3840002, ThermoFisher Scientific, Waltham, MA), 1% Penicillin/Streptomycin/L-Glutamine (catalog #10378016, ThermoFisher Scientific, Waltham, MA), and 0.05 mM 2-mercaptoethanol (catalog #21985-023, ThermoFisher Scientific, Waltham, MA). RPMI8226, GA-10, DoHH-2 were maintained in RPMI-1640 medium supplemented with 10% heat-inactivated fetal bovine serum (catalog #A3840002, ThermoFisher Scientific, Waltham, MA) and 1% Penicillin/Streptomycin/L-Glutamine (catalog #10378016, ThermoFisher Scientific, Waltham, MA). All cells were grown at 37° C., 5% $CO_2$, and 95% humidity. Cells were expanded until reaching one million five hundred thousand cells per mL at which time they were subcultured or harvested for assay use.

For cell proliferation assay appropriate number of cells (Forty thousand cells for H929; Twenty thousand cells for RPMI8226, and GA-10; Eight thousand cells for DoHH-2) were seeded per well in 200 µL in respective medium were dispensed into a 96-well black clear bottom plate. A serial dilution of test compound was added in triplicate and plates were incubated for 72 or 120 h at 37° C., 5% $CO_2$, and 95% humidity. Several standard of care agents clinically used to treat multiple myeloma were used for combination studies (lenalidomide (catalog #S1029, Selleckchem, Houston, TX), bortezomib (catalog #S1013, Selleckchem, Houston, TX), dexamethasone (catalog #S1322, Selleckchem, Houston, TX), ibrutinib (Pharmacyclics, Sunnyvale, CA)). At the end of the incubation for H929, RPMI8226, and GA-10, 40 µL of a 440 mM solution of resazurin (Sigma, St. Louis, MO) in PBS was added to each well of the plate and plates were incubated for an additional 7 h at 37° C., 5% $CO_2$, and 95% humidity. Plates were read on a Synergy2 or equivalent reader (Biotek, Winooski VT) using an excitation of 540 nm and an emission of 600 nm. At the end of the incubation of DoHH-2, cell viability was determined using CellTiter-Glo® assay (Promega, Madison, WI). Luminescence was measured using EnVision MultiLabel Reader (PerkinElmer, Waltham, MA). Data was analyzed using GraphPad Prism software (GraphPad, San Diego, CA) to calculate $IC_{50}$ values.

Compound 16, in combination with standard of care (SOC) agents that treat multiple myeloma or B cell lymphomas, exhibits additivity or synergy for inhibition of cell proliferation. Representative graphs are shown in FIG. 6.

Example 191

CCRF-CEM Xenograft Pharmacokinetic/Pharmacodynamic (PK/PD) Model

The CCRF-CEM xenograft model was performed in compliance with all the laws, regulations and guidelines of the National Institutes of Health (NIH) and with the approval of the Animal Care and Use Committee of Labcorp (Ann Arbor, MI), an AAALAC accredited facility. Food and water were provided ad libitum. All mice were observed for clinical signs at least once daily. Female Envigo C.B-17 SCID (6-7 weeks old) were inoculated subcutaneously just below the right high axilla with ten million cells in Dulbecco's Phosphate Buffered Saline, using a 27-gauge needle and syringe. When tumor burdens reached 200 mm$^3$ on average on day 22, mice were randomly assigned into groups such that the mean tumor burden for all groups was within 10% of the overall mean tumor burden for the study population. Groups were treated on days 23-24 as follows: on day 23 vehicle control (dosed orally and IP to mimic combination group) (n=9); ASNase (Abcam, Cambridge, UK) dosed IP at 1000 U/kg/day (n=9). On day 24 vehicle control dosed orally (dosed orally and IP to mimic combination group) (n=9); Compound 16 dosed orally at 50 mg/kg (n=10) and ASNase (Abcam, Cambridge, UK) dosed IP at 1000 U/kg (n=9) 2 h prior to sample harvest; Compound 16 dosed orally at 25 mg/kg (n=10) and ASNase (Abcam, Cambridge, UK) dosed IP at 1000 U/kg (n=9) 2 h prior to sample harvest at 2, 6, and 10 h post Compound 16 dose. Blood samples were collected in K2EDTA tubes and processed into plasma, snap frozen in liquid nitrogen then stored at −80° C. Plasma samples were subjected to pharmacokinetic analysis using liquid chromatography coupled with tandem mass spectrometry analysis (Cayman Chemical, Ann Arbor, MI). Tumors and pancreatic tissues were harvested and powdered over liquid nitrogen in covaris bags and stored at −80° C. Fr tissue sample processing roughly 30 mg of tumor or pancreatic tissue was lysed in mPER lysis buffer (Thermo Fisher Scientific, Waltham, MA) supplemented with 3× Halt protease inhibitor, 3× Halt phosphatase inhibitor, 3× Sigma phosphatase inhibitor cocktail 2 and 3×EDTA on ice then homogenized using Bead Ruptor 96 (Omni, Kennesaw, GA). Samples were then centrifuged at 21,000 g for 10 min at 4° C. Cleared lysates were then transferred to ice-chilled conical bottom 96-well plates, sealed then stored at −80° C. Next day, samples were thawed on ice followed by centrifugation at 3739 g for 10 min at 4° C. Cleared lysates were then transferred to ice-chilled round bottom 96-well plates. Protein concentrations were determined using BCA protein assay kit (Thermo Fisher Scientific, Waltham, MA). Lysates were normalized to 10 µg/µl prior to boiling in 4×SDS-sample buffer and reducing agent. Samples were resolved using SDS-PAGE then analyzed using Western blot to quantify phospho-GCN2 (Thr899) (Abcam, Cambridge, UK), total GCN2, ATF4 and beta-Actin (Cell Signaling Technology, Danvers, MA). Membranes are imaged with LI-COR Odyssey CLx Imaging System (LI-COR, Lincoln, NE). Data is analyzed using GraphPad Prism software (GraphPad, San Diego, CA) to calculate % inhibition.

Figures 7A, 7B:
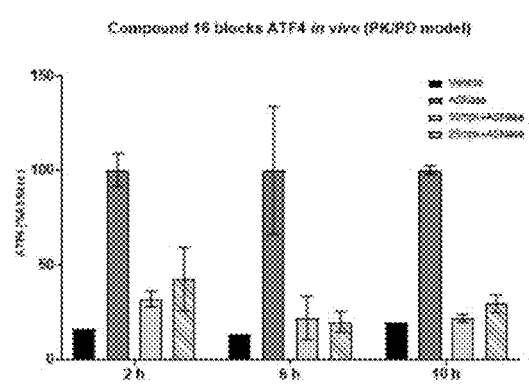
FIGS. 7A and 7B show effects of Compound 16 in combination with asparaginase on ATF4 levels, measuring GCN2 activity, in an in vivo PK/PD model using Western blot analysis. Corresponding plasma levels of Compound 16 were determined at the PD time points of 2, 6, and 10 hours post dose.

Compound 16, in combination with ASNase, inhibits GCN2-mediated ATF4 levels in a CCRF-CEM leukemia xenograft model. As shown in FIG. 7, Compound 16 inhibited ATF4 levels by 81 to 98% compared to vehicle control when dosed at 50 mg/kg orally, and inhibited ATF4 levels by 69 to 92% compared to vehicle control when dosed at 25 mg/kg orally. Corresponding plasma levels of Compound 16 were determined at the PD time points of 2, 6, and 10 hours post dose.

Example 192

MV-4-11 Xenograft Efficacy Model

The MV-4-11 acute myeloid leukemia xenograft model was performed in compliance with all the laws, regulations, and guidelines of the National Institutes of Health (NIH) and with the approval of the Animal Care and Use Committee of Crown Bioscience (Taicang, China), an AAALAC accredited facility. Food and water were provided ad libitum. All mice were observed for clinical signs at least once daily. Female NOD/SCID (6-9 weeks old; Vital River Laboratories Research Models and Services (Beijing, China)) were inoculated subcutaneously right front flank region with five million cells in Dulbecco's Phosphate Buffered Saline:Matrigel (1:1), using a 27-gauge needle and syringe. When tumor burdens reached 150 mm$^3$ on average on day 7, mice were randomly assigned into groups such that the mean tumor burden for all groups was within 10% of the overall mean tumor burden for the study population. Groups were treated on days 7-21 as follows: vehicle control (dosed orally and IP to mimic combination group (n=10); Compound 16 dosed orally at 25 mg/kg/day (n=10); Leunase (Kyowa Kirin, Japan) dosed IP at 1000 U/kg/day (n=10); Leunase (Kyowa Kirin, Japan) dosed IP at 1000 U/kg/day (n=10) and Compound 16 dosed orally at 25 mg/kg/day (n=10). Tumor volume and body weight were measured three times per week. Tumor burden (mg) was estimated from caliper measurements by the formula: tumor burden (mg=mm$^3$)= (length×width$^2$)/2.

Figure 8:
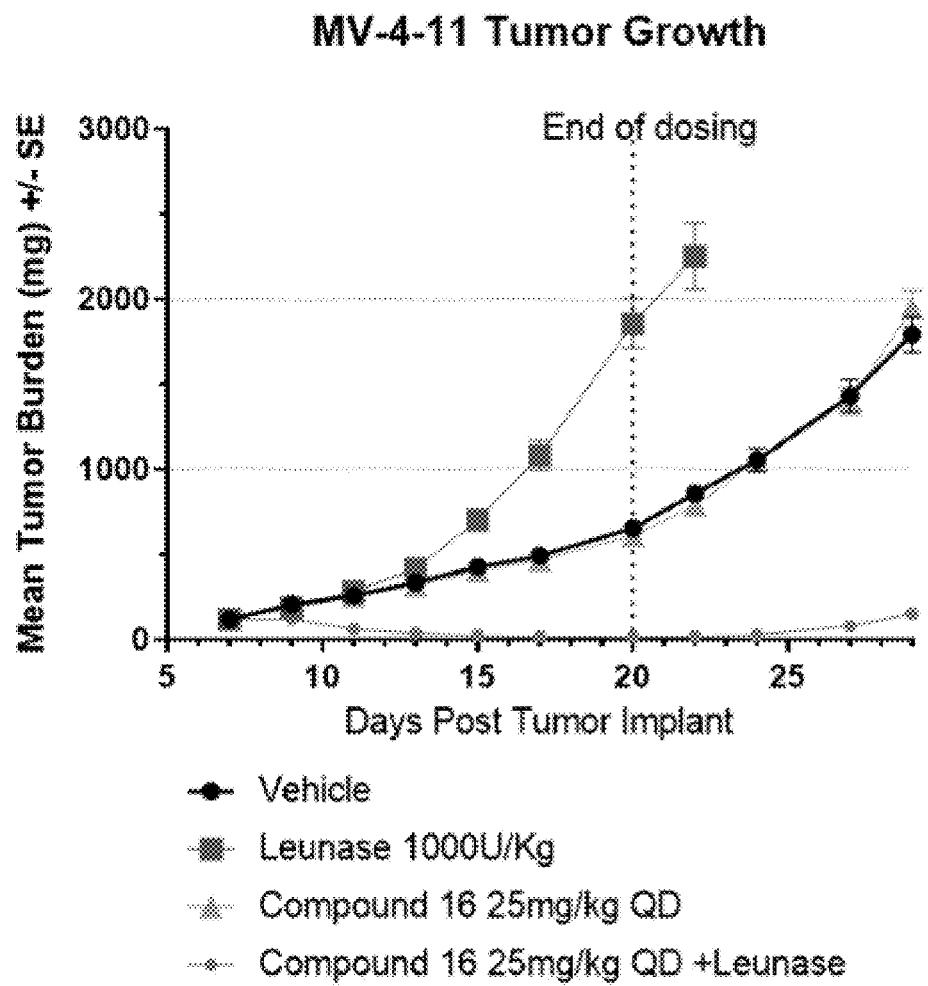
FIG. 8 depicts a plot showing the effect of Compound 16 in combination with asparaginase on tumor growth in an MV-4-11 xenograft model.

Compound 16, in combination with ASNase, inhibits MV-4-11 tumor growth when dosed orally. As shown in FIG. 8, Compound 16 induced tumor regression when dosed at 25 mg/kg/day for 14 days in combination with Leunase dosed at 1000 U/kg.

EQUIVALENTS

While specific embodiments have been discussed, the above specification is illustrative and not restrictive. Many variations of the embodiments will become apparent to those skilled in the art upon review of this specification. The full scope of what is disclosed should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A compound represented by Formula I-R:

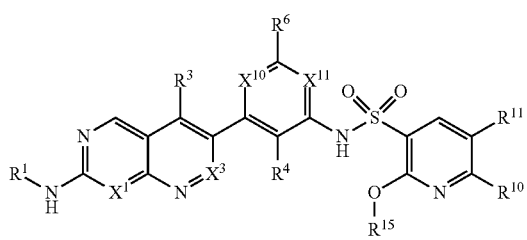

Formula I-R or a pharmaceutically acceptable salt, enantiomer, stereoisomer, or tautomer thereof, wherein:

$X^1$ is selected from the group consisting of CH and N;
$X^3$ is selected from the group consisting of C—O-$L^2$-$E^2$, C-$L^2$-$E^2$, and C—N($R^2$)-$L^2$-$E^2$
$X^{10}$ is selected from the group consisting of $CR^5$ and N;
$X^{11}$ is selected from the group consisting of $CR^7$ and N;
$R^1$ is selected from the group consisting of alkyl, (C=O) $R^{13}$, cycloalkyl, alkoxyalkyl, cycloalkoxyalkyl, aminoalkyl, heterocyclyl, heterocyclylalkyl, aryl, heteroaryl, and heteroarylalkyl,
wherein each of aryl and heteroaryl is optionally substituted with one or more occurrences of a substituent independently selected from the group consisting of haloalkyl, alkyl, haloalkoxy, alkoxy, halo, amino, amido, acyl, alkoxyalkyl, hydroxy, hydroxyalkyl, cyano, cyanoalkyl, and heterocyclyl, and
wherein heterocyclyl is optionally substituted with one or more occurrences of a substituent independently selected from the group consisting of alkyl, alkoxy, alkoxyalkyl, amido, amino, aminoalkyl, acyl, haloalkyl, haloalkoxy, halo, hydroxy, hydroxyalkyl, oxo, cyano, cyanoalkyl, and sulfonyl;

R² is selected from the group consisting of H and alkyl;
R³ is selected from the group consisting of H, alkyl, and halo;
R⁴ and R⁵ are each independently selected from the group consisting of halo, H, alkoxy, alkylamino, amino, alkyl, haloalkyl and CN;
R⁶ is selected from the group consisting of halo, H, and alkyl;
R⁷ is selected from the group consisting of H and F;
R¹⁰ and R¹¹ are each independently selected from the group consisting of hydroxyalkyl, hydroxycycloalkyl, alkoxyalkyl, alkoxycycloalkyl, amino, aminoalkyl, aminocycloalkyl, aminocarbonyl, acylamino, halo, cyano, alkoxy, alkylamino, H, cyanoalkyl, alkyl, cycloalkyl, haloalkyl, cycloalkoxy, cycloalkylamino, heterocyclyl, alkoxycarbonyl, and heterocyclylalkyl;
R¹³ is selected from the group consisting of H, alkyl, cycloalkyl, alkoxyalkyl, cycloalkoxyalkyl, aminoalkyl, heterocyclyl, heterocyclylalkyl, aryl, heteroaryl, and heteroarylalkyl,
wherein each of aryl and heteroaryl is optionally substituted with one or more occurrences of a substituent independently selected from the group consisting of haloalkyl, alkyl, haloalkoxy, alkoxy, halo, amino, amido, acyl, alkoxyalkyl, hydroxy, hydroxyalkyl, cyano, cyanoalkyl, and heterocyclyl, and
wherein heterocyclyl is optionally substituted with one or more occurrences of a substituent independently selected from the group consisting of alkyl, alkoxy, alkoxyalkyl, amido, amino, aminoalkyl, acyl, haloalkyl, haloalkoxy, halo, hydroxy, hydroxyalkyl, oxo, cyano, cyanoalkyl, and sulfonyl;
R¹⁵ is selected from the group consisting of alkyl, cycloalkyl, and heterocycyl;
L² is selected from the group consisting of a direct bond and $C_1$-$C_6$alkyl, wherein $C_1$-$C_6$alkyl is optionally substituted with $(E^{21})_p$;
E² is selected from the group consisting of hydroxy, alkoxy, alkoxyalkyl, cyano, halo, sulfonyl, H, alkyl, amino, amido, acyl, haloalkoxy, haloalkyl, and heterocyclyl,
wherein heterocyclyl is optionally substituted with one or more occurrences of a substituent independently selected from the group consisting of alkyl, alkoxy, amido, amino, acyl, haloalkyl, haloalkoxy, halo, hydroxy, hydroxyalkyl, oxo, cyano, and cyanoalkyl;
$E^{21}$, at each occurrence, is independently selected from the group consisting of H, alkyl, cycloalkyl, alkoxy, cyano, cyanoalkyl, haloalkoxy, haloalkyl, hydroxy, hydroxyalkyl, and halo, and
each p is independently 0, 1 or 2.

2. The compound of claim 1, wherein R¹ is selected from the group consisting of

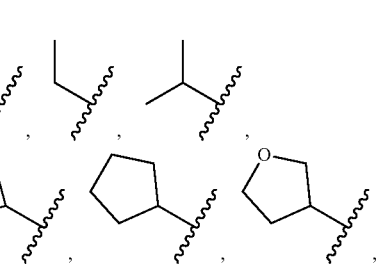

-continued

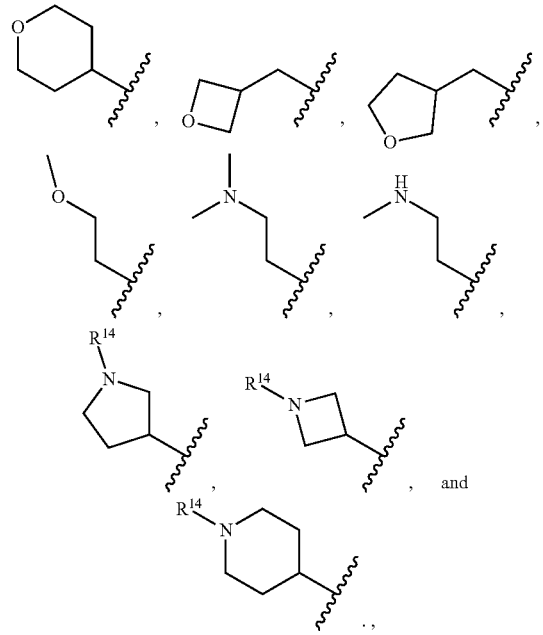

wherein each occurrence of R¹⁴ is independently selected from the group consisting of H, alkyl, alkoxyalkyl, haloalkyl, hydroxyalkyl, and cyanoalkyl.

3. The compound of claim 1, wherein X¹ is N.
4. The compound of claim 1, wherein X¹ is CH.
5. The compound of claim 1, wherein X³ is C—N(R²)-L²-E².
6. The compound of claim 1, wherein X¹⁰ is N and X¹¹ is CR⁷.
7. The compound of claim 1, wherein X¹⁰ and X¹¹ are N.
8. The compound of claim 1, wherein X¹⁰ is CR⁵ and X¹¹ is N.
9. The compound of claim 1, wherein R³ is selected from the group consisting of H, $C_1$-$C_6$ alkyl, and halo.
10. The compound of claim 1, wherein R⁴ is selected from the group consisting of H, F, Cl, Me, OMe, CF₃, and CN.
11. The compound of claim 1, wherein R⁵ is selected from the group consisting of H, F, Cl, Me, OMe, CF₃, and CN.
12. The compound of claim 1, wherein R⁶ is independently selected from the group consisting of H, F, Cl, and Me.
13. The compound of claim 1, wherein R¹⁵ is selected from the group consisting of $C_1$-$C_6$ alkyl, $C_3$-$C_6$ cycloalkyl, and $C_3$-$C_6$ heterocyclyl.
14. A compound selected from the group consisting of:

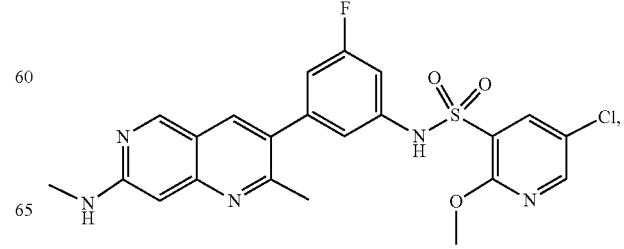

341 -continued

342 -continued

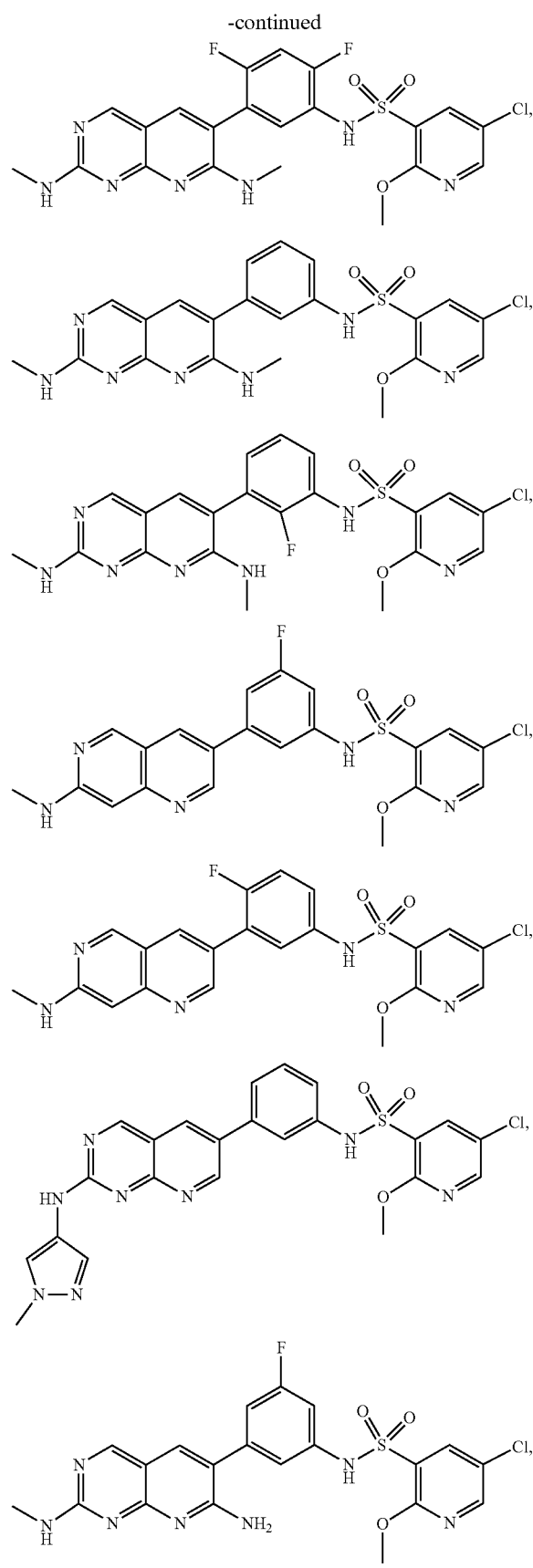
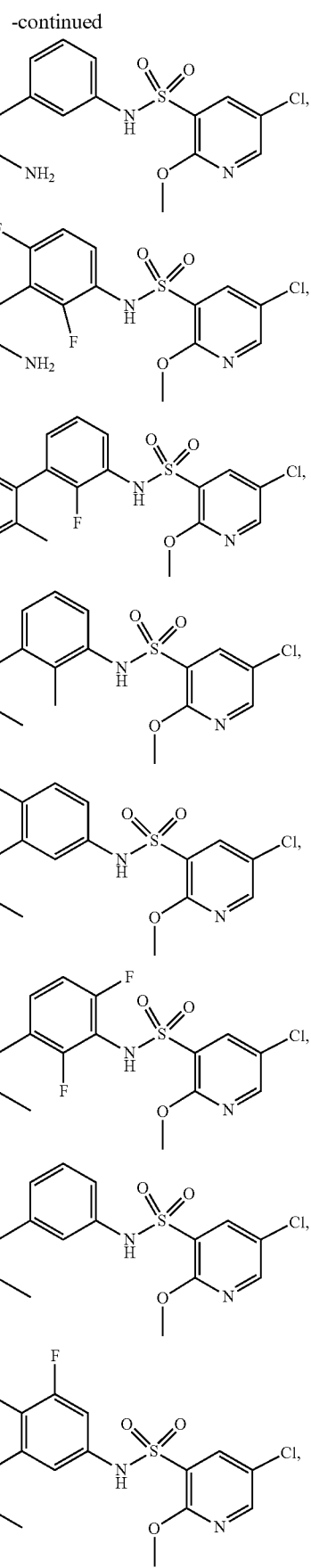

345
-continued
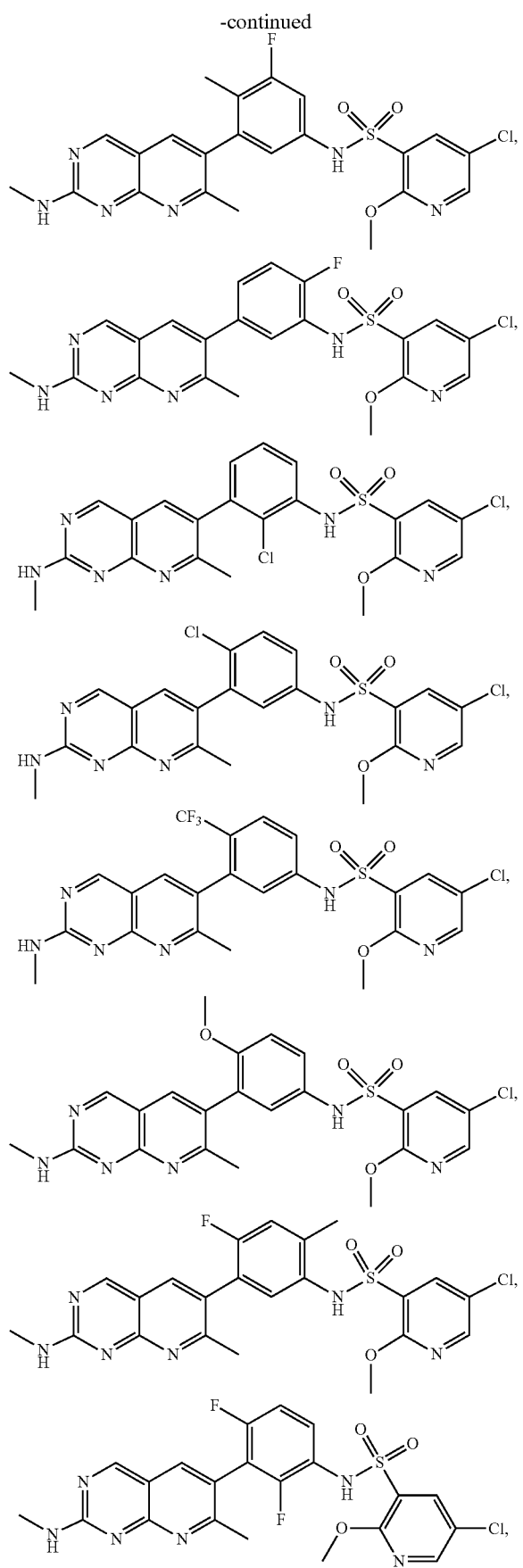
346
-continued
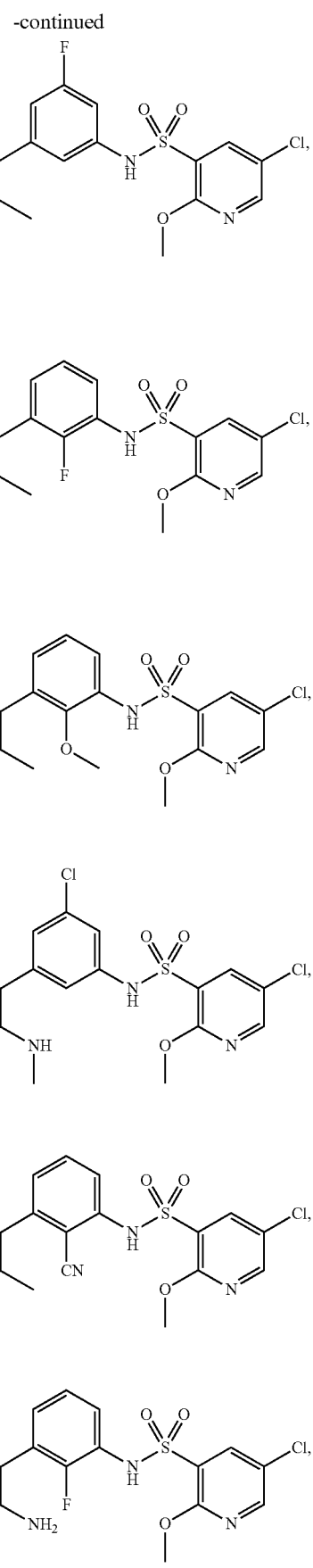

347
-continued
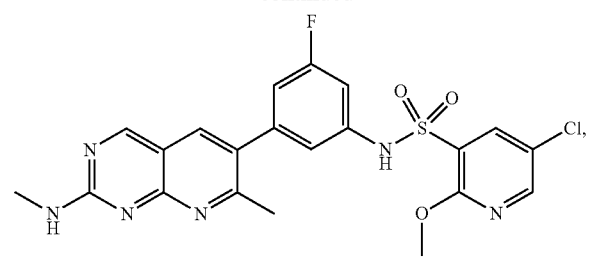
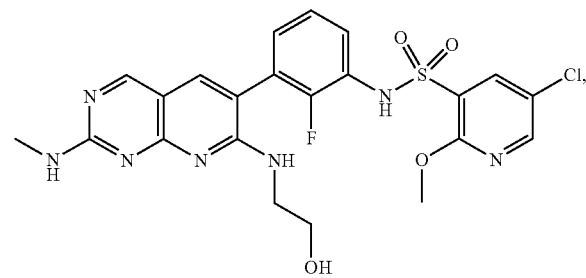
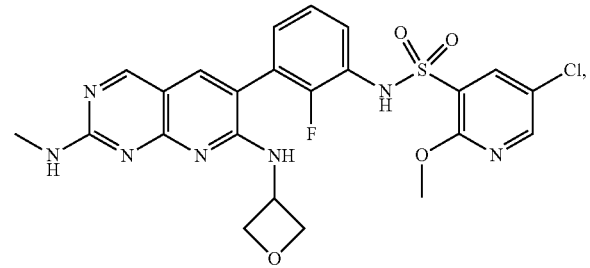
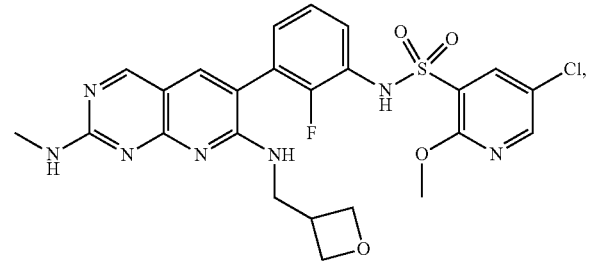
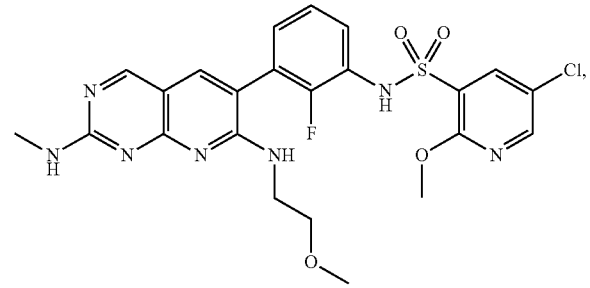
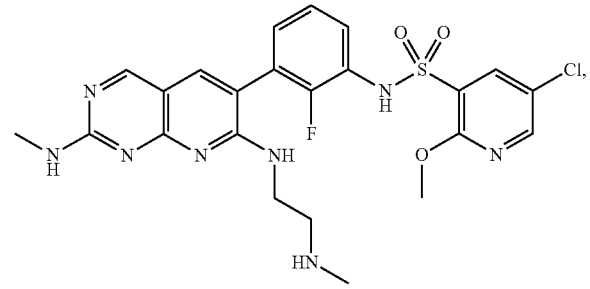
348
-continued
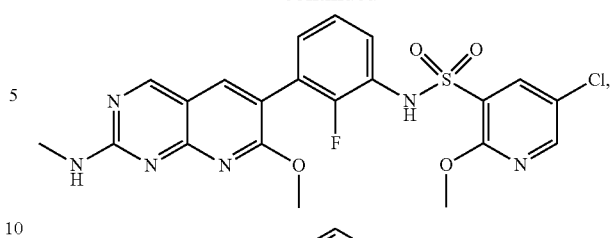
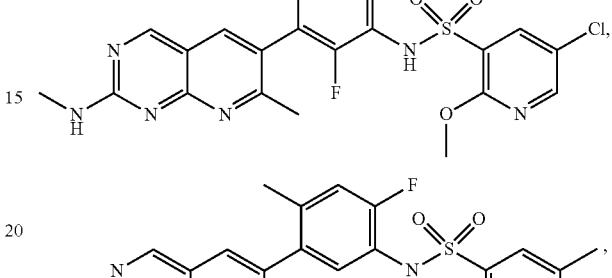
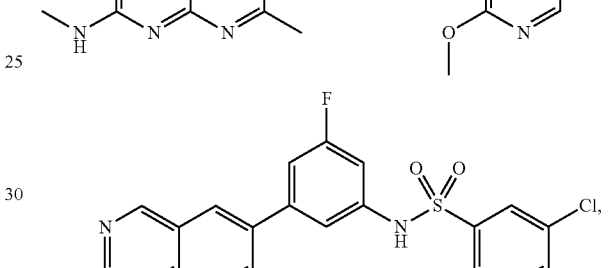
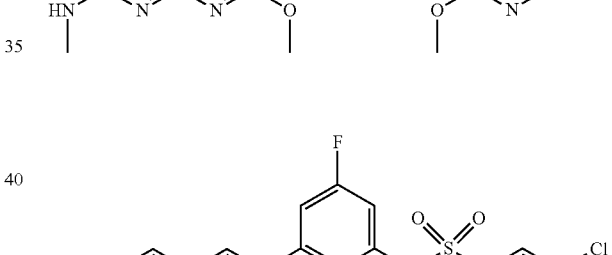
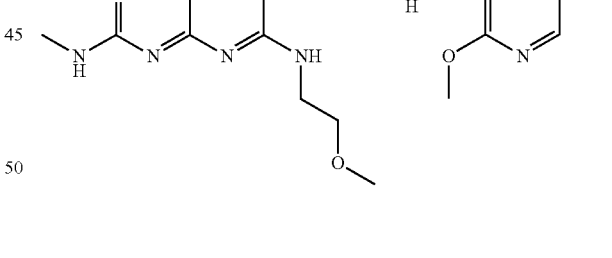
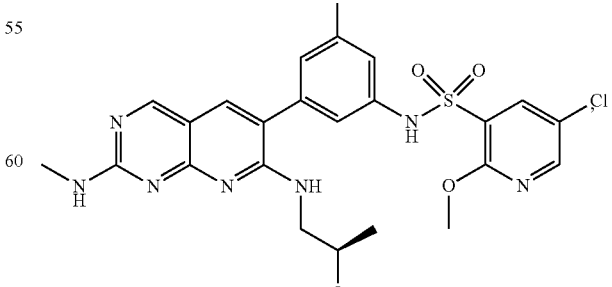

349
-continued
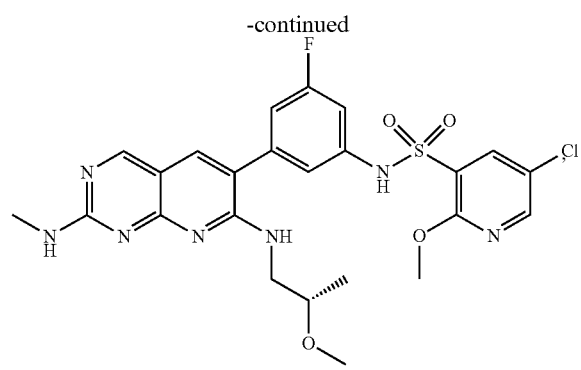
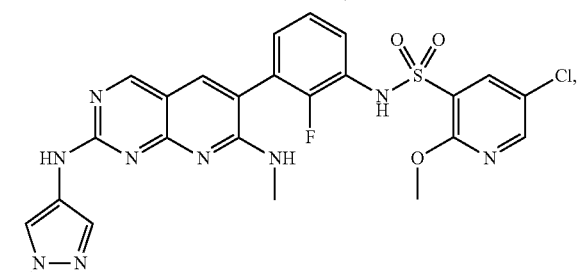
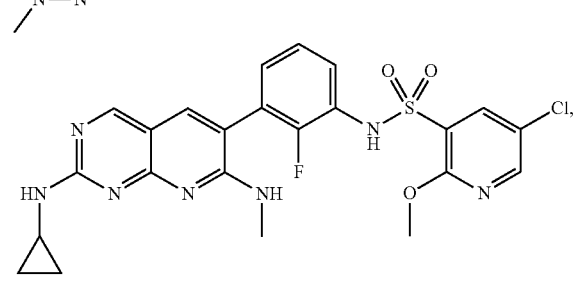
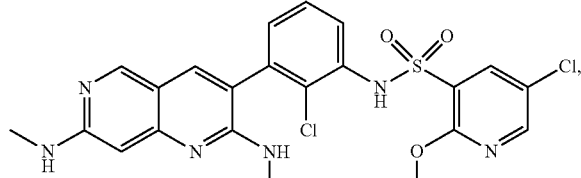
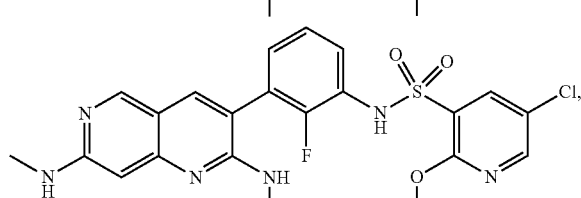
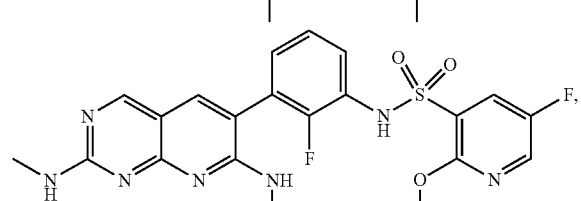
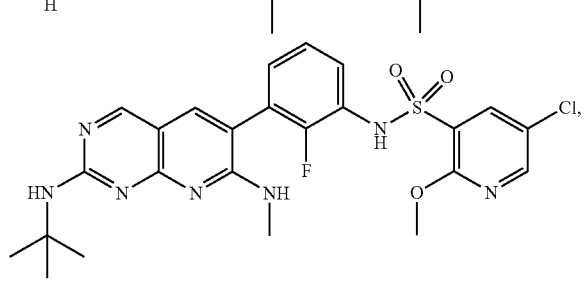
350
-continued
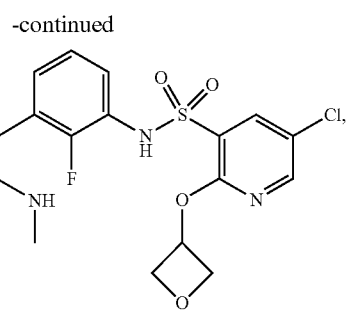
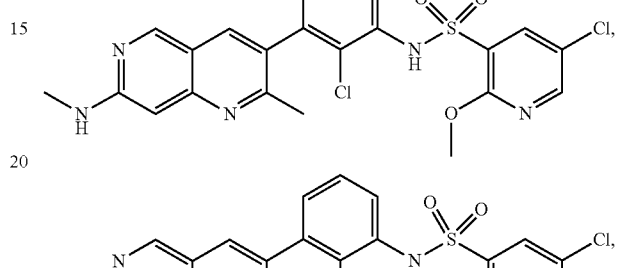
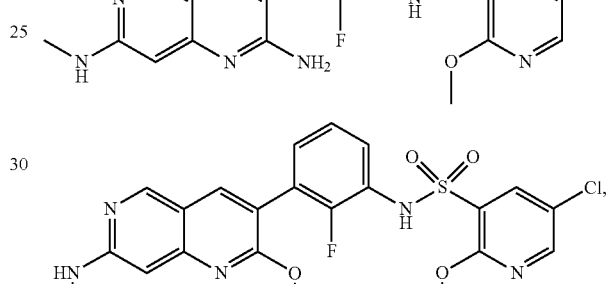
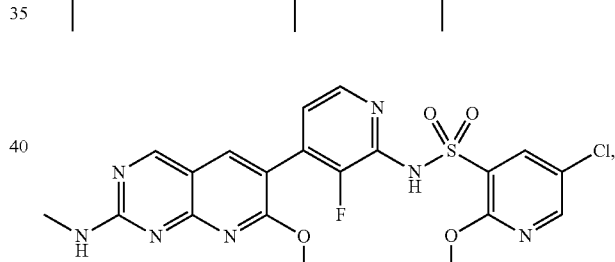
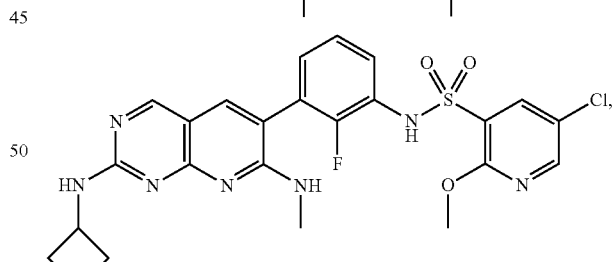
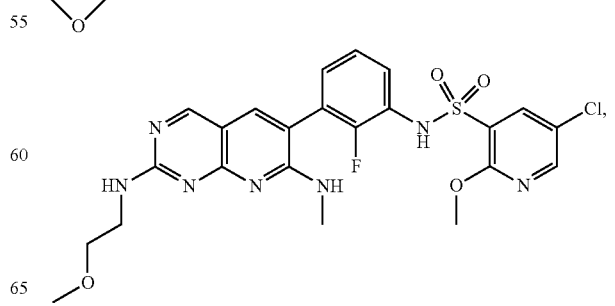

-continued
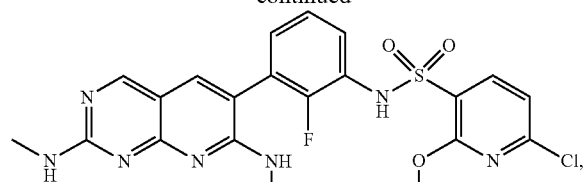
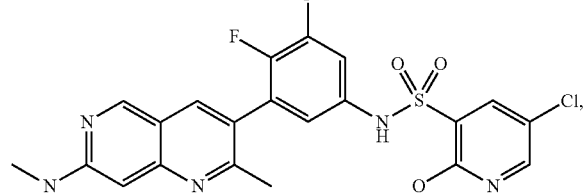
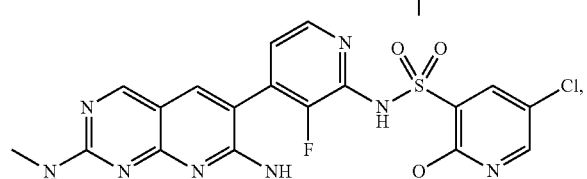
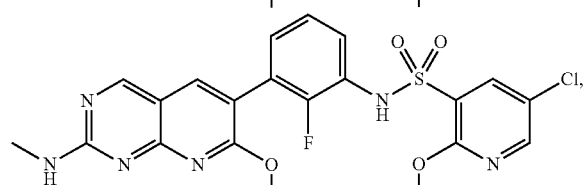
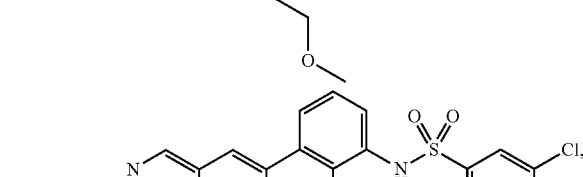
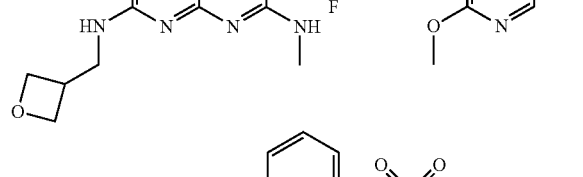
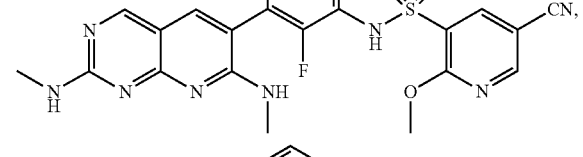
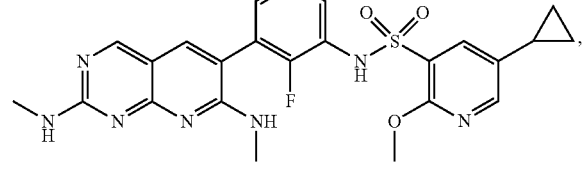
-continued
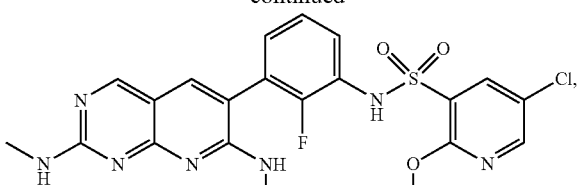
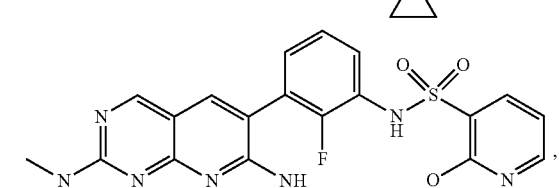
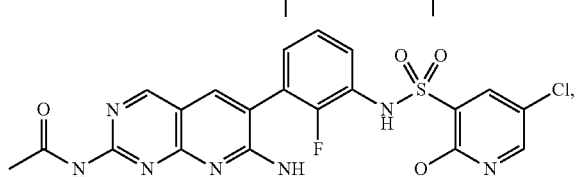
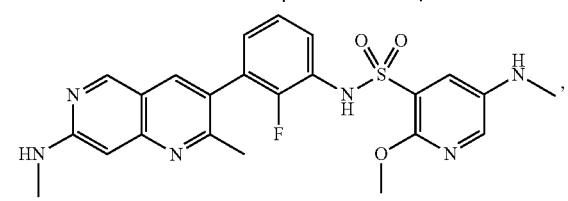
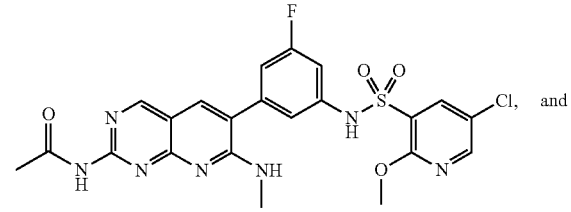
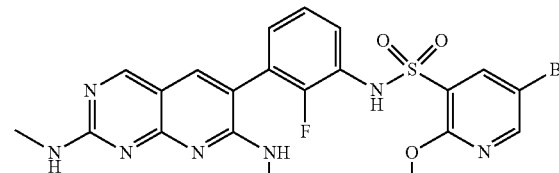
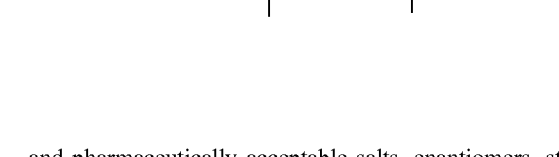
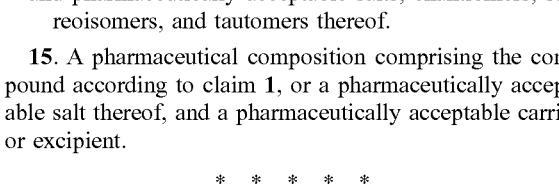
and pharmaceutically acceptable salts, enantiomers, stereoisomers, and tautomers thereof.
15. A pharmaceutical composition comprising the compound according to claim 1, or a pharmaceutically acceptable salt thereof, and a pharmaceutically acceptable carrier or excipient.
* * * * *

UNITED STATES PATENT AND TRADEMARK OFFICE
CERTIFICATE OF CORRECTION

PATENT NO. : 11,912,668 B2  
APPLICATION NO. : 17/528478  
DATED : February 27, 2024  
INVENTOR(S) : Daniel L. Flynn et al.

Page 1 of 2

It is certified that error appears in the above-identified patent and that said Letters Patent is hereby corrected as shown below:

In the Claims

In Claim 14, Column 342, Line 15, replace " 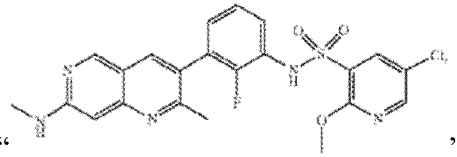 " with 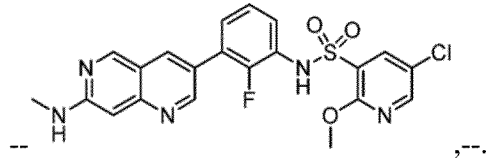 ,--.

In Claim 14, Column 344, Line 15, replace " 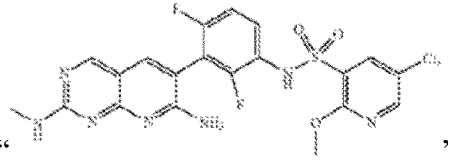 " with 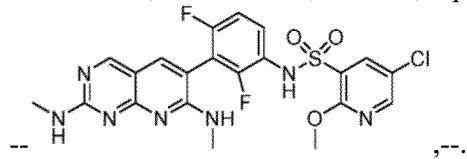 ,--.

Signed and Sealed this  
Twenty-third Day of April, 2024

Katherine Kelly Vidal  
*Director of the United States Patent and Trademark Office*

CERTIFICATE OF CORRECTION (continued)
U.S. Pat. No. 11,912,668 B2

In Claim 14, Column 344, Line 40, replace " 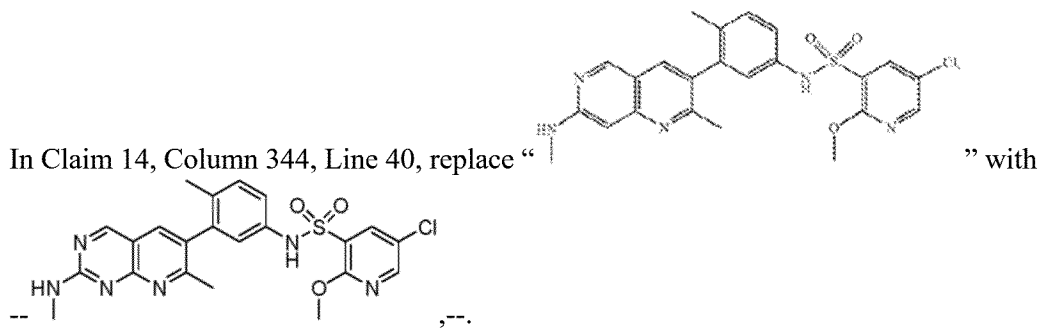 " with --[structure],--.

SEQUENCE LISTING

<160> NUMBER OF SEQ ID NOS: 2

<210> SEQ ID NO 1
<211> LENGTH: 1894
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 1

```
Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ala Met Gly Ser Gly Ile Gln Arg Pro Thr
225                 230                 235                 240

Ser Thr Ser Ser Leu Val Met Ala Gly Gly Arg Gly Ala Pro Gly Arg
                245                 250                 255

Gly Arg Asp Glu Pro Pro Glu Ser Tyr Pro Gln Arg Gln Asp His Glu
            260                 265                 270

Leu Gln Ala Leu Glu Ala Ile Tyr Gly Ala Asp Phe Gln Asp Leu Arg
        275                 280                 285

Pro Asp Ala Cys Gly Pro Val Lys Glu Pro Pro Glu Ile Asn Leu Val
    290                 295                 300

Leu Tyr Pro Gln Gly Leu Thr Gly Glu Glu Val Tyr Val Lys Val Asp
305                 310                 315                 320

Leu Arg Val Lys Cys Pro Pro Thr Tyr Pro Asp Val Val Pro Glu Ile
                325                 330                 335

Glu Leu Lys Asn Ala Lys Gly Leu Ser Asn Glu Ser Val Asn Leu Leu
            340                 345                 350

Lys Ser Arg Leu Glu Glu Leu Ala Lys Lys His Cys Gly Glu Val Met
        355                 360                 365

Ile Phe Glu Leu Ala Tyr His Val Gln Ser Phe Leu Ser Glu His Asn
    370                 375                 380

Lys Pro Pro Pro Lys Ser Phe His Glu Glu Met Leu Glu Arg Arg Ala
385                 390                 395                 400
```

```
Gln Glu Glu Gln Gln Arg Leu Leu Glu Ala Lys Arg Lys Glu Glu Gln
                405                 410                 415

Glu Gln Arg Glu Ile Leu His Glu Ile Gln Arg Lys Glu Glu Ile
            420                 425                 430

Lys Glu Glu Lys Lys Arg Lys Glu Met Ala Lys Gln Glu Arg Leu Glu
            435                 440                 445

Ile Ala Ser Leu Ser Asn Gln Asp His Thr Ser Lys Lys Asp Pro Gly
450                 455                 460

Gly His Arg Thr Ala Ala Ile Leu His Gly Gly Ser Pro Asp Phe Val
465                 470                 475                 480

Gly Asn Gly Lys His Arg Ala Asn Ser Ser Gly Arg Ser Arg Arg Glu
                485                 490                 495

Arg Gln Tyr Ser Val Cys Asn Ser Glu Asp Ser Pro Gly Ser Cys Glu
                500                 505                 510

Ile Leu Tyr Phe Asn Met Gly Ser Pro Asp Gln Leu Met Val His Lys
                515                 520                 525

Gly Lys Cys Ile Gly Asp Glu Gln Leu Gly Lys Leu Val Tyr Asn Ala
                530                 535                 540

Leu Glu Thr Ala Thr Gly Gly Phe Val Leu Leu Tyr Glu Trp Val Leu
545                 550                 555                 560

Gln Trp Gln Lys Lys Met Gly Pro Phe Leu Thr Ser Gln Glu Lys Glu
                565                 570                 575

Lys Ile Asp Lys Cys Lys Lys Gln Ile Gln Gly Thr Glu Thr Glu Phe
                580                 585                 590

Asn Ser Leu Val Lys Leu Ser His Pro Asn Val Val Arg Tyr Leu Ala
                595                 600                 605

Met Asn Leu Lys Glu Gln Asp Asp Ser Ile Val Val Asp Ile Leu Val
610                 615                 620

Glu His Ile Ser Gly Val Ser Leu Ala Ala His Leu Ser His Ser Gly
625                 630                 635                 640

Pro Ile Pro Val His Gln Leu Arg Arg Tyr Thr Ala Gln Leu Leu Ser
                645                 650                 655

Gly Leu Asp Tyr Leu His Ser Asn Ser Val Val His Lys Val Leu Ser
                660                 665                 670

Ala Ser Asn Val Leu Val Asp Ala Glu Gly Thr Val Lys Ile Thr Asp
                675                 680                 685

Tyr Ser Ile Ser Lys Arg Leu Ala Asp Ile Cys Lys Glu Asp Val Phe
                690                 695                 700

Glu Gln Thr Arg Val Arg Phe Ser Asp Asn Ala Leu Pro Tyr Lys Thr
705                 710                 715                 720

Gly Lys Lys Gly Asp Val Trp Arg Leu Gly Leu Leu Leu Leu Ser Leu
                725                 730                 735

Ser Gln Gly Gln Glu Cys Gly Glu Tyr Pro Val Thr Ile Pro Ser Asp
                740                 745                 750

Leu Pro Ala Asp Phe Gln Asp Phe Leu Lys Lys Cys Val Cys Leu Asp
                755                 760                 765

Asp Lys Glu Arg Trp Ser Pro Gln Gln Leu Leu Lys His Ser Phe Ile
                770                 775                 780

Asn Pro Gln Pro Lys Met Pro Leu Val Glu Gln Ser Pro Glu Asp Ser
785                 790                 795                 800

Gly Gly Gln Asp Tyr Val Glu Thr Val Ile Pro Ser Asn Arg Leu Pro
                805                 810                 815
```

```
Ser Ala Ala Phe Phe Ser Glu Thr Gln Arg Gln Phe Ser Arg Tyr Phe
                820                 825                 830

Ile Glu Phe Glu Glu Leu Gln Leu Leu Gly Lys Gly Ala Phe Gly Ala
            835                 840                 845

Val Ile Lys Val Gln Asn Lys Leu Asp Gly Cys Cys Tyr Ala Val Lys
        850                 855                 860

Arg Ile Pro Ile Asn Pro Ala Ser Arg Gln Phe Arg Arg Ile Lys Gly
865                 870                 875                 880

Glu Val Thr Leu Leu Ser Arg Leu His His Glu Asn Ile Val Arg Tyr
                885                 890                 895

Tyr Asn Ala Trp Ile Glu Arg His Glu Arg Pro Ala Gly Pro Gly Thr
            900                 905                 910

Pro Pro Pro Asp Ser Gly Pro Leu Ala Lys Asp Asp Arg Ala Ala Arg
        915                 920                 925

Gly Gln Pro Ala Ser Asp Thr Asp Gly Leu Asp Ser Val Glu Ala Ala
    930                 935                 940

Ala Pro Pro Pro Ile Leu Ser Ser Ser Val Glu Trp Ser Thr Ser Gly
945                 950                 955                 960

Glu Arg Ser Ala Ser Ala Arg Phe Pro Ala Thr Gly Pro Gly Ser Ser
                965                 970                 975

Asp Asp Glu Asp Asp Asp Glu Asp Glu His Gly Gly Val Phe Ser Gln
            980                 985                 990

Ser Phe Leu Pro Ala Ser Asp Ser  Glu Ser Asp Ile Ile  Phe Asp Asn
        995                 1000                 1005

Glu Asp  Glu Asn Ser Lys Ser  Gln Asn Gln Asp Glu  Asp Cys Asn
    1010                 1015                 1020

Glu Lys  Asn Gly Cys His Glu  Ser Glu Pro Ser Val  Thr Thr Glu
    1025                 1030                 1035

Ala Val  His Tyr Leu Tyr Ile  Gln Met Glu Tyr Cys  Glu Lys Ser
    1040                 1045                 1050

Thr Leu  Arg Asp Thr Ile Asp  Gln Gly Leu Tyr Arg  Asp Thr Val
    1055                 1060                 1065

Arg Leu  Trp Arg Leu Phe Arg  Glu Ile Leu Asp Gly  Leu Ala Tyr
    1070                 1075                 1080

Ile His  Glu Lys Gly Met Ile  His Arg Asp Leu Lys  Pro Val Asn
    1085                 1090                 1095

Ile Phe  Leu Asp Ser Asp Asp  His Val Lys Ile Gly  Asp Phe Gly
    1100                 1105                 1110

Leu Ala  Thr Asp His Leu Ala  Phe Ser Ala Asp Ser  Lys Gln Asp
    1115                 1120                 1125

Asp Gln  Thr Gly Asp Leu Ile  Lys Ser Asp Pro Ser  Gly His Leu
    1130                 1135                 1140

Thr Gly  Met Val Gly Thr Ala  Leu Tyr Val Ser Pro  Glu Val Gln
    1145                 1150                 1155

Gly Ser  Thr Lys Ser Ala Tyr  Asn Gln Lys Val Asp  Leu Phe Ser
    1160                 1165                 1170

Leu Gly  Ile Ile Phe Phe Glu  Met Ser Tyr His Pro  Met Val Thr
    1175                 1180                 1185

Ala Ser  Glu Arg Ile Phe Val  Leu Asn Gln Leu Arg  Asp Pro Thr
    1190                 1195                 1200

Ser Pro  Lys Phe Pro Glu Asp  Phe Asp Asp Gly Glu  His Ala Lys
    1205                 1210                 1215

Gln Lys  Ser Val Ile Ser Trp  Leu Leu Asn His Asp  Pro Ala Lys
```

-continued

```
            1220                1225                1230
Arg Pro Thr Ala Thr Glu Leu Leu Lys Ser Glu Leu Leu Pro Pro
            1235                1240                1245
Pro Gln Met Glu Glu Ser Glu Leu His Glu Val Leu His His Thr
            1250                1255                1260
Leu Thr Asn Val Asp Gly Lys Ala Tyr Arg Thr Met Met Ala Gln
            1265                1270                1275
Ile Phe Ser Gln Arg Ile Ser Pro Ala Ile Asp Tyr Thr Tyr Asp
            1280                1285                1290
Ser Asp Ile Leu Lys Gly Asn Phe Ser Ile Arg Thr Ala Lys Met
            1295                1300                1305
Gln Gln His Val Cys Glu Thr Ile Ile Arg Ile Phe Lys Arg His
            1310                1315                1320
Gly Ala Val Gln Leu Cys Thr Pro Leu Leu Leu Pro Arg Asn Arg
            1325                1330                1335
Gln Ile Tyr Glu His Asn Glu Ala Ala Leu Phe Met Asp His Ser
            1340                1345                1350
Gly Met Leu Val Met Leu Pro Phe Asp Leu Arg Ile Pro Phe Ala
            1355                1360                1365
Arg Tyr Val Ala Arg Asn Asn Ile Leu Asn Leu Lys Arg Tyr Cys
            1370                1375                1380
Ile Glu Arg Val Phe Arg Pro Arg Lys Leu Asp Arg Phe His Pro
            1385                1390                1395
Lys Glu Leu Leu Glu Cys Ala Phe Asp Ile Val Thr Ser Thr Thr
            1400                1405                1410
Asn Ser Phe Leu Pro Thr Ala Glu Ile Ile Tyr Thr Ile Tyr Glu
            1415                1420                1425
Ile Ile Gln Glu Phe Pro Ala Leu Gln Glu Arg Asn Tyr Ser Ile
            1430                1435                1440
Tyr Leu Asn His Thr Met Leu Leu Lys Ala Ile Leu Leu His Cys
            1445                1450                1455
Gly Ile Pro Glu Asp Lys Leu Ser Gln Val Tyr Ile Ile Leu Tyr
            1460                1465                1470
Asp Ala Val Thr Glu Lys Leu Thr Arg Arg Glu Val Glu Ala Lys
            1475                1480                1485
Phe Cys Asn Leu Ser Leu Ser Ser Asn Ser Leu Cys Arg Leu Tyr
            1490                1495                1500
Lys Phe Ile Glu Gln Lys Gly Asp Leu Gln Asp Leu Met Pro Thr
            1505                1510                1515
Ile Asn Ser Leu Ile Lys Gln Lys Thr Gly Ile Ala Gln Leu Val
            1520                1525                1530
Lys Tyr Gly Leu Lys Asp Leu Glu Glu Val Val Gly Leu Leu Lys
            1535                1540                1545
Lys Leu Gly Ile Lys Leu Gln Val Leu Ile Asn Leu Gly Leu Val
            1550                1555                1560
Tyr Lys Val Gln Gln His Asn Gly Ile Ile Phe Gln Phe Val Ala
            1565                1570                1575
Phe Ile Lys Arg Arg Gln Arg Ala Val Pro Glu Ile Leu Ala Ala
            1580                1585                1590
Gly Gly Arg Tyr Asp Leu Leu Ile Pro Gln Phe Arg Gly Pro Gln
            1595                1600                1605
Ala Leu Gly Pro Val Pro Thr Ala Ile Gly Val Ser Ile Ala Ile
            1610                1615                1620
```

```
Asp Lys Ile Ser Ala Ala Val Leu Asn Met Glu Glu Ser Val Thr
        1625                1630                1635

Ile Ser Ser Cys Asp Leu Leu Val Val Ser Val Gly Gln Met Ser
        1640                1645                1650

Met Ser Arg Ala Ile Asn Leu Thr Gln Lys Leu Trp Thr Ala Gly
        1655                1660                1665

Ile Thr Ala Glu Ile Met Tyr Asp Trp Ser Gln Ser Gln Glu Glu
        1670                1675                1680

Leu Gln Glu Tyr Cys Arg His His Glu Ile Thr Tyr Val Ala Leu
        1685                1690                1695

Val Ser Asp Lys Glu Gly Ser His Val Lys Val Lys Ser Phe Glu
        1700                1705                1710

Lys Glu Arg Gln Thr Glu Lys Arg Val Leu Glu Thr Glu Leu Val
        1715                1720                1725

Asp His Val Leu Gln Lys Leu Arg Thr Lys Val Thr Asp Glu Arg
        1730                1735                1740

Asn Gly Arg Glu Ala Ser Asp Asn Leu Ala Val Gln Asn Leu Lys
        1745                1750                1755

Gly Ser Phe Ser Asn Ala Ser Gly Leu Phe Glu Ile His Gly Ala
        1760                1765                1770

Thr Val Val Pro Ile Val Ser Val Leu Ala Pro Glu Lys Leu Ser
        1775                1780                1785

Ala Ser Thr Arg Arg Arg Tyr Glu Thr Gln Val Gln Thr Arg Leu
        1790                1795                1800

Gln Thr Ser Leu Ala Asn Leu His Gln Lys Ser Ser Glu Ile Glu
        1805                1810                1815

Ile Leu Ala Val Asp Leu Pro Lys Glu Thr Ile Leu Gln Phe Leu
        1820                1825                1830

Ser Leu Glu Trp Asp Ala Asp Glu Gln Ala Phe Asn Thr Thr Val
        1835                1840                1845

Lys Gln Leu Leu Ser Arg Leu Pro Lys Gln Arg Tyr Leu Lys Leu
        1850                1855                1860

Val Cys Asp Glu Ile Tyr Asn Ile Lys Val Glu Lys Lys Val Ser
        1865                1870                1875

Val Leu Phe Leu Tyr Ser Tyr Arg Asp Asp Tyr Tyr Arg Ile Leu
        1880                1885                1890

Phe

<210> SEQ ID NO 2
<211> LENGTH: 779
<212> TYPE: PRT
<213> ORGANISM: Homo sapiens

<400> SEQUENCE: 2

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80
```

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Lys Tyr Asp Ser Val Ser Gly Glu Ala Asn Asp Ser Ser Trp
225                 230                 235                 240

Asn Asp Ile Lys Asn Ser Gly Tyr Ile Ser Arg Tyr Leu Thr Asp Phe
                245                 250                 255

Glu Pro Ile Gln Cys Leu Gly Arg Gly Gly Phe Gly Val Val Phe Glu
            260                 265                 270

Ala Lys Asn Lys Val Asp Asp Cys Asn Tyr Ala Ile Lys Arg Ile Arg
        275                 280                 285

Leu Pro Asn Arg Glu Leu Ala Arg Glu Lys Val Met Arg Glu Val Lys
    290                 295                 300

Ala Leu Ala Lys Leu Glu His Pro Gly Ile Val Arg Tyr Phe Asn Ala
305                 310                 315                 320

Trp Leu Glu Ala Pro Pro Glu Lys Trp Gln Glu Lys Met Asp Glu Ile
                325                 330                 335

Trp Leu Lys Asp Glu Ser Thr Asp Trp Pro Leu Ser Ser Pro Ser Pro
            340                 345                 350

Met Asp Ala Pro Ser Val Lys Ile Arg Arg Met Asp Pro Phe Ser Thr
        355                 360                 365

Lys Glu His Ile Glu Ile Ile Ala Pro Ser Pro Gln Arg Ser Arg Ser
    370                 375                 380

Phe Ser Val Gly Ile Ser Cys Asp Gln Thr Ser Ser Glu Ser Gln
385                 390                 395                 400

Phe Ser Pro Leu Glu Phe Ser Gly Met Asp His Glu Asp Ile Ser Glu
                405                 410                 415

Ser Val Asp Ala Ala Tyr Asn Leu Gln Asp Ser Cys Leu Thr Asp Cys
            420                 425                 430

Asp Val Glu Asp Gly Thr Met Asp Gly Asn Asp Glu Gly His Ser Phe
        435                 440                 445

Glu Leu Cys Pro Ser Glu Ala Ser Pro Tyr Val Arg Ser Arg Glu Arg
    450                 455                 460

Thr Ser Ser Ser Ile Val Phe Glu Asp Ser Gly Cys Asp Asn Ala Ser
465                 470                 475                 480

Ser Lys Glu Glu Pro Lys Thr Asn Arg Leu His Ile Gly Asn His Cys
                485                 490                 495
```

```
Ala Asn Lys Leu Thr Ala Phe Lys Pro Thr Ser Ser Lys Ser Ser
        500             505             510
Glu Ala Thr Leu Ser Ile Ser Pro Pro Arg Pro Thr Thr Leu Ser Leu
        515             520             525
Asp Leu Thr Lys Asn Thr Thr Glu Lys Leu Gln Pro Ser Ser Pro Lys
        530             535             540
Val Tyr Leu Tyr Ile Gln Met Gln Leu Cys Arg Lys Glu Asn Leu Lys
545             550             555             560
Asp Trp Met Asn Gly Arg Cys Thr Ile Glu Arg Glu Arg Ser Val
            565             570             575
Cys Leu His Ile Phe Leu Gln Ile Ala Glu Ala Val Glu Phe Leu His
        580             585             590
Ser Lys Gly Leu Met His Arg Asp Leu Lys Pro Ser Asn Ile Phe Phe
        595             600             605
Thr Met Asp Asp Val Val Lys Val Gly Asp Phe Gly Leu Val Thr Ala
        610             615             620
Met Asp Gln Asp Glu Glu Glu Gln Thr Val Leu Thr Pro Met Pro Ala
625             630             635             640
Tyr Ala Arg His Thr Gly Gln Val Gly Thr Lys Leu Tyr Met Ser Pro
            645             650             655
Glu Gln Ile His Gly Asn Ser Tyr Ser His Lys Val Asp Ile Phe Ser
            660             665             670
Leu Gly Leu Ile Leu Phe Glu Leu Leu Tyr Pro Phe Ser Thr Gln Met
        675             680             685
Glu Arg Val Arg Thr Leu Thr Asp Val Arg Asn Leu Lys Phe Pro Pro
        690             695             700
Leu Phe Thr Gln Lys Tyr Pro Cys Glu Tyr Val Met Val Gln Asp Met
705             710             715             720
Leu Ser Pro Ser Pro Met Glu Arg Pro Glu Ala Ile Asn Ile Ile Glu
            725             730             735
Asn Ala Val Phe Glu Asp Leu Asp Phe Pro Gly Lys Thr Val Leu Arg
            740             745             750
Gln Arg Ser Arg Ser Leu Ser Ser Ser Gly Thr Lys His Ser Arg Gln
        755             760             765
Ser Asn Asn Ser His Ser Pro Leu Pro Ser Asn
770             775
```